US009988440B2

(12) United States Patent
Johnson et al.

(10) Patent No.: US 9,988,440 B2
(45) Date of Patent: *Jun. 5, 2018

(54) COMPOSITIONS COMPRISING ANTIBODIES TARGETING FACTOR P

(71) Applicant: NOVARTIS AG, Basel (CH)

(72) Inventors: Leslie Ngozi Anuna Johnson, Revere, MA (US); Ute Jaeger, Munich (DE); Yong-In Kim, Westborough, MA (US); Christian Carsten Silvester Kunz, Munich (DE); Igor Splawski, Winchester, MA (US); Michael Roguska, Ashland, MA (US); Joy Ghosh, Brookline, MA (US); Barbara Brannetti, Basel (CH); Michael Stefanidakis, Brookline, MA (US); Sha-Mei Liao, Lexington, MA (US)

(73) Assignee: NOVARTIS AG, Basel (CH)

( * ) Notice: Subject to any disclaimer, the term of this patent is extended or adjusted under 35 U.S.C. 154(b) by 365 days.

This patent is subject to a terminal disclaimer.

(21) Appl. No.: 14/309,330

(22) Filed: Jun. 19, 2014

(65) Prior Publication Data
US 2015/0158936 A1 Jun. 11, 2015

Related U.S. Application Data

(63) Continuation of application No. PCT/IB2012/057394, filed on Dec. 17, 2012.

(60) Provisional application No. 61/578,458, filed on Dec. 21, 2011.

(51) Int. Cl.
*A61K 39/395* (2006.01)
*C07K 16/18* (2006.01)
*G01N 33/68* (2006.01)
*C07K 16/24* (2006.01)
*A61K 39/00* (2006.01)

(52) U.S. Cl.
CPC .......... *C07K 16/18* (2013.01); *A61K 39/3955* (2013.01); *C07K 16/24* (2013.01); *G01N 33/6863* (2013.01); *A61K 2039/505* (2013.01); *A61K 2039/507* (2013.01); *C07K 2317/21* (2013.01); *C07K 2317/30* (2013.01); *C07K 2317/33* (2013.01); *C07K 2317/40* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,074,642 | A | 6/2000 | Wang et al. |
|---|---|---|---|
| 6,333,034 | B1 | 12/2001 | Gupta-Bansal et al. |
| 6,355,245 | B1 | 3/2002 | Evans et al. |
| 7,011,952 | B2 | 3/2006 | Hageman et al. |
| 7,108,982 | B1 | 9/2006 | Hageman |
| 7,285,269 | B2 | 10/2007 | Babcook et al. |
| 7,344,846 | B2 | 3/2008 | Hageman et al. |
| 7,351,524 | B2 | 4/2008 | Hageman et al. |
| 7,423,128 | B2 | 9/2008 | Gazit-Bornstein et al. |
| 7,514,539 | B2 | 4/2009 | O'Neil et al. |
| 8,088,896 | B2 | 1/2012 | Tesar et al. |
| 8,168,758 | B2 | 5/2012 | Tamburini et al. |
| 8,241,628 | B2 | 8/2012 | Diefenbach-Streiber et al. |
| 8,435,512 | B2 | 5/2013 | Bansal |
| 9,051,365 | B2 * | 6/2015 | Johnson ............. C07K 16/18 |
| 2005/0169921 | A1 | 8/2005 | Bell et al. |
| 2005/0191298 | A1 | 9/2005 | Bell et al. |
| 2006/0115476 | A1 | 6/2006 | Tedesco et al. |
| 2006/0263819 | A1 | 11/2006 | Hageman et al. |
| 2007/0065433 | A1 | 3/2007 | Mollnes et al. |
| 2007/0116710 | A1 | 5/2007 | Bell et al. |
| 2007/0123466 | A1 | 5/2007 | Salmon et al. |
| 2007/0196367 | A1 | 8/2007 | Dinu |
| 2007/0274989 | A1 | 11/2007 | Fung et al. |
| 2008/0131418 | A1 | 6/2008 | Hageman et al. |
| 2008/0200645 | A1 | 8/2008 | Kotwal et al. |
| 2008/0274453 | A1 | 11/2008 | Hageman |
| 2009/0017031 | A1 | 1/2009 | Fung |
| 2009/0162357 | A1 | 6/2009 | Cabezas et al. |
| 2009/0214538 | A1 | 8/2009 | Fung et al. |
| 2009/0269356 | A1 | 10/2009 | Epstein et al. |
| 2010/0034809 | A1 | 2/2010 | Diefenbach-Streiber et al. |
| 2010/0087393 | A1 | 4/2010 | Bansal |

(Continued)

FOREIGN PATENT DOCUMENTS

| CN | 102170906 A | 8/2011 |
|---|---|---|
| EP | 1153302 B1 | 10/2006 |

(Continued)

OTHER PUBLICATIONS

Schreiber et al., "Initiation of the alternative pathway of complement: recognition of activators by bound C3b and assembly of the entire pathway from six isolated proteins," Proc Natl Acad Sci U S A. 75(8):3948-52 (Aug. 1978).
Blondin et al., "Inhibition of complement activation by natural sulfated polysaccharides (fucans) from brown seaweed." Molecular Immunol. 31(4):247-253 (1994).
Fredrikson et al., Molecular characterization of properdin deficiency type III: dysfunction produced by a single point mutation in exon 9 of the structural gene causing a tyrosine to aspartic acid interchange. J Immunol. 15;157(8):3666-71 (Oct. 1996).
Sahu et al., "Inhibition of human complement by a C3-binding peptide isolated from a phage-displayed random peptide library," J Immunol. 157(2):884-891 (1996).
Wolf-Schnurrbusch et al., Complement Factor P in choroidal neovascular membranes of patients with age-related macular degeneration. Retina 9(7):966-73 (Jul.-Aug. 2009).
Whiteman et al., Association of activated properdin with complexes of properdin with C3. J Immunol. 15;147(4):1344-51 (Aug. 1991).
Seitsonen et al., Screening of DNA-variants in the properdin gene (CFP) in age-related macular degeneration (AMD). Mol Immunol. 47(6):1334-6 (Mar. 2010).
Gupta-Bansal et al., "Inhibition of complement alternative pathway function with anti-properdin monoclonal antibodies," Molecular Immunology 37(5):191-201 (Apr. 1, 2000).

(Continued)

*Primary Examiner* — Phillip Gambel
(74) *Attorney, Agent, or Firm* — Sherwin Y. Chan

(57) ABSTRACT

The present invention relates to antibodies or antigen binding fragments thereof that bind to complement Factor P and used thereof as well as combinations of anti-Factor P antibodies with antibodies or antigen binding fragments thereof that bind to complement component 5 (C5).

33 Claims, 6 Drawing Sheets

(56) References Cited

U.S. PATENT DOCUMENTS

| | | |
|---|---|---|
| 2011/0008340 A1 | 1/2011 | Bansal |
| 2012/0258095 A1 | 10/2012 | Demopulos et al. |

FOREIGN PATENT DOCUMENTS

| | | |
|---|---|---|
| EP | 1804064 A1 | 7/2007 |
| EP | 1287364 B1 | 10/2008 |
| EP | 2026073 A1 | 2/2009 |
| JP | 3734266 B2 | 10/2005 |
| JP | 2006518750 A | 8/2006 |
| JP | 2009514888 A | 4/2009 |
| JP | 2011529700 A | 12/2011 |
| WO | 95/29697 A1 | 11/1995 |
| WO | 01/84144 A1 | 11/2001 |
| WO | 02/30985 A2 | 4/2002 |
| WO | 02/086085 A2 | 10/2002 |
| WO | WO2004075838 A2 | 9/2004 |
| WO | 2005/074607 A2 | 8/2005 |
| WO | 2006/052591 A2 | 5/2006 |
| WO | 2006052591 A2 | 5/2006 |
| WO | 2007/056227 A2 | 5/2007 |
| WO | 2007/106585 A1 | 9/2007 |
| WO | 2008/069889 A2 | 6/2008 |
| WO | 2008/154018 A2 | 12/2008 |
| WO | 2009/029669 A1 | 3/2009 |
| WO | 2009110918 A1 | 9/2009 |
| WO | 2009/121065 A2 | 10/2009 |
| WO | 2010/015608 A1 | 2/2010 |
| WO | 2011/109494 A2 | 9/2011 |
| WO | 2011-112850 A2 | 9/2011 |
| WO | 2011/112850 A2 | 9/2011 |
| WO | 2013/006449 A2 | 1/2013 |
| WO | 2013/093762 A1 | 6/2013 |

OTHER PUBLICATIONS

Gehrs et al., "Complement, Age-Related Macular Degeneration and a Vision of the Future," Archives of Ophthalmology 128(3):349-358 (Mar. 2010).
Chen et al., "Enhancement and destruction of antibody function by somatic mutation: unequal occurrence is controlled by V gene combinatorial associations," EMBO J. 14(12):2784-2794 (1995).
Colman, P.M., "Effects of amino acid sequence changes on antibody-antigen interactions," Res Immunol. 145(1):33-6 (1995).
Kussie et al., A single engineered amino acid substitution changes antibody fine specificity. J Immunol. Jan. 1, 1994;152(1):146-52.
Rudikoff et al., Single amino acid substitution altering antigen-binding specificity. Proc Natl Acad Sci U S A. Mar. 1982;79(6):1979-83.
Holm et al., "Functional mapping and single chain construction of the anti-cytokeratin 8 monoclonal antibody TS1," Molecular Immunology 44:1075-1084 (2007).
Holt et al., "Domain antibodies: proteins for therapy," Trends in Biotechnology 21(11):484-490(Nov. 2003).
Liu et al., "Fine mapping of the antigen-antibody interaction of scFv215, a recombinant antibody inhibiting RNA polymerase II from Drosophila melanogaster," Journal of Molecular Recognition 12:103-111 (1999).
MacCallum et al., "Antibody-antigen Interactions: Contact Analysis and Binding Site Topography," J. Mol. Bio. 262:732-745 (1996).
Maynard and Georgiou, "Antibody Engineering," Annu. Rev. Biomed. Eng. 02:339-76 (2000).
Pini et al., "Design and Use of a Phage Display Library," The Journal of Biological Chemistry 273(34):21769-21779 (1998).
Rothe et al., "The Human Combinatorial Antibody Library HuCAL Gold Combines Diversification of All Six CDRs According to the Natural Immune System with a Novel Display Method for Efficient Selection of High-Affinity Antibodies" J. Mol. Biol. 376:1182-1200 (2008).
Rother et al., "Discovery and development of the complement inhibitor eculizumab for the treatment of paroxysmal nocturnal hemoglobunuria," Nature Biotechnology 25(11):1256-1264 (Nov. 2007).
Schildbach et al., "Contribution of a single heavy chain residue to specificity of an anti-digoxin monoclonal antibody," Protein Science 3:737-749 (1994).
Thurman et al., "The Central Role of the Alternative Complement Pathway in Human Disease," The Journal of Immunology 176:1305-1310 (2006).
Vajdos et al., "Comprehensive functional maps of the antigen-binding site of the Antigen-binding Site of an Anti-ErbB2 Antibody Obtained with Shotgun Scanning Mutagenesis" J. Mol. Biol. 320:415-428 (2002).
Wu et al., "Humanization of a Murine Monoclonal Antibody by Simultaneous Optimization of Framework and CDR Residues," J. Mol. Biol 294:151-162 (1999).
Xiang et al., "Study of B72.3 Combining Sites by Molecular Modeling and Site-Directed Mutagenesis," Protein Engineering 13(5):339-344 (2000).
Schildbach et al., "Heavy Chain Position 50 Is a Determinant of Affinity and Specificity for the Anti-digoxin Antibody 26-10," The Journal of Biological Chemistry 268(29):21739-21747 (1983).
Brown et al., "Tolerance to single, but not multiple, amino acid replacements in antibody VH CDR 2," The Journal of Immunology 156(9):3285-3291 (1996).
Casset et al., "A peptide mimetic of an Anti-CD4 monoclonal antibody by rational design," Biochemical and Biophysical Research Communications 307:198-205 (2003).
Cicchetti et al., "Immune parameters relevant to neural xenograft survival in the primate brain," Xenotransplantation 10(1):41-49 (2003).
Davies et al., "Affinity improvement of single antibody VH domains: residues in all three hypervariable regions affect antigen binding," Immunotechnology 2(3):169-179 (1996).
De Pascallis et al., "Grafting of Abbreviated Complementarity-Determining Regions Containing Specificity-Determining Residues Essential for Ligand Contact to Engineer a Less Immunogenic Humanized Monoclonal Antibody" The Journal of Immunology 169:3076-3084 (2002).
Giusti et al., "Somatic diversification of S107 from an antiphosphocholine to an anti-DNA autoantibody is due to a single base change in its heavy chain variable region," Proc. Natl. Acad. Sci. USA 84:2926-2930 (May 1987).
Holers, "The spectrum of complement alternative pathway-mediated diseases," Immunological Reviews 223:300-316 (2008).

* cited by examiner

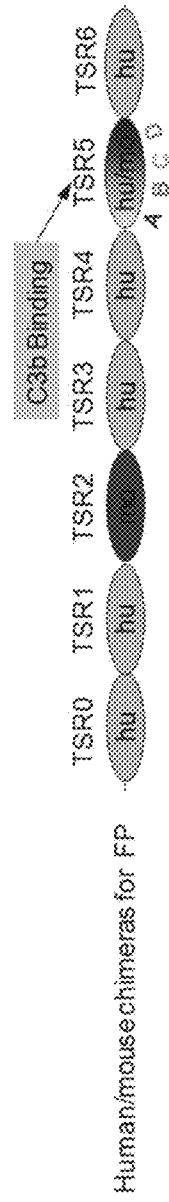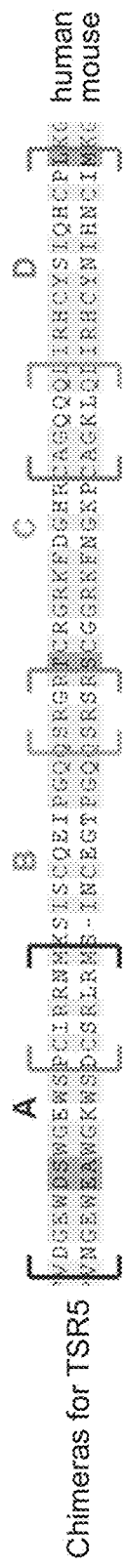
FIG. 1A
FIG. 1B

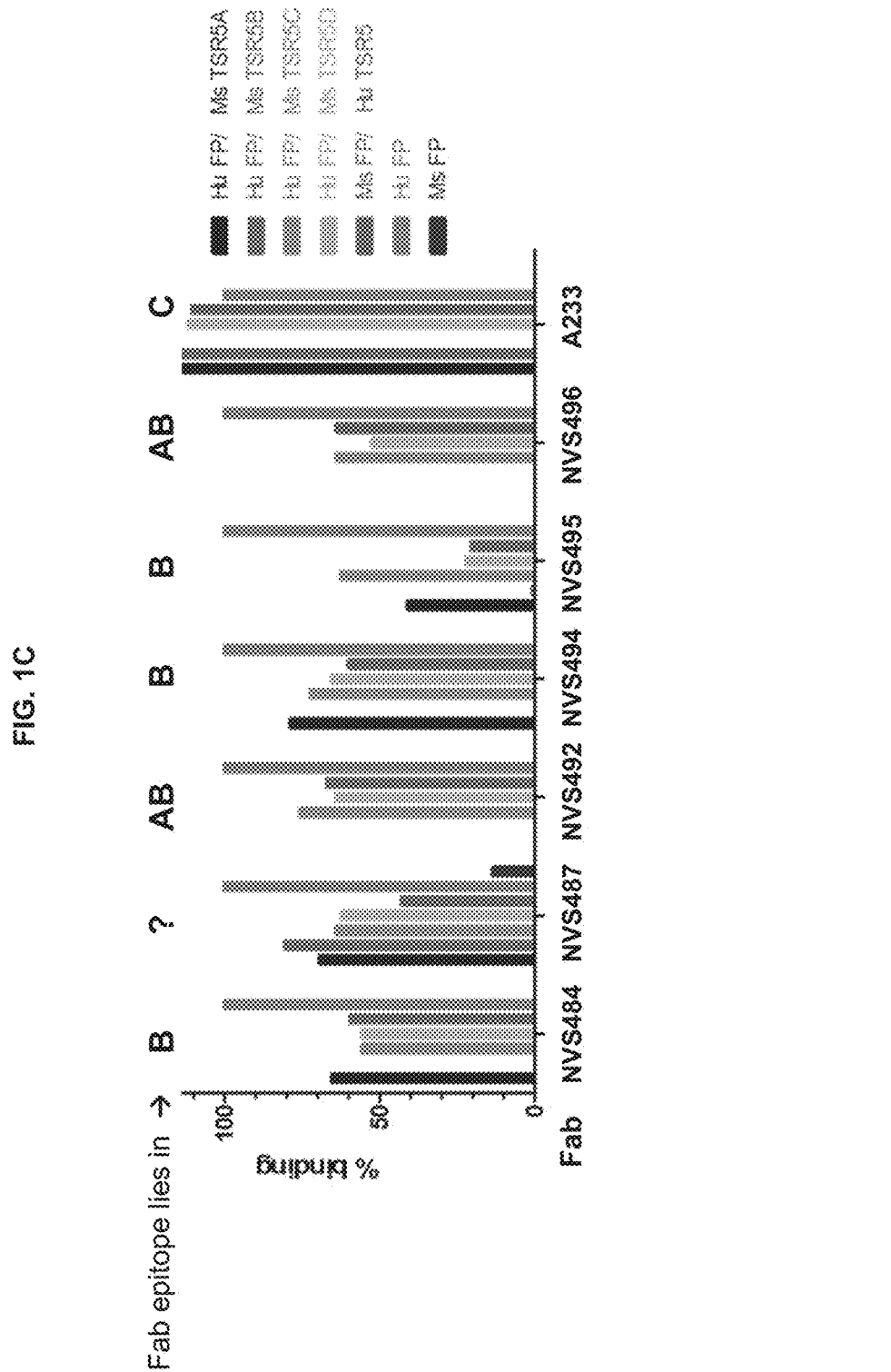

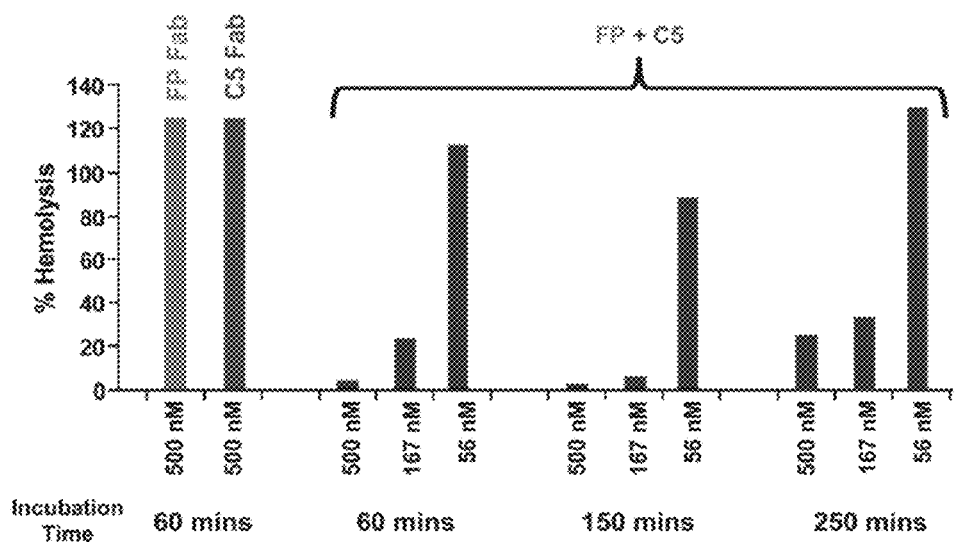

# COMPOSITIONS COMPRISING ANTIBODIES TARGETING FACTOR P

CROSS REFERENCE TO RELATED APPLICATIONS

This application claims the benefit of U.S. Patent Application No. 61/578,458, filed on Dec. 21, 2011, the entire contents of which are hereby incorporated by reference in their entirety.

BACKGROUND OF THE INVENTION

Age related macular degeneration (AMD) is a progressive disease and a leading cause of vision loss and blindness in Americans aged 65 and older. AMD primarily affects the macula; a part of the retina responsible for high visual acuity needed to read or drive. The majority of AMD patients suffer from an early stage of the disease which is characterized by the presence of extracellular retinal deposits called drusen. Drusen are extracellular retinal deposits of cell debris, inflammatory mediators, and extracellular matrix components. The late stages of AMD manifest as a dry or wet form, both are associated with vision loss. Dry AMD, also known as geographic atrophy, appears on ophthalmoscopic examination as clearly demarcated regions corresponding to local areas of retinal pigmented epithelium (RPE) loss. Wet AMD is associated with neovascularization of the chorioid, causing a loss of integrity in Bruch's membrane and vessel growth in the retina, where they can often hemorrhage. This leakage causes permanent damage to retinal cells which die off and create blind spots in the central vision.

The innate human system is composed of the complement pathway. The complement pathway serves to defend against pyogenic bacterial infection bridging innate and adaptive immunity; and disposing of products of immune complexes and inflammatory injury. The complement is a system of more than 30 proteins involved in cascade reactions in plasma and cell surfaces. The complement system and its complement components are involved in various immune processes. For example, complement C5b-9 complex, also termed the terminal complex or the membrane attack complex (MAC), plays an important role in cell death by inducing membrane permeability damages.

There are three known complement activation pathways: the classical, lectin, and alternative pathways. All three pathways lead to the cleavage of C3 by C3 convertase and subsequent cleavage of C5 by the C5 convertase, releasing C3a, C5a, and C5b. Factor P is a key regulator of the alternative complement pathway. It is proposed to have two major functions in viva First, Factor P stabilizes the C3 and C5 convertases by binding to C3b of the convertase enzyme and thereby prolongs the half life of C3 convertase. Second, Factor P may determine which cells will be lysed by attaching to a cell surface and functioning as a template on which convertases can form, leading to activation of the alternative complement pathway and lysis of the cell.

Recent work has demonstrated that complement components C3 and C5 are principal constituents of drusen in patients with AMD. Mulling, R. F. et al. (2000) FASEB J 14, 835-46 Their presence as well as that of the membrane attack complex (MAC) C5b-9 and other acute phase reactant proteins in RPE cells overlying drusen has been speculated to be involved in the process that can trigger complement activation and formation of MAC. Johnson, L et al. (2001) Exp Eye Res 73, 887-896. Thus, there is growing evidence that complement components are more than mere mediators of innate immunity.

Nutritional intervention has been prescribed to inhibit progression of dry AMD to wet AMD. At present the only FDA approved treatments for wet AMD include photodynamic therapy (PDT), an anti-VEGF aptamer, such as pegaptanib, and anti-VEGF antibodies, ranibizumab. These drugs or therapies are typically administered to patients who have already suffered substantial vision loss.

There remains a need to develop an effective treatment for AMD, particularly dry AMD to replace or supplement current treatments. Particularly, there is a need for treatments which can provide early detection, prevention or restoration of vision loss.

SUMMARY OF THE INVENTION

The present invention relates to an isolated antibody, or antigen binding fragment thereof, that binds to human or cynomolgus Factor P, wherein said antibody binds to the TSR5 domain (SEQ ID NO: 406). For example, the antibodies, or antigen binding fragments described herein bind to a region of the TSR5 domain comprising the sequence of SEQ ID NO: 407, more specifically said antibodies also bind a region of the Factor P TSR5 domain comprising the amino acid sequence KSISC (SEQ ID NO: 408). In certain embodiments, the isolated antibodies, or antigen binding fragments thereof, bind to a Factor P epitope comprising the amino acid sequence of SEQ ID NO: 407. In other embodiments, the isolated antibodies, or antigen binding fragments thereof, bind to a Factor P epitope comprising the amino acid sequence of SEQ ID NO: 408.

The isolated antibodies, or antigen binding fragments, described herein bind Factor P, with a KD of less than or equal to 1.2 nM. For example, the isolated antibodies or antigen binding fragments described herein may bind to human or cynomolgus Factor P with a KD of less than or equal to 1.1 nM, less than or equal to 1 nM, less than or equal to 600 pM, less than or equal to 500 pM, less than or equal to 400 pM, less than or equal to 300 pM, less than or equal to 200 pM, less than or equal to 100 pM, less than or equal to 75 pM, less than or equal to 50 pM, less than or equal to 40 pM, less than or equal to 30 pM, less than or equal to 20 pM, or less than or equal to 10 pM.

The binding affinity of isolated antibodies and antigen binding fragments described herein can be determined by solution equilibrium titration (SET). Methods for SET are known in the art and are described in further detail below. Alternatively, binding affinity of the isolated antibodies, or fragments, described herein can be determined by BIACORE™ assay. Methods for BIACORE™ kinetic assays are known in the art and are described in further detail below.

The isolated antibodies and antigen binding fragments described herein can be used to inhibit the alternative complement pathway. For example, an isolated antibody or antigen binding fragment thereof can inhibit the alternative complement pathway as measure by an in vitro hemolytic assay with an IC50 of less than or equal to 25 nm, less than or equal to 20 nM, less than or equal to 16 nM, less than or equal to 15 nM, less than or equal to 14 nM, less than or equal to 13 nM, less than or equal to 12 nM, less than or equal to 11 nM, less than or equal to 10 nM, less than or equal to 9 nM, less than or equal to 8 nM, less than or equal to 7 nM. More specifically, an isolated antibody or antigen binding fragment thereof as described herein can inhibit the alternative complement pathway in human as measure by an in vitro hemolytic assay with an IC50 of less than or equal to 16 nm, or less than or equal to 9 nm.

An isolated antibody or antigen binding fragment thereof as described herein can inhibit the alternative complement pathway as measure by an in vitro C3b deposition assay with an IC50 of less than or equal to 10 nm, less than or equal to 7 nM, less than or equal to 6 nM, less than or equal to 5 nM, less than or equal to 4 nM, less than or equal to 3 nM, less than or equal to 2 nM, less than or equal to 1 nM, less than or equal to 15 nM, less than or equal to 1 nM, less than or equal to 0.5 nM, or less than or equal to 0.1 nM. More specifically, an isolated antibody or antigen binding fragment thereof as described herein can inhibit the alternative complement pathway in human as measure by an in vitro C3b deposition assay with an IC50 of less than or equal to 3 nm, or less than or equal to 2 nM.

An isolated antibody or antigen binding fragment thereof as described herein can inhibit the alternative complement pathway with an IC50 of less than or equal to 25 nm, less than or equal to 20 nM, less than or equal to 15 nM, less than or equal to 10 nM, less than or equal to 9 nM, less than or equal to 8 nM, less than or equal to 7 nM, or less than or equal to 6 nM, as measure by deposition of the complement membrane attack complex. More specifically, an isolated antibody or fragment thereof as described herein can inhibit the alternative complement pathway in human with an IC50 of less than or equal to 25 nm, or less than or equal to 7.5 nM, as measure by deposition of the complement membrane attack complex.

An isolated antibody or antigen binding fragment thereof as described herein can inhibit the alternative complement pathway with an IC50 of less than or equal to 80 nM, less than or equal to 50 nM, less than or equal to 45 nM, or less than or equal to 35 nM, as measure by generation of C3a.

An isolated antibody or antigen binding fragment thereof as described herein may also inhibit the alternative complement pathway with an IC50 of less than or equal to 80 nM, less than or equal to 50 nM, less than or equal to 45 nM, or less than or equal to 35 nM, as measure by generation of iC3b.

An isolated antibody or antigen binding fragment thereof as described herein may also inhibit the alternative complement pathway with an IC50 of less than or equal to 80 nM, less than or equal to 50 nM, less than or equal to 45 nM, or less than or equal to 35 nM, as measure by generation of C5a.

An isolated antibody or antigen binding fragment thereof as described herein may also inhibit the alternative complement pathway with an IC50 of less than or equal to 80 nM, less than or equal to 50 nM, less than or equal to 45 nM, or less than or equal to 35 nM, as measure by generation of C5b.

An isolated antibody or antigen binding fragment thereof as described herein may also inhibit the alternative complement pathway by destabilizing and/or blocking the activity of C3 and/or C5 convertase, as measured by a decrease in production of C3a, C3b, iC3b, C5a, and/or C5b.

An isolated antibody or antigen binding fragment thereof as described herein may also inhibit the generation of C5a with an IC50 of less than or equal to 80 nM, less than or equal to 50 nM, less than or equal to 45 nM, or less than or equal to 35 nM.

The isolated antibodies, or antigen binding fragment thereof, may also block Factor P binding to C3b and/or prevent Factor P binding to the cell surface or to DNA or oligonucleotides.

Another aspect of the invention includes an isolated antibody, or antigen binding fragment thereof, that specifically binds to human, cynomolgus, rat and/or rabbit Factor P. In a further aspect, the isolated antibody, or antigen binding fragment, competes for binding with an antibody, or antigen binding fragment, described in Table 1.

The isolated antibodies, or antigen binding fragments thereof, as described herein can be a monoclonal antibodies, a human or humanized antibodies, a chimeric antibodies, single chain antibodies, Fab fragments, Fv fragments, F(ab')2 fragments, or ScFv fragments, and/or IgG isotypes.

The isolated antibodies, or antigen binding fragments thereof, as described herein can also include a framework in which an amino acid has been substituted into the antibody framework from the respective human VH or VL germline sequences.

Another aspect of the invention includes an isolated antibody or antigen binding fragment thereof having the heavy and light chain sequences of Fabs described in Table 1. For example, the isolated antibody or antigen binding fragment thereof can have the heavy and light chain sequences of Fab NVS962, NVS963, NVS964, NVS965, NVS966, NVS967, NVS962-G, NVS962-S, NVS962-T, NVS962-Q, NVS962-S31A, NVS965-Q, NVS965-S, NVS965-T, NVS804, NVS805, NVS806, NVS807, or NVS808.

A further aspect of the invention includes an isolated antibody or antigen binding fragment thereof having the heavy and light chain variable domain sequences of Fabs described in Table 1. For example, the isolated antibody or antigen binding fragment there of can have the heavy and light chain variable domain sequence of Fab NVS962, NVS963, NVS964, NVS965, NVS966, NVS967, NVS962-G, NVS962-S, NVS962-T, NVS962-Q, NVS962-S31A, NVS965-Q, NVS965-S, NVS965-T, NVS804, NVS805, NVS806, NVS807, or NVS808.

The invention also relates to an isolated antibody or antigen binding fragment thereof that includes a heavy chain CDR1 selected from the group consisting of SEQ ID NOs 1, 15, 29, 43, 57, 71, 85, 99, 113, 127, 141, 155, 169, 183, 197, 211, 225, 239, 253, and 267; a heavy chain CDR2 selected from the group consisting of SEQ ID NOs: 2, 16, 30, 44, 58, 72, 86, 100, 114, 128, 142, 156, 170, 184, 198, 212, 226, 240, 254, and 268; and a heavy chain CDR3 selected from the group consisting of SEQ ID NOs: 3, 17, 31, 45, 59, 73, 87, 101, 115, 129, 143, 157, 171, 185, 199, 213, 227, 241, 255, and 269, wherein the isolated antibody or antigen binding fragment thereof binds to human Factor P. In another aspect, the isolated antibody or antigen binding fragment thereof further includes a light chain CDR1 selected from the group consisting of SEQ ID NOs: 4, 18, 32, 46, 60, 74, 88, 102, 116, 130, 144, 158, 172, 186, 200, 214, 228, 242, 256, and 270; a light chain CDR2 selected from the group consisting of SEQ ID NOs 5, 19, 33, 47, 61, 75, 89, 103, 117, 131, 145, 159, 173, 187, 201, 215, 229, 243, 257, and 271; and a light chain CDR3 selected from the group consisting of SEQ ID NOs 6, 20, 34, 48, 62, 76, 90, 104, 118, 132, 146, 160, 174, 188, 202, 216, 230, 244, 258, and 272.

The invention also relates to an isolated antibody or antigen binding fragment thereof that includes a light chain CDR1 selected from the group consisting of SEQ ID NOs: 4, 18, 32, 46, 60, 74, 88, 102, 116, 130, 144, 158, 172, 186, 200, 214, 228, 242, 256, and 270; a light chain CDR2 selected from the group consisting of SEQ ID NOs 5, 19, 33, 47, 61, 75, 89, 103, 117, 131, 145, 159, 173, 187, 201, 215, 229, 243, 257, and 271; and a light chain CDR3 selected from the group consisting of SEQ ID NOs 6, 20, 34, 48, 62, 76, 90, 104, 118, 132, 146, 160, 174, 188, 202, 216, 230, 244, 258, and 272, wherein the isolated antibody or antigen binding fragment thereof binds to human Factor P.

The invention also relates to an isolated antibody or antigen binding fragment thereof that binds Factor P having HCDR1, HCDR2, HCDR3 and LCDR1, LCDR2, LCDR3, wherein HCDR1, HCDR2, HCDR3 comprises SEQ ID NOs: 1, 2, 3, and LCDR1, LCDR2, LCDR3 comprises SEQ ID NOs: 4, 5, 6; or HCDR1, HCDR2, HCDR3 and LCDR1, LCDR2, LCDR3, wherein HCDR1, HCDR2, HCDR3 comprises SEQ ID NOs 15, 16, 17, and LCDR1, LCDR2, LCDR3 comprises SEQ ID NOs: 18, 19, 20; or HCDR1, HCDR2, HCDR3 and LCDR1, LCDR2, LCDR3, wherein HCDR1, HCDR2, HCDR3 comprises SEQ ID NOs 29, 30, 31, and LCDR1, LCDR2, LCDR3 comprises SEQ ID NOs: 32, 33, 34; or HCDR1, HCDR2, HCDR3 and LCDR1, LCDR2, LCDR3, wherein HCDR1, HCDR2, HCDR3 comprises SEQ ID NOs 43, 44, 45, and LCDR1, LCDR2, LCDR3 comprises SEQ ID NOs: 46, 47, 48; or HCDR1, HCDR2, HCDR3 and LCDR1, LCDR2, LCDR3, wherein HCDR1, HCDR2, HCDR3 comprises SEQ ID NOs 57, 58, 59, and LCDR1, LCDR2, LCDR3 comprises SEQ ID NOs: 60, 61, 62; or HCDR1, HCDR2, HCDR3 and LCDR1, LCDR2, LCDR3, wherein HCDR1, HCDR2, HCDR3 comprises SEQ ID NOs 71, 72, 73, and LCDR1, LCDR2, LCDR3 comprises SEQ ID NOs: 74, 75, 76; or HCDR1, HCDR2, HCDR3 and LCDR1, LCDR2, LCDR3, wherein HCDR1, HCDR2, HCDR3 comprises SEQ ID NOs 85, 86, 87, and LCDR1, LCDR2, LCDR3 comprises SEQ ID NOs: 88, 89, 90; or HCDR1, HCDR2, HCDR3 and LCDR1, LCDR2, LCDR3, wherein HCDR1, HCDR2, HCDR3 comprises SEQ ID NOs 99, 100, 101, and LCDR1, LCDR2, LCDR3 comprises SEQ ID NOs: 102, 103, 104; or HCDR1, HCDR2, HCDR3 and LCDR1, LCDR2, LCDR3, wherein HCDR1, HCDR2, HCDR3 comprises SEQ ID NOs 113, 114, 115, and LCDR1, LCDR2, LCDR3 comprises SEQ ID NOs: 116, 117, 118; or HCDR1, HCDR2, HCDR3 and LCDR1, LCDR2, LCDR3, wherein HCDR1, HCDR2, HCDR3 comprises SEQ ID NOs 127, 128, 129, and LCDR1, LCDR2, LCDR3 comprises SEQ ID NOs: 130, 131, 132; or HCDR1, HCDR2, HCDR3 and LCDR1, LCDR2, LCDR3, wherein HCDR1, HCDR2, HCDR3 comprises SEQ ID NOs 141, 142, 143, and LCDR1, LCDR2, LCDR3 comprises SEQ ID NOs: 144, 145, 146; or HCDR1, HCDR2, HCDR3 and LCDR1, LCDR2, LCDR3, wherein HCDR1, HCDR2, HCDR3 comprises SEQ ID NOs 155, 156, 157, and LCDR1, LCDR2, LCDR3 comprises SEQ ID NOs: 158, 159, 160; or HCDR1, HCDR2, HCDR3 and LCDR1, LCDR2, LCDR3, wherein HCDR1, HCDR2, HCDR3 comprises SEQ ID NOs 169, 170, 171, and LCDR1, LCDR2, LCDR3 comprises SEQ ID NOs: 172, 173, 174; or HCDR1, HCDR2, HCDR3 and LCDR1, LCDR2, LCDR3, wherein HCDR1, HCDR2, HCDR3 comprises SEQ ID NOs 183, 184, 185, and LCDR1, LCDR2, LCDR3 comprises SEQ ID NOs: 186, 187, 188; or HCDR1, HCDR2, HCDR3 and LCDR1, LCDR2, LCDR3, wherein HCDR1, HCDR2, HCDR3 comprises SEQ ID NOs 197, 198, 199, and LCDR1, LCDR2, LCDR3 comprises SEQ ID NOs: 200, 201, 202; or HCDR1, HCDR2, HCDR3 and LCDR1, LCDR2, LCDR3, wherein HCDR1, HCDR2, HCDR3 comprises SEQ ID NOs 211, 212, 213, and LCDR1, LCDR2, LCDR3 comprises SEQ ID NOs: 214, 215, 216; or HCDR1, HCDR2, HCDR3 and LCDR1, LCDR2, LCDR3, wherein HCDR1, HCDR2, HCDR3 comprises SEQ ID NOs 225, 226, 227, and LCDR1, LCDR2, LCDR3 comprises SEQ ID NOs: 228, 229, 230; or HCDR1, HCDR2, HCDR3 and LCDR1, LCDR2, LCDR3, wherein HCDR1, HCDR2, HCDR3 comprises SEQ ID NOs 239, 240, 241, and LCDR1, LCDR2, LCDR3 comprises SEQ ID NOs: 242, 243, 244; or HCDR1, HCDR2, HCDR3 and LCDR1, LCDR2, LCDR3, wherein HCDR1, HCDR2, HCDR3 comprises SEQ ID NOs 253, 254, 255, and LCDR1, LCDR2, LCDR3 comprises SEQ ID NOs: 256, 257, 258; or HCDR1, HCDR2, HCDR3 and LCDR1, LCDR2, LCDR3, wherein HCDR1, HCDR2, HCDR3 comprises SEQ ID NOs 267, 268, 269, and LCDR1, LCDR2, LCDR3 comprises SEQ ID NOs: 270, 271, 272.

In one embodiment of the invention the isolated antibody or antigen binding fragment thereof includes a heavy chain variable domain sequence selected from the group consisting of SEQ ID NOs: 7, 21, 35, 49, 63, 77, 91, 105, 119, 133, 147, 161, 175, 189, 203, 217, 231, 245, 259 and 273. In another embodiment, the isolated antibody or antigen binding fragment further comprises a light chain variable domain sequence wherein the heavy chain variable domain and light chain variable domain combine to form and antigen binding site for Factor P. In a further embodiment the isolated antibody or antigen binding fragment further includes a light chain variable domain sequence selected from SEQ ID NOs: 8, 22, 36, 50, 64, 78, 92, 106, 120, 134, 148, 162, 176, 190, 204, 218, 232, 246, 260, and 274 wherein said isolated antibody or antigen binding fragment thereof binds Factor P.

The invention also relates to an isolated antibody or antigen binding fragment thereof that includes a light chain variable domain sequence selected from the group consisting of SEQ ID NOs: 8, 22, 36, 50, 64, 78, 92, 106, 120, 134, 148, 162, 176, 190, 204, 218, 232, 246, 260, and 274, wherein said isolated antibody or antigen binding fragment thereof binds to human Factor P. In one embodiment, the isolated antibody or antigen binding fragment further comprises a heavy chain variable domain sequence wherein the light chain variable domain and heavy chain variable domain combine to form and antigen binding site for Factor P.

In another embodiment of the invention, the isolated antibody or antigen binding fragment thereof that binds Factor P, may have heavy and light chain variable domains comprising the sequences of SEQ ID NOs: 7 and 8; 21 and 22; 35 and 36; 49 and 50; 63 and 64; 77 and 78; 91 and 92; 104 and 105; 118 and 119; 132 and 133; 146 and 147; 160 and 161; 174 and 175; 188 and 189; 202 and 203; 216 and 217; 230 and 231; 244 and 245; 258 and 259; or 272 and 273, respectively.

The invention further relates to an isolated antibody or antigen binding fragment thereof, that includes a heavy chain variable domain having at least 90% sequence identity to a sequence selected from the group consisting of SEQ ID NOs: 7, 21, 35, 49, 63, 77, 91, 105, 119, 133, 147, 161, 175, 189, 203, 217, 231, 245, 259 and 273, wherein said antibody binds to Factor P. In one aspect, the isolated antibody or antigen binding fragment thereof also includes a light chain variable domain having at least 95% sequence identity to a sequence selected from the group consisting of SEQ ID NOs 8, 22, 36, 50, 64, 78, 92, 106, 120, 134, 148, 162, 176, 190, 204, 218, 232, 246, 260, and 274.

In another embodiment the isolated antibody or antigen binding fragment thereof, may include a light chain variable domain having at least 90% sequence identity to a sequence selected from the group consisting of SEQ ID NOs 8, 22, 36, 50, 64, 78, 92, 106, 120, 134, 148, 162, 176, 190, 204, 218, 232, 246, 260, and 274, wherein said antibody binds Factor P.

In another embodiment the isolated antibody, or antigen binding fragment thereof, that binds to Factor P may have a heavy chain comprising the sequence of SEQ ID NO: 9, 23, 37, 51, 65, 79, 93, 107, 121, 135, 149, 163, 177, 191, 205, 219, 233, 247, 261 or 275. In a further embodiment, the isolated antibody also includes a light chain that can combine with the heavy chain to form an antigen binding site to human Factor P. In a further embodiment, the isolated antibody or antigen binding fragment thereof includes a light chain having a sequence comprising SEQ ID NO: 10, 24, 38, 52, 66, 80, 94, 108, 122, 136, 150, 164, 178, 192, 206, 220, 234, 248, 262, or 276.

The invention still further relates to an isolated antibody or antigen binding fragment thereof that includes a heavy chain having at least 90% sequence identity to a sequence selected from the group consisting of SEQ ID NOs 9, 23, 37, 51, 65, 79, 93, 107, 121, 135, 149, 163, 177, 191, 205, 219, 233, 247, 261 and 275, wherein said antibody binds to Factor P. In one aspect, the isolated antibody or antigen binding fragment thereof also includes a light chain having at least 95% sequence identity to a sequence selected from the group consisting of SEQ ID NOs 10, 24, 38, 52, 66, 80, 94, 108, 122, 136, 150, 164, 178, 192, 206, 220, 234, 248, 262, and 276.

The invention still further relates to an isolated antibody or antigen binding fragment thereof that includes a light chain having at least 90% sequence identity to a sequence selected from the group consisting of SEQ ID NOs 9, 23, 37, 51, 65, 79, 93, 107, 121, 135, 149, 163, 177, 191, 205, 219, 233, 247, 261 and 275, wherein said antibody binds Factor P.

The invention also relates to compositions comprising the isolated antibody, or antigen binding fragment thereof, described herein. As well as, antibody compositions in combination with a pharmaceutically acceptable carrier. Specifically, the invention further includes pharmaceutical compositions comprising an antibody or antigen binding fragment thereof of Table 1, such as, for example antibody NVS962, NVS963, NVS964, NVS965, NVS966, NVS967, NVS962-G, NVS962-S, NVS962-T, NVS962-Q, NVS962-S31A, NVS965-Q, NVS965-S, NVS965-T, NVS804, NVS805, NVS806, NVS807, or NVS808. The invention also relates to pharmaceutical compositions comprising a combination of two or more of the isolated antibodies or antigen binding fragments thereof of Table 1.

The invention also relates to an isolated nucleic acid comprising a sequence encoding a polypeptide that includes a heavy chain variable domain having at least 90% sequence identity to a sequence selected from the group consisting of SEQ ID NOs: 7, 21, 35, 49, 63, 77, 91, 105, 119, 133, 147, 161, 175, 189, 203, 217, 231, 245, 259 and 273.

The invention also relates to an isolated nucleic acid comprising a sequence encoding a polypeptide that includes a light chain variable domain having at least 90% sequence identity to a sequence selected from the group consisting of SEQ ID NOs 8, 22, 36, 50, 64, 78, 92, 106, 120, 134, 148, 162, 176, 190, 204, 218, 232, 246, 260, and 274.

The invention also relates to a vector that includes one or more of the nucleic acid molecules described herein.

The invention also relates to an isolated host cell that includes a recombinant DNA sequence encoding a heavy chain of the antibody described above, and a second recombinant DNA sequence encoding a light chain of the antibody described above, wherein said DNA sequences are operably linked to a promoter and are capable of being expressed in the host cell. It is contemplated that the antibody can be a human monoclonal antibody. It is also contemplated that the host cell is a non-human mammalian cell.

The invention also relates to a method of inhibiting the complement mediated cell death wherein the method includes the step of contacting a cell with an effective amount of a composition comprising the isolated antibody or antigen binding fragments thereof described herein. It is contemplated that the cell is a human cell. It is further contemplated that the cell is in a subject. It is still further contemplated that the subject is human.

The invention still further relates to a method of inhibiting the alternative complement pathway in a cell wherein the method includes the step of contacting the cell with an effective amount of a composition comprising the isolated antibody or antigen binding fragments thereof described herein. In one aspect, it is contemplated that the cell is a human cell. It is further contemplated that the cell is in a subject. It is still further contemplated that the subject is human.

The invention also relates to a method of inhibiting the formation of membrane attack complex in a cell wherein the method includes the step of contacting the cell with an effective amount of a composition comprising the isolated antibody or antigen binding fragments thereof described herein. It is contemplated that the cell is a human cell. It is further contemplated that the cell is in a subject. It is still further contemplated that the subject is human.

Any of the foregoing isolated antibodies or antigen binding fragments thereof may be a monoclonal antibody or antigen binding fragment thereof.

In one aspect, the invention provides a first antibody, or antigen binding fragment thereof, that binds Factor P, and a second antibody, or antigen binding fragment thereof, that binds C5, wherein said combination inhibits the alternative complement pathway. In one aspect the first and second antibodies can be in combination as a composition.

Such a combination can be used to inhibit ocular inflammation. Ocular inflammation can be determined by measuring neutrophil accumulation and/or macrophage recruitment in the retina.

In one aspect, such a combination can be used to inhibit neutrophil accumulation in the retina, or macrophage recruitment in the retina.

In one aspect, the antibody in such a combination that binds Factor P, binds a region of Factor P comprising SEQ ID NO: 408. Alternatively or in combination, such an antibody binds a region of Factor P comprising SEQ ID NO: 407.

In a further aspect, the combination of antibodies or binding fragments thereof that bind Factor P and C5 include a first antibody or antigen binding fragment selected from Table 1 and a second antibody or antigen-binding fragment selected from Table 2. In one aspect, the first antibody, or antigen binding fragment thereof binds the same epitope as is an antibody described in Table 1 and the second antibody, or antigen binding fragment thereof, binds the same epitope as is an antibody described in Table 2.

In one aspect, the invention provides a first antibody, or antigen binding fragment thereof that comprises a heavy chain CDR1, 2, 3, and a light chain CDR1, 2, 3, selected from the group consisting of a) a heavy chain variable region HCDR1, HCDR2 and HCDR3 as set forth in SEQ ID NOs: 1, 2, and 3, respectively, and light chain variable region LCDR1, LCDR2, and LCDR3 as set forth in SEQ ID NOs: 4, 5, and 6, respectively; b) a heavy chain variable region HCDR1, HCDR2 and HCDR3 as set forth in SEQ ID NOs: 15, 16, and 17, respectively, and light chain variable region LCDR1, LCDR2, and LCDR3 as set forth in SEQ ID NOs: 18, 19, and 20, respectively; c) a heavy chain variable region HCDR1, HCDR2 and HCDR3 as set forth in SEQ ID NOs: 29, 30, and 31, respectively, and light chain variable region LCDR1, LCDR2, and LCDR3 as set forth in SEQ ID NOs: 32, 33, and 34, respectively; d) a heavy chain variable region HCDR1, HCDR2 and HCDR3 as set forth in SEQ ID NOs: 43, 44, and 45, respectively, and light chain variable region LCDR1, LCDR2, and LCDR3 as set forth in SEQ ID NOs: 46, 47, and 48, respectively; e) a heavy chain variable region HCDR1, HCDR2 and HCDR3 as set forth in SEQ ID NOs: 57, 58, and 59, respectively, and light chain variable region LCDR1, LCDR2, and LCDR3 as set forth in SEQ ID NOs: 60, 61, and 62, respectively; f) a heavy chain variable region HCDR1, HCDR2 and HCDR3 as set forth in SEQ ID NOs: 71, 72, and 73, respectively, and light chain variable region LCDR1, LCDR2, and LCDR3 as set forth in SEQ ID NOs: 74, 75, and 76, respectively; g) a heavy chain variable region HCDR1, HCDR2 and HCDR3 as set forth in SEQ ID NOs: 85, 86, and 87, respectively, and light chain variable region LCDR1, LCDR2, and LCDR3 as set forth in SEQ ID NOs: 88, 89, and 90, respectively; h) a heavy chain variable region HCDR1, HCDR2 and HCDR3 as set forth in SEQ ID NOs: 99, 100, and 101, respectively, and light chain variable region LCDR1, LCDR2, and LCDR3 as set forth in SEQ ID NOs: 102, 103, and 104, respectively; i) a heavy chain variable region HCDR1, HCDR2 and HCDR3 as set forth in SEQ ID NOs: 113, 114, and 115, respectively, and light chain variable region LCDR1, LCDR2, and LCDR3 as set forth in SEQ ID NOs: 116, 117, and 118, respectively; j) a heavy chain variable region HCDR1, HCDR2 and HCDR3 as set forth in SEQ ID NOs: 127, 128, and 129, respectively, and light chain variable region LCDR1, LCDR2, and LCDR3 as set forth in SEQ ID NOs: 130, 131, and 132, respectively; k) a heavy chain variable region HCDR1, HCDR2 and HCDR3 as set forth in SEQ ID NOs: 141, 142, and 143, respectively, and light chain variable region LCDR1, LCDR2, and LCDR3 as set forth in SEQ ID NOs: 144, 145, and 146, respectively; l) a heavy chain variable region HCDR1, HCDR2 and HCDR3 as set forth in SEQ ID NOs: 155, 156, and 157, respectively, and light chain variable region LCDR1, LCDR2, and LCDR3 as set forth in SEQ ID NOs: 158, 159, and 160, respectively; m) a heavy chain variable region HCDR1, HCDR2 and HCDR3 as set forth in SEQ ID NOs: 169, 170, and 171, respectively, and light chain variable region LCDR1, LCDR2, and LCDR3 as set forth in SEQ ID NOs: 172, 173, and 174, respectively; n) a heavy chain variable region HCDR1, HCDR2 and HCDR3 as set forth in SEQ ID NOs: 183, 184, and 185, respectively, and light chain variable region LCDR1, LCDR2, and LCDR3 as set forth in SEQ ID NOs: 186, 187, and 188, respectively; o) a heavy chain variable region HCDR1, HCDR2 and HCDR3 as set forth in SEQ ID NOs: 197, 198, and 199, respectively, and light chain variable region LCDR1, LCDR2, and LCDR3 as set forth in SEQ ID NOs: 200, 201, and 202, respectively; p) a heavy chain variable region HCDR1, HCDR2 and HCDR3 as set forth in SEQ ID NOs: 211, 212, and 213, respectively, and light chain variable region LCDR1, LCDR2, and LCDR3 as set forth in SEQ ID NOs: 214, 215, and 216, respectively; q) a heavy chain variable region HCDR1, HCDR2 and HCDR3 as set forth in SEQ ID NOs: 225, 226, and 227, respectively, and light chain variable region LCDR1, LCDR2, and LCDR3 as set forth in SEQ ID NOs: 228, 229, and 230, respectively; r) a heavy chain variable region HCDR1, HCDR2 and HCDR3 as set forth in SEQ ID NOs: 239, 240, and 241, respectively, and light chain variable region LCDR1, LCDR2, and LCDR3 as set forth in SEQ ID NOs: 242, 243, and 244, respectively; s) a heavy chain variable region HCDR1, HCDR2 and HCDR3 as set forth in SEQ ID NOs: 253, 254, and 255, respectively, and light chain variable region LCDR1, LCDR2, and LCDR3 as set forth in SEQ ID NOs: 256, 257, and 258, respectively; and t) a heavy chain variable region HCDR1, HCDR2 and HCDR3 as set forth in SEQ ID NOs: 267, 268, and 269, respectively, and light chain variable region LCDR1, LCDR2, and LCDR3 as set forth in SEQ ID NOs: 270, 271, and 272, respectively, and wherein the second antibody or antigen binding fragment thereof comprises a heavy chain CDR1, 2, 3 and light chain CDR1, 2, 3 selected from the group consisting of: a) a heavy chain variable region HCDR1, HCDR2 and HCDR3 as set forth in SEQ ID NOs: 410, 411, and 412, respectively, and light chain variable region LCDR1, LCDR2, and LCDR3 as set forth in SEQ ID NOs: 413, 414, and 415, respectively; b) a heavy chain variable region HCDR1, HCDR2 and HCDR3 as set forth in SEQ ID NOs: 426, 427, and 428, respectively, and light chain variable region LCDR1, LCDR2, and LCDR3 as set forth in SEQ ID NOs: 429, 430, and 431, respectively; c) a heavy chain variable region HCDR1, HCDR2 and HCDR3 as set forth in SEQ ID NOs: 442, 443, and 444, respectively, and light chain variable region LCDR1, LCDR2, and LCDR3 as set forth in SEQ ID NOs: 445, 446, and 447, respectively; d) a heavy chain variable region HCDR1, HCDR2 and HCDR3 as set forth in SEQ ID NOs: 426, 458, and 428, respectively, and light chain variable region LCDR1, LCDR2, and LCDR3 as set forth in SEQ ID NOs: 429, 430, and 459, respectively; and e) a heavy chain variable region HCDR1, HCDR2 and HCDR3 as set forth in SEQ ID NOs: 470, 471, and 472, respectively, and light chain variable region LCDR1, LCDR2, and LCDR3 as set forth in SEQ ID NOs: 473, 474 and 475, respectively.

In one aspect, the invention relates to a first and second antibody or antigen binding fragment thereof (which may be in combination as a composition) where the first antibody or antigen binding fragment thereof includes heavy and light chain variable regions having amino acid sequences at least 90% identical to SEQ ID NOs: 7 and 8; SEQ ID NOs: 21 and 22; SEQ ID NOs: 35 and 36; SEQ ID NOs: 49 and 50; SEQ ID NOs: 63 and 64; SEQ ID NOs: 77 and 78; SEQ ID NOs: 91 and 92; SEQ ID NOs: 105 and 106; SEQ ID NOs: 119 and 120; SEQ ID NOs: 133 and 134; SEQ ID NOs: 147 and 148; SEQ ID NOs: 161 and 162; SEQ ID NOs: 175 and 176; SEQ ID NOs: 189 and 190; SEQ ID NOs: 203 and 204; SEQ ID NOs: 217 and 218; SEQ ID NOs: 231 and 232; SEQ ID NOs: 245 and 246; SEQ ID NOs: 259 and 260; or SEQ ID NOs: 273 and 274, respectively, and wherein the second antibody or antigen binding fragment thereof includes heavy and light chain variable regions having amino acid sequences at least 90% identical to SEQ ID NOs: 416 and 417; SEQ ID NOs: 432 and 433; SEQ ID NOs: 448 and 449; SEQ ID NOs: 460 and 461; or SEQ ID NOs: 476 and 477, respectively.

In one aspect, the invention relates to a first and second antibody or antigen binding fragment thereof (which may be in combination as a composition) where the first antibody or antigen binding fragment thereof includes heavy and light chain variable regions having amino acid sequences selected from SEQ ID NOs: 7 and 8; SEQ ID NOs: 21 and 22; SEQ ID NOs: 35 and 36; SEQ ID NOs: 49 and 50; SEQ ID NOs: 63 and 64; SEQ ID NOs: 77 and 78; SEQ ID NOs: 91 and 92; SEQ ID NOs: 105 and 106; SEQ ID NOs: 119 and 120; SEQ ID NOs: 133 and 134; SEQ ID NOs: 147 and 148; SEQ ID NOs: 161 and 162; SEQ ID NOs: 175 and 176; SEQ ID NOs: 189 and 190; SEQ ID NOs: 203 and 204; SEQ ID NOs: 217 and 218; SEQ ID NOs: 231 and 232; SEQ ID NOs: 245 and 246; SEQ ID NOs: 259 and 260; or SEQ ID NOs: 273 and 274, respectively, and wherein the second antibody or antigen binding fragment thereof includes heavy and light chain variable regions having amino acid sequences selected from SEQ ID NOs: 416 and 417; SEQ ID NOs: 432 and 433; SEQ ID NOs: 448 and 449; SEQ ID NOs: 460 and 461; or SEQ ID NOs: 476 and 477, respectively.

In a further aspect, the invention includes a first and second antibody or antigen binding fragment thereof (which may be in combination as a composition) in which (a) the first antibody, or antigen binding fragment thereof includes a heavy chain variable region comprising SEQ ID NO: 7, 21, 35, 49, 63, 77, 91, 105, 119, 133, 147, 161, 175, 189, 203, 217, 231, 245, 259, or 273 and further includes a light chain variable region, wherein said heavy chain variable region and said light chain variable region combine to form an antigen binding site to Factor P and (b) wherein the second antibody or antigen binding fragment thereof includes a heavy chain variable region comprising SEQ ID NO: 416, 432, 448, 460 or 476 and further includes a light chain variable region, wherein said heavy chain variable region and said light chain variable region combine to form an antigen binding site to C5. In a further aspect, the first antibody or antigen binding fragment thereof includes the light chain variable region sequence of SEQ ID NO: 8, 22, 36, 50, 64, 78, 92, 106, 120, 134, 148, 162, 176, 190, 204, 218, 232, 246, 260, or 274, and the second antibody or antigen binding fragment thereof includes the light chain variable region sequence of SEQ ID NO: 417, 433, 449, 461 or 477.

In a further aspect, the invention includes a first and second antibody or antigen binding fragment thereof (which may be in combination as a composition) in which (a) the first antibody or antigen binding fragment thereof includes a light chain variable domain comprising SEQ ID NO: 8, 22, 36, 50, 64, 78, 92, 106, 120, 134, 148, 162, 176, 190, 204, 218, 232, 246, 260, or 274 and further includes a heavy chain variable domain, wherein the light chain variable domain and the heavy chain variable domain combine to form an antigen binding site to Factor P and (b) wherein the second antibody or antigen binding fragment thereof includes a light chain variable region comprises a light chain variable domain includes SEQ ID NO: 417, 433, 449, 461 or 477 and further comprises a heavy chain variable domain, wherein the light chain variable domain and the heavy chain variable domain combine to form an antigen binding site to C5.

In one aspect, the invention includes a first and second antibody or antigen binding fragment thereof (which may be in combination as a composition) in which (a) the first antibody, or antigen binding fragment thereof includes a heavy chain of SEQ ID NO: 9, 23, 37, 51, 65, 79, 93, 107, 121, 135, 149, 163, 177, 191, 205, 219, 233, 247, 261 or 275 and further includes a light chain, wherein the heavy chain and the light chain combine to form an antigen binding site to Factor P and (b) wherein the second antibody or antigen binding fragment thereof includes a heavy chain of SEQ ID NO: 418, 434, 450, 462, or 478 and further includes a light chain, wherein the heavy chain and the light chain combine to form an antigen binding site to C5. In a further aspect, the first antibody or antigen binding fragment thereof includes a light chain of SEQ ID NO: 10, 24, 38, 52, 66, 80, 94, 108, 122, 136, 150, 164, 178, 192, 206, 220, 234, 248, 262 or 276, and wherein the second antibody or antigen binding fragment thereof includes a light chain of SEQ ID NO: 419, 435, 451, 463, or 479.

In one aspect, the invention includes a first and second antibody or antigen binding fragment thereof (which may be in combination as a composition) in which (a) the first antibody, or antigen binding fragment thereof includes a light chain of SEQ ID NO: 10, 24, 38, 52, 66, 80, 94, 108, 122, 136, 150, 164, 178, 192, 206, 220, 234, 248, 262 or 276 and further includes a heavy chain, wherein the light chain and the heavy chain combine to form an antigen binding site to Factor P and (b) wherein the second antibody or antigen binding fragment thereof includes a light chain of SEQ ID NO: 419, 435, 451, 463, or 479 and further includes a heavy chain, wherein the light chain and the heavy chain combine to form an antigen binding site to C5.

In one aspect, the invention includes a first and second antibody or antigen binding fragment thereof (which may be in combination as a composition) wherein the first antibody, or antigen binding fragment thereof includes a heavy chain with an amino acid sequence having at least 90% sequence identity to SEQ ID NO: 9, 23, 37, 51, 65, 79, 93, 107, 121, 135, 149, 163, 177, 191, 205, 219, 233, 247, 261 or 275 and further includes a light chain with an amino acid sequence having at least 90% sequence identity to SEQ ID NO: 10, 24, 38, 52, 66, 80, 94, 108, 122, 136, 150, 164, 178, 192, 206, 220, 234, 248, 262 or 276 and wherein the second antibody or antigen binding fragment thereof includes a heavy chain with an amino acid sequence having at least 90% sequence identity to SEQ ID NO: 418, 434, 450, 462, or 478 and further includes a light chain with an amino acid sequence having at least 90% sequence identity to SEQ ID NO: 419, 435, 451, 463, or 479.

In a further aspect, the invention includes a first and second antibody or antigen binding fragment thereof (which may be in combination as a composition) wherein the first antibody, or antigen binding fragment thereof includes a heavy chain with an amino acid sequence selected from SEQ ID NO: 9, 23, 37, 51, 65, 79, 93, 107, 121, 135, 149, 163, 177, 191, 205, 219, 233, 247, 261 or 275 and further includes a light chain with an amino acid sequence selected from SEQ ID NO: 10, 24, 38, 52, 66, 80, 94, 108, 122, 136, 150, 164, 178, 192, 206, 220, 234, 248, 262 or 276 and wherein the second antibody or antigen binding fragment thereof includes a heavy chain with an amino acid sequence selected from SEQ ID NO: 418, 434, 450, 462, or 478 and further includes a light chain with an amino acid sequence selected from SEQ ID NO: 419, 435, 451, 463, or 479.

In a further aspect, the invention includes a first and second antibody or antigen binding fragment thereof (which may be in combination as a composition) wherein the first antibody, or antigen binding fragment thereof includes a heavy chain and a light chain with an amino acid sequence having at least 90% sequence identity, respectively, to SEQ ID NO: 9 and 10, 23 and 24, 37 and 38, 51 and 52, 65 and 66, 79 and 80, 93 and 94, 107 and 108, 121 and 122, 135 and 136, 149 and 150, 163 and 164, 177 and 178, 191 and 192, 205 and 206, 219 and 220, 233 and 234, 247 and 248, 261 and 262, or 275 and 276; and wherein the second antibody or antigen binding fragment thereof includes a heavy chain and a light chain with an amino acid sequence having at least 90% sequence identity, respectively, to SEQ ID NOs: 418 and 419, 434 and 435; 450 and 451; 462 and 463; or 478 and 479.

In a still further aspect, the invention includes a first and second antibody or antigen binding fragment thereof (which may be in combination as a composition) wherein the first antibody, or antigen binding fragment thereof includes a heavy chain and a light chain with an amino acid sequence, respectively, selected from SEQ ID NO: 9 and 10, 23 and 24, 37 and 38, 51 and 52, 65 and 66, 79 and 80, 93 and 94, 107 and 108, 121 and 122, 135 and 136, 149 and 150, 163 and 164, 177 and 178, 191 and 192, 205 and 206, 219 and 220, 233 and 234, 247 and 248, 261 and 262, or 275 and 276; and wherein the second antibody or antigen binding fragment thereof includes a heavy chain and a light chain with an amino acid sequence, respectively, selected from SEQ ID NOs: 418 and 419, 434 and 435; 450 and 451; 462 and 463; or 478 and 479.

The invention further relates to an isolated nucleic acid molecule comprising a nucleotide sequence encoding the first and/or second antibody or antigen binding fragment thereof as described herein. Such a nucleic acid sequence can be included in a vector, which may, in turn be included in a host cell which, in one aspect, is capable of expressing such nucleic acid sequence.

The invention further relates to a method of treating age related macular degeneration in a subject comprising administering to said subject, an effective amount of a first and second antibody or antigen binding fragment thereof, either singly, or in combination as a composition. The subject may be a human.

The invention further relates to a method of inhibiting the alternative complement pathway in a subject comprising administering to said subject an effective amount of a first and second antibody or antigen binding fragment thereof, either singly, or in combination as a composition. The subject may be a human.

BRIEF DESCRIPTION OF THE DRAWINGS

FIG. 1A-1C depicts the Factor P binding site. FIG. 1A illustrates the relative position TSR5 domain of Factor P and the TSR5 sequence fragments: A, B, C and D. FIG. 1B shows the human TSR5 sequence (SEQ ID NO:486) aligned with the mouse sequence (SEQ ID NO:487). Brackets indicate the sequence fragments of TSR5. FIG. 1C illustrates the antibodies bind to region B of TSR5.

FIG. 2 shows the results of a hemolytic assay demonstrating inhibition of the alternative complement pathway in 20% human serum.

DETAILED DESCRIPTION

Figure 3:
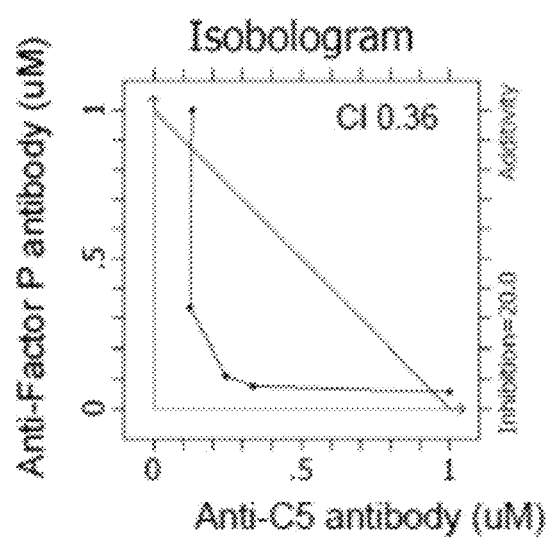
FIG. 3 shows an isobologram generated using the data from the hemolytic assay depicted in FIG. 2.

The present invention is based, in part, on the discovery of antibody molecules that specifically bind to both human and cynomolgus Factor P. The invention relates to both full IgG format antibodies as well as antigen binding fragments thereof, such as Fab fragments (e.g., see antibodies NVS965-S, NVS962-S, NVS804 and NVS807).

Accordingly, the present invention provides antibodies that specifically bind to Factor P (e.g., human Factor P, cynomolgus Factor P, rat Factor P, rabbit Factor P), pharmaceutical compositions, production methods, and methods of use of such antibodies and compositions.

Definitions

Unless defined otherwise, all technical and scientific terms used herein have the same meaning as commonly understood by those of ordinary skill in the art to which this invention pertains.

The term "antibody" as used herein means a whole antibodies and any antigen binding fragment (i. e., "antigen-binding portion") or single chains thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen binding portion" or "antigen binding fragment" of an antibody, as used herein, refers to one or more fragments of an intact antibody that retain the ability to specifically bind to a given antigen (e.g., Factor P). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703, 199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an IgG antibody or fragment thereof (e.g., a Fab fragment) refers to an antibody having a KD of $10^{-8}$ M or less, $10^{-9}$ M or less, or $10^{-10}$ M, or $10^{-11}$ M or less, or $10^{-12}$ M or less, or $10^{-13}$ M or less for a target antigen. However, high affinity binding can vary for other antibody isotypes. For example, high affinity binding for an IgM isotype refers to an antibody having a KD of $10^{-7}$ M or less, or $10^{-8}$ M or less.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., a Factor P-binding antibody) refers to a binding reaction that is determinative of the presence of a cognate antigen (e.g., a human Factor P or cynomolgus Factor P) in a heterogeneous population of proteins and other biologics. The phrases "an antibody recognizing an antigen" and "an antibody specific for an antigen" are used interchangeably herein with the term "an antibody which binds specifically to an antigen".

The term "conditions or disorders associated with macular degeneration" refers to any of a number of conditions in which the retinal macula degenerates or becomes dysfunctional, e.g., as a consequence of decreased growth of cells of the macula, increased death or rearrangement of the cells of the macula (e.g., RPE cells), loss of normal biological function, or a combination of these events. Macular degeneration results in the loss of integrity of the histoarchitecture of the cells and/or extracellular matrix of the normal macula and/or the loss of function of the cells of the macula. Examples of macular degeneration-related disorder include AMD, North Carolina macular dystrophy, Sorsby's fundus dystrophy, Stargardt's disease, pattern dystrophy, Best disease, dominant drusen, and malattia leventinese (radial drusen). The term also encompasses extramacular changes that occur prior to, or following dysfunction and/or degeneration of the macula. Thus, the term "macular degeneration-related disorder" also broadly includes any condition which alters or damages the integrity or function of the macula (e.g., damage to the RPE or Bruch's membrane). For example, the term encompasses retinal detachment, chorioretinal degenerations, retinal degenerations, photoreceptor degenerations, RPE degenerations, mucopolysaccharidoses, rod-cone dystrophies, cone-rod dystrophies and cone degenerations.

The term "complement component", "complement proteins" or "complement component proteins" refers to the molecules that are involved in activation of the complement system. The classical pathway components include, e.g., C1q, C1r, C1s, C4, C2, C3, C5, C6, C7, C8, C9, and C5b-9 complex (membrane attack complex: MAC). The alternative pathway components include, e.g., Factor B, Factor D, Factor H, Factor I and Properdin.

The term "cellular activities regulated by the complement pathway" include cell damage resulting from the C5b-9 attack complex, vascular permeability changes, contraction and migration of smooth muscle cells, T cell proliferation, immune adherence, aggregation of dendritic cells, monocytes, granulocyte and platelet, phagocytosis, migration and activation of neutrophils (PMN) and macrophages.

Further, activation of the complement pathways results in the increase of proinflammatory response contributed by the by-products within the complement pathway. Disorders associated with activation of the complement pathway include nephritis, asthma, reperfusion injury, hemodialysis, rheumatoid arthritis, systemic lupus, psoriasis, multiple sclerosis, transplantation, Alzheimer's disease, aHUS, MPGN II, or any other complement-mediated disease. Disorders associated with macular degeneration include AMD, North Carolina macular dystrophy, Sorsby's fundus dystrophy, Stargardt's disease, pattern dystrophy, Best disease, dominant drusen, and malattia leventinese (radial drusen), extramacular changes that occur prior to, or following dysfunction and/or degeneration of the macula, retinal detachment, chorioretinal degenerations, retinal degenerations, photoreceptor degenerations, RPE degenerations, mucopolysaccharidoses, rod-cone dystrophies, cone-rod dystrophies and cone degenerations.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "Factor P protein" or "Factor P antigen" or "Factor P" are used interchangeably, and refers to the Factor P protein in different species. For example, human Factor P has the sequence as set out in Table 1: SEQ ID NO: 401. Human Factor P can be obtained from Complement Tech, Tyler, Tex. Cynomolgus Factor P can be purified from cynomolgus serum (protocol adapted from Nakano et al., (1986) J Immunol Methods 90:77-83). Examples of Factor P protein from other species are provided in Table 1, SEQ ID NOs: 402, 403, 404 or 405, as well as Factor P protein binding domains and fragments (e.g.: SEQ ID NOs: 406, 407 or 408). Factor P is also know in the art as "Properdin".

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "inhibit (or inhibits) the alternative complement pathway" refers to the ability of Factor P antibodies to interfere with activation of the alternative complement pathway. Specifically, "inhibit" refers to a statistically significant decrease (i.e., p<0.05) in alternative complement activation as measured by one or more assays as described herein, including MAC formation, hemolytic assay, or C3b deposition assay in a cell or subject following contact with an anti-Factor P antibody or fragment thereof as described herein relative to a control. As used herein, "inhibit (or inhibits) the alternative complement pathway" can also refer to a clinically relevant improvement in visual function or retinal anatomy following treatment with an anti-Factor P antibody described herein in a patient diagnosed with age related macular degeneration as described below.

The term "isolated antibody" refers to an antibody that is substantially free of other antibodies having different antigenic specificities (e.g., an isolated antibody that specifically binds Factor P is substantially free of antibodies that specifically bind antigens other than Factor P). An isolated antibody that specifically binds Factor P may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of Kd to Ka (i.e. Kd/Ka) and is expressed as a molar concentration (M). $K_D$ values for antibodies can be determined using methods well established in the art. Methods for determining the $K_D$ of an antibody include measuring surface plasmon resonance using a biosensor system such as a BIACORE™ system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g.: mammals and non-mammals) such as, non-human primates (e.g.: cynomolgus monkey), sheep, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*).

As used herein, the term "treating" or "treatment" of any disease or disorder (i.e., AMD) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder. "Prevention" as it relates to AMD means any action that prevents or slows a worsening in visual function, retinal anatomy, and/or an AMD disease parameter, as described below, in a patient at risk for said worsening. More specifically, "treatment" of AMD means any action that results in the improvement or preservation of visual function and/or reginal anatomy. Methods for assessing treatment and/or prevention of disease are known in the art and described hereinbelow.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Factor P Antibodies & Antigen Binding Fragments

The present invention provides antibodies that specifically bind to Factor P. In some embodiments, the present invention provides antibodies that specifically bind to human, cynomolgus, rat and/or rabbit Factor P. Antibodies of the invention include, but are not limited to, the human monoclonal antibodies and Fabs, isolated as described in the Examples.

The present invention provides antibodies that specifically bind a Factor P protein (e.g., human and/or cynomolgus Factor P), wherein the antibodies comprise a VH domain having an amino acid sequence of SEQ ID NO: 7, 21, 35, 49, 63, 77, 91, 105, 119, 133, 147, 161, 175, 189, 203, 217, 231, 245, 259 or 273. The present invention also provides antibodies that specifically bind to a Factor P protein, wherein the antibodies comprise a VH CDR having an amino acid sequence of any one of the VH CDRs listed in Table 1, infra. In particular, the invention provides antibodies that specifically bind to a Factor P protein (e.g., human and/or cynomolgus Factor P), wherein the antibodies comprise (or alternatively, consist of) one, two, three, or more VH CDRs having an amino acid sequence of any of the VH CDRs listed in Table 1, infra.

The present invention provides antibodies that specifically bind to a Factor P protein, said antibodies comprising a VL domain having an amino acid sequence of SEQ ID NO: 8, 22, 36, 50, 64, 78, 92, 106, 120, 134, 148, 162, 176, 190, 204, 218, 232, 246, 260, or 274. The present invention also provides antibodies that specifically bind to a Factor P protein (e.g., human and/or cynomolgus Factor P), said antibodies comprising a VL CDR having an amino acid sequence of any one of the VL CDRs listed in Table 1, infra. In particular, the invention provides antibodies that specifically bind to a Factor P protein (e.g., human and/or cynomolgus Factor P), said antibodies comprising (or alternatively, consisting of) one, two, three or more VL CDRs having an amino acid sequence of any of the VL CDRs listed in Table 1, infra.

Other antibodies of the invention include amino acids that have been mutated, yet have at least 60, 70, 80, 85, 90 or 95 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full length heavy chain, and the full length light chain of the antibodies that specifically bind to a Factor P protein (e.g., human and/or cynomolgus Factor P). Such nucleic acid sequences can be optimized for expression in mammalian cells (for example, Table 1 shows the optimized nucleic acid sequences for the heavy chain and light chain of antibodies of the invention).

TABLE 1

Examples of Factor P Antibodies, Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| NVS962 | |
| CDRH1 | 1/281<br>SYAIS (Kabat)/GGTFNSY (Chothia) |
| CDRH2 | 2/282<br>RIIPIFGTANYAQKFQG (Kabat)/IPIFGT (Chothia) |
| CDRH3 | 3/283<br>HGGYSFDS (Kabat)/HGGYSFDS (Chothia) |
| CDRL1 | 4/284<br>SGDNLGSKYVD (Kabat)/DNLGSKY (Chothia) |
| CDRL2 | 5/285<br>SDNNRPS (Kabat)/SDN (Chothia) |
| CDRL3 | 6/286<br>QTYTSGNNYL (Kabat)/YTSGNNYL (Chothia) |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| VH | 7<br>EVQLVQSGAEVKKPGSSVKVSCKASGGTFNSYAISWVRQAPGQGLEWM<br>GRIIPIFGTANYAQKFQGRVTITADESTSTAYMELSSLRSEDTAVYYC<br>ARHGGYSFDSWGQGTLVTVSS |
| VL | 8<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVL |
| HEAVY CHAIN | 9<br>EVQLVQSGAEVKKPGSSVKVSCKASGGTFNSYAISWVRQAPGQGLEWM<br>GRIIPIFGTANYAQKFQGRVTITADESTSTAYMELSSLRSEDTAVYYC<br>ARHGGYSFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 10<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 7 | 11<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAACAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING SEQ.ID.NO: 8 | 12<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTA |
| PN ENCODING SEQ.ID.NO: 9 | 13<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAACAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING SEQ.ID.NO: 10 | 14<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | TACAGCTGCCAGGTCACGCATGAAGGGAGCACCGTGGAGAAGACAGTG<br>GCCCCTACAGAATGTTCA |

NVS963

| | |
|---|---|
| CDRH1 | 15/287<br>SYAIS (Kabat)/GGTFSSY (Chothia) |
| CDRH2 | 16/288<br>PINPYYGDAIYAQKFQG (Kabat)/NPYYGD (Chothia) |
| CDRH3 | 17/289<br>YYSDYMDY (Kabat)/YYSDYMDY (Chothia) |
| CDRL1 | 18/290<br>TGSSSNIGAGYDVH (Kabat)/SSSNIGAGYD (Chothia) |
| CDRL2 | 19/291<br>DNSHRPS (Kabat)/DNS (Chothia) |
| CDRL3 | 20/292<br>ASYDESAHS (Kabat)/YDESAHS (Chothia) |
| VH | 21<br>EVQLVQSGAEVKKPGSSVKVSCKASGGTFSSYAISWVRQAPGQGLEWM<br>GPINPYYGDAIYAQKFQGRVTITADESTSTAYMELSSLRSEDTAVYYC<br>ARYYSDYMDYWGQGTLVTVSS |
| VL | 22<br>QSVLTQPPSVSGAPGQRVTISCTGSSSNIGAGYDVHWYQQLPGTAPKL<br>LIHDNSHRPSGVPDRFSGSKSGTSASLAITGLQSEDEADYYCASYDES<br>AHSVFGGGTKLTVL |
| HEAVY CHAIN | 23<br>EVQLVQSGAEVKKPGSSVKVSCKASGGTFSSYAISWVRQAPGQGLEWM<br>GPINPYYGDAIYAQKFQGRVTITADESTSTAYMELSSLRSEDTAVYYC<br>ARYYSDYMDYWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 24<br>QSVLTQPPSVSGAPGQRVTISCTGSSSNIGAGYDVHWYQQLPGTAPKL<br>LIHDNSHRPSGVPDRFSGSKSGTSASLAITGLQSEDEADYYCASYDES<br>AHSVFGGGTKLTVLGQPKAAPSVTLFPPSSEELQANKATLVCLISDFY<br>PGAVTVAWKADSSPVKAGVETTTPSKQSNNKYAASSYLSLTPEQWKSH<br>RSYSCQVTHEGSTVEKTVAPTECS |
| PN ENCODING SEQ.ID.NO: 21 | 25<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTTAGCAGCTAC<br>GCCATCAGCTGGGTGCGCCAGGCTCCAGGACAGGGCCTGGAATGGATG<br>GGCCCCATCAACCCCTACTACGGCGACGCCATCTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGC<br>GCCCGGTACTACAGCGACTACATGGACTACTGGGGCCAGGGCACCCTG<br>GTGACCGTGAGCTCA |
| PN ENCODING SEQ.ID.NO: 22 | 26<br>CAGTCAGTGCTGACCCAGCCTCCCTCTGTGTCTGGCGCCCCTGGCCAG<br>AGAGTGACCATCAGCTGCACCGGCTCCAGCAGCAACATCGGAGCTGGA<br>TACGACGTGCACTGGTATCAGCAGCTGCCCGGCACAGCCCCTAAGCTG<br>CTGATCCACGACAACAGCCACAGACCCAGCGGCGTGCCCGATAGATTC<br>AGCGGCAGCAAGAGCGGCACCAGCGCCAGCCTGGCCATCACCGGCCTG<br>CAGAGCGAGGACGAGGCCGACTACTACTGCGCCAGCTACGACGAGAGC<br>GCCCACAGCGTGTTCGGAGGCGGAACAAAGTTAACCGTCCTA |
| PN ENCODING SEQ.ID.NO: 23 | 27<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTTAGCAGCTAC<br>GCCATCAGCTGGGTGCGCCAGGCTCCAGGACAGGGCCTGGAATGGATG<br>GGCCCCATCAACCCCTACTACGGCGACGCCATCTACGCCCAGAAATTC<br>CAGGGCAGAGTGACCATCACCGCCGACGAGAGCACCAGCACCGCCTAC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | ATGGAACTGAGCAGCCTGAGAAGCGAGGACACCGCCGTGTACTACTGC<br>GCCCGGTACTACAGCGACTACATGGACTACTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING SEQ.ID.NO: 24 | 28<br>CAGTCAGTGCTGACCCAGCCTCCCTCTGTGTCTGGCGCCCCTGGCCAG<br>AGAGTGACCATCAGCTGCACCGGCTCCAGCAGCAACATCGGAGCTGGA<br>TACGACGTGCACTGGTATCAGCAGCTGCCCGGCACAGCCCCTAAGCTG<br>CTGATCCACGACAACAGCCACAGACCCAGCGGCGTGCCCGATAGATTC<br>AGCGGCAGCAAGAGCGGCACCAGCGCCAGCCTGGCCATCACCGGCCTG<br>CAGAGCGAGGACGAGGCCGACTACTACTGCGCCAGCTACGACGAGAGC<br>GCCCACAGCGTGTTCGGAGGCGGAACAAAGTTAACCGTCCTAGGTCAG<br>CCCAAGGCTGCCCCCTCGGTCACTCTGTTCCCGCCCTCCTCTGAGGAG<br>CTTCAAGCCAACAAGGCCACACTGGTGTGTCTCATAAGTGACTTCTAC<br>CCGGGAGCCGTGACAGTGGCCTGGAAGGCAGATAGCAGCCCCGTCAAG<br>GCGGGAGTGGAGACCACCACACCCTCCAAACAAAGCAACAACAAGTAC<br>GCGGCCAGCAGCTATCTGAGCCTGACGCCTGAGCAGTGGAAGTCCCAC<br>AGAAGCTACAGCTGCCAGGTCACGCATGAAGGGAGCACCGTGGAGAAG<br>ACAGTGGCCCCTACAGAATGTTCA |

NVS964

| CDRH1 | 29/293<br>SHYMH (Kabat)/GYTFTSH (Chothia) |
|---|---|
| CDRH2 | 30/294<br>KINADLGDTNYAQKFQG (Kabat)/NADLGD (Chothia) |
| CDRH3 | 31/295<br>DGIEHGGHYYWGYLFDI (Kabat)/DGIEHGGHYYWGYLFDI (Chothia) |
| CDRL1 | 32/296<br>SGDSIREYYVH (Kabat)/DSIREYY (Chothia) |
| CDRL2 | 33/297<br>DDTNRPS (Kabat)/DDT (Chothia) |
| CDRL3 | 34/298<br>AAWDFSPAI (Kabat)/WDFSPAI (Chothia) |
| VH | 35<br>EVQLVQSGAEVKKPGASVKVSCKASGYTFTSHYMHWVRQAPGQGLEWM<br>GKINADLGDTNYAQKFQGRVTMTRDTSISTAYMELSSLRSEDTAVYYC<br>ARDGIEHGGHYYWGYLFDIWGQGTLVTVSS |
| VL | 36<br>SYELTQPPSVSVAPGQTARISCSGDSIREYYVHWYQQKPGQAPVLVIG<br>DDTNRPSGIPERFSGSNSGNTATLTISGTQAEDEADYYCAAWDFSPAI<br>VFGGGTKLTVL |
| HEAVY CHAIN | 37<br>EVQLVQSGAEVKKPGASVKVSCKASGYTFTSHYMHWVRQAPGQGLEWM<br>GKINADLGDTNYAQKFQGRVTMTRDTSISTAYMELSSLRSEDTAVYYC<br>ARDGIEHGGHYYWGYLFDIWGQGTLVTVSSASTKGPSVFPLAPSSKST<br>SGGTAALGCLVKDYFPEPVTVSWNSGALTSGVHTFPAVLQSSGLYSLS<br>SVVTVPSSSLGTQTYICNVNHKPSNTKVDKRVEPKSC |
| LIGHT CHAIN | 38<br>SYELTQPPSVSVAPGQTARISCSGDSIREYYVHWYQQKPGQAPVLVIG<br>DDTNRPSGIPERFSGSNSGNTATLTISGTQAEDEADYYCAAWDFSPAI<br>VFGGGTKLTVLGQPKAAPSVTLFPPSSEELQANKATLVCLISDFYPGA<br>VTVAWKADSSPVKAGVETTTPSKQSNNKYAASSYLSLTPEQWKSHRSY<br>SCQVTHEGSTVEKTVAPTECS |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| PN ENCODING SEQ.ID.NO: 35 | 39<br>GAGGTGCAGCTGGTGCAGAGCGGAGCCGAAGTGAAGAAACCTGGCGCC<br>AGCGTGAAGGTGTCCTGCAAGGCCAGCGGCTACACCTTCACCAGCCAC<br>TACATGCACTGGGTGCGCCAGGCTCCAGGACAGGGCCTGGAATGGATG<br>GGCAAGATCAACGCCGACCTGGGCGACACCAACTACGCCCAGAAATTC<br>CAGGGCAGAGTGACCATGACCCGGGACACCAGCATCAGCACCGCCTAC<br>ATGGAACTGAGCAGCCTGAGAAGCGAGGACACCGCCGTGTACTACTGC<br>GCCAGGGACGGCATCGAGCACGGCGGCCACTACTACTGGGGCTACCTG<br>TTCGACATCTGGGGCCAGGGCACCCTGGTGACCGTGAGCTCA |
| PN ENCODING SEQ.ID.NO: 36 | 40<br>AGCTACGAGCTGACTCAGCCCCCTTCTGTGTCTGTGGCCCCTGGCCAG<br>ACCGCCAGAATCAGCTGCAGCGGCGACAGCATCCGGGAGTACTACGTG<br>CACTGGTATCAGCAGAAGCCCGGCCAGGCTCCTGTGCTGGTGATCGGC<br>GACGACACCAACAGACCCAGCGGCATCCCCGAGAGATTCAGCGGCAGC<br>AACAGCGGCAATACCGCCACCCTGACCATCAGCGGCACCCAGGCCGAG<br>GACGAGGCCGATTACTACTGCGCCGCCTGGGACTTCAGCCCTGCCATC<br>GTGTTCGGAGGCGGAACAAAGTTAACCGTCCTA |
| PN ENCODING SEQ.ID.NO: 37 | 41<br>GAGGTGCAGCTGGTGCAGAGCGGAGCCGAAGTGAAGAAACCTGGCGCC<br>AGCGTGAAGGTGTCCTGCAAGGCCAGCGGCTACACCTTCACCAGCCAC<br>TACATGCACTGGGTGCGCCAGGCTCCAGGACAGGGCCTGGAATGGATG<br>GGCAAGATCAACGCCGACCTGGGCGACACCAACTACGCCCAGAAATTC<br>CAGGGCAGAGTGACCATGACCCGGGACACCAGCATCAGCACCGCCTAC<br>ATGGAACTGAGCAGCCTGAGAAGCGAGGACACCGCCGTGTACTACTGC<br>GCCAGGGACGGCATCGAGCACGGCGGCCACTACTACTGGGGCTACCTG<br>TTCGACATCTGGGGCCAGGGCACCCTGGTGACCGTGAGCTCAGCATCC<br>ACCAAGGGTCCATCGGTCTTCCCCCTGGCACCCTCCTCCAAGAGCACC<br>TCTGGGGGCACAGCGGCCCTGGGCTGCCTGGTCAAGGACTACTTCCCC<br>GAACCGGTGACGGTGTCGTGGAACTCAGGCGCCCTGACCAGCGGCGTG<br>CACACCTTCCCGGCTGTCCTACAGTCCTCAGGACTCTACTCCCTCAGC<br>AGCGTGGTGACCGTGCCCTCCAGCAGCTTGGGCACCCAGACCTACATC<br>TGCAACGTGAATCACAAGCCCAGCAACACCAAGGTGGACAAGAGAGTT<br>GAGCCCAAATCTTGT |
| PN ENCODING SEQ.ID.NO: 38 | 42<br>AGCTACGAGCTGACTCAGCCCCCTTCTGTGTCTGTGGCCCCTGGCCAG<br>ACCGCCAGAATCAGCTGCAGCGGCGACAGCATCCGGGAGTACTACGTG<br>CACTGGTATCAGCAGAAGCCCGGCCAGGCTCCTGTGCTGGTGATCGGC<br>GACGACACCAACAGACCCAGCGGCATCCCCGAGAGATTCAGCGGCAGC<br>AACAGCGGCAATACCGCCACCCTGACCATCAGCGGCACCCAGGCCGAG<br>GACGAGGCCGATTACTACTGCGCCGCCTGGGACTTCAGCCCTGCCATC<br>GTGTTCGGAGGCGGAACAAAGTTAACCGTCCTAGGTCAGCCCAAGGCT<br>GCCCCCTCGGTCACTCTGTTCCCGCCCTCCTCTGAGGAGCTTCAAGCC<br>AACAAGGCCACACTGGTGTGTCTCATAAGTGACTTCTACCCGGGAGCC<br>GTGACAGTGGCCTGGAAGGCAGATAGCAGCCCCGTCAAGGCGGGAGTG<br>GAGACCACCACACCCTCCAAACAAAGCAACAACAAGTACGCGGCCAGC<br>AGCTATCTGAGCCTGACGCCTGAGCAGTGGAAGTCCCACAGAAGCTAC<br>AGCTGCCAGGTCACGCATGAAGGGAGCACCGTGGAGAAGACAGTGGCC<br>CCTACAGAATGTTCA |

NVS966

| CDRH1 | 43/299<br>NYWIG (Kabat)/GYSFTNY (Chothia) |
|---|---|
| CDRH2 | 44/300<br>RIDPGESLTNYAPSFQG (Kabat)/DPGESL (Chothia) |
| CDRH3 | 45/301<br>TGVADVDMPFAH (Kabat)/TGVADVDMPFAH (Chothia) |
| CDRL1 | 46/302<br>SGDNLGSYYVN (Kabat)/DNLGSYY (Chothia) |
| CDRL2 | 47/303<br>GDSERPS (Kabat)/GDS (Chothia) |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| CDRL3 | 48/304<br>GSWDITSF (Kabat)/WDITSF (Chothia) |
| VH | 49<br>EVQLVQSGAEVKKPGESLKISCKGSGYSFTNYWIGWVRQMPGKGLEWM<br>GRIDPGESLTNYAPSFQGQVTISADKSISTAYLQWSSLKASDTAMYYC<br>ARTGVADVDMPFAHWGQGTLVTVSS |
| VL | 50<br>SYVLTQPPSVSVAPGKTARISCSGDNLGSYYVNWYQQKPGQAPVLVIY<br>GDSERPSGIPERFSGSNSGNTATLTISRAQAGDEADYYCGSWDITSFV<br>FGGGTKLTVL |
| HEAVY CHAIN | 51<br>EVQLVQSGAEVKKPGESLKISCKGSGYSFTNYWIGWVRQMPGKGLEWM<br>GRIDPGESLTNYAPSFQGQVTISADKSISTAYLQWSSLKASDTAMYYC<br>ARTGVADVDMPFAHWGQGTLVTVSSASTKGPSVFPLAPSSKSTSGGTA<br>ALGCLVKDYFPEPVTVSWNSGALTSGVHTFPAVLQSSGLYSLSSVVTV<br>PSSSLGTQTYICNVNHKPSNTKVDKRVEPKSC |
| LIGHT CHAIN | 52<br>SYVLTQPPSVSVAPGKTARISCSGDNLGSYYVNWYQQKPGQAPVLVIY<br>GDSERPSGIPERFSGSNSGNTATLTISRAQAGDEADYYCGSWDITSFV<br>FGGGTKLTVLGQPKAAPSVTLFPPSSEELQANKATLVCLISDFYPGAV<br>TVAWKADSSPVKAGVETTTPSKQSNNKYAASSYLSLTPEQWKSHRSYS<br>CQVTHEGSTVEKTVAPTECS |
| PN ENCODING SEQ.ID.NO: 49 | 53<br>GAGGTGCAGCTGGTGCAGAGCGGAGCCGAAGTGAAGAAGCCTGGCGAG<br>AGCCTGAAGATCAGCTGCAAGGGCAGCGGCTACAGCTTCACCAACTAC<br>TGGATCGGCTGGGTGCGCCAGATGCCTGGCAAGGGCCTGGAATGGATG<br>GGCAGAATCGACCCCGGCGAGTCCCTGACCAACTACGCCCCCAGCTTC<br>CAGGGCCAGGTGACAATCAGCGCCGACAAGAGCATCAGCACCGCCTAT<br>CTGCAGTGGAGCAGCCTGAAGGCCAGCGACACCGCCATGTACTACTGC<br>GCCAGAACCGGCGTGGCCGACGTGGACATGCCTTTTGCCCACTGGGGC<br>CAGGGCACCCTGGTGACCGTGAGCTCA |
| PN ENCODING SEQ.ID.NO: 50 | 54<br>AGCTACGTGCTGACTCAGCCCCCTTCTGTGTCTGTGGCCCCTGGCAAG<br>ACCGCCAGAATCAGCTGCAGCGGCGACAACCTGGGCAGCTACTACGTG<br>AACTGGTATCAGCAGAAGCCCGGCCAGGCTCCCGTGCTGGTGATCTAC<br>GGCGACAGCGAGAGGCCTAGCGGCATCCCCGAGCGGTTCAGCGGCAGC<br>AACAGCGGCAATACCGCCACCCTGACCATCTCTAGAGCCCAGGCCGGC<br>GACGAGGCCGATTACTACTGCGGCTCCTGGGACATCACCAGCTTCGTG<br>TTCGGAGGCGGAACAAAGTTAACCGTCCTA |
| PN ENCODING SEQ.ID.NO: 51 | 55<br>GAGGTGCAGCTGGTGCAGAGCGGAGCCGAAGTGAAGAAGCCTGGCGAG<br>AGCCTGAAGATCAGCTGCAAGGGCAGCGGCTACAGCTTCACCAACTAC<br>TGGATCGGCTGGGTGCGCCAGATGCCTGGCAAGGGCCTGGAATGGATG<br>GGCAGAATCGACCCCGGCGAGTCCCTGACCAACTACGCCCCCAGCTTC<br>CAGGGCCAGGTGACAATCAGCGCCGACAAGAGCATCAGCACCGCCTAT<br>CTGCAGTGGAGCAGCCTGAAGGCCAGCGACACCGCCATGTACTACTGC<br>GCCAGAACCGGCGTGGCCGACGTGGACATGCCTTTTGCCCACTGGGGC<br>CAGGGCACCCTGGTGACCGTGAGCTCAGCCTCCACCAAGGGTCCATCG<br>GTCTTCCCCCTGGCACCCTCCTCCAAGAGCACCTCTGGGGGCACAGCG<br>GCCCTGGGCTGCCTGGTCAAGGACTACTTCCCCGAACCGGTGACGGTG<br>TCGTGGAACTCAGGCGCCCTGACCAGCGGCGTGCACACCTTCCCGGCT<br>GTCCTACAGTCCTCAGGACTCTACTCCCTCAGCAGCGTGGTGACCGTG<br>CCCTCCAGCAGCTTGGGCACCCAGACCTACATCTGCAACGTGAATCAC<br>AAGCCCAGCAACACCAAGGTGGACAAGAGAGTTGAGCCCAAATCTTGT |
| PN ENCODING SEQ.ID.NO: 52 | 56<br>AGCTACGTGCTGACTCAGCCCCCTTCTGTGTCTGTGGCCCCTGGCAAG<br>ACCGCCAGAATCAGCTGCAGCGGCGACAACCTGGGCAGCTACTACGTG<br>AACTGGTATCAGCAGAAGCCCGGCCAGGCTCCCGTGCTGGTGATCTAC<br>GGCGACAGCGAGAGGCCTAGCGGCATCCCCGAGCGGTTCAGCGGCAGC<br>AACAGCGGCAATACCGCCACCCTGACCATCTCTAGAGCCCAGGCCGGC<br>GACGAGGCCGATTACTACTGCGGCTCCTGGGACATCACCAGCTTCGTG<br>TTCGGAGGCGGAACAAAGTTAACCGTCCTAGGTCAGCCCAAGGCTGCC<br>CCCTCGGTCACTCTGTTCCCGCCCTCCTCTGAGGAGCTTCAAGCCAAC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | AAGGCCACACTGGTGTGTCTCATAAGTGACTTCTACCCGGGAGCCGTG<br>ACAGTGGCCTGGAAGGCAGATAGCAGCCCCGTCAAGGCGGGAGTGGAG<br>ACCACCACACCCTCCAAACAAAGCAACAACAAGTACGCGGCCAGCAGC<br>TATCTGAGCCTGACGCCTGAGCAGTGGAAGTCCCACAGAAGCTACAGC<br>TGCCAGGTCACGCATGAAGGGAGCACCGTGGAGAAGACAGTGGCCCCT<br>ACAGAATGTTCA |

NVS965

| | |
|---|---|
| CDRH1 | 57/305<br>SYAIS (Kabat)/GGTFNSY (Chothia) |
| CDRH2 | 58/306<br>RIIPIFGTANYAQKFQG (Kabat)/IPIFGT (Chothia) |
| CDRH3 | 59/307<br>HGGYSFDS (Kabat)/HGGYSFDS (Chothia) |
| CDRL1 | 60/308<br>SGDNLGSKYVD (Kabat)/DNLGSKY (Chothia) |
| CDRL2 | 61/309<br>SDNNRPS (Kabat)/SDN (Chothia) |
| CDRL3 | 62/310<br>ATYDSSPRTE (Kabat)/YDSSPRTE (Chothia) |
| VH | 63<br>EVQLVQSGAEVKKPGSSVKVSCKASGGTFNSYAISWVRQAPGQGLEWM<br>GRIIPIFGTANYAQKFQGRVTITADESTSTAYMELSSLRSEDTAVYYC<br>ARHGGYSFDSWGQGTLVTVSS |
| VL | 64<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVL |
| HEAVY CHAIN | 65<br>EVQLVQSGAEVKKPGSSVKVSCKASGGTFNSYAISWVRQAPGQGLEWM<br>GRIIPIFGTANYAQKFQGRVTITADESTSTAYMELSSLRSEDTAVYYC<br>ARHGGYSFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 66<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 63 | 67<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAACAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING SEQ.ID.NO: 64 | 68<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | GACGAGGCCGACTACTACTGCGCCACCTACGACAGCAGCCCCAGAACC GAGGTGTTCGGAGGCGGAACAAAGTTAACCGTCCTA |
| PN ENCODING SEQ.ID.NO: 65 | 69<br>GAGGTGCAGCTGGTGCAGAGCGGAGCCGAAGTGAAGAAACCCGGCAGC AGCGTGAAGGTGTCCTGCAAGGCCAGCGGCGGCACCTTCAACAGCTAC GCCATCAGCTGGGTGCGCCAGGCTCCTGGACAGGGCCTGGAATGGATG GGCCGGATCATCCCCATCTTCGGCACCGCCAACTACGCCCAGAAATTC CAGGGCAGAGTGACCATCACCGCCGACGAGAGCACCAGCACGGCCTAC ATGGAACTGAGCAGCCTGAGAAGCGAGGACACCGCCGTGTACTACTGT GCCCGGCACGGCGGCTACAGCTTCGATAGCTGGGGCCAGGGCACCCTG GTGACCGTGAGCTCAGCCTCCACCAAGGGTCCATCGGTCTTCCCCCTG GCACCCTCCTCCAAGAGCACCTCTGGGGGCACAGCGGCCCTGGGCTGC CTGGTCAAGGACTACTTCCCCGAACCGGTGACGGTGTCGTGGAACTCA GGCGCCCTGACCAGCGGCGTGCACACCTTCCCGGCTGTCCTACAGTCC TCAGGACTCTACTCCCTCAGCAGCGTGGTGACCGTGCCCTCCAGCAGC TTGGGCACCCAGACCTACATCTGCAACGTGAATCACAAGCCCAGCAAC ACCAAGGTGGACAAGAGAGTTGAGCCCAAATCTTGT |
| PN ENCODING SEQ.ID.NO: 66 | 70<br>AGCTACGTGCTGACTCAGCCCCCTTCTGTGTCTGTGGCCCCTGGCAAG ACCGCCAGAATCAGCTGCAGCGGCGACAACCTGGGCAGCAAATACGTG GACTGGTATCAGCAGAAGCCCGGCCAGGCTCCCGTGCTGGTGATCTAC AGCGACAACAACCGGCCCAGCGGCATCCCTGAGCGGTTCAGCGGCAGC AACAGCGGCAATACCGCCACCCTGACCATCAGCCGGCACCCAGGCCATG GACGAGGCCGACTACTACTGCGCCACCTACGACAGCAGCCCCAGAACC GAGGTGTTCGGAGGCGGAACAAAGTTAACCGTCCTAGGTCAGCCCAAG GCTGCCCCCTCGGTCACTCTGTTCCCGCCCTCCTCTGAGGAGCTTCAA GCCAACAAGGCCACACTGGTGTGTCTCATAAGTGACTTCTACCCGGGA GCCGTGACAGTGGCCTGGAAGGCAGATAGCAGCCCCGTCAAGGCGGGA GTGGAGACCACCACACCCTCCAAACAAAGCAACAACAAGTACGCGGCC AGCAGCTATCTGAGCCTGACGCCTGAGCAGTGGAAGTCCCACAGAAGC TACAGCTGCCAGGTCACGCATGAAGGGAGCACCGTGGAGAAGACAGTG GCCCCTACAGAATGTTCA |

NVS967

| CDRH1 | 71/311<br>SHYMH (Kabat)/GYTFTSH (Chothia) |
|---|---|
| CDRH2 | 72/312<br>NINPVDGGTEYAQKFQG (Kabat)/NPVDGG (Chothia) |
| CDRH3 | 73/313<br>DGIEHGGHYYWGYLFDI (Kabat)/DGIEHGGHYYWGYLFDI (Chothia) |
| CDRL1 | 74/314<br>SGDSIREYYVH (Kabat)/DSIREYY (Chothia) |
| CDRL2 | 75/315<br>DDTNRPS (Kabat)/DDT (Chothia) |
| CDRL3 | 76/316<br>AAWDFSPAI (Kabat)/WDFSPAI (Chothia) |
| VH | 77<br>EVQLVQSGAEVKKPGASVKVSCKASGYTFTSHYMHWVRQAPGQGLEWM GNINPVDGGTEYAQKFQGRVTMTRDTSISTAYMELSSLRSEDTAVYYC ARDGIEHGGHYYWGYLFDIWGQGTLVTVSS |
| VL | 78<br>SYVLTQPPSVSVAPGKTARISCSGDSIREYYVHWYQQKPGQAPVLVIG DDTNRPSGIPERFSGSNSGNTATLTISRAQAGDEADYYCAAWDFSPAI VFGGGTKLTVL |
| HEAVY CHAIN | 79<br>EVQLVQSGAEVKKPGASVKVSCKASGYTFTSHYMHWVRQAPGQGLEWM GNINPVDGGTEYAQKFQGRVTMTRDTSISTAYMELSSLRSEDTAVYYC ARDGIEHGGHYYWGYLFDIWGQGTLVTVSSASTKGPSVFPLAPSSKST SGGTAALGCLVKDYFPEPVTVSWNSGALTSGVHTFPAVLQSSGLYSLS SVVTVPSSSLGTQTYICNVNHKPSNTKVDKRVEPKSC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| LIGHT CHAIN | 80<br>SYVLTQPPSVSVAPGKTARISCSGDSIREYYVHWYQQKPGQAPVLVIG<br>DDTNRPSGIPERFSGSNSGNTATLTISRAQAGDEADYYCAAWDFSPAI<br>VFGGGTKLTVLGQPKAAPSVTLFPPSSEELQANKATLVCLISDFYPGA<br>VTVAWKADSSPVKAGVETTTPSKQSNNKYAASSYLSLTPEQWKSHRSY<br>SCQVTHEGSTVEKTVAPTECS |
| PN ENCODING SEQ.ID.NO: 77 | 81<br>GAGGTGCAGCTGGTGCAGAGCGGAGCCGAAGTGAAGAAACCTGGCGCC<br>AGCGTGAAGGTGTCCTGCAAGGCCAGCGGCTACACCTTCACCAGCCAC<br>TACATGCACTGGGTGCGCCAGGCTCCAGGACAGGGCCTGGAATGGATG<br>GGCAACATCAACCCCGTGGACGGCGGCACCGAGTACGCCCAGAAATTC<br>CAGGGCAGAGTGACCATGACCCGGGACACCAGCATCAGCACCGCCTAC<br>ATGGAACTGAGCAGCCTGAGAAGCGAGGACACCGCCGTGTACTACTGC<br>GCCAGGGACGGCATCGAGCACGGCGGCCACTACTACTGGGGCTACCTG<br>TTCGACATCTGGGGCCAGGGCACCCTGGTGACCGTGAGCTCA |
| PN ENCODING SEQ.ID.NO: 78 | 82<br>TCTTACGTGCTGACTCAGCCCCCTTCTGTGTCTGTGGCCCCTGGCAAG<br>ACCGCCAGAATCAGCTGCAGCGGCGACAGCATCCGGGAGTACTACGTG<br>CACTGGTATCAGCAGAAGCCCGGCCAGGCTCCTGTGCTGGTGATCGGC<br>GACGACACCAACAGACCCAGCGGCATCCCCGAGAGATTCAGCGGCAGC<br>AACAGCGGCAATACCGCCACCCTGACCATCTCTAGAGCCCAGGCCGGC<br>GACGAGGCCGATTACTACTGCGCCGCCTGGGACTTCAGCCCTGCCATC<br>GTGTTCGGAGGCGGAACAAAGTTAACCGTCCTA |
| PN ENCODING SEQ.ID.NO: 79 | 83<br>GAGGTGCAGCTGGTGCAGAGCGGAGCCGAAGTGAAGAAACCTGGCGCC<br>AGCGTGAAGGTGTCCTGCAAGGCCAGCGGCTACACCTTCACCAGCCAC<br>TACATGCACTGGGTGCGCCAGGCTCCAGGACAGGGCCTGGAATGGATG<br>GGCAACATCAACCCCGTGGACGGCGGCACCGAGTACGCCCAGAAATTC<br>CAGGGCAGAGTGACCATGACCCGGGACACCAGCATCAGCACCGCCTAC<br>ATGGAACTGAGCAGCCTGAGAAGCGAGGACACCGCCGTGTACTACTGC<br>GCCAGGGACGGCATCGAGCACGGCGGCCACTACTACTGGGGCTACCTG<br>TTCGACATCTGGGGCCAGGGCACCCTGGTGACCGTGAGCTCAGCCTCC<br>ACCAAGGGTCCATCGGTCTTCCCCCTGGCACCCTCCTCCAAGAGCACC<br>TCTGGGGGCACAGCGGCCCTGGGCTGCCTGGTCAAGGACTACTTCCCC<br>GAACCGGTGACGGTGTCGTGGAACTCAGGCGCCCTGACCAGCGGCGTG<br>CACACCTTCCCGGCTGTCCTACAGTCCTCAGGACTCTACTCCCTCAGC<br>AGCGTGGTGACCGTGCCCTCCAGCAGCTTGGGCACCCAGACCTACATC<br>TGCAACGTGAATCACAAGCCCAGCAACACCAAGGTGGACAAGAGAGTT<br>GAGCCCAAATCTTGT |
| PN ENCODING SEQ.ID.NO: 80 | 84<br>TCTTACGTGCTGACTCAGCCCCCTTCTGTGTCTGTGGCCCCTGGCAAG<br>ACCGCCAGAATCAGCTGCAGCGGCGACAGCATCCGGGAGTACTACGTG<br>CACTGGTATCAGCAGAAGCCCGGCCAGGCTCCTGTGCTGGTGATCGGC<br>GACGACACCAACAGACCCAGCGGCATCCCCGAGAGATTCAGCGGCAGC<br>AACAGCGGCAATACCGCCACCCTGACCATCTCTAGAGCCCAGGCCGGC<br>GACGAGGCCGATTACTACTGCGCCGCCTGGGACTTCAGCCCTGCCATC<br>GTGTTCGGAGGCGGAACAAAGTTAACCGTCCTAGGTCAGCCCAAGGCT<br>GCCCCCTCGGTCACTCTGTTCCCGCCCTCCTCTGAGGAGCTTCAAGCC<br>AACAAGGCCACACTGGTGTGTCTCATAAGTGACTTCTACCCGGGAGCC<br>GTGACAGTGGCCTGGAAGGCAGATAGCAGCCCCGTCAAGGCGGGAGTG<br>GAGACCACCACACCCTCCAAACAAAGCAACAACAAGTACGCGGCCAGC<br>AGCTATCTGAGCCTGACGCCTGAGCAGTGGAAGTCCCACAGAAGCTAC<br>AGCTGCCAGGTCACGCATGAAGGGAGCACCGTGGAGAAGACAGTGGCC<br>CCTACAGAATGTTCA |
| NVS807 | |
| CDRH1 | 85/317<br>SYAIS (Kabat)/GGTFSSY (Chothia) |
| CDRH2 | 86/318<br>RIIPIFGTANYAQKFQG (Kabat)/IPIFGT (Chothia) |
| CDRH3 | 87/319<br>HGGYSYFDS (Kabat)/HGGYYFDS (Chothia) |

TABLE 1-continued

Examples of Factor P Antibodies, Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| CDRL1 | 88/320<br>SGDNLGSKYVD (Kabat)/DNLGSKY (Chothia) |
| CDRL2 | 89/321<br>SDNNRPS (Kabat)/SDN (Chothia) |
| CDRL3 | 90/322<br>QTYTSGNNYL (Kabat)/YTSGNNYL (Chothia) |
| VH | 91<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYYFDSWGQGTLVTVSS |
| VL | 92<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVL |
| HEAVY CHAIN | 93<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYYFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 94<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 91 | 95<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACTACTTCGATAGCTGGGGCCAGGGCACCCTG<br>GTGACCGTGAGCTCA |
| PN ENCODING SEQ.ID.NO: 92 | 96<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTA |
| PN ENCODING SEQ.ID.NO: 93 | 97<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACTACTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING SEQ.ID.NO: 94 | 98<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | GACTGGTATCAGCAGAAGCCCGGCCAGGCTCCCGTGCTGGTGATCTAC AGCGACAACAACCGGCCCAGCGGCATCCCTGAGCGGTTCAGCGGCAGC AACAGCGGCAATACCGCCACCCTGACCATCAGCGGCACCCAGGCCGAG GACGAGGCCGACTACTACTGCCAGACCTACACCAGCGGCAACAACTAC CTGGTGTTCGGAGGCGGAACAAAGTTAACCGTCCTAGGTCAGCCCAAG GCTGCCCCCTCGGTCACTCTGTTCCCGCCCTCCTCTGAGGAGCTTCAA GCCAACAAGGCCACACTGGTGTGTCTCATAAGTGACTTCTACCCGGGA GCCGTGACAGTGGCCTGGAAGGCAGATAGCAGCCCCGTCAAGGCGGGA GTGGAGACCACCACACCCTCCAAACAAAGCAACAACAAGTACGCGGCC AGCAGCTATCTGAGCCTGACGCCTGAGCAGTGGAAGTCCCACAGAAGC TACAGCTGCCAGGTCACGCATGAAGGGAGCACCGTGGAGAAGACAGTG GCCCCTACAGAATGTTCA |

NVS808

| CDRH1 | 99/323 SYAIS (Kabat)/GGTFSSY (Chothia) |
|---|---|
| CDRH2 | 100/324 RIIPIFGTANYAQKFQG (Kabat)/IPIFGT (Chothia) |
| CDRH3 | 101/325 HGGYIFDS (Kabat)/HGGYIFDS (Chothia) |
| CDRL1 | 102/326 SGDNLGSKYVD (Kabat)/DNLGSKY (Chothia) |
| CDRL2 | 103/327 SDNNRPS (Kabat)/SDN (Chothia) |
| CDRL3 | 104/328 QTYTSGNNYL (Kabat)/YTSGNNYL (Chothia) |
| VH | 105 EVQLVQSGAEVKKPGSSVKVSCKASGGTFSSYAISWVRQAPGQGLEWM GRIIPIFGTANYAQKFQGRVTITADESTSTAYMELSSLRSEDTAVYYC ARHGGYIFDSWGQGTLVTVSS |
| VL | 106 SYELTQPPSVSVAPGQTARISCSGDNLGSKYVDWYQQKPGQAPVLVIY SDNNRPSGIPERFSGSNSGNTATLTISGTQAEDEADYYCQTYTSGNNY LVFGGGTKLTVL |
| HEAVY CHAIN | 107 EVQLVQSGAEVKKPGSSVKVSCKASGGTFSSYAISWVRQAPGQGLEWM GRIIPIFGTANYAQKFQGRVTITADESTSTAYMELSSLRSEDTAVYYC ARHGGYIFDSWGQGTLVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSC |
| LIGHT CHAIN | 108 SYELTQPPSVSVAPGQTARISCSGDNLGSKYVDWYQQKPGQAPVLVIY SDNNRPSGIPERFSGSNSGNTATLTISGTQAEDEADYYCQTYTSGNNY LVFGGGTKLTVLGQPKAAPSVTLFPPSSEELQANKATLVCLISDFYPG AVTVAWKADSSPVKAGVETTTPSKQSNNKYAASSYLSLTPEQWKSHRS YSCQVTHEGSTVEKTVAPTECS |
| PN ENCODING SEQ.ID.NO: 105 | 109 GAGGTGCAGCTGGTGCAGAGCGGAGACCGAAGTGAAGAAACCCGGCAGC AGCGTGAAGGTGTCCTGCAAGGCCAGCGGCGGCACCTTCAGCAGCTAC GCCATCAGCTGGGTGCGCCAGGCTCCTGGACAGGGCCTGGAATGGATG GGCCGGATCATCCCCATCTTCGGCACCGCCAACTACGCCCAGAAATTC CAGGGCAGAGTGACCATCACCGCCGACGAGAGCACCAGCACCGCCTAC ATGGAACTGAGCAGCCTGAGAAGCGAGGACACCGCCGTGTACTACTGT GCCCGGCACGGCGGCTACATTTTCGATAGCTGGGGCCAGGGCACCCTG GTGACCGTGAGCTCA |
| PN ENCODING SEQ.ID.NO: 106 | 110 AGCTACGAGCTGACTCAGCCCCCTTCTGTGTCTGTGGCCCCTGGCCAG ACCGCCAGAATCAGCTGCAGCGGCGACAACCTGGGCAGCAAATACGTG GACTGGTATCAGCAGAAGCCCGGCCAGGCTCCCGTGCTGGTGATCTAC AGCGACAACAACCGGCCCAGCGGCATCCCTGAGCGGTTCAGCGGCAGC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | AACAGCGGCAATACCGCCACCCTGACCATCAGCGGCACCCAGGCCGAG GACGAGGCCGACTACTACTGCCAGACCTACACCAGCGGCAACAACTAC CTGGTGTTCGGAGGCGGAACAAAGTTAACCGTCCTA |
| PN ENCODING SEQ.ID.NO: 107 | 111<br>GAGGTGCAGCTGGTGCAGAGCGGAGCCGAAGTGAAGAAACCCGGCAGC AGCGTGAAGGTGTCCTGCAAGGCCAGCGGCGGCACCTTCAGCAGCTAC GCCATCAGCTGGGTGCGCCAGGCTCCTGGACAGGGCCTGGAATGGATG GGCCGGATCATCCCCATCTTCGGCACCGCCAACTACGCCCAGAAATTC CAGGGCAGAGTGACCATCACCGCCGACGAGAGCACCAGCACCGCCTAC ATGGAACTGAGCAGCCTGAGAAGCGAGGACACCGCCGTGTACTACTGT GCCCGGCACGGCGGCTACATTTTCGATAGCTGGGGCCAGGGCACCCTG GTGACCGTGAGCTCAGCCTCCACCAAGGGTCCATCGGTCTTCCCCCTG GCACCCTCCTCCAAGAGCACCTCTGGGGGCACAGCGGCCCTGGGCTGC CTGGTCAAGGACTACTTCCCCGAACCGGTGACGGTGTCGTGGAACTCA GGCGCCCTGACCAGCGGCGTGCACACCTTCCCGGCTGTCCTACAGTCC TCAGGACTCTACTCCCTCAGCAGCGTGGTGACCGTGCCCTCCAGCAGC TTGGGCACCCAGACCTACATCTGCAACGTGAATCACAAGCCCAGCAAC ACCAAGGTGGACAAGAGAGTTGAGCCCAAATCTTGT |
| PN ENCODING SEQ.ID.NO: 108 | 112<br>AGCTACGAGCTGACTCAGCCCCCTTCTGTGTCTGTGGCCCCTGGCCAG ACCGCCAGAATCAGCTGCAGCGGCGACAACCTGGGCAGCAAATACGTG GACTGGTATCAGCAGAAGCCCGGCCAGGCTCCCGTGCTGGTGATCTAC AGCGACAACAACCGGCCCAGCGGCATCCCTGAGCGGTTCAGCGGCAGC AACAGCGGCAATACCGCCACCCTGACCATCAGCGGCACCCAGGCCGAG GACGAGGCCGACTACTACTGCCAGACCTACACCAGCGGCAACAACTAC CTGGTGTTCGGAGGCGGAACAAAGTTAACCGTCCTAGGTCAGCCCAAG GCTGCCCCCTCGGTCACTCTGTTCCCGCCCTCCTCTGAGGAGCTTCAA GCCAACAAGGCCACACTGGTGTGTCTCATAAGTGACTTCTACCCGGGA GCCGTGACAGTGGCCTGGAAGGCAGATAGCAGCCCCGTCAAGGCGGGA GTGGAGACCACCACACCCTCCAAACAAAGCAACAACAAGTACGCGGCC AGCAGCTATCTGAGCCTGACGCCTGAGCAGTGGAAGTCCCACAGAAGC TACAGCTGCCAGGTCACGCATGAAGGGAGCACCGTGGAGAAGACAGTG GCCCCTACAGAATGTTCA |

NVS806

| CDRH1 | 113/329<br>SYAIS (Kabat)/GGTFSSY (Chothia) |
|---|---|
| CDRH2 | 114/330<br>RIIPIFGTANYAQKFQG (Kabat)/IPIFGT (Chothia) |
| CDRH3 | 115/331<br>HGGYVFDS (Kabat)/HGGYVFDS (Chothia) |
| CDRL1 | 116/332<br>SGDNLGSKYVD (Kabat)/DNLGSKY (Chothia) |
| CDRL2 | 117/333<br>SDNNRPS (Kabat)/SDN (Chothia) |
| CDRL3 | 118/334<br>QTYTSGNNYL (Kabat)/YTSGNNYL (Chothia) |
| VH | 119<br>EVQLVQSGAEVKKPGSSVKVSCKASGGTFSSYAISWVRQAPGQGLEWM GRIIPIFGTANYAQKFQGRVTITADESTSTAYMELSSLRSEDTAVYYC ARHGGYVFDSWGQGTLVTVSS |
| VL | 120<br>SYELTQPPSVSVAPGQTARISCSGDNLGSKYVDWYQQKPGQAPVLVIY SDNNRPSGIPERFSGSNSGNTATLTISGTQAEDEADYYCQTYTSGNNY LVFGGGTKLTVL |
| HEAVY CHAIN | 121<br>EVQLVQSGAEVKKPGSSVKVSCKASGGTFSSYAISWVRQAPGQGLEWM GRIIPIFGTANYAQKFQGRVTITADESTSTAYMELSSLRSEDTAVYYC ARHGGYVFDSWGQGTLVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| LIGHT CHAIN | 122<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 119 | 123<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACGTCTTCGATAGCTGGGGCCAGGGCACCCTG<br>GTGACCGTGAGCTCA |
| PN ENCODING SEQ.ID.NO: 120 | 124<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTA |
| PN ENCODING SEQ.ID.NO: 121 | 125<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACGTCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING SEQ.ID.NO: 122 | 126<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS804

| CDRH1 | 127/335<br>SYAIS (Kabat)/GGTFSSY (Chothia) |
|---|---|
| CDRH2 | 128/336<br>RIIPIFGTANYAQKFQG (Kabat)/IPIFGT (Chothia) |
| CDRH3 | 129/337<br>HGGYVFDS (Kabat)/HGGYIFDS (Chothia) |

TABLE 1-continued

Examples of Factor P Antibodies, Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| CDRL1 | 130/338<br>SGDNLGSKYVD (Kabat)/DNLGSKY (Chothia) |
| CDRL2 | 131/339<br>SDNNRPS (Kabat)/SDN (Chothia) |
| CDRL3 | 132/340<br>ATYDSSPRTE (Kabat)/YDSSPRTE (Chothia) |
| VH | 133<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYIFDSWGQGTLVTVSS |
| VL | 134<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVL |
| HEAVY CHAIN | 135<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYIFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 136<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 133 | 137<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACATTTTCGATAGCTGGGGCCAGGGCACCCTG<br>GTGACCGTGAGCTCA |
| PN ENCODING SEQ.ID.NO: 134 | 138<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTA |
| PN ENCODING SEQ.ID.NO: 135 | 139<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACATTTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING SEQ.ID.NO: 136 | 140<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG |

TABLE 1-continued

Examples of Factor P Antibodies, Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS809

| | |
|---|---|
| CDRH1 | 141/341<br>SYAIS (Kabat)/GGTFSSY (Chothia) |
| CDRH2 | 142/342<br>RIIPIFGTANYAQKFQG (Kabat)/IPIFGT (Chothia) |
| CDRH3 | 143/343<br>HGGYYFDS (Kabat)/HGGYYFDS (Chothia) |
| CDRL1 | 144/344<br>SGDNLGSKYVD (Kabat)/DNLGSKY (Chothia) |
| CDRL2 | 145/345<br>SDNNRPS (Kabat)/SDN (Chothia) |
| CDRL3 | 146/346<br>ATYDSSPRTE (Kabat)/YDSSPRTE (Chothia) |
| VH | 147<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYYFDSWGQGTLVTVSS |
| VL | 148<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVL |
| HEAVY CHAIN | 149<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYYFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 150<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING<br>SEQ.ID.NO: 147 | 151<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACTACTTCGATAGCTGGGGCCAGGGCACCCTG<br>GTGACCGTGAGCTCA |
| PN ENCODING<br>SEQ.ID.NO: 148 | 152<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTA |
| PN ENCODING<br>SEQ.ID.NO: 149 | 153<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACTACTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING<br>SEQ.ID.NO: 150 | 154<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS805

| | |
|---|---|
| CDRH1 | 155/347<br>SYAIS (Kabat)/GGTFSSY (Chothia) |
| CDRH2 | 156/348<br>RIIPIFGTANYAQKFQG (Kabat)/IPIFGT (Chothia) |
| CDRH3 | 157/349<br>HGGYVFDS (Kabat)/HGGYVFDS (Chothia) |
| CDRL1 | 158/350<br>SGDNLGSKYVD (Kabat)/DNLGSKY (Chothia) |
| CDRL2 | 159/351<br>SDNNRPS (Kabat)/SDN (Chothia) |
| CDRL3 | 160/352<br>ATYDSSPRTE (Kabat)/YDSSPRTE (Chothia) |
| VH | 161<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYVFDSWGQGTLVTVSS |
| VL | 162<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVL |
| HEAVY CHAIN | 163<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYVFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| LIGHT CHAIN | 164<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING<br>SEQ.ID.NO: 161 | 165<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACGTCTTCGATAGCTGGGGCCAGGGCACCCTG<br>GTGACCGTGAGCTCA |
| PN ENCODING<br>SEQ.ID.NO: 162 | 166<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTA |
| PN ENCODING<br>SEQ.ID.NO: 163 | 167<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACGTCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING<br>SEQ.ID.NO: 164 | 168<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS962-S

| CDRH1 | 169/353<br>SYAIS (Kabat)/GGTFSSY (Chothia) |
|---|---|
| CDRH2 | 170/354<br>RIIPIFGTANYAQKFQG (Kabat)/IPIFGT (Chothia) |
| CDRH3 | 171/355<br>HGGYSFDS (Kabat)/HGGYSFDS (Chothia) |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| CDRL1 | 172/356<br>SGDNLGSKYVD (Kabat)/DNLGSKY (Chothia) |
| CDRL2 | 173/357<br>SDNNRPS (Kabat)/SDN (Chothia) |
| CDRL3 | 174/358<br>QTYTSGNNYL (Kabat)/YTSGNNYL (Chothia) |
| VH | 175<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYSFDSWGQGTLVTVSS |
| VL | 176<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVL |
| HEAVY CHAIN | 177<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYSFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 178<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 175 | 179<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING SEQ.ID.NO: 176 | 180<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTA |
| PN ENCODING SEQ.ID.NO: 177 | 181<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING SEQ.ID.NO: 178 | 182<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS962-Q

| CDRH1 | 183/359<br>SYAIS (Kabat)/GGTFQSY (Chothia) |
| CDRH2 | 184/360<br>RIIPIFGTANYAQKFQG (Kabat)/IPIFGT (Chothia) |
| CDRH3 | 185/361<br>HGGYSFDS (Kabat)/HGGYSFDS (Chothia) |
| CDRL1 | 186/362<br>SGDNLGSKYVD (Kabat)/DNLGSKY (Chothia) |
| CDRL2 | 187/363<br>SDNNRPS (Kabat)/SDN (Chothia) |
| CDRL3 | 188/364<br>QTYTSGNNYL (Kabat)/YTSGNNYL (Chothia) |
| VH | 189<br>EVQLVQSGAEVKKPGSSVKVSCKASGGTFQSYAISWVRQAPGQGLEWM<br>GRIIPIFGTANYAQKFQGRVTITADESTSTAYMELSSLRSEDTAVYYC<br>ARHGGYSFDSWGQGTLVTVSS |
| VL | 190<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVL |
| HEAVY CHAIN | 191<br>EVQLVQSGAEVKKPGSSVKVSCKASGGTFQSYAISWVRQAPGQGLEWM<br>GRIIPIFGTANYAQKFQGRVTITADESTSTAYMELSSLRSEDTAVYYC<br>ARHGGYSFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 192<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 189 | 193<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCCAAAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING SEQ.ID.NO: 190 | 194<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | AACAGCGGCAATACCGCCACCCTGACCATCAGCGGCACCCAGGCCGAG GACGAGGCCGACTACTACTGCCAGACCTACACCAGCGGCAACAACTAC CTGGTGTTCGGAGGCGGAACAAAGTTAACCGTCCTA |
| PN ENCODING SEQ.ID.NO: 191 | 195<br>GAGGTGCAGCTGGTGCAGAGCGGAGCCGAAGTGAAGAAACCCGGCAGC AGCGTGAAGGTGTCCTGCAAGGCCAGCGGCGGCACCTTCCAAAGCTAC GCCATCAGCTGGGTGCGCCAGGCTCCTGGACAGGGCCTGGAATGGATG GGCCGGATCATCCCCATCTTCGGCACCGCCAACTACGCCCAGAAATTC CAGGGCAGAGTGACCATCACCGCCGACGAGAGCACCAGCACCGCCTAC ATGGAACTGAGCAGCCTGAGAAGCGAGGACACCGCCGTGTACTACTGT GCCCGGCACGGCGGCTACAGCTTCGATAGCTGGGGCCAGGGCACCCTG GTGACCGTGAGCTCAGCCTCCACCAAGGGTCCATCGGTCTTCCCCCTG GCACCCTCCTCCAAGAGCACCTCTGGGGGCACAGCGGCCCTGGGCTGC CTGGTCAAGGACTACTTCCCCGAACCGGTGACGGTGTCGTGGAACTCA GGCGCCCTGACCAGCGGCGTGCACACCTTCCCGGCTGTCCTACAGTCC TCAGGACTCTACTCCCTCAGCAGCGTGGTGACCGTGCCCTCCAGCAGC TTGGGCACCCAGACCTACATCTGCAACGTGAATCACAAGCCCAGCAAC ACCAAGGTGGACAAGAGAGTTGAGCCCAAATCTTGT |
| PN ENCODING SEQ.ID.NO: 192 | 196<br>AGCTACGAGCTGACTCAGCCCCCTTCTGTGTCTGTGGCCCCTGGCCAG ACCGCCAGAATCAGCTGCAGCGGCGACAACCTGGGCAGCAAATACGTG GACTGGTATCAGCAGAAGCCCGGCCAGGCTCCCGTGCTGGTGATCTAC AGCGACAACAACCGGCCCAGCGGCATCCCTGAGCGGTTCAGCGGCAGC AACAGCGGCAATACCGCCACCCTGACCATCAGCGGCACCCAGGCCGAG GACGAGGCCGACTACTACTGCCAGACCTACACCAGCGGCAACAACTAC CTGGTGTTCGGAGGCGGAACAAAGTTAACCGTCCTAGGTCAGCCCAAG GCTGCCCCCTCGGTCACTCTGTTCCCGCCCTCCTCTGAGGAGCTTCAA GCCAACAAGGCCACACTGGTGTGTCTCATAAGTGACTTCTACCCGGGA GCCGTGACAGTGGCCTGGAAGGCAGATAGCAGCCCCGTCAAGGCGGGA GTGGAGACCACCACACCCTCCAAACAAAGCAACAACAAGTACGCGGCC AGCAGCTATCTGAGCCTGACGCCTGAGCAGTGGAAGTCCCACAGAAGC TACAGCTGCCAGGTCACGCATGAAGGGAGCACCGTGGAGAAGACAGTG GCCCCTACAGAATGTTCA |

NVS962-S31A

| CDRH1 | 197/365<br>SYAIS (Kabat)/GGTFNAY (Chothia) |
|---|---|
| CDRH2 | 198/366<br>RIIPIFGTANYAQKFQG (Kabat)/IPIFGT (Chothia) |
| CDRH3 | 199/367<br>HGGYSFDS (Kabat)/HGGYSFDS (Chothia) |
| CDRL1 | 200/368<br>SGDNLGSKYVD (Kabat)/DNLGSKY (Chothia) |
| CDRL2 | 201/369<br>SDNNRPS (Kabat)/SDN (Chothia) |
| CDRL3 | 202/370<br>QTYTSGNNYL (Kabat)/YTSGNNYL (Chothia) |
| VH | 203<br>EVQLVQSGAEVKKPGSSVKVSCKASGGTFNAYAISWVRQAPGQGLEWM GRIIPIFGTANYAQKFQGRVTITADESTSTAYMELSSLRSEDTAVYYC ARHGGYSFDSWGQGTLVTVSS |
| VL | 204<br>SYELTQPPSVSVAPGQTARISCSGDNLGSKYVDWYQQKPGQAPVLVIY SDNNRPSGIPERFSGSNSGNTATLTISGTQAEDEADYYCQTYTSGNNY LVFGGGTKLTVL |
| HEAVY CHAIN | 205<br>EVQLVQSGAEVKKPGSSVKVSCKASGGTFNAYAISWVRQAPGQGLEWM GRIIPIFGTANYAQKFQGRVTITADESTSTAYMELSSLRSEDTAVYYC ARHGGYSFDSWGQGTLVTVSSASTKGPSVFPLAPSSKSTSGGTAALGC LVKDYFPEPVTVSWNSGALTSGVHTFPAVLQSSGLYSLSSVVTVPSSS LGTQTYICNVNHKPSNTKVDKRVEPKSC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| LIGHT CHAIN | 206<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 203 | 207<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAACGCCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING SEQ.ID.NO: 204 | 208<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTA |
| PN ENCODING SEQ.ID.NO: 205 | 209<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAACGCCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING SEQ.ID.NO: 206 | 210<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS962-G

| | |
|---|---|
| CDRH1 | 211/371<br>SYAIS (Kabat)/GGTFGSY (Chothia) |
| CDRH2 | 212/372<br>RIIPIFGTANYAQKFQG (Kabat)/IPIFGT (Chothia) |
| CDRH3 | 213/373<br>HGGYSFDS (Kabat)/HGGYSFDS (Chothia) |

TABLE 1-continued

Examples of Factor P Antibodies, Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| CDRL1 | 214/374<br>SGDNLGSKYVD (Kabat)/DNLGSKY (Chothia) |
| CDRL2 | 215/375<br>SDNNRPS (Kabat)/SDN (Chothia) |
| CDRL3 | 216/376<br>QTYTSGNNYL (Kabat)/YTSGNNYL (Chothia) |
| VH | 217<br>EVQLVQSGAEVKKPGSSVKVSCKASGGTFGSYAISWVRQAPGQGLEWM<br>GRIIPIFGTANYAQKFQGRVTITADESTSTAYMELSSLRSEDTAVYYC<br>ARHGGYSFDSWGQGTLVTVSS |
| VL | 218<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVL |
| HEAVY CHAIN | 219<br>EVQLVQSGAEVKKPGSSVKVSCKASGGTFGSYAISWVRQAPGQGLEWM<br>GRIIPIFGTANYAQKFQGRVTITADESTSTAYMELSSLRSEDTAVYYC<br>ARHGGYSFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 220<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 217 | 221<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCGGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING SEQ.ID.NO: 218 | 222<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTA |
| PN ENCODING SEQ.ID.NO: 219 | 223<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCGGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING SEQ.ID.NO: 220 | 224<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS962-T

| | |
|---|---|
| CDRH1 | 225/377<br>SYAIS (Kabat)/GGTFTSY (Chothia) |
| CDRH2 | 226/378<br>RIIPIFGTANYAQKFQG (Kabat)/IPIFGT (Chothia) |
| CDRH3 | 227/379<br>HGGYSFDS (Kabat)/HGGYSFDS (Chothia) |
| CDRL1 | 228/380<br>SGDNLGSKYVD (Kabat)/DNLGSKY (Chothia) |
| CDRL2 | 229/381<br>SDNNRPS (Kabat)/SDN (Chothia) |
| CDRL3 | 230/382<br>QTYTSGNNYL (Kabat)/YTSGNNYL (Chothia) |
| VH | 231<br>EVQLVQSGAEVKKPGSSVKVSCKASGGTFTSYAISWVRQAPGQGLEWM<br>GRIIPIFGTANYAQKFQGRVTITADESTSTAYMELSSLRSEDTAVYYC<br>ARHGGYSFDSWGQGTLVTVSS |
| VL | 232<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVL |
| HEAVY CHAIN | 233<br>EVQLVQSGAEVKKPGSSVKVSCKASGGTFTSYAISWVRQAPGQGLEWM<br>GRIIPIFGTANYAQKFQGRVTITADESTSTAYMELSSLRSEDTAVYYC<br>ARHGGYSFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 234<br>SYELTQPPSVSVAPGQTARISCSGDNLGSKYVDWYQQKPGQAPVLVIY<br>SDNNRPSGIPERFSGSNSGNTATLTISGTQAEDEADYYCQTYTSGNNY<br>LVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 231 | 235<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCACCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING SEQ.ID.NO: 232 | 236<br>AGCTACGAGCTGACTCAGCCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTA |
| PN ENCODING<br>SEQ.ID.NO: 233 | 237<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCACCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING<br>SEQ.ID.NO: 234 | 238<br>AGCTACGAGCTGACTCAGCCCCTTCTGTGTCTGTGGCCCCTGGCCAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCGAG<br>GACGAGGCCGACTACTACTGCCAGACCTACACCAGCGGCAACAACTAC<br>CTGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS965-T

| CDRH1 | 239/383<br>SYAIS (Kabat)/GGTFTSY (Chothia) |
|---|---|
| CDRH2 | 240/384<br>RIIPIFGTANYAQKFQG (Kabat)/IPIFGT (Chothia) |
| CDRH3 | 241/385<br>HGGYSFDS (Kabat)/HGGYSFDS (Chothia) |
| CDRL1 | 242/386<br>SGDNLGSKYVD (Kabat)/DNLGSKY (Chothia) |
| CDRL2 | 243/387<br>SDNNRPS (Kabat)/SDN (Chothia) |
| CDRL3 | 244/388<br>ATYDSSPRTE (Kabat)/YDSSPRTE (Chothia) |
| VH | 245<br>EVQLVQSGAEVKKPGSSVKVSCKASGGTFTSYAISWVRQAPGQGLEWM<br>GRIIPIFGTANYAQKFQGRVTITADESTSTAYMELSSLRSEDTAVYYC<br>ARHGGYSFDSWGQGTLVTVSS |
| VL | 246<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVL |
| HEAVY CHAIN | 247<br>EVQLVQSGAEVKKPGSSVKVSCKASGGTFTSYAISWVRQAPGQGLEWM<br>GRIIPIFGTANYAQKFQGRVTITADESTSTAYMELSSLRSEDTAVYYC<br>ARHGGYSFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |

TABLE 1-continued

Examples of Factor P Antibodies, Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| LIGHT CHAIN | 248<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING<br>SEQ.ID.NO: 245 | 249<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCACCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING<br>SEQ.ID.NO: 246 | 250<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTA |
| PN ENCODING<br>SEQ.ID.NO: 247 | 251<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCACCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING<br>SEQ.ID.NO: 248 | 252<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS965-Q

| CDRH1 | 253/389<br>SYAIS (Kabat)/GGTFQSY (Chothia) |
|---|---|
| CDRH2 | 254/390<br>RIIPIFGTANYAQKFQG (Kabat)/IPIFGT (Chothia) |
| CDRH3 | 255/391<br>HGGYSFDS (Kabat)/HGGYSFDS (Chothia) |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| CDRL1 | 256/392<br>SGDNLGSKYVD (Kabat)/DNLGSKY (Chothia) |
| CDRL2 | 257/393<br>SDNNRPS (Kabat)/SDN (Chothia) |
| CDRL3 | 258/394<br>ATYDSSPRTE (Kabat)/YDSSPRTE (Chothia) |
| VH | 259<br>EVQLVQSGAEVKKPGSSVKVSCKASGGTFQSYAISWVRQAPGQGLEWM<br>GRIIPIFGTANYAQKFQGRVTITADESTSTAYMELSSLRSEDTAVYYC<br>ARHGGYSFDSWGQGTLVTVSS |
| VL | 260<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVL |
| HEAVY CHAIN | 261<br>EVQLVQSGAEVKKPGSSVKVSCKASGGTFQSYAISWVRQAPGQGLEWM<br>GRIIPIFGTANYAQKFQGRVTITADESTSTAYMELSSLRSEDTAVYYC<br>ARHGGYSFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 262<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 259 | 263<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCCAAAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING SEQ.ID.NO: 260 | 264<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTA |
| PN ENCODING SEQ.ID.NO: 261 | 265<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCCAAAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING SEQ.ID.NO: 262 | 266<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |

NVS965-S

| CDRH1 | 267/395<br>SYAIS (Kabat)/GGTFSSY (Chothia) |
|---|---|
| CDRH2 | 268/396<br>RIIPIFGTANYAQKFQG (Kabat)/IPIFGT (Chothia) |
| CDRH3 | 269/397<br>HGGYSFDS (Kabat)/HGGYSFDS (Chothia) |
| CDRL1 | 270/398<br>SGDNLGSKYVD (Kabat)/DNLGSKY (Chothia) |
| CDRL2 | 271/399<br>SDNNRPS (Kabat)/SDN (Chothia) |
| CDRL3 | 272/400<br>ATYDSSPRTE (Kabat)/YDSSPRTE (Chothia) |
| VH | 273<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYSFDSWGQGTLVTVSS |
| VL | 274<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVL |
| HEAVY CHAIN | 275<br>EVQLVQSGAEVKKPGSSVKVSCKASGGTFSSYAISWVRQAPGQGLEWM<br>GRIIPIFGTANYAQKFQGRVTITADESTSTAYMELSSLRSEDTAVYYC<br>ARHGGYSFDSWGQGTLVTVSSASTKGPSVFPLAPSSKSTSGGTAALGC<br>LVKDYFPEPVTVSWNSGALTSGVHTFPAVLQSSGLYSLSSVVTVPSSS<br>LGTQTYICNVNHKPSNTKVDKRVEPKSC |
| LIGHT CHAIN | 276<br>SYVLTQPPSVSVAPGKTARISCSGDNLGSKYVDWYQQKPGQAPVLVIY<br>SDNNRPSGIPERFSGSNSGNTATLTISGTQAMDEADYYCATYDSSPRT<br>EVFGGGTKLTVLGQPKAAPSVTLFPPSSEELQANKATLVCLISDFYPG<br>AVTVAWKADSSPVKAGVETTTPSKQSNNKYAASSYLSLTPEQWKSHRS<br>YSCQVTHEGSTVEKTVAPTECS |
| PN ENCODING SEQ.ID.NO: 273 | 277<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCA |
| PN ENCODING SEQ.ID.NO: 274 | 278<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC |

TABLE 1-continued

Examples of Factor P Antibodies,
Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
| | AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTA |
| PN ENCODING<br>SEQ.ID.NO: 275 | 279<br>GAGGTGCAGCTGGTGCAGAGCGGAGCCGAAGTGAAGAAACCCGGCAGC<br>AGCGTGAAGGTGTCCTGCAAGGCCAGCGGCGGCACCTTCAGCAGCTAC<br>GCCATCAGCTGGGTGCGCCAGGCTCCTGGACAGGGCCTGGAATGGATG<br>GGCCGGATCATCCCCATCTTCGGCACCGCCAACTACGCCCAGAAATTC<br>CAGGGCAGAGTGACCATCACCGCCGACGAGAGCACCAGCACCGCCTAC<br>ATGGAACTGAGCAGCCTGAGAAGCGAGGACACCGCCGTGTACTACTGT<br>GCCCGGCACGGCGGCTACAGCTTCGATAGCTGGGGCCAGGGCACCCTG<br>GTGACCGTGAGCTCAGCCTCCACCAAGGGTCCATCGGTCTTCCCCCTG<br>GCACCCTCCTCCAAGAGCACCTCTGGGGGCACAGCGGCCCTGGGCTGC<br>CTGGTCAAGGACTACTTCCCCGAACCGGTGACGGTGTCGTGGAACTCA<br>GGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGC<br>TTGGGCACCCAGACCTACATCTGCAACGTGAATCACAAGCCCAGCAAC<br>ACCAAGGTGGACAAGAGAGTTGAGCCCAAATCTTGT |
| PN ENCODING<br>SEQ.ID.NO: 276 | 280<br>AGCTACGTGCTGACTCAGCCCCCTTCTGTGTCTGTGGCCCCTGGCAAG<br>ACCGCCAGAATCAGCTGCAGCGGCGACAACCTGGGCAGCAAATACGTG<br>GACTGGTATCAGCAGAAGCCCGGCCAGGCTCCCGTGCTGGTGATCTAC<br>AGCGACAACAACCGGCCCAGCGGCATCCCTGAGCGGTTCAGCGGCAGC<br>AACAGCGGCAATACCGCCACCCTGACCATCAGCGGCACCCAGGCCATG<br>GACGAGGCCGACTACTACTGCGCCACCTACGACAGCAGCCCCAGAACC<br>GAGGTGTTCGGAGGCGGAACAAAGTTAACCGTCCTAGGTCAGCCCAAG<br>GCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGA<br>GCCGTGACAGTGGCCTGGAAGGCAGATAGCAGCCCCGTCAAGGCGGGA<br>GTGGAGACCACCACACCCTCCAAACAAAGCAACAACAAGTACGCGGCC<br>AGCAGCTATCTGAGCCTGACGCCTGAGCAGTGGAAGTCCCACAGAAGC<br>TACAGCTGCCAGGTCACGCATGAAGGGAGCACCGTGGAGAAGACAGTG<br>GCCCCTACAGAATGTTCA |
| Human Factor P<br>NP_001138724.1 | 401<br>PVLCFTQYEESSGKCKGLLGGGVSVEDCCLNTAFAYQKRSGGLCQPCR<br>SPRWSLWSTWAPCSVTCSEGSQLRYRRCVGWNGQCSGKVAPGTLEWQL<br>QACEDQQCCPEMGGWSGWGPWEPCSVTCSKGTRTRRRACNHPAPKCGG<br>HCPGQAQESEACDTQQVCPTHGAWATWGPWTPCSASCHGGPHEPKETR<br>SRKCSAPEPSQKPPGKPCPGLAYEQRRCTGLPPCPVAGGWGPWGPVSP<br>CPVTCGLGQTMEQRTCNHPVPQHGGPFCAGDATRTHICNTAVPCPVDG<br>EWDSWGEWSPCIRRNMKSISCQEEIPGQQSRGRTCRGRKFDGHRCAGQQ<br>QDIRHCYSIQHCPLKGSWSEWSTWGLCMPPCGPNPTRARQRLCTPLLP<br>KYPPTVSMVEGQGEKNVTFWGRPLPRCEELQGQKLVVEEKRPCLHVPA<br>CKDPEEEEL |
| Chimpanzee<br>Factor P<br>XP_001136665.1 | 402<br>MITEGAQAPCLLLPPLLLLLTLPATGSDPVLCFTQYEESSGKCKGLLG<br>GGVSVKDCCLNTAYAYQERNGGLCQPCRSPRWSLWSTWAPCSVTCSEG<br>SQLRYRRCVGWNGQCSERVALGTLEWQLQACEDKQCCPEMGGWSDWGP<br>WEPCSVTCSKGMRTRRRACNHPAPKCGGHCPGEAQESEACDTQQVCPT<br>HGAWAAWGPWSPCSGSCHGGPHEPKETRSRTCSAPEPSQKPPGKPCPG<br>PAYEHRKCTGLPPCPVAGGWGPWGPVSPCPVTCGLGQTIERRTCNRPV<br>PQHGGPSCAGDATRTHICNTAAPCPVDGEWDLWGQWSTCVRRNMKSIS<br>CEEIPGQQSRWRTCKGRKFDGHRCTGQQQDIRHCYSIQHCPLKGSWSE<br>WSTWGLCMPPCGPNPTRARQRLCTPLLPKYPPTVSMVEGQGEKNVTFW<br>GRPLPRCEELQGQKLVVEEKRPCLHVPACKDPEEEKL |
| Rat Factor P<br>NP_001100227.1 | 403<br>MPVGMQAPQWLLLLLLILPTTGSDPVLCFTQYEEPSGRCKGLLGRDIR<br>VEDCCLNTAYAFQEHDGGLCQSCRSPQWSAWSSWGPCSVTCSEGSQLR<br>HRRCVGRGGQCSEKAAPGTLEWQLQACEDQLCCPEMGGWSEWGPWGPC<br>SVTCSKGTQTRQRLCDNPAPKCGGHCPGEAQQSQACDTQKICPTHGAW<br>ASWGPWSACSGSCLGGAQEPKETRSRSCSAPAPSHQPPGKPCSGTAYE<br>HRGCSGLPPCPVAGGWGPWGPSSPCPVTCGLGQTLERRTCDHPVPRHG<br>GPFCAGDATRKHVCNTAMPCPVNGEWEAWGKWSHCSRVRMKSISCDEI<br>PGQQSRSRSCGGRKFDGQPCTGKLQDIRHCYDIHNCVLKGSWSQWSTW |

TABLE 1-continued

Examples of Factor P Antibodies, Fabs and Factor P Proteins

| AMINO ACID SEQUENCE OR POLYNUCLEOTIDE (PN) | SEQUENCE IDENTIFIER (SEQ.ID.NO:) AND SEQUENCE |
|---|---|
|  | GLCTPPCGPNPTRVRQRLCTPLLPKYSPTVSMVEGQGEKNVTFWGIPR PLCEVLQGQKLVVEEKRPCLHVPSCRDPEEKKP |
| Rabbit Factor P XP_002719931.1 | 404 MPAQAQPPLPLLLLPLLLTLPATGADPVVCFTEYDEPSGKCKGLLGGG VSVEHCCLNAAYAFQEPGSGLCHACRSPLWSPWSAWAPCSVTCSEGSQ LRHRRCVGQGGPCSEKAAPGTLQWQLQACEDQPCCPEIGGWSDWGPWR PCSVTCSKGTKTRQRACDRPAPKCGGRCPGEAQESEACDTKQVCPTHG LWAAWGPWSPCSGSCHGGPQVPKETRSRTCSAPEPSKQPPGKPCSGPA YEEQSCAGLPPCPVAGGWGPWGPVSSCSVTCGLGKTLEKRTCDHPVPQ HGGPFCTGDATRTHICNTAVPCPVNGEWEAWGEWSECSRPGRKSISCE EVPGQQRRTRVCKGRKFDGQRCAGEYQDIRHCYNIQRCRLKGSWLEWS SWGLCTPPCGPSPTRTRQRLCTALLPKFPPTISLVEGQGEKNVTFWGK PWPQCEQLQGQKLVVEEKRPCLHVPACKDPEEKP |
| Mouse Factor P NP_032849.2 | 405 MPAEMQAPQWLLLLLVILPATGSDPVLCFTQYEESSGRCKGLLGRDIR VEDCCLNAAYAFQEHDGGLCQACRSPQWSAWSLWGPCSVTCSEGSQLR HRRCVGRGGQCSENVAPGTLEWQLQACEDQPCCPEMGGWSEWGPWGPC SVTCSKGTQIRQRVCDNPAPKCGGHCPGEAQQSQACDTQKTCPTHGAW ASWGPWSPCSGSCLGGAQEPKETRSRSCSAPAPSHQPPGKPCSGPAYE HKACSGLPPCPVAGGWGPWSPLSPCSVTCGLGQTLEQRTCDHPAPRHG GPFCAGDATRNQMCNKAVPCPVNGEWEAWGKWSDCSRLRMSINCEGTP GQQSRSRSCGGRKFNGKPCAGKLQDIRHCYNIHNCIMKGSWSQWSTWS LCTPPCSPNATRVRQRLCTPLLPKYPPTVSMVEGQGEKNVTFWGTPRP LCEALQGQKLVVEEKRSCLHVPVCKDPEEKKP |
| TSR5 Domain of SEQ ID NO: 401 | 406 VDGEWDSWGEWSPCIRRNMKSISCQEIPGQQSRGRTCRGRKFDGHRCA GQQQDIRHCYSIQHCP |
| Region B of TSR 5 domain | 407 PCIRRNMKSISCQEIPGQQSRGR |
| Region of TSR 5 binding domain | 408 KSISC |
| TSR5 Domain of mouse SEQ ID NO: 405 | 409 VNGEWEAWGKWSDCSRLRMSINCEGTPGQQSRSRSCGGRKFNGKPCAG KLQDIRHCYNIHNCI |

TABLE 2

Examples of C5 Antibodies, Fabs and C5 Proteins

| Antibody 8109 | Sequence Identifier (SEQ ID NO:) |
|---|---|
| CDRH1 | 410 SYAIS |
| CDRH2 | 411 GIGPFFGTANYAQKFQG |
| CDRH3 | 412 DTPYFDY |
| CDRL1 | 413 SGDSIPNYYVY |
| CDRL2 | 414 DDSNRPS |
| CDRL3 | 415 QSFDSSLNAEV |

TABLE 2-continued

Examples of C5 Antibodies,
Fabs and C5 Proteins

| | | |
|---|---|---|
| VH | 416 | EVQLVQSGAEVKKPGSSVKVSCKASGGTFSSYAISWVRQAPGQGLEWMGGIGPFFGTANYAQK FQGRVTITADESTSTAYMELSSLRSEDTAVYYCARDTPYFDYWGQGTLVTVSS |
| VL | 417 | SYELTQPLSVSVALGQTARITCSGDSIPNYYVYWYQQKPGQAPVLVIYDDSNRPSGIPERFSG SNSGNTATLTISRAQAGDEADYYCQSFDSSLNAEVFGGGTKLTVL |
| Heavy chain | 418 | EVQLVQSGAEVKKPGSSVKVSCKASGGTFSSYAISWVRQAPGQGLEWMGGIGPFFGTANYAQK FQGRVTITADESTSTAYMELSSLRSEDTAVYYCARDTPYFDYWGQGTLVTVSSASTKGPSVFP LAPSSKSTSGGTAALGCLVKDYFPEPVTVSWNSGALTSGVHTFPAVLQSSGLYSLSSVVTVPS SSLGTQTYICNVNHKPSNTKVDKRVEPKSCDKTHTCPPCPAPEAAGGPSVFLFPPKPKDTLMI SRTPEVTCVVVDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLVKGFYPSDIAV EWESNGQPENNYKTTPPVLDSDGSFFLYSKLTVDKSRWQQGNVFSCSVMHEALHNHYTQKSLS LSPGK |
| Light chain | 419 | SYELTQPLSVSVALGQTARITCSGDSIPNYYVYWYQQKPGQAPVLVIYDDSNRPSGIPERFSG SNSGNTATLTISRAQAGDEADYYCQSFDSSLNAEVFGGGTKLTVLGQPKAAPSVTLFPPSSEE LQANKATLVCLISDFYPGAVTVAWKADSSPVKAGVETTTPSKQSNNKYAASSYLSLTPEQWKS HRSYSCQVTHEGSTVEKTVAPTECS |
| PN encoding SEQ ID NO: 416 | 420 | GAGGTGCAATTGGTTCAGTCTGGCGCGGAAGTGAAAAAACCGGGCAGCAGCGTGAAAGTGAGC TGCAAAGCCTCCGGAGGCACTTTTTCTTCTTATGCCATTTCTTGGGTGCGCCAAGCCCCTGGG CAGGGTCTCGAGTGGATGGGCGGTATCGGTCCGTTTTTTGGCACTGCGAATTACGCGCAGAAG TTTCAGGGCCGGGTGACCATTACCGCGGATGAAAGCACCAGCACCGCGTATATGGAACTGAGC AGCCTGCGTAGCGAAGATACGGCCGTGTATTATTGCGCGCGTGATACTCCTTATTTTGATTAT TGGGGCCAAGGCACCCTGGTGACGGTTAGCTCA |
| PN encoding SEQ ID NO: 417 | 421 | TCCTATGAACTCACACAGCCCCTGAGCGTGAGCGTGGCCCTGGGCCAGACCGCCCGGATCACC TGCTCCGGCGACAGCATCCCCAACTACTACGTGTACTGGTACCAGCAGAAGCCCGGCCAGGCC CCCGTGCTGGTGATCTACGACGACAGCAACCGGCCCAGCGGCATCCCCGAGCGGTTCAGCGGC AGCAACAGCGGCAACACCGCCACCCTGACCATTTCCAGAGCACAGGCAGGCGACGAGGCCGAC TACTACTGCCAGAGCTTCGACAGCAGCCTGAACGCCGAGGTGTTCGGCGGAGGGACCAAGTTA ACCGTCCTA |
| PN encoding SEQ ID NO: 418 | 422 | GAGGTGCAATTGGTTCAGTCTGGCGCGGAAGTGAAAAAACCGGGCAGCAGCGTGAAAGTGAGC TGCAAAGCCTCCGGAGGCACTTTTTCTTCTTATGCCATTTCTTGGGTGCGCCAAGCCCCTGGG CAGGGTCTCGAGTGGATGGGCGGTATCGGTCCGTTTTTTGGCACTGCGAATTACGCGCAGAAG TTTCAGGGCCGGGTGACCATTACCGCGGATGAAAGCACCAGCACCGCGTATATGGAACTGAGC AGCCTGCGTAGCGAAGATACGGCCGTGTATTATTGCGCGCGTGATACTCCTTATTTTGATTAT TGGGGCCAAGGCACCCTGGTGACGGTTAGCTCAGCCTCCACCAAGGGTCCATCGGTCTTCCCC CTGGCACCCTCCTCCAAGAGCACCTCTGGGGGCACAGCGGCCCTGGGCTGCCTGGTCAAGGAC TACTTCCCCGAACCGGTGACGGTGTCGTGGAACTCAGGCGCCCTGACCAGCGGCGTGCACACC TTCCCGGCTGTCCTACAGTCCTCAGGACTCTACTCCCTCAGCAGCGTGGTGACCGTGCCCTCC AGCAGCTTGGGCACCCAGACCTACATCTGCAACGTGAATCACAAGCCCAGCAACACCAAGGTG GACAAGAGAGTTGAGCCCAAATCTTGTGACAAAACTCACACATGCCCACCGTGCCCAGCACCT GAAGCAGCGGGGGGACCGTCAGTCTTCCTCTTCCCCCCAAAACCCAAGGACACCCTCATGATC TCCCGGACCCCTGAGGTCACATGCGTGGTGGTGGACGTGAGCCACGAAGACCCTGAGGTCAAG TTCAACTGGTACGTGGACGGCGTGGAGGTGCATAATGCCAAGACAAAGCCGCGGGAGGAGCAG TACAACAGCACGTACCGGGTGGTCAGCGTCCTCACCGTCCTGCACCAGGACTGGCTGAATGGC AAGGAGTACAAGTGCAAGGTCTCCAACAAAGCCCTCCCAGCCCCCATCGAGAAAACCATCTCC AAAGCCAAAGGGCAGCCCCGAGAACCACAGGTGTACACCCTGCCCCCATCCCGGGAGGAGATG ACCAAGAACCAGGTCAGCCTGACCTGCCTGGTCAAAGGCTTCTATCCCAGCGACATCGCCGTG GAGTGGGAGAGCAATGGGCAGCCGGAGAACAACTACAAGACCACGCCTCCCGTGCTGGACTCC GACGGCTCCTTCTTCCTCTACAGCAAGCTCACCGTGGACAAGAGCAGGTGGCAGCAGGGGAAC GTCTTCTCATGCTCCGTGATGCATGAGGCTCTGCACAACCACTACACGCAGAAGAGCCTCTCC CTGTCTCCGGGTAAA |
| PN encoding SEQ ID NO: 419 | 423 | TCCTATGAACTCACACAGCCCCTGAGCGTGAGCGTGGCCCTGGGCCAGACCGCCCGGATCACC TGCTCCGGCGACAGCATCCCCAACTACTACGTGTACTGGTACCAGCAGAAGCCCGGCCAGGCC CCCGTGCTGGTGATCTACGACGACAGCAACCGGCCCAGCGGCATCCCCGAGCGGTTCAGCGGC AGCAACAGCGGCAACACCGCCACCCTGACCATTTCCAGAGCACAGGCAGGCGACGAGGCCGAC TACTACTGCCAGAGCTTCGACAGCAGCCTGAACGCCGAGGTGTTCGGCGGAGGGACCAAGTTA ACCGTCCTAGGTCAGCCCAAGGCTGCCCCCTCGGTCACTCTGTTCCCGCCCTCCTCTGAGGAG CTTCAAGCCAACAAGGCCACACTGGTGTGTCTCATAAGTGACTTCTACCCGGGAGCCGTGACA GTGGCCTGGAAGGCAGATAGCAGCCCCGTCAAGGCGGGAGTGGAGACCACCACACCCTCCAAA CAAAGCAACAACAAGTACGCGGCCAGCAGCTATCTGAGCCTGACGCCTGAGCAGTGGAAGTCC CACAGAAGCTACAGCTGCCAGGTCACGCATGAAGGGAGCACCGTGGAGAAGACAGTGGCCCCT ACAGAATGTTCA |

TABLE 2-continued

Examples of C5 Antibodies, Fabs and C5 Proteins

| | |
|---|---|
| Optimized PN encoding SEQ ID NO: 418 | 424<br>GAGGTGCAGCTGGTGCAGAGCGGAGCCGAGGTGAAGAAGCCCGGTAGCAGCGTCAAGGTGTCC<br>TGCAAGGCCAGCGGCGGCACCTTCAGCAGCTACGCCATCAGCTGGGTGCGGCAGGCCCCAGGC<br>CAGGGCCTGGAGTGGATGGGCGGCATCGGCCCATTCTTCGGCACCGCCAACTACGCCCAGAAG<br>TTCCAGGGCAGGGTCACCATCACCGCCGACGAGAGCACCAGCACCGCCTACATGGAGCTGTCC<br>AGCCTGAGAAGCGAGGACACCGCCGTGTACTACTGCGCCAGAGACACCCCCTACTTCGACTAC<br>TGGGGCCAGGGCACCCTGGTGACCGTGAGCAGCGCTAGCACCAAGGGCCCCAGCGTGTTCCCC<br>CTGGCCCCCAGCAGCAAGAGCACCTCCGGCGGCACAGCCGCCCTGGGCTGCCTGGTGAAGGAC<br>TACTTCCCCGAGCCCGTGACCGTGTCCTGGAACAGCGGAGCCCTGACCAGCGGCGTGCACACC<br>TTCCCCGCCGTGCTGCAGAGCAGCGGCCTGTACAGCCTGTCCAGCGTGGTGACAGTGCCCAGC<br>AGCAGCCTGGGCACCCAGACCTACATCTGCAACGTGAACCACAAGCCCAGCAACACCAAGGTG<br>GACAAGAGAGTGGAGCCCAAGAGCTGCGACAAGACCCACACCTGCCCCCCCTGCCCAGCCCCC<br>GAAGCTGCAGGCGGCCCTTCCGTGTTCCTGTTCCCCCCCAAGCCCAAGGACACCCTGATGATC<br>AGCAGGACCCCCGAGGTGACCTGCGTGGTGGTGGACGTGAGCCACGAGGACCCAGAGGTGAAG<br>TTCAACTGGTACGTGGACGGCGTGGAGGTGCACAACGCCAAGACCAAGCCCAGAGAGGAGCAG<br>TACAACAGCACCTACAGGGTGGTGTCCGTGCTGACCGTGCTGCACCAGGACTGGCTGAACGGC<br>AAAGAATACAAGTGCAAGGTCTCCAACAAGGCCCTGCCTGCCCCCATCGAAAAGACCATCAGC<br>AAGGCCAAGGGCCAGCCACGGGAGCCCCAGGTGTACACCCTGCCCCCTTCTCGGGAGGAGATG<br>ACCAAGAACCAGGTGTCCCTGACCTGTCTGGTGAAGGGCTTCTACCCCAGCGACATCGCCGTG<br>GAGTGGGAGAGCAACGGCCAGCCCGAGAACAACTACAAGACCACCCCCCCAGTGCTGGACAGC<br>GACGGCAGCTTCTTCCTGTACAGCAAGCTGACCGTGGACAAGAGCAGGTGGCAGCAGGGCAAC<br>GTGTTCAGCTGCAGCGTGATGCACGAGGCCCTGCACAACCACTACACCCAGAAGAGCCTGAGC<br>CTGTCACCCGGCAAG |
| Optimized PN encoding SEQ ID NO: 419 | 425<br>AGCTACGAGCTGACCCAGCCCCTGAGCGTGAGCGTGGCCCTGGGCCAGACCGCCAGGATCACC<br>TGCAGCGGCGACAGCATCCCCAACTACTACGTGTACTGGTATCAGCAGAAGCCCGGCCAGGCC<br>CCCGTGCTGGTGATCTACGACGACAGCAACAGGCCCAGCGGCATCCCCGAGAGGTTCAGCGGC<br>AGCAACAGCGGCAACACCGCCACCCTGACCATCAGCGGAGCCCAGGCCGGCGACGAGGCCGAC<br>TACTACTGCCAGAGCTTCGACAGCTCACTGAACGCCGAGGTGTTCGGCGGAGGGACCAAGCTG<br>ACCGTGCTGGGCCAGCCTAAGGCTGCCCCCAGCGTGACCCTGTTCCCCCCCAGCAGCGAGGAG<br>CTGCAGGCCAACAAGGCCACCCTGGTGTGCCTGATCAGCGACTTCTACCCAGGCGCCGTGACC<br>GTGGCCTGGAAGGCCGACAGCAGCCCCGTGAAGGCCGGCGTGGAGACCACCACCCCCAGCAAG<br>CAGAGCAACAACAAGTACGCCGCCAGCAGCTACCTGAGCCTGACCCCCGAGCAGTGGAAGAGC<br>CACAGGTCCTACAGCTGCCAGGTGACCCACGAGGGCAGCACCGTGGAAAAGACCGTGGCCCCA<br>ACCGAGTGCAGC |
| Antibody 8110 | Sequence Identifier (SEQ ID NO:) and Sequence or comments |
| CDRH1 | 426<br>NYIS |
| CDRH2 | 427<br>IIDPDDSYTEYSPSFQG |
| CDRH3 | 428<br>YEYGGFDI |
| CDRL1 | 429<br>SGDNIGNSYVH |
| CDRL2 | 430<br>KDNDRPS |
| CDRL3 | 431<br>GTYDIESYV |
| VH | 432<br>EVQLVQSGAEVKKPGESLKISCKGSGYSFTNYISWVRQMPGKGLEWMGIIDPDDSYTEYSPSF<br>QGQVTISADKSISTAYLQWSSLKASDTAMYYCARYEYGGFDIWGQGTLVTVSS |
| VL | 433<br>SYELTQPPSVSVAPGQTARISCSGDNIGNSYVHWYQQKPGQAPVLVIYKDNDRPSGIPERFSG<br>SNSGNTATLTISGTQAEDEADYYCGTYDIESYVFGGGTKLTVL |
| Heavy chain | 434<br>EVQLVQSGAEVKKPGESLKISCKGSGYSFTNYISWVRQMPGKGLEWMGIIDPDDSYTEYSPSF<br>QGQVTISADKSISTAYLQWSSLKASDTAMYYCARYEYGGFDIWGQGTLVTVSSASTKGPSVFP<br>LAPSSKSTSGGTAALGCLVKDYFPEPVTVSWNSGALTSGVHTFPAVLQSSGLYSLSSVVTVPS<br>SSLGTQTYICNVNHKPSNTKVDKRVEPKSCDKTHTCPPCPAPEAAGGPSVFLFPPKPKDTLMI<br>SRTPEVTCVVVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEALHNHYTQKSLS<br>LSPGK |

TABLE 2-continued

Examples of C5 Antibodies,
Fabs and C5 Proteins

| | | |
|---|---|---|
| Light chain | 435 | SYELTQPPSVSVAPGQTARISCSGDNIGNSYVHWYQQKPGQAPVLVIYKDNDRPSGIPERFSG SNSGNTATLTISGTQAEDEADYYCGTYDIESYVFGGGTKLTVLGQPKAAPSVTLFPPSSEELQ ANKATLVCLISDFYPGAVTVAWKADSSPVKAGVETTTPSKQSNNKYAASSYLSLTPEQWKSHR SYSCQVTHEGSTVEKTVAPTECS |
| PN encoding SEQ ID NO: 432 | 436 | GAGGTGCAATTGGTTCAGAGCGGCGCGGAAGTGAAAAAACCGGGCGAAAGCCTGAAAATTAGC TGCAAAGGTTCCGGATATTCCTTTACTAATTATATTTCTTGGGTGCGCCAGATGCCTGGGAAG GGTCTCGAGTGGATGGGCATTATTGATCCTGATGATTCTTATACTGAGTATTCTCCTTCTTTT CAGGGTCAGGTCACCATTAGCGCGGATAAAAGCATTAGCACCGCGTATCTTCAATGGAGCAGC CTGAAAGCGAGCGATACGGCCATGTATTATTGCGCGCGTTATGAGTATGGTGGTTTTGATATT TGGGGCCAAGGCACCCTGGTGACGGTTAGCTCA |
| PN encoding SEQ ID NO: 434 | 437 | AGTTACGAACTGACCCAGCCGCCTTCAGTGAGCGTTGCACCAGGTCAGACCGCGCGTATCTCG TGTAGCGGCGATAATATTGGTAATTCTTATGTTCATTGGTACCAGCAGAAACCCGGGCAGGCG CCAGTTCTTGTGATTTATAAGGATAATGATCGTCCCTCAGGCATCCCGGAACGCTTTAGCGGA TCCAACAGCGGCAACACCGCGACCCTGACCATTAGCGGCACTCAGGCGGAAGACGAAGCGGAT TATTATTGCGGTACTTATGATATTGAGTCTTATGTGTTTGGCGGCGGCACGAAGTTAACCGTC CTA |
| PN encoding SEQ ID NO: 435 | 438 | GAGGTGCAATTGGTTCAGAGCGGCGCGGAAGTGAAAAAACCGGGCGAAAGCCTGAAAATTAGC TGCAAAGGTTCCGGATATTCCTTTACTAATTATATTTCTTGGGTGCGCCAGATGCCTGGGAAG GGTCTCGAGTGGATGGGCATTATTGATCCTGATGATTCTTATACTGAGTATTCTCCTTCTTTT CAGGGTCAGGTCACCATTAGCGCGGATAAAAGCATTAGCACCGCGTATCTTCAATGGAGCAGC CTGAAAGCGAGCGATACGGCCATGTATTATTGCGCGCGTTATGAGTATGGTGGTTTTGATATT TGGGGCCAAGGCACCCTGGTGACGGTTAGCTCAGCCTCCACCAAGGGTCCATCGGTCTTCCCC CTGGCACCCTCCTCCAAGAGCACCTCTGGGGGCACAGCGGCCCTGGGCTGCCTGGTCAAGGAC TACTTCCCCGAACCGGTGACGGTGTCGTGGAACTCAGGCGCCCTGACCAGCGGCGTGCACACC TTCCCGGCTGTCCTACAGTCCTCAGGACTCTACTCCCTCAGCAGCGTGGTGACCGTGCCCTCC AGCAGCTTGGGCACCCAGACCTACATCTGCAACGTGAATCACAAGCCCAGCAACACCAAGGTG GACAAGAGAGTTGAGCCCAAATCTTGTGACAAAACTCACACATGCCCACCGTGCCCAGCACCT GAAGCAGCGGGGGGACCGTCAGTCTTCCTCTTCCCCCCAAAACCCAAGGACACCCTCATGATC TCCCGGACCCCTGAGGTCACATGCGTGGTGGTGGACGTGAGCCACGAAGACCCTGAGGTCAAG TTCAACTGGTACGTGGACGGCGTGGAGGTGCATAATGCCAAGACAAAGCCGCGGGAGGAGCAG TACAACAGCACGTACCGGGTGGTCAGCGTCCTCACCGTCCTGCACCAGGACTGGCTGAATGGC AAGGAGTACAAGTGCAAGGTCTCCAACAAAGCCCTCCCAGCCCCCATCGAGAAAACCATCTCC AAAGCCAAAGGGCAGCCCCGAGAACCACAGGTGTACACCCTGCCCCCATCCCGGGAGGAGATG ACCAAGAACCAGGTCAGCCTGACCTGCCTGGTCAAAGGCTTCTATCCCAGCGACATCGCCGTG GAGTGGGAGAGCAATGGGCAGCCGGAGAACAACTACAAGACCACGCCTCCCGTGCTGGACTCC GACGGCTCCTTCTTCCTCTACAGCAAGCTCACCGTGGACAAGAGCAGGTGGCAGCAGGGGAAC GTCTTCTCATGCTCCGTGATGCATGAGGCTCTGCACAACCACTACACGCAGAAGAGCCTCTCC CTGTCTCCGGGTAAA |
| PN encoding SEQ ID NO: 436 | 439 | AGTTACGAACTGACCCAGCCGCCTTCAGTGAGCGTTGCACCAGGTCAGACCGCGCGTATCTCG TGTAGCGGCGATAATATTGGTAATTCTTATGTTCATTGGTACCAGCAGAAACCCGGGCAGGCG CCAGTTCTTGTGATTTATAAGGATAATGATCGTCCCTCAGGCATCCCGGAACGCTTTAGCGGA TCCAACAGCGGCAACACCGCGACCCTGACCATTAGCGGCACTCAGGCGGAAGACGAAGCGGAT TATTATTGCGGTACTTATGATATTGAGTCTTATGTGTTTGGCGGCGGCACGAAGTTAACCGTC CTAGGTCAGCCCAAGGCTGCCCCCTCGGTCACTCTGTTCCCGCCCTCCTCTGAGGAGCTTCAA GCCAACAAGGCCACACTGGTGTGTCTCATAAGTGACTTCTACCCGGGAGCCGTGACAGTGGCC TGGAAGGCAGATAGCAGCCCCGTCAAGGCGGGAGTGGAGACCACCACACCCTCCAAACAAAGC AACAACAAGTACGCGGCCAGCAGCTATCTGAGCCTGACGCCTGAGCAGTGGAAGTCCCACAGA AGCTACAGCTGCCAGGTCACGCATGAAGGGAGCACCGTGGAGAAGACAGTGGCCCCTACAGAA TGTTCA |
| Optimized PN encoding SEQ ID NO: 434 | 440 | GAGGTGCAGCTGGTGCAGAGCGGAGCCGAGGTGAAAAAGCCCGGTGAGAGCCTGAAGATCAGC TGCAAGGGCAGCGGCTACAGCTTCACCAACTACATCAGCTGGGTGCGGCAGATGCCCGGCAAG GGCCTGGAGTGGATGGGCATCATCGACCCCGACGACAGCTACACCGAGTACGGCGGCTTCGAC ATC TGGGGCCAGGGCACCCTGGTGACCGTCAGCTCAGCTAGCACCAAGGGCCCCAGCGTGTTCCCC CTGGCCCCCAGCAGCAAGAGCACCTCCGGCGGCACAGCCGCCCTGGGCTGCCTGGTGAAGGAC TACTTCCCCGAGCCCGTGACCGTGTCCTGGAACAGCGGAGCCCTGACCAGCGGCGTGCACACC TTCCCCGCCGTGCTGCAGAGCAGCGGCCTGTACAGCCTGTCCAGCGTGGTGACAGTGCCCAGC AGCAGCCTGGGCACCCAGACCTACATCTGCAACGTGAACCACAAGCCCAGCAACACCAAGGTG GACAAGAGAGTGGAGCCCAAGAGCTGCGACAAGACCCACACCTGCCCCCCTGCCCAGCCCCC GAAGCTGCAGGCGGCCCTTCCGTGTTCCTGTTCCCCCCAAGCCCAAGGACACCCTGATGATC AGCAGGACCCCCGAGGTGACCTGCGTGGTGGTGGACGTGAGCCACGAGGACCCAGAGGTGAAG TTCAACTGGTACGTGGACGGCGTGGAGGTGCACAACGCCAAGACCAAGCCCAGAGAGGAGCAG TACAACAGCACCTACAGGGTGGTGTCCGTGCTGACCGTGCTGCACCAGGACTGGCTGAACGGC AAGGAATACAAGTGCAAGGTCTCCAACAAGGCCCTGCCTGCCCCCATCGAAAAGACCATCAGC |

TABLE 2-continued

Examples of C5 Antibodies, Fabs and C5 Proteins

| | |
|---|---|
| | AAGGCCAAGGGCCAGCCACGGGAGCCCCAGGTGTACACCCTGCCCCCTTCTCGGGAGGAGATG<br>ACCAAGAACCAGGTGTCCCTGACCTGTCTGGTGAAGGGCTTCTACCCCAGCGACATCGCCGTG<br>GAGTGGGAGAGCAACGGCCAGCCCGAGAACAACTACAAGACCACCCCCCCAGTGCTGGACAGC<br>GACGGCAGCTTCTTCCTGTACAGCAAGCTGACCGTGGACAAGAGCAGGTGGCAGCAGGGCAAC<br>GTGTTCAGCTGCAGCGTGATGCACGAGGCCCTGCACAACCACTACACCCAGAAGAGCCTGAGC<br>CTGTCACCCGGCAAG |
| Optimized PN encoding SEQ ID NO: 435 | 441<br>AGCTACGAGCTGACCCAGCCCCCCAGCGTGAGCGTGGCCCCAGGCCAGACCGCCAGGATCAGC<br>TGCAGCGGCGACAACATCGGCAACAGCTACGTGCACTGGTATCAGCAGAAGCCCGGCCAGGCC<br>CCCGTGCTGGTGATCTACAAGGACAACGACAGGCCCAGCGGCATCCCCGAGAGGTTCAGCGGC<br>AGCAACTCCGGCAACACCGCCACCCTGACCATCAGCGGCACCCAGGCCGAGGACGAGGCCGAC<br>TACTACTGCGGCACCTACGACATCGAGTCATACGTGTTCGGCGGAGGGACCAAGCTGACCGTG<br>CTGGGCCAGCCTAAGGCTGCCCCCAGCGTGACCCTGTTCCCCCCCAGCAGCGAGGAGCTGCAG<br>GCCAACAAGGCCACCCTGGTGTGCCTGATCAGCGACTTCTACCCAGGCGCCGTGACCGTGGCC<br>TGGAAGGCCGACAGCAGCCCCGTGAAGGCCGGCGTGGAGACCACCACCCCCAGCAAGCAGAGC<br>AACAACAAGTACGCCGCCAGCAGCTACCTGAGCCTGACCCCCGAGCAGTGGAAGAGCCACAGG<br>TCCTACAGCTGCCAGGTGACCCACGAGGGCAGCACCGTGGAAAAGACCGTGGCCCCAACCGAG<br>TGCAGC |
| Antibody 8111 | Sequence Identifier (SEQ ID NO:) and Sequence or comments |
| CDRH1 | 442<br>TSGGGVS |
| CDRH2 | 443<br>NIDDADIKDYSPSLKS |
| CDRH3 | 444<br>GPYGFDS |
| CDRL1 | 445<br>TGTSSDIGTYNYVS |
| CDRL2 | 446<br>DDSNRPS |
| CDRL3 | 447<br>QSYDSQSIV |
| VH | 448<br>EVTLKESGPALVKPTQTLTLTCTFSGFSLSTSGGGVSWIRQPPGKALEWLANIDDADIKDYSP<br>SLKSRLTISKDTSKNQVVLTMTNMDPVDTATYYCARGPYGFDSWGQGTLVTVSS |
| VL | 449<br>ESALTQPASVSGSPGQSITISCTGTSSDIGTYNYVSWYQQHPGKAPKLMIYDDSNRPSGVSNR<br>FSGSKSGNTASLTISGLQAEDEADYYCQSYDSQSIVFGGGTKLTVL |
| Heavy chain | 450<br>EVTLKESGPALVKPTQTLTLTCTFSGFSLSTSGGGVSWIRQPPGKALEWLANIDDADIKDYSP<br>SLKSRLTISKDTSKNQVVLTMTNMDPVDTATYYCARGPYGFDSWGQGTLVTVSSASTKGPSVF<br>PLAPSSKSTSGGTAALGCLVKDYFPEPVTVSWNSGALTSGVHTFPAVLQSSGLYSLSSVVTVP<br>SSSLGTQTYICNVNHKPSNTKVDKRVEPKSCDKTHTCPPCPAPEAAGGPSVFLFPPKPKDTLM<br>ISRTPEVTCVVVDVSHEDPEVKFNWYVDGVEVHNAKTKPREEQYNSTYRVVSVLTVLHQDWLN<br>GKEYKCKVSNKALPAPIEKTISKAKGQPREPQVYTLPPSREEMTKNQVSLTCLVKGFYPSDIA<br>VEWESNGQPENNYKTTPPVLDSDGSFFLYSKLTVDKSRWQQGNVFSCSVMHEALHNHYTQKSL<br>SLSPGK |
| Light chain | 451<br>ESALTQPASVSGSPGQSITISCTGTSSDIGTYNYVSWYQQHPGKAPKLMIYDDSNRPSGVSNR<br>FSGSKSGNTASLTISGLQAEDEADYYCQSYDSQSIVFGGGTKLTVLGQPKAAPSVTLFPPSSE<br>ELQANKATLVCLISDFYPGAVTVAWKADSSPVKAGVETTTPSKQSNNKYAASSYLSLTPEQWK<br>SHRSYSCQVTHEGSTVEKTVAPTECS |
| PN encoding SEQ ID NO: 448 | 452<br>GAGGTGACATTGAAAGAAAGCGGCCCGGCCCTGGTGAAACCGACCCAAACCCTGACCCTGACC<br>TGTACCTTTTCCGGATTTAGCCTGTCTACTTCTGGTGGTGGTGTGTCTTGGATTCGCCAGCCG<br>CCTGGGAAAGCCCTCGAGTGGCTGGCTAATATTGATGATGCTGATATTAAGGATTATTCTCCT<br>TCTCTTAAGTCTCGTCTGACCATTAGCAAAGATACTTCGAAAAATCAGGTGGTGCTGACTATG<br>ACCAACATGGACCCGGTGGATACGGCCACCTATTATTGCGCGCGTGGTCCTTATGGTTTTGAT<br>TCTTGGGGCCAAGGCACCCTGGTGACGGTTAGCTCA |
| PN encoding SEQ ID NO: 449 | 453<br>GAAAGCGCACTGACCCAGCCAGCTTCAGTGAGCGGCTCACCAGGTCAGAGCATTACCATCTCG<br>TGTACGGGTACTAGCAGCGATATTGGTACTTATAATTATGTGTCTTGGTACCAGCAGCATCCC<br>GGGAAGGCGCCGAAACTTATGATTTATGATGATTCTAATCGTCCCTCAGGCGTGAGCAACCGT<br>TTTAGCGGATCCAAAAGCGGCAACACCGCGAGCCTGACCATTAGCGGCCTGCAAGCGGAAGAC |

TABLE 2-continued

Examples of C5 Antibodies,
Fabs and C5 Proteins

|  |  |
|---|---|
|  | GAAGCGGATTATTATTGCCAGTCTTATGATTCTCAGTCTATTGTGTTTGGCGGCGGCACGAAG<br>TTAACCGTCCTA |
| PN encoding<br>SEQ ID<br>NO: 450 | 454<br>GAGGTGACATTGAAAGAAAGCGGCCCGGCCCTGGTGAAACCGACCCAAACCCTGACCCTGACC<br>TGTACCTTTTCCGGATTTAGCCTGTCTACTTCTGGTGGTGGTGTGTCTTGGATTCGCCAGCCG<br>CCTGGGAAAGCCCTCGAGTGGCTGGCTAATATTGATGATGCTGATATTAAGGATTATTCTCCT<br>TCTCTTAAGTCTCGTCTGACCATTAGCAAAGATACTTCGAAAAATCAGGTGGTGCTGACTATG<br>ACCAACATGGACCCGGTGGATACGGCCACCTATTATTGCGCGCGTGGTCCTTATGGTTTTGAT<br>TCTTGGGGCCAAGGCACCCTGGTGACGGTTAGCTCAGCCTCCACCAAGGGTCCATCGGTCTTC<br>CCCCTGGCACCCTCCTCAAGAGCACCTCTGGGGGCACAGCGGCCCTGGGCTGCCTGGTCAAG<br>GACTACTTCCCCGAACCGGTGACGGTGTCGTGGAACTCAGGCGCCCTGACCAGCGGCGTGCAC<br>ACCTTCCCGGCTGTCCTACAGTCCTCAGGACTCTACTCCCTCAGCAGCGTGGTGACCGTGCCC<br>TCCAGCAGCTTGGGCACCCAGACCTACATCTGCAACGTGAATCACAAGCCCAGCAACACCAAG<br>GTGGACAAGAGAGTTGAGCCCAAATCTTGTGACAAAACTCACACATGCCCACCGTGCCCAGCA<br>CCTGAAGCAGCGGGGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGAAGACCCTGAGGTC<br>AAGTTCAACTGGTACGTGGACGGCGTGGAGGTGCATAATGCCAAGACAAAGCCGCGGGAGGAG<br>CAGTACAACAGCACGTACCGGGTGGTCAGCGTCCTCACCGTCCTGCACCAGGACTGGCTGAAT<br>GGCAAGGAGTACAAGTGCAAGGTCTCCAACAAAGCCCTCCCAGCCCCCATCGAGAAAACCATC<br>TCCAAAGCCAAAGGGCAGCCCCGAGAACCACAGGTGTACACCCTGCCCCCATCCCGGGAGGAG<br>ATGACCAAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTGCTGGAC<br>TCCGACGGCTCCTTCTTCCTCTACAGCAAGCTCACCGTGGACAAGAGCAGGTGGCAGCAGGGG<br>AACGTCTTCTCATGCTCCGTGATGCATGAGGCTCTGCACAACCACTACACGCAGAAGAGCCTC<br>TCCCTGTCTCCGGGTAAA |
| PN encoding<br>SEQ ID<br>NO: 451 | 455<br>GAAAGCGCACTGACCCAGCCAGCTTCAGTGAGCGGCTCACCAGGTCAGAGCATTACCATCTCG<br>TGTACGGGTACTAGCAGCGATATTGGTACTTATAATTATGTGCTTTGGTACCAGCAGCATCCC<br>GGGAAGGCGCCGAAACTTATGATTTATGATGATTCTAATCGTCCCTCAGGCGTGAGCAACCGT<br>TTTAGCGGATCCAAAAGCGGCAACACCGCGAGCCTGACCATTAGCGGCCTGCAAGCGGAAGAC<br>GAAGCGGATTATTATTGCCAGTCTTATGATTCTCAGTCTATTGTGTTTGGCGGCGGCACGAAG<br>TTAACCGTCCTAGGTCAGCCCAAGGCTGCCCCCTCGGTCACTCTGTTCCCGCCCTCCTCTGAG<br>GAGCTTCAAGCCAACAAGGCCACACTGGTGTGTCTCATAAGTGACTTCTACCCGGGAGCCGTG<br>ACAGTGGCCTGGAAGGCAGATAGCAGCCCCGTCAAGGCGGGAGTGGAGACCACCACACCCTCC<br>AAACAAAGCAACAACAAGTACGCGGCCAGCAGCTATCTGAGCCTGACGCCTGAGCAGTGGAAG<br>TCCCACAGAAGCTACAGCTGCCAGGTCACGCATGAAGGGAGCACCGTGGAGAAGACAGTGGCC<br>CCTACAGAATGTTCA |
| Optimized PN<br>encoding SEQ<br>ID NO: 448 | 456<br>GAGGTGACCCTGAAGGAGAGCGGCCCCAGCCCTGGTGAAGCCCACCCAGACCCTGACCCTGACT<br>TGCACCTTCAGCGGCTTCAGCCTGAGCACCAGCGGAGGGGGCGTGAGCTGGATCAGGCAGCCC<br>CCAGGTAAGGCCCTGGAGTGGCTGGCCAATATCGACGACGCCGATATCAAGGACTACAGCCCC<br>AGCCTGAAGAGCAGGCTGACCATCAGCAAGGACACCAGCAAGAACCAGGTGGTGCTGACCATG<br>ACCAATATGGACCCCGTGGACACCGCCACCTACTACTGCGCCAGAGGCCCCTACGGCTTCGAC<br>AGCTGGGGCCAGGGCACCCTGGTGACCGTCAGCTCAGCTAGCACCAAGGGCCCCAGCGTGTTC<br>CCCCTGGCCCCCAGCAGCAAGAGCACCTCCGGCGGCACAGCCGCCCTGGGCTGCCTGGTGAAG<br>GACTACTTCCCCGAGCCCGTGACCGTGTCCTGGAACAGCGGAGCCCTGACCAGCGGCGTGCAC<br>ACCTTCCCCGCCGTGCTGCAGAGCAGCGGCCTGTACAGCCTGTCCAGCGTGGTGACAGTGCCC<br>AGCAGCAGCCTGGGCACCCAGACCTACATCTGCAACGTGAACCACAAGCCCAGCAACACCAAG<br>GTGGACAAGAGAGTGGAGCCCAAGAGCTGCGACAAGACCCACACCTGCCCCCCCTGCCCAGCC<br>CCCGAAGCTGCAGGCGGCCCTTCCGTGTTCCTGTTCCCCCCCAAGCCCAAGGACACCCTGATG<br>ATCAGCAGGACCCCCGAGGTGACCTGCGTGGTGGTGGACGTGAGCCACGAGGACCCAGAGGTG<br>AAGTTCAACTGGTACGTGGACGGCGTGGAGGTGCACAACGCCAAGACCAAGCCCAGAGAGGAG<br>CAGTACAACAGCACCTACAGGGTGGTGTCCGTGCTGACCGTGCTGCACCAGGACTGGCTGAAC<br>GGCAAAGAATACAAGTGCAAGGTCTCCAACAAGGCCCTGCCTGCCCCCATCGAAAAGACCATC<br>AGCAAGGCCAAGGGCCAGCCACGGGAGCCCCAGGTGTACACCCTGCCCCCTTCTCGGGAGGAG<br>ATGACCAAGAACCAGGTGTCCCTGACCTGTCTGGTGAAGGGCTTCTACCCCAGCGACATCGCC<br>GTGGAGTGGGAGAGCAACGGCCAGCCCGAGAACAACTACAAGACCACCCCCCCAGTGCTGGAC<br>AGCGACGGCAGCTTCTTCCTGTACAGCAAGCTGACCGTGGACAAGAGCAGGTGGCAGCAGGGC<br>AACGTGTTCAGCTGCAGCGTGATGCACGAGGCCCTGCACAACCACTACACCCAGAAGAGCCTG<br>AGCCTGTCACCCGGCAAG |
| Optimized PN<br>encoding SEQ<br>ID NO: 449 | 457<br>GAGAGCGCCCTGACCCAGCCCGCCAGCGTGAGCGGCAGCCCAGGCCAGTCTATCACAATCAGC<br>TGCACCGGCACCTCCAGCGATATCGGCACCTACAACTACGTGAGCTGGTATCAGCAGCACCCC<br>GGCAAGGCCCCCAAGCTGATGATCTACGACGACAGCAACAGGCCCAGCGGCGTGAGCAACAGG<br>TTCAGCGGCAGCAAGAGCGGCAACACCGCCAGCCTGACAATCAGCGGCCTGCAGGCCGAGGAC<br>GAGGCCGACTACTACTGCCAGAGCTACGACAGCCAGTCAATCGTGTTCGGCGGAGGGACCAAG<br>CTGACCGTGCTGGGCCAGCCTAAGGCTGCCCCCAGCGTGACCCTGTTCCCCCCCAGCAGCGAG<br>GAGCTGCAGGCCAACAAGGCCACCCTGGTGTGCCTGATCAGCGACTTCTACCCAGGCGCCGTG<br>ACCGTGGCCTGGAAGGCCGACAGCAGCCCCGTGAAGGCCGGCGTGGAGACCACCACCCCCAGC<br>AAGCAGAGCAACAACAAGTACGCCGCCAGCAGCTACCTGAGCCTGACCCCCGAGCAGTGGAAG<br>AGCCACAGGTCCTACAGCTGCCAGGTGACCCACGAGGGCAGCACCGTGGAAAAGACCGTGGCC<br>CCAACCGAGTGCAGC |

TABLE 2-continued

Examples of C5 Antibodies, Fabs and C5 Proteins

| Antibody 8113 | Sequence Identifier (SEQ ID NO:) and Sequence or comments |
|---|---|
| CDRH1 | SEQ ID NO: 426 |
| CDRH2 | 458<br>IIDPDDSYTRYSPSFQG |
| CDRH3 | SEQ ID NO: 428 |
| CDRL1 | SEQ ID NO: 429 |
| CDRL2 | SEQ ID NO: 430 |
| CDRL3 | 459<br>ATWGSEDQV |
| VH | 460<br>EVQLVQSGAEVKKPGESLKISCKGSGYSFTNYISWVRQMPGKGLEWMGIIDPDDSYTRYSPSF<br>QGQVTISADKSISTAYLQWSSLKASDTAMYYCARYEYGGFDIWGQGTLVTVSS |
| VL | 461<br>SYELTQPPSVSVAPGQTARISCSGDNIGNSYVHWYQQKPGQAPVLVIYKDNDRPSGIPERFSG<br>SNSGNTATLTISGTQAEDEADYYCATWGSEDQVFGGGTKLTVL |
| Heavy chain | 462<br>EVQLVQSGAEVKKPGESLKISCKGSGYSFTNYISWVRQMPGKGLEWMGIIDPDDSYTRYSPSF<br>QGQVTISADKSISTAYLQWSSLKASDTAMYYCARYEYGGFDIWGQGTLVTVSSASTKGPSVFP<br>LAPSSKSTSGGTAALGCLVKDYFPEPVTVSWNSGALTSGVHTFPAVLQSSGLYSLSSVVTVPS<br>SSLGTQTYICNVNHKPSNTKVDKRVEPKSCDKTHTCPPCPAPEAAGGPSVFLFPPKPKDTLMI<br>SRTPEVTCVVVDVSHEDPEVKFNWYVDGVEVHNAKTKPREEQYNSTYRVVSVLTVLHQDWLNG<br>KEYKCKVSNKALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEALHNHYTQKSLS<br>LSPGK |
| Light chain | 463<br>SYELTQPPSVSVAPGQTARISCSGDNIGNSYVHWYQQKPGQAPVLVIYKDNDRPSGIPERFSG<br>SNSGNTATLTISGTQAEDEADYYCATWGSEDQVFGGGTKLTVLGQPKAAPSVTLFPPSSEELQ<br>ANKATLVCLISDFYPGAVTVAWKADSSPVKAGVETTTPSKQSNNKYAASSYLSLTPEQWKSHR<br>SYSCQVTHEGSTVEKTVAPTECS |
| PN encoding<br>SEQ ID<br>NO: 460 | 464<br>GAGGTGCAATTGGTTCAGAGCGGCGCGGAAGTGAAAAAACCGGGCGAAAGCCTGAAAATTAGC<br>TGCAAAGGTTCCGGATATTCCTTTACTAATTATATTTCTTGGGTGCGCCAGATGCCTGGGAAG<br>GTCTCGAGTGGATGGGCATTATCGATCCGGATGATAGCTATACCCGTTATTCTCCGAGCTTT<br>CAGGGACAGGTGACCATTAGCGCGGATAAAAGCATTAGCACCGCGTATCTTCAATGGAGCAGC<br>CTGAAAGCGAGCGATACGGCCATGTATTATTGCGCGCGTTATGAGTATGGTGGTTTTGATATT<br>TGGGGCCAAGGCACCCTGGTGACGGTTAGCTCA |
| PN encoding<br>SEQ ID<br>NO: 461 | 465<br>AGTTACGAACTGACCCAGCCGCCTTCAGTGAGCGTTGCACCAGGTCAGACCGCGCGTATCTCG<br>TGTAGCGGCGATAATATTGGTAATTCTTATGTTCATTGGTACCAGCAGAAACCCGGGCAGGCG<br>CCAGTTCTTGTGATTTATAAGGATAATGATCGTCCCTCAGGCATCCCGGAACGCTTTAGCGGA<br>TCCAACAGCGGCAACACCGCGACCCTGACCATTAGCGGCACTCAGGCGGAAGACGAAGCGGAT<br>TATTATTGCGCTACTTGGGGTTCTGAGGATCAGGTGTTTGGCGGCGGCACGAAGTTAACCGTC<br>CTA |
| PN encoding<br>SEQ ID<br>NO: 462 | 466<br>GAGGTGCAATTGGTTCAGAGCGGCGCGGAAGTGAAAAAACCGGGCGAAAGCCTGAAAATTAGC<br>TGCAAAGGTTCCGGATATTCCTTTACTAATTATATTTCTTGGGTGCGCCAGATGCCTGGGAAG<br>GTCTCGAGTGGATGGGCATTATCGATCCGGATGATAGCTATACCCGTTATTCTCCGAGCTTT<br>CAGGGACAGGTGACCATTAGCGCGGATAAAAGCATTAGCACCGCGTATCTTCAATGGAGCAGC<br>CTGAAAGCGAGCGATACGGCCATGTATTATTGCGCGCGTTATGAGTATGGTGGTTTTGATATT<br>TGGGGCCAAGGCACCCTGGTGACGGTTAGCTCAGCTTCCACCAAGGGTCCATCGGTCTTCCCC<br>CTGGCACCCTCCTCCAAGAGCACCTCTGGGGGCACAGCGGCCCTGGGCTGCCTGGTCAAGGAC<br>TACTTCCCCGAACCGGTGACGGTGTCGTGGAACTCAGGCGCCCTGACCAGCGGCGTGCACACC<br>TTCCCGGCTGTCCTACAGTCCTCAGGACTCTACTCCCTCAGCAGCGTGGTGACCGTGCCCTCC<br>AGCAGCTTGGGCACCCAGACCTACATCTGCAACGTGAATCACAAGCCCAGCAACACCAAGGTG<br>GACAAGAGAGTTGAGCCCAAATCTTGTGACAAAACTCACACATGCCCACCGTGCCCAGCACCT<br>GAAGCAGCGGGGGGACCGTCAGTCTTCCTCTTCCCCCCAAAACCCAAGGACACCCTCATGATC<br>TCCCGGACCCCTGAGGTCACATGCGTGGTGGTGGACGTGAGCCACGAAGACCCTGAGGTCAAG<br>TTCAACTGGTACGTGGACGGCGTGGAGGTGCATAATGCCAAGACAAAGCCGCGGGAGGAGCAG<br>TACAACAGCACGTACCGGGTGGTCAGCGTCCTCACCGTCCTGCACCAGGACTGGCTGAATGGC<br>AAGGAGTACAAGTGCAAGGTCTCCAACAAAGCCCTCCCAGCCCCCATCGAGAAAACCATCTCC<br>AAAGCCAAAGGGCAGCCCCGAGAACCACAGGTGTACACCCTGCCCCCATCCCGGGAGGAGATG<br>ACCAAGAACCAGGTCAGCCTGACCTGCCTGGTCAAAGGCTTCTATCCCAGCGACATCGCCGTG<br>GAGTGGGAGAGCAATGGGCAGCCGGAGAACAACTACAAGACCACGCCTCCCGTGCTGGACTCC |

TABLE 2-continued

Examples of C5 Antibodies, Fabs and C5 Proteins

| | |
|---|---|
| | GACGGCTCCTTCTTCCTCTACAGCAAGCTCACCGTGGACAAGAGCAGGTGGCAGCAGGGGAAC<br>GTCTTCTCATGCTCCGTGATGCATGAGGCTCTGCACAACCACTACACGCAGAAGAGCCTCTCC<br>CTGTCTCCGGGTAAA |
| PN encoding<br>SEQ ID<br>NO: 463 | 467<br>AGTTACGAACTGACCCAGCCGCCTTCAGTGAGCGTTGCACCAGGTCAGACCGCGCGTATCTCG<br>TGTAGCGGCGATAATATTGGTAATTCTTATGTTCATTGGTACCAGCAGAAACCCGGGCAGGCG<br>CCAGTTCTTGTGATTTATAAGGATAATGATCGTCCCTCAGGCATCCCGGAACGCTTTAGCGGA<br>TCCAACAGCGGCAACACCGCGACCCTGACCATTAGCGGCACTCAGGCGGAAGACGAAGCGGAT<br>TATTATTGCGCTACTTGGGGTTCTGAGGATCAGGTGTTTGGCGGCGGCACGAAGTTAACCGTC<br>CTAGGTCAGCCCAAGGCTGCCCCCTCGGTCACTCTGTTCCCGCCCTCCTCTGAGGAGCTTCAA<br>GCCAACAAGGCCACACTGGTGTGTCTCATAAGTGACTTCTACCCGGGAGCCGTGACAGTGGCC<br>TGGAAGGCAGATAGCAGCCCCGTCAAGGCGGGAGTGGAGACCACCACACCCTCCAAACAAAGC<br>AACAACAAGTACGCGGCCAGCAGCTATCTGAGCCTGACGCCTGAGCAGTGGAAGTCCCACAGA<br>AGCTACAGCTGCCAGGTCACGCATGAAGGGAGCACCGTGGAGAAGACAGTGGCCCCTACAGAA<br>TGTTCA |
| Optimized PN<br>encoding SEQ<br>ID NO: 462 | 468<br>GAGGTGCAGCTGGTGCAGAGCGGAGCCGAGGTGAAAAAGCCCGGTGAGAGCCTGAAGATCAGC<br>TGCAAGGGCAGCGGCTACAGCTTCACCAACTACATCAGCTGGGTGCGGCAGATGCCCGGCAAG<br>GGCCTGGAGTGGATGGGCATCATCGACCCCGACGACAGCTACACCAGGTACAGCCCCAGCTTC<br>CAGGGCCAGGTGACCATCAGCGCCGACAAGAGCATCAGCACCGCCTACCTGCAGTGGAGCAGC<br>CTGAAGGCCAGCGACACCGCCATGTACTACTGCGCCAGATACGAGTACGGCGGCTTCGACATC<br>TGGGGCCAGGGCACCCTGGTGACCGTCAGCTCAGCTAGCACCAAGGGCCCCAGCGTGTTCCCC<br>CTGGCCCCCAGCAGCAAGAGCACCTCCGGCGGCACAGCCGCCCTGGGCTGCCTGGTGAAGGAC<br>TACTTCCCCGAGCCCGTGACCGTGTCCTGGAACAGCGGAGCCCTGACCAGCGGCGTGCACACC<br>TTCCCCGCCGTGCTGCAGAGCAGCGGCCTGTACAGCCTGTCCAGCGTGGTGACAGTGCCCAGC<br>AGCAGCCTGGGCACCCAGACCTACATCTGCAACGTGAACCACAAGCCCAGCAACACCAAGGTG<br>GACAAGAGAGTGGAGCCCAAGAGCTGCGACAAGACCCACACCTGCCCCCCTGCCCAGCCCCC<br>GAAGCTGCAGGCGGCCCTTCCGTGTTCCTGTTCCCCCCCAAGCCCAAGGACACCCTGATGATC<br>AGCAGGACCCCCGAGGTGACCTGCGTGGTGGTGGACGTGAGCCACGAGGACCCAGAGGTGAAG<br>TTCAACTGGTACGTGGACGGCGTGGAGGTGCACAACGCCAAGACCAAGCCCAGAGAGGAGCAG<br>TACAACAGCACCTACAGGGTGGTGTCCGTGCTGACCGTGCTGCACCAGGACTGGCTGAACGGC<br>AAAGAATACAAGTGCAAGGTCTCCAACAAGGCCCTGCCTGCCCCCATCGAAAAGACCATCAGC<br>AAGGCCAAGGGCCAGCCACGGGAGCCCCAGGTGTACACCCTGCCCCCTTCTCGGGAGGAGATG<br>ACCAAGAACCAGGTGTCCCTGACCTGTCTGGTGAAGGGCTTCTACCCCAGCGACATCGCCGTG<br>GAGTGGGAGAGCAACGGCCAGCCCGAGAACAACTACAAGACCACCCCCCCAGTGCTGGACAGC<br>GACGGCAGCTTCTTCCTGTACAGCAAGCTGACCGTGGACAAGAGCAGGTGGCAGCAGGGCAAC<br>GTGTTCAGCTGCAGCGTGATGCACGAGGCCCTGCACAACCACTACACCCAGAAGAGCCTGAGC<br>CTGTCACCCGGCAAG |
| Optimized PN<br>encoding SEQ<br>ID NO: 463 | 469<br>AGCTACGAGCTGACCCAGCCCCCCAGCGTGAGCGTGGCCCCAGGCCAGACCGCCAGGATCAGC<br>TGCAGCGGCGACAATATCGGCAACAGCTACGTGCACTGGTATCAGCAGAAGCCCGGCCAGGCC<br>CCCGTGCTGGTGATCTACAAGGACAACGACAGGCCCAGCGGCATCCCCGAGAGGTTCAGCGGC<br>AGCAACTCCGGCAACACCGCCACCCTGACAATCAGCGGCACCCAGGCCGAGGACGAGGCCGAC<br>TACTACTGCGCCACCTGGGGCTCAGAGGACCAGGTGTTCGGCGGAGGGACCAAGCTGACCGTG<br>CTGGGCCAGCCTAAGGCTGCCCCCAGCGTGACCCTGTTCCCCCCCAGCAGCGAGGAGCTGCAG<br>GCCAACAAGGCCACCCTGGTGTGCCTGATCAGCGACTTCTACCCAGGCGCCGTGACCGTGGCC<br>TGGAAGGCCGACAGCAGCCCCGTGAAGGCCGGCGTGGAGACCACCACCCCCAGCAAGCAGAGC<br>AACAACAAGTACGCCGCCAGCAGCTACCTGAGCCTGACCCCCGAGCAGTGGAAGAGCCACAGG<br>TCCTACAGCTGCCAGGTGACCCACGAGGGCAGCACCGTGGAAAAGACCGTGGCCCCAACCGAG<br>TGCAGC |
| Antibody 8114 | Sequence Identifier (SEQ ID NO:) and Sequence or comments |
| CDRH1 | 470<br>SYYIG |
| CDRH2 | 471<br>IIDPTDSQTAYSPSFQG |
| CDRH3 | 472<br>YMMRGFDH |
| CDRL1 | 473<br>SGDSLGDYYAY |
| CDRL2 | 474<br>KDNNRPS |
| CDRL3 | 475<br>QTWDTGESGV |

TABLE 2-continued

Examples of C5 Antibodies,
Fabs and C5 Proteins

| | | |
|---|---|---|
| VH | 476 | EVQLVQSGAEVKKPGESLKISCKGSGYSFTSYYIGWVRQMPGKGLEWMGIIDPTDSQTAYSPS FQGQVTISADKSISTAYLQWSSLKASDTAMYYCARYMMRGFDHWGQGTLVTVSS |
| VL | 477 | SYELTQPPSVSVAPGQTARISCSGDSLGDYYAYWYQQKPGQAPVLVIYKDNNRPSGIPERFSG SNSGNTATLTISGTQAEDEADYYCQTWDTGESGVFGGGTKLTVL |
| Heavy chain | 478 | EVQLVQSGAEVKKPGESLKISCKGSGYSFTSYYIGWVRQMPGKGLEWMGIIDPTDSQTAYSPS FQGQVTISADKSISTAYLQWSSLKASDTAMYYCARYMMRGFDHWGQGTLVTVSSASTKGPSVF PLAPSSKSTSGGTAALGCLVKDYFPEPVTVSWNSGALTSGVHTFPAVLQSSGLYSLSSVVTVP SSSLGTQTYICNVNHKPSNTKVDKRVEPKSCDKTHTCPPCPAPEAAGGPSVFLFPPKPKDTLM ISRTPEVTCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQKSL SLSPGK |
| Light chain | 479 | SYELTQPPSVSVAPGQTARISCSGDSLGDYYAYWYQQKPGQAPVLVIYKDNNRPSGIPERFSG SNSGNTATLTISGTQAEDEADYYCQTWDTGESGVFGGGTKLTVLGQPKAAPSVTLFPPSSEEL QANKATLVCLISDFYPGAVTVAWKADSSPVKAGVETTTPSKQSNNKYAASSYLSLTPEQWKSH RSYSCQVTHEGSTVEKTVAPTECS |
| PN encoding SEQ ID NO: 476 | 480 | GAGGTGCAATTGGTTCAGAGCGGCGCGGAAGTGAAAAAACCGGGCGAAAGCCTGAAAATTAGC TGCAAAGGTTCCGGATATTCCTTTACTTCTTATTATATTGGTTGGGTGCGCCAGATGCCTGGG AAGGGTCTCGAGTGGATGGGCATTATTGATCCTACTGATTCTCAGACTGCTTATTCTCCTTCT TTTCAGGGTCAGGTGACCATTAGCGCGGATAAAAGCATTAGCACCGCGTATCTTCAATGGAGC AGCCTGAAAGCGAGCGATACGGCCATGTATTATTGCGCGCGTTATATGATGCGTGGTTTTGAT CATTGGGGCCAAGGCACCCTGGTGACGGTTAGCTCA |
| PN encoding SEQ ID NO: 478 | 481 | AGTTACGAACTGACCCAGCCGCCTTCAGTGAGCGTTGCACCAGGTCAGACCGCGCGTATCTCG TGTAGCGGCGATTCTCTTGGTGATTATTATGCTTATTGGTACCAGCAGAAACCCGGGCAGGCG CCAGTTCTTGTGATTTATAAGGATAATAATCGTCCCTCAGGCATCCCGGAACGCTTTAGCGGA TCCAACAGCGGCAACACCGCGACCCTGACCATTAGCGGCACTCAGGCGGAAGACGAAGCGGAT TATTATTGCCAGACTTGGGATACTGGTGAGTCTGGTGTGTTTGGCGGCGGCACGAAGTTAACC GTCCTA |
| PN encoding SEQ ID NO: 479 | 482 | GAGGTGCAATTGGTTCAGAGCGGCGCGGAAGTGAAAAAACCGGGCGAAAGCCTGAAAATTAGC TGCAAAGGTTCCGGATATTCCTTTACTTCTTATTATATTGGTTGGGTGCGCCAGATGCCTGGG AAGGGTCTCGAGTGGATGGGCATTATTGATCCTACTGATTCTCAGACTGCTTATTCTCCTTCT TTTCAGGGTCAGGTGACCATTAGCGCGGATAAAAGCATTAGCACCGCGTATCTTCAATGGAGC AGCCTGAAAGCGAGCGATACGGCCATGTATTATTGCGCGCGTTATATGATGCGTGGTTTTGAT CATTGGGGCCAAGGCACCCTGGTGACGGTTAGCTCAGCCTCCACCAAGGGTCCATCGGTCTTC CCCCTGGCACCCTCCTCCAAGAGCACCTCTGGGGGCACAGCGGCCCTGGGCTGCCTGGTCAAG GACTACTTCCCCGAACCGGTGACGGTGTCGTGGAACTCAGGCGCCCTGACCAGCGGCGTGCAC ACCTTCCCGGCTGTCCTACAGTCCTCAGGACTCTACTCCCTCAGCAGCGTGGTGACCGTGCCC TCCAGCAGCTTGGGCACCCAGACCTACATCTGCAACGTGAATCACAAGCCCAGCAACACCAAG GTGGACAAGAGAGTTGAGCCCAAATCTTGTGACAAAACTCACACATGCCCACCGTGCCCAGCA CCTGAAGCAGCGGGGGGACCGTCAGTCTTCCTCTTCCCCCCAAAACCCAAGGACACCCTCATG ATCTCCCGGACCCCTGAGGTCACATGCGTGGTGGTGGACGTGAGCCACGAAGACCCTGAGGTC AAGTTCAACTGGTACGTGGACGGCGTGGAGGTGCATAATGCCAAGACAAAGCCGCGGGAGGAG CAGTACAACAGCACGTACCGGGTGGTCAGCGTCCTCACCGTCCTGCACCAGGACTGGCTGAAT GGCAAGGAGTACAAGTGCAAGGTCTCCAACAAAGCCCTCCCAGCCCCCATCGAGAAAACCATC TCCAAAGCCAAAGGGCAGCCCCGAGAACCACAGGTGTACACCCTGCCCCCATCCCGGGAGGAG ATGACCAAGAACCAGGTCAGCCTGACCTGCCTGGTCAAAGGCTTCTATCCCAGCGACATCGCC GTGGAGTGGGAGAGCAATGGGCAGCCGGAGAACAACTACAAGACCACGCCTCCCGTGCTGGAC TCCGACGGCTCCTTCTTCCTCTACAGCAAGCTCACCGTGGACAAGAGCAGGTGGCAGCAGGGG AACGTCTTCTCATGCTCCGTGATGCATGAGGCTCTGCACAACCACTACACGCAGAAGAGCCTC TCCCTGTCTCCGGGTAAA |
| PN encoding SEQ ID NO: 480 | 483 | AGTTACGAACTGACCCAGCCGCCTTCAGTGAGCGTTGCACCAGGTCAGACCGCGCGTATCTCG TGTAGCGGCGATTCTCTTGGTGATTATTATGCTTATTGGTACCAGCAGAAACCCGGGCAGGCG CCAGTTCTTGTGATTTATAAGGATAATAATCGTCCCTCAGGCATCCCGGAACGCTTTAGCGGA TCCAACAGCGGCAACACCGCGACCCTGACCATTAGCGGCACTCAGGCGGAAGACGAAGCGGAT TATTATTGCCAGACTTGGGATACTGGTGAGTCTGGTGTGTTTGGCGGCGGCACGAAGTTAACC GTCCTAGGTCAGCCCAAGGCTGCCCCCTCGGTCACTCTGTTCCCGCCCTCCTCTGAGGAGCTT CAAGCCAACAAGGCCACACTGGTGTGTCTCATAAGTGACTTCTACCCGGGAGCCGTGACAGTG GCCTGGAAGGCAGATAGCAGCCCCGTCAAGGCGGGAGTGGAGACCACCACACCCTCCAAACAA AGCAACAACAAGTACGCGGCCAGCAGCTATCTGAGCCTGACGCCTGAGCAGTGGAAGTCCCAC AGAAGCTACAGCTGCCAGGTCACGCATGAAGGGAGCACCGTGGAGAAGACAGTGGCCCCTACA GAATGTTCA |

TABLE 2-continued

Examples of C5 Antibodies, Fabs and C5 Proteins

| | |
|---|---|
| Optimized PN encoding SEQ ID NO: 479 | 484<br>GAGGTGCAGCTGGTGCAGAGCGGAGCCGAGGTGAAAAAGCCCGGTGAGAGCCTGAAGATCAGC<br>TGCAAGGGCAGCGGCTACAGCTTCACCAGCTACTACATCGGCTGGGTGCGGCAGATGCCCGGC<br>AAGGGCCTGGAGTGGATGGGCATCATCGACCCCACCGACAGCCAGACCGCCTACAGCCCCAGC<br>TTCCAGGGCCAGGTGACCATCAGCGCCGACAAGAGCATCAGCACCGCCTACCTGCAGTGGAGC<br>AGCCTGAAGGCCAGCGACACCGCCATGTACTACTGCGCCCGGTACATGATGAGGGGCTTCGAC<br>CACTGGGGTCAGGGCACCCTGGTGACCGTCAGCTCAGCTAGCACCAAGGGCCCCAGCGTGTTC<br>CCCCTGGCCCCCAGCAGCAAGAGCACCTCCGGCGGCACAGCCGCCCTGGGCTGCCTGGTGAAG<br>GACTACTTCCCCGAGCCCGTGACCGTGTCCTGGAACAGCGGAGCCCTGACCAGCGGCGTGCAC<br>ACCTTCCCCGCCGTGCTGCAGAGCAGCGGCCTGTACAGCCTGTCCAGCGTGGTGACAGTGCCC<br>AGCAGCAGCCTGGGCACCCAGACCTACATCTGCAACGTGAACCACAAGCCCAGCAACACCAAG<br>GTGGACAAGAGAGTGGAGCCCAAGAGCTGCGACAAGACCCACACCTGCCCCCCCTGCCCAGCC<br>CCCGAAGCTGCAGGCGGCCCTTCCGTGTTCCTGTTCCCCCCCAAGCCCAAGGACACCCTGATG<br>ATCAGCAGGACCCCCGAGGTGACCTGCGTGGTGGTGGACGTGAGCCACGAGGACCCAGAGGTG<br>AAGTTCAACTGGTACGTGGACGGCGTGGAGGTGCACAACGCCAAGACCAAGCCCAGAGAGGAG<br>CAGTACAACAGCACCTACAGGGTGGTGTCCGTGCTGACCGTGCTGCACCAGGACTGGCTGAAC<br>GGCAAAGAATACAAGTGCAAGGTCTCCAACAAGGCCCTGCCTGCCCCCATCGAAAAGACCATC<br>AGCAAGGCCAAGGGCCAGCCACGGGAGCCCCAGGTGTACACCCTGCCCCCTTCTCGGGAGGAG<br>ATGACCAAGAACCAGGTGTCCCTGACCTGTCTGGTGAAGGGCTTCTACCCCAGCGACATCGCC<br>GTGGAGTGGGAGAGCAACGGCCAGCCCGAGAACAACTACAAGACCACCCCCCCAGTGCTGGAC<br>AGCGACGGCAGCTTCTTCCTGTACAGCAAGCTGACCGTGGACAAGAGCAGGTGGCAGCAGGGC<br>AACGTGTTCAGCTGCAGCGTGATGCACGAGGCCCTGCACAACCACTACACCCAGAAGAGCCTG<br>AGCCTGTCACCCGGCAAG |
| Optimized PN encoding SEQ ID NO: 480 | 485<br>AGCTACGAGCTGACCCAGCCCCCCAGCGTGAGCGTGGCCCCAGGCCAGACCGCCAGGATCAGC<br>TGCAGCGGCGACAGCCTGGGCGACTACTACGCCTACTGGTATCAGCAGAAGCCCGGCCAGGCC<br>CCCGTGCTGGTGATCTACAAGGACAACAACAGGCCCAGCGGCATCCCCGAGAGGTTCAGCGGC<br>AGCAACAGCGGCAACACCGCCACCCTGACAATCAGCGGCACCCAGGCCGAGGACGAGGCCGAC<br>TACTACTGCCAGACCTGGGACACCGGCGAGTCAGGCGTGTTCGGCGGAGGGACCAAGCTGACC<br>GTGCTGGGTCAGCCTAAGGCTGCCCCCAGCGTGACCCTGTTCCCCCCCAGCAGCGAGGAGCTG<br>CAGGCCAACAAGGCCACCCTGGTGTGCCTGATCAGCGACTTCTACCCAGGCGCCGTGACCGTG<br>GCCTGGAAGGCCGACAGCAGCCCCGTGAAGGCCGGCGTGGAGACCACCACCCCCAGCAAGCAG<br>AGCAACAACAAGTACGCCGCCAGCAGCTACCTGAGCCTGACCCCCGAGCAGTGGAAGAGCCAC<br>AGGTCCTACAGCTGCCAGGTGACCCACGAGGGCAGCACCGTGGAAAAGACCGTGGCCCCAACC<br>GAGTGCAGC |

Other antibodies of the invention include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen binding activity.

Since each of these antibodies can bind to Factor P, the VH, VL, full length light chain, and full length heavy chain sequences (amino acid sequences and the nucleotide sequences encoding the amino acid sequences) can be "mixed and matched" to create other Factor P-binding antibodies of the invention. Such "mixed and matched" Factor P-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated antibody or antigen binding region thereof having: a heavy chain variable domain comprising an amino acid sequence selected from the group consisting of SEQ ID NOs: 7, 21, 35, 49, 63, 77, 91, 105, 119, 133, 147, 161, 175, 189, 203, 217, 231, 245, 259 and 273, and a light chain variable domain comprising an amino acid sequence selected from the group consisting of SEQ ID NOs: 8, 22, 36, 50, 64, 78, 92, 106, 120, 134, 148, 162, 176, 190, 204, 218, 232, 246, 260, and 274 wherein the antibody specifically binds to Factor P (e.g., human and/or cynomolgus Factor P).

In another aspect, the invention provides (i) an isolated antibody having: a full length heavy chain comprising an amino acid sequence that has been optimized for expression in a mammalian cell selected from the group consisting of SEQ ID NOs: 9, 23, 37, 51, 65, 79, 93, 107, 121, 135, 149, 163, 177, 191, 205, 219, 233, 247, 261 and 275, and a full length light chain comprising an amino acid sequence that has been optimized for expression in a mammalian cell selected from the group consisting of SEQ ID NOs: 10, 24, 38, 52, 66, 80, 94, 108, 122, 136, 150, 164, 178, 192, 206, 220, 234, 248, 262 and 276; or (ii) a functional protein comprising an antigen binding portion thereof.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme).

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

In another aspect, the present invention provides Factor P binding antibodies that comprise the heavy chain and light chain CDR1s, CDR2s, and CDR3s as described in Table 1, or combinations thereof. The amino acid sequences of the VH CDR1 s of the antibodies are shown in SEQ ID NOs: 1, 15, 29, 43, 57, 71, 85, 99, 113, 127, 141, 155, 169, 183, 197, 211, 225, 239, 253, or 267. The amino acid sequences of the VH CDR2s of the antibodies and are shown in SEQ ID NOs: 2, 16, 30, 44, 58, 72, 86, 100, 114, 128, 142, 156, 170, 184, 198, 212, 226, 240, 254, or 268. The amino acid sequences of the VH CDR3s of the antibodies are shown in SEQ ID NOs: 3, 17, 31, 45, 59, 73, 87, 101, 115, 129, 143, 157, 171, 185, 199, 213, 227, 241, 255, or 269. The amino acid sequences of the VL CDR1s of the antibodies are shown in SEQ ID NOs: 4, 18, 32, 46, 60, 74, 88, 102, 116, 130, 144, 158, 172, 186, 200, 214, 228, 242, 256, or 270. The amino acid sequences of the VL CDR2s of the antibodies are shown in SEQ ID NOs: 5, 19, 33, 47, 61, 75, 89, 103, 117, 131, 145, 159, 173, 187, 201, 215, 229, 243, 257, or 271. The amino acid sequences of the VL CDR3s of the antibodies are shown in SEQ ID NOs: 6, 20, 34, 48, 62, 76, 90, 104, 118, 132, 146, 160, 174, 188, 202, 216, 230, 244, 258, or 272. These CDR regions are delineated using the Kabat system.

Alternatively, as defined using the Chothia system (Al-Lazikani et al., (1997) JMB 273, 927-948) the amino acid sequences of the VH CDR1s of the antibodies are shown in SEQ ID NOs: 281, 287, 293, 299, 305, 311, 317, 323, 329, 335, 341, 347, 353, 359, 365, 371, 377, 383, 389, or 395. The amino acid sequences of the VH CDR2s of the antibodies and are shown in SEQ ID NOs: 282, 288, 294, 300, 306, 312, 318, 324, 330, 336, 342, 348, 354, 360, 366, 372, 378, 384, 390, or 396. The amino acid sequences of the VH CDR3s of the antibodies are shown in SEQ ID NOs: 283, 289, 295, 301, 307, 313, 319, 325, 331, 337, 343, 349, 355, 361, 367, 373, 379, 385, 391, or 397. The amino acid sequences of the VL CDR1s of the antibodies are shown in SEQ ID NOs: 284, 290, 296, 302, 308, 314, 320, 326, 332, 338, 344, 350, 356, 362, 368, 374, 380, 386, 392, or 398. The amino acid sequences of the VL CDR2s of the antibodies are shown in SEQ ID NOs: 285, 291, 297, 303, 309, 315, 321, 327, 333, 339, 345, 351, 357, 363, 369, 375, 381, 387, 393, or 399. The amino acid sequences of the VL CDR3s of the antibodies are shown in SEQ ID NOs: 286, 292, 298, 304, 310, 316, 322, 328, 334, 340, 346, 352, 358, 364, 370, 376, 382, 388, 394, or 400.

Given that each of these antibodies can bind to Factor P and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody preferably contains a VH CDR1, 2 and 3 and a VL CDR1, 2 and 3 to create other Factor P binding molecules of the invention. Such "mixed and matched" Factor P binding antibodies can be tested using the binding assays known in the art and those described in the Examples (e.g., ELISAs, SET, BIA-CORE™). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention. In addition to the foregoing, in one embodiment, the antigen binding fragments of the antibodies described herein can comprise a VH CDR1, 2, and 3, or a VL CDR 1, 2, and 3, wherein the fragment binds to Factor P as a single variable domain.

In certain embodiments of the invention, the antibodies or antigen binding fragments thereof may have the heavy and light chain sequences of the Fabs described in Table 1. More specifically, the antibody or antigen binding fragment thereof may have the heavy and light sequence of Fab NVS962, NVS963, NVS964, NVS965, NVS966, NVS967, NVS805, NVS806, NVS807, NVS808, NVS809, NVS962-S, NVS962-Q, NVS962-S31A, NVS962-G, NVS962-T, NVS965-S, NVS965-T, or NVS965-Q.

In other embodiments of the invention the antibody or antigen binding fragment in that specifically binds Factor P comprises a heavy chain variable region CDR1, a heavy chain variable region CDR2, a heavy chain variable region CDR3, a light chain variable region CDR1, a light chain variable region CDR2, and a light chain variable region CDR3 as defined by Kabat and described in Table 1. In still other embodiments of the invention the antibody or antigen binding fragment in that specifically binds Factor P comprises a heavy chain variable region CDR1, a heavy chain variable region CDR2, a heavy chain variable region CDR3, a light chain variable region CDR1, a light chain variable region CDR2, and a light chain variable region CDR3 as defined by Chothia and described in Table 1.

In a specific embodiment, the invention includes an antibody that specifically binds to Factor P comprising a heavy chain variable region CDR1 of SEQ ID NO:1; a heavy chain variable region CDR2 of SEQ ID NO: 2; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 6. In another specific embodiment, the invention includes an antibody that specifically binds to Factor P comprising a heavy chain variable region CDR1 of SEQ ID NO: 15; a heavy chain variable region CDR2 of SEQ ID NO: 16; a heavy chain variable region CDR3 of SEQ ID NO: 17; a light chain variable region CDR1 of SEQ ID NO: 18; a light chain variable region CDR2 of SEQ ID NO: 19; and a light chain variable region CDR3 of SEQ ID NO: 20. In another specific embodiment, the invention includes an antibody that specifically binds to Factor P comprising a heavy chain variable region CDR1 of SEQ ID NO: 29; a heavy chain variable region CDR2 of SEQ ID NO: 30; a heavy chain variable region CDR3 of SEQ ID NO: 31; a light chain variable region CDR1 of SEQ ID NO: 32; a light chain variable region CDR2 of SEQ ID NO: 33; and a light chain variable region CDR3 of SEQ ID NO: 34. In another specific embodiment, the invention includes an antibody that specifically binds to Factor P comprising a heavy chain variable region CDR1 of SEQ ID NO: 43; a heavy chain variable region CDR2 of SEQ ID NO: 44; a heavy chain variable region CDR3 of SEQ ID NO: 45; a light chain variable region CDR1 of SEQ ID NO: 46; a light chain variable region CDR2 of SEQ ID NO: 47; and a light chain variable region CDR3 of SEQ ID NO: 48. In another specific embodiment, the invention includes an antibody that specifically binds to Factor P comprising a heavy chain variable region CDR1 of SEQ ID NO: 57; a heavy chain variable region CDR2 of SEQ ID NO: 58; a heavy chain variable region CDR3 of SEQ ID NO: 59; a light chain variable region CDR1 of SEQ ID NO: 60; a light chain variable region CDR2 of SEQ ID NO: 61; and a light chain variable region CDR3 of SEQ ID NO: 62. In another specific embodiment, the invention includes an antibody that specifically binds to Factor P comprising a heavy chain variable region CDR1 of SEQ ID NO: 71; a heavy chain variable region CDR2 of SEQ ID NO: 72; a heavy chain variable region CDR3 of SEQ ID NO: 73; a light chain variable region CDR1 of SEQ ID NO: 74; a light chain variable region CDR2 of SEQ ID NO: 75; and a light chain variable region CDR3 of SEQ ID NO: 76. In another specific embodiment, the invention includes an antibody that specifically binds to Factor P comprising a heavy chain variable region CDR1 of SEQ ID NO: 85; a heavy chain variable region CDR2 of SEQ ID NO: 86; a heavy chain variable region CDR3 of SEQ ID NO: 87; a light chain variable region CDR1 of SEQ ID NO: 88; a light chain variable region CDR2 of SEQ ID NO: 89; and a light chain variable region CDR3 of SEQ ID NO: 90. In another specific embodiment, the invention includes an antibody that specifically binds to Factor P comprising a heavy chain variable region CDR1 of SEQ ID NO: 99; a heavy chain variable region CDR2 of SEQ ID NO: 100; a heavy chain variable region CDR3 of SEQ ID NO: 101; a light chain variable region CDR1 of SEQ ID NO: 102; a light chain variable region CDR2 of SEQ ID NO: 103; and a light chain variable region CDR3 of SEQ ID NO: 104. In another specific embodiment, the invention includes an antibody that specifically binds to Factor P comprising a heavy chain variable region CDR1 of SEQ ID NO: 113; a heavy chain variable region CDR2 of SEQ ID NO: 114; a heavy chain variable region CDR3 of SEQ ID NO: 115; a light chain variable region CDR1 of SEQ ID NO: 116; a light chain variable region CDR2 of SEQ ID NO: 117; and a light chain variable region CDR3 of SEQ ID NO: 118. In another specific embodiment, the invention includes an antibody that specifically binds to Factor P comprising a heavy chain variable region CDR1 of SEQ ID NO: 127; a heavy chain variable region CDR2 of SEQ ID NO: 128; a heavy chain variable region CDR3 of SEQ ID NO: 129; a light chain variable region CDR1 of SEQ ID NO: 130; a light chain variable region CDR2 of SEQ ID NO: 131; and a light chain variable region CDR3 of SEQ ID NO: 132. In another specific embodiment, the invention includes an antibody that specifically binds to Factor P comprising a heavy chain variable region CDR1 of SEQ ID NO: 141; a heavy chain variable region CDR2 of SEQ ID NO: 142; a heavy chain variable region CDR3 of SEQ ID NO: 143; a light chain variable region CDR1 of SEQ ID NO: 144; a light chain variable region CDR2 of SEQ ID NO: 145; and a light chain variable region CDR3 of SEQ ID NO: 146. In another specific embodiment, the invention includes an antibody that specifically binds to Factor P comprising a heavy chain variable region CDR1 of SEQ ID NO: 155; a heavy chain variable region CDR2 of SEQ ID NO: 156; a heavy chain variable region CDR3 of SEQ ID NO: 157; a light chain variable region CDR1 of SEQ ID NO: 158; a light chain variable region CDR2 of SEQ ID NO: 159; and a light chain variable region CDR3 of SEQ ID NO: 160. In another specific embodiment, the invention includes an antibody that specifically binds to Factor P comprising a heavy chain variable region CDR1 of SEQ ID NO: 169; a heavy chain variable region CDR2 of SEQ ID NO: 170; a heavy chain variable region CDR3 of SEQ ID NO: 171; a light chain variable region CDR1 of SEQ ID NO: 172; a light chain variable region CDR2 of SEQ ID NO: 173; and a light chain variable region CDR3 of SEQ ID NO: 174. In another specific embodiment, the invention includes an antibody that specifically binds to Factor P comprising a heavy chain variable region CDR1 of SEQ ID NO: 183; a heavy chain variable region CDR2 of SEQ ID NO: 184; a heavy chain variable region CDR3 of SEQ ID NO: 185; a light chain variable region CDR1 of SEQ ID NO: 186; a light chain variable region CDR2 of SEQ ID NO: 187; and a light chain variable region CDR3 of SEQ ID NO: 188. In another specific embodiment, the invention includes an antibody that specifically binds to Factor P comprising a heavy chain variable region CDR1 of SEQ ID NO: 197; a heavy chain variable region CDR2 of SEQ ID NO: 198; a heavy chain variable region CDR3 of SEQ ID NO: 199; a light chain variable region CDR1 of SEQ ID NO: 200; a light chain variable region CDR2 of SEQ ID NO: 201; and a light chain variable region CDR3 of SEQ ID NO: 202. In another specific embodiment, the invention includes an antibody that specifically binds to Factor P comprising a heavy chain variable region CDR1 of SEQ ID NO: 211; a heavy chain variable region CDR2 of SEQ ID NO: 212; a heavy chain variable region CDR3 of SEQ ID NO: 213; a light chain variable region CDR1 of SEQ ID NO: 214; a light chain variable region CDR2 of SEQ ID NO: 215; and a light chain variable region CDR3 of SEQ ID NO: 216. In another specific embodiment, the invention includes an antibody that specifically binds to Factor P comprising a heavy chain variable region CDR1 of SEQ ID NO: 225; a heavy chain variable region CDR2 of SEQ ID NO: 226; a heavy chain variable region CDR3 of SEQ ID NO: 227; a light chain variable region CDR1 of SEQ ID NO: 228; a light chain variable region CDR2 of SEQ ID NO: 229; and a light chain variable region CDR3 of SEQ ID NO: 230. In another specific embodiment, the invention includes an antibody that specifically binds to Factor P comprising a heavy chain variable region CDR1 of SEQ ID NO: 239; a heavy chain variable region CDR2 of SEQ ID NO: 240; a heavy chain variable region CDR3 of SEQ ID NO: 241; a light chain variable region CDR1 of SEQ ID NO: 242; a light chain variable region CDR2 of SEQ ID NO: 243; and a light chain variable region CDR3 of SEQ ID NO: 244. In another specific embodiment, the invention includes an antibody that specifically binds to Factor P comprising a heavy chain variable region CDR1 of SEQ ID NO: 253; a heavy chain variable region CDR2 of SEQ ID NO: 254; a heavy chain variable region CDR3 of SEQ ID NO: 255; a light chain variable region CDR1 of SEQ ID NO: 256; a light chain variable region CDR2 of SEQ ID NO: 257; and a light chain variable region CDR3 of SEQ ID NO: 258. In another specific embodiment, the invention includes an antibody that specifically binds to Factor P comprising a heavy chain variable region CDR1 of SEQ ID NO: 267; a heavy chain variable region CDR2 of SEQ ID NO: 268; a heavy chain variable region CDR3 of SEQ ID NO: 269; a light chain variable region CDR1 of SEQ ID NO: 270; a light chain variable region CDR2 of SEQ ID NO: 271; and a light chain variable region CDR3 of SEQ ID NO: 271.

In another specific embodiment, the invention includes an antibody that specifically binds to Factor P comprising a heavy chain variable region CDR1 of SEQ ID NO: 281; a heavy chain variable region CDR2 of SEQ ID NO: 282; a heavy chain variable region CDR3 of SEQ ID NO: 283; a light chain variable region CDR1 of SEQ ID NO: 284; a light chain variable region CDR2 of SEQ ID NO: 285; and a light chain variable region CDR3 of SEQ ID NO: 286. In another specific embodiment, the invention includes an antibody that specifically binds to Factor P comprising a heavy chain variable region CDR1 of SEQ ID NO: 287; a heavy chain variable region CDR2 of SEQ ID NO: 288; a heavy chain variable region CDR3 of SEQ ID NO: 289; a light chain variable region CDR1 of SEQ ID NO: 290; a light chain variable region CDR2 of SEQ ID NO: 291; and a light chain variable region CDR3 of SEQ ID NO: 292. In another specific embodiment, the invention includes an antibody that specifically binds to Factor P comprising a heavy chain variable region CDR1 of SEQ ID NO: 293; a heavy chain variable region CDR2 of SEQ ID NO: 294; a heavy chain variable region CDR3 of SEQ ID NO: 295; a light chain variable region CDR1 of SEQ ID NO: 296; a light chain variable region CDR2 of SEQ ID NO: 297; and a light chain variable region CDR3 of SEQ ID NO: 298. In another specific embodiment, the invention includes an antibody that specifically binds to Factor P comprising a heavy chain variable region CDR1 of SEQ ID NO: 299; a heavy chain variable region CDR2 of SEQ ID NO: 300; a heavy chain variable region CDR3 of SEQ ID NO: 301; a light chain variable region CDR1 of SEQ ID NO: 302; a light chain variable region CDR2 of SEQ ID NO: 303; and a light chain variable region CDR3 of SEQ ID NO: 304. In another specific embodiment, the invention includes an antibody that specifically binds to Factor P comprising a heavy chain variable region CDR1 of SEQ ID NO: 305; a heavy chain variable region CDR2 of SEQ ID NO: 306; a heavy chain variable region CDR3 of SEQ ID NO: 307; a light chain variable region CDR1 of SEQ ID NO: 308; a light chain variable region CDR2 of SEQ ID NO: 309; and a light chain variable region CDR3 of SEQ ID NO: 310. In another specific embodiment, the invention includes an antibody that specifically binds to Factor P comprising a heavy chain variable region CDR1 of SEQ ID NO: 311; a heavy chain variable region CDR2 of SEQ ID NO: 312; a heavy chain variable region CDR3 of SEQ ID NO: 313; a light chain variable region CDR1 of SEQ ID NO: 314; a light chain variable region CDR2 of SEQ ID NO: 315; and a light chain variable region CDR3 of SEQ ID NO: 316. In another specific embodiment, the invention includes an antibody that specifically binds to Factor P comprising a heavy chain variable region CDR1 of SEQ ID NO: 317; a heavy chain variable region CDR2 of SEQ ID NO: 318; a heavy chain variable region CDR3 of SEQ ID NO: 319; a light chain variable region CDR1 of SEQ ID NO: 320; a light chain variable region CDR2 of SEQ ID NO: 321; and a light chain variable region CDR3 of SEQ ID NO: 322. In another specific embodiment, the invention includes an antibody that specifically binds to Factor P comprising a heavy chain variable region CDR1 of SEQ ID NO: 323; a heavy chain variable region CDR2 of SEQ ID NO: 324; a heavy chain variable region CDR3 of SEQ ID NO: 325; a light chain variable region CDR1 of SEQ ID NO: 326; a light chain variable region CDR2 of SEQ ID NO: 327; and a light chain variable region CDR3 of SEQ ID NO: 328. In another specific embodiment, the invention includes an antibody that specifically binds to Factor P comprising a heavy chain variable region CDR1 of SEQ ID NO: 329; a heavy chain variable region CDR2 of SEQ ID NO: 330; a heavy chain variable region CDR3 of SEQ ID NO: 331; a light chain variable region CDR1 of SEQ ID NO: 332; a light chain variable region CDR2 of SEQ ID NO: 333; and a light chain variable region CDR3 of SEQ ID NO: 334. In another specific embodiment, the invention includes an antibody that specifically binds to Factor P comprising a heavy chain variable region CDR1 of SEQ ID NO: 335; a heavy chain variable region CDR2 of SEQ ID NO: 336; a heavy chain variable region CDR3 of SEQ ID NO: 337; a light chain variable region CDR1 of SEQ ID NO: 338; a light chain variable region CDR2 of SEQ ID NO: 339; and a light chain variable region CDR3 of SEQ ID NO: 340. In another specific embodiment, the invention includes an antibody that specifically binds to Factor P comprising a heavy chain variable region CDR1 of SEQ ID NO: 341; a heavy chain variable region CDR2 of SEQ ID NO: 342; a heavy chain variable region CDR3 of SEQ ID NO: 343; a light chain variable region CDR1 of SEQ ID NO: 344; a light chain variable region CDR2 of SEQ ID NO: 345; and a light chain variable region CDR3 of SEQ ID NO: 346. In another specific embodiment, the invention includes an antibody that specifically binds to Factor P comprising a heavy chain variable region CDR1 of SEQ ID NO: 347; a heavy chain variable region CDR2 of SEQ ID NO: 348; a heavy chain variable region CDR3 of SEQ ID NO: 349; a light chain variable region CDR1 of SEQ ID NO: 350; a light chain variable region CDR2 of SEQ ID NO: 351; and a light chain variable region CDR3 of SEQ ID NO: 352. In another specific embodiment, the invention includes an antibody that specifically binds to Factor P comprising a heavy chain variable region CDR1 of SEQ ID NO: 353; a heavy chain variable region CDR2 of SEQ ID NO: 354; a heavy chain variable region CDR3 of SEQ ID NO: 355; a light chain variable region CDR1 of SEQ ID NO: 356; a light chain variable region CDR2 of SEQ ID NO: 357; and a light chain variable region CDR3 of SEQ ID NO: 358. In another specific embodiment, the invention includes an antibody that specifically binds to Factor P comprising a heavy chain variable region CDR1 of SEQ ID NO: 359; a heavy chain variable region CDR2 of SEQ ID NO: 360; a heavy chain variable region CDR3 of SEQ ID NO: 361; a light chain variable region CDR1 of SEQ ID NO: 362; a light chain variable region CDR2 of SEQ ID NO: 363; and a light chain variable region CDR3 of SEQ ID NO: 364. In another specific embodiment, the invention includes an antibody that specifically binds to Factor P comprising a heavy chain variable region CDR1 of SEQ ID NO: 365; a heavy chain variable region CDR2 of SEQ ID NO: 366; a heavy chain variable region CDR3 of SEQ ID NO: 367; a light chain variable region CDR1 of SEQ ID NO: 368; a light chain variable region CDR2 of SEQ ID NO: 369; and a light chain variable region CDR3 of SEQ ID NO: 370. In another specific embodiment, the invention includes an antibody that specifically binds to Factor P comprising a heavy chain variable region CDR1 of SEQ ID NO: 371; a heavy chain variable region CDR2 of SEQ ID NO: 372; a heavy chain variable region CDR3 of SEQ ID NO: 373; a light chain variable region CDR1 of SEQ ID NO: 374; a light chain variable region CDR2 of SEQ ID NO: 375; and a light chain variable region CDR3 of SEQ ID NO: 376. In another specific embodiment, the invention includes an antibody that specifically binds to Factor P comprising a heavy chain variable region CDR1 of SEQ ID NO: 377; a heavy chain variable region CDR2 of SEQ ID NO: 378; a heavy chain variable region CDR3 of SEQ ID NO: 379; a light chain variable region CDR1 of SEQ ID NO: 380; a light chain variable region CDR2 of SEQ ID NO: 381; and a light chain variable region CDR3 of SEQ ID NO: 382. In another specific embodiment, the invention includes an antibody that specifically binds to Factor P comprising a heavy chain variable region CDR1 of SEQ ID NO: 383; a heavy chain variable region CDR2 of SEQ ID NO: 384; a heavy chain variable region CDR3 of SEQ ID NO: 385; a light chain variable region CDR1 of SEQ ID NO: 386; a light chain variable region CDR2 of SEQ ID NO: 387; and a light chain variable region CDR3 of SEQ ID NO: 388. In another specific embodiment, the invention includes an antibody that specifically binds to Factor P comprising a heavy chain variable region CDR1 of SEQ ID NO: 389; a heavy chain variable region CDR2 of SEQ ID NO: 390; a heavy chain variable region CDR3 of SEQ ID NO: 391; a light chain variable region CDR1 of SEQ ID NO: 392; a light chain variable region CDR2 of SEQ ID NO: 393; and a light chain variable region CDR3 of SEQ ID NO: 394. In another specific embodiment, the invention includes an antibody that specifically binds to Factor P comprising a heavy chain variable region CDR1 of SEQ ID NO: 395; a heavy chain variable region CDR2 of SEQ ID NO: 396; a heavy chain variable region CDR3 of SEQ ID NO: 397; a light chain variable region CDR1 of SEQ ID NO: 398; a light chain variable region CDR2 of SEQ ID NO: 399; and a light chain variable region CDR3 of SEQ ID NO: 400.

In certain embodiments, the invention includes antibodies or antigen binding fragments that specifically binds to Factor P as described in Table 1. In a preferred embodiment, the antibody, or antigen binding fragment, that binds Factor P is Fab NVS962, NVS963, NVS964, NVS965, NVS966, NVS967, NVS804, NVS805, NVS806, NVS807, NVS808, NVS809, NVS962-S, NVS962-Q, NVS962-G, NVS962-T, NVS962-S31A, NVS965-T, NVS965-Q, or NVS965-S.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described below, as well as DP47 and DPK9.

Homologous Antibodies

In yet another embodiment, the present invention provides an antibody, or an antigen binding fragment thereof, comprising amino acid sequences that are homologous to the sequences described in Table 1, and the antibody binds to a Factor P protein (e.g., human and/or cynomolgus Factor P), and retains the desired functional properties of those antibodies described in Table 1.

For example, the invention provides an isolated antibody, or a functional antigen binding fragment thereof, comprising a heavy chain variable domain and a light chain variable domain, wherein the heavy chain variable domain comprises an amino acid sequence that is at least 80%, at least 90%, or at least 95% identical to an amino acid sequence selected from the group consisting of SEQ ID NOs: 7, 21, 35, 49, 63, 77, 91, 105, 119, 133, 147, 161, 175, 189, 203, 217, 231, 245, 259 and 273; the light chain variable domain comprises an amino acid sequence that is at least 80%, at least 90%, or at least 95% identical to an amino acid sequence selected from the group consisting of SEQ ID NOs: 8, 22, 36, 50, 64, 78, 92, 106, 120, 134, 148, 162, 176, 190, 204, 218, 232, 246, 260, and 274; and the antibody specifically binds to Factor P (e.g., human and/or cynomolgus Factor P).

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except for an amino acid substitution in no more than 1, 2, 3, 4 or 5 amino acid positions. An antibody having VH and VL regions having high (i. e., 80% or greater) identity to the VH and VL regions of those described in Table 1 can be obtained by mutagenesis (e.g., site-directed or PCR-mediated mutagenesis) of nucleic acid molecules encoding SEQ ID NOs: 7, 21, 35, 49, 63, 77, 91, 105, 119, 133, 147, 161, 175, 189, 203, 217, 231, 245, 259 or 273 and SEQ ID NOs: 8, 22, 36, 50, 64, 78, 92, 106, 120, 134, 148, 162, 176, 190, 204, 218, 232, 246, 260, or 274, respectively, followed by testing of the encoded altered antibody for retained function using the functional assays described herein.

In other embodiments, the full length heavy chain and/or full length light chain amino acid sequences may be 50% 60%, 70%, 80%, 90%, 95%, 96%, 97%, 98% or 99% identical to the sequences set forth in Table 1. An antibody having a full length heavy chain and full length light chain having high (i.e., 80% or greater) identity to the full length heavy chains of any of SEQ ID NOs: 9, 23, 37, 51, 65, 79, 93, 107, 121, 135, 149, 163, 177, 191, 205, 219, 233, 247, 261 or 275, and full length light chains of any of SEQ ID NOs 10, 24, 38, 52, 66, 80, 94, 108, 122, 136, 150, 164, 178, 192, 206, 220, 234, 248, 262, or 276, can be obtained by mutagenesis (e.g., site-directed or PCR-mediated mutagenesis) of nucleic acid molecules encoding such polypeptides, followed by testing of the encoded altered antibody for retained function using the functional assays described herein.

In other embodiments, the full length heavy chain and/or full length light chain nucleotide sequences may be 60%, 70%, 80%, 90%, 95%, 96%, 97%, 98% or 99% identical to the sequences set forth in Table 1.

In other embodiments, the variable regions of heavy chain and/or the variable regions of light chain nucleotide sequences may be 60%, 70%, 80%, 90%, 95%, 96%, 97%, 98% or 99% identical to the sequences set forth in Table 1.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the Factor P-binding antibodies of the invention. Accordingly, the invention provides an isolated antibody, or a antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 1, 15, 29, 43, 57, 71, 85, 99, 113, 127, 141, 155, 169, 183, 197, 211, 225, 239, 253, and 267, and conservative modifications thereof; the heavy chain variable region CDR2 amino acid sequences are selected from the group consisting of SEQ ID NOs: 2, 16, 30, 44, 58, 72, 86, 100, 114, 128, 142, 156, 170, 184, 198, 212, 226, 240, 254, and 268, and conservative modifications thereof; the heavy chain variable region CDR3 amino acid sequences are selected from the group consisting of SEQ ID NOs: 3, 17, 31, 45, 59, 73, 87, 101, 115, 129, 143, 157, 171, 185, 199, 213, 227, 241, 255, and 269, and conservative modifications thereof; the light chain variable regions CDR1 amino acid sequences are selected from the group consisting of SEQ ID NOs: 4, 18, 32, 46, 60, 74, 88, 102, 116, 130, 144, 158, 172, 186, 200, 214, 228, 242, 256, and 270, and conservative modifications thereof; the light chain variable regions CDR2 amino acid sequences are selected from the group consisting of SEQ ID NOs: 5, 19, 33, 47, 61, 75, 89, 103, 117, 131, 145, 159, 173, 187, 201, 215, 229, 243, 257, and 271, and conservative modifications thereof; the light chain variable regions of CDR3 amino acid sequences are selected from the group consisting of SEQ ID NOs: 6, 20, 34, 48, 62, 76, 90, 104, 118, 132, 146, 160, 174, 188, 202, 216, 230, 244, 258, and 272, and conservative modifications thereof; and the antibody or antigen binding fragment thereof specifically binds to Factor P.

In other embodiments, the antibody of the invention is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the Factor P binding antibodies of the invention. Accordingly, the invention provides an isolated antibody optimized for expression in a mammalian cell consisting of a full length heavy chain and a full length light chain wherein the full length heavy chain has amino acid sequences selected from the group of SEQ ID NOs: 9, 23, 37, 51, 65, 79, 93, 107, 121, 135, 149, 163, 177, 191, 205, 219, 233, 247, 261 and 275, and conservative modifications thereof; and the full length light chain has amino acid sequences selected from the group of SEQ ID NOs: 10, 24, 38, 52, 66, 80, 94, 108, 122, 136, 150, 164, 178, 192, 206, 220, 234, 248, 262, and 276, and conservative modifications thereof; and the antibody specifically binds to Factor P (e.g., human and/or cynomolgus Factor P).

Antibodies that Bind to the Same Epitope

The present invention provides antibodies that bind to the same epitope as the Factor P binding antibodies described in Table 1. Additional antibodies can therefore be identified based on their ability to compete (e.g., to competitively inhibit the binding of, in a statistically significant manner) with other antibodies of the invention in Factor P binding assays (such as those described in the Examples). The ability of a test antibody to inhibit the binding of antibodies of the present invention to a Factor P protein demonstrates that the test antibody can compete with that antibody for binding to Factor P; such an antibody may, according to non-limiting theory, bind to the same or a related (e.g., a structurally similar or spatially proximal) epitope on the Factor P protein as the antibody with which it competes. In a certain embodiment, the antibody that binds to the same epitope on Factor P as the antibodies of the present invention is a human monoclonal antibody. Such human monoclonal antibodies can be prepared and isolated as described herein. As used herein, an antibody "competes" for binding when the competing antibody inhibits Factor P binding of an antibody or antigen binding fragment of the invention by more than 50%, in the presence of an equimolar concentration of competing antibody.

In other embodiments the antibodies or antigen binding fragments of the invention bind the Thrombospondin type 5 repeat (TSR 5) domain of Factor P (SEQ ID NO: 406). In other embodiments the antibodies or antigen binding fragments of the invention bind a region of the Factor P TSR5 domain comprising SEQ ID NO: 407. Still in other embodiments the region comprises SEQ ID NO: 408.

In other embodiments of the invention the isolated antibodies or antigen binding fragments bind an epitope comprising SEQ ID NO: 407, and in other embodiments the epitope comprises SEQ ID NO: 408. In other embodiments of the invention, the antibodies or antigen binding fragments bind a peptide according to SEQ ID NO: 407 and in still other embodiments the Factor P epitope includes SEQ ID NO: 408.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i. e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated antibody, or an antigen binding fragment thereof, comprising a heavy chain variable region comprising CDR1 sequences having an amino acid sequence selected from the group consisting of SEQ ID NOs: 1, 15, 29, 43, 57, 71, 85, 99, 113, 127, 141, 155, 169, 183, 197, 211, 225, 239, 253, and 267; CDR2 sequences having an amino acid sequence selected from the group consisting of SEQ ID NOs: 2, 16, 30, 44, 58, 72, 86, 100, 114, 128, 142, 156, 170, 184, 198, 212, 226, 240, 254, and 268; CDR3 sequences having an amino acid sequence selected from the group consisting of SEQ ID NOs: 3, 17, 31, 45, 59, 73, 87, 101, 115, 129, 143, 157, 171, 185, 199, 213, 227, 241, 255, and 269, respectively; and a light chain variable region having CDR1 sequences having an amino acid sequence selected from the group consisting of SEQ ID NOs: 4, 18, 32, 46, 60, 74, 88, 102, 116, 130, 144, 158, 172, 186, 200, 214, 228, 242, 256, and 270; CDR2 sequences having an amino acid sequence selected from the group consisting of SEQ ID NOs: 5, 19, 33, 47, 61, 75, 89, 103, 117, 131, 145, 159, 173, 187, 201, 215, 229, 243, 257, and 271; and CDR3 sequences consisting of an amino acid sequence selected from the group consisting of SEQ ID NOs: 6, 20, 34, 48, 62, 76, 90, 104, 118, 132, 146, 160, 174, 188, 202, 216, 230, 244, 258, and 272, respectively. Thus, such antibodies contain the VH and VL CDR sequences of monoclonal antibodies, yet may contain different framework sequences from these antibodies.

Alternatively, another embodiment of the invention pertains to an isolated antibody, or an antigen binding fragment thereof, comprising a heavy chain variable region comprising CDR1 sequences having an amino acid sequence selected from the group consisting of SEQ ID NOs: 281, 287, 293, 299, 305, 311, 317, 323, 329, 335, 341, 347, 353, 359, 365, 371, 377, 383, 389, and 395; CDR2 sequences having an amino acid sequence selected from the group consisting of SEQ ID NOs: 282, 288, 294, 300, 306, 312, 318, 324, 330, 336, 342, 348, 354, 360, 366, 372, 378, 384, 390, and 396; CDR3 sequences having an amino acid sequence selected from the group consisting of SEQ ID NOs: 283, 289, 295, 301, 307, 313, 319, 325, 331, 337, 343, 349, 355, 361, 367, 373, 379, 385, 391, and 397, respectively; and a light chain variable region having CDR1 sequences having an amino acid sequence selected from the group consisting of SEQ ID NOs: 284, 290, 296, 302, 308, 314, 320, 326, 332, 338, 344, 350, 356, 362, 368, 374, 380, 386, 392, and 398; CDR2 sequences having an amino acid sequence selected from the group consisting of SEQ ID NOs: 285, 291, 297, 303, 309, 315, 321, 327, 333, 339, 345, 351, 357, 363, 369, 375, 381, 387, 393, and 399; and CDR3 sequences consisting of an amino acid sequence selected from the group consisting of SEQ ID NOs: 286, 292, 298, 304, 310, 316, 322, 328, 334, 340, 346, 352, 358, 364, 370, 376, 382, 388, 394, and 400, respectively. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180, 370 to Queen et al). Frameworks that can be utilized as scaffolds on which to build the antibodies and antigen binding fragments described herein include, but are not limited to VH1A, VH1B, VH3, Vk1, VI2, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the invention relates to isolated Factor P binding antibodies, or antigen binding fragments thereof, comprising a heavy chain variable region comprising an amino acid sequence selected from the group consisting of SEQ ID NOs: 7, 21, 35, 49, 63, 77, 91, 105, 119, 133, 147, 161, 175, 189, 203, 217, 231, 245, 259 and 273, or an amino acid sequence having one, two, three, four or five amino acid substitutions, deletions or additions in the framework region of such sequences, and further comprising a light chain variable region having an amino acid sequence selected from the group consisting of SEQ ID NOs: 8, 22, 36, 50, 64, 78, 92, 106, 120, 134, 148, 162, 176, 190, 204, 218, 232, 246, 260, and 274, or an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated Factor P-binding antibodies, or antigen binding fragments thereof, consisting of a heavy chain variable region having a VH CDR1 region consisting of an amino acid sequence selected from the group having SEQ ID NOs: 1, 15, 29, 43, 57, 71, 85, 99, 113, 127, 141, 155, 169, 183, 197, 211, 225, 239, 253, and 267 or an amino acid sequence having one, two, three, four or five amino acid substitutions, deletions or additions as compared to SEQ ID NOs: 1, 15, 29, 43, 57, 71, 85, 99, 113, 127, 141, 155, 169, 183, 197, 211, 225, 239, 253, or 267; a VH CDR2 region having an amino acid sequence selected from the group consisting of SEQ ID NOs: 2, 16, 30, 44, 58, 72, 86, 100, 114, 128, 142, 156, 170, 184, 198, 212, 226, 240, 254, and 268 or an amino acid sequence having one, two, three, four or five amino acid substitutions, deletions or additions as compared to SEQ ID NOs: 2, 16, 30, 44, 58, 72, 86, 100, 114, 128, 142, 156, 170, 184, 198, 212, 226, 240, 254, or 268; a VH CDR3 region having an amino acid sequence selected from the group consisting of SEQ ID NOs: 3, 17, 31, 45, 59, 73, 87, 101, 115, 129, 143, 157, 171, 185, 199, 213, 227, 241, 255, and 269, or an amino acid sequence having one, two, three, four or five amino acid substitutions, deletions or additions as compared to SEQ ID NOs: 3, 17, 31, 45, 59, 73, 87, 101, 115, 129, 143, 157, 171, 185, 199, 213, 227, 241, 255, or 269; a VL CDR1 region having an amino acid sequence selected from the group consisting of SEQ ID NOs: 4, 18, 32, 46, 60, 74, 88, 102, 116, 130, 144, 158, 172, 186, 200, 214, 228, 242, 256, and 270, or an amino acid sequence having one, two, three, four or five amino acid substitutions, deletions or additions as compared to SEQ ID NOs: 4, 18, 32, 46, 60, 74, 88, 102, 116, 130, 144, 158, 172, 186, 200, 214, 228, 242, 256, or 270; a VL CDR2 region having an amino acid sequence selected from the group consisting of SEQ ID NOs: 5, 19, 33, 47, 61, 75, 89, 103, 117, 131, 145, 159, 173, 187, 201, 215, 229, 243, 257, and 271, or an amino acid sequence having one, two, three, four or five amino acid substitutions, deletions or additions as compared to SEQ ID NOs: 5, 19, 33, 47, 61, 75, 89, 103, 117, 131, 145, 159, 173, 187, 201, 215, 229, 243, 257, or 271; and a VL CDR3 region having an amino acid sequence selected from the group consisting of SEQ ID NOs: 6, 20, 34, 48, 62, 76, 90, 104, 118, 132, 146, 160, 174, 188, 202, 216, 230, 244, 258, and 272, or an amino acid sequence having one, two, three, four or five amino acid substitutions, deletions or additions as compared to SEQ ID NOs: 6, 20, 34, 48, 62, 76, 90, 104, 118, 132, 146, 160, 174, 188, 202, 216, 230, 244, 258, or 272.

Accordingly, in another embodiment, the invention provides isolated Factor P-binding antibodies, or antigen binding fragments thereof, consisting of a heavy chain variable region having a VH CDR1 region consisting of an amino acid sequence selected from the group having SEQ ID NOs: 281, 287, 293, 299, 305, 311, 317, 323, 329, 335, 341, 347, 353, 359, 365, 371, 377, 383, 389, and 395 or an amino acid sequence having one, two, three, four or five amino acid substitutions, deletions or additions as compared to SEQ ID NOs: 281, 287, 293, 299, 305, 311, 317, 323, 329, 335, 341, 347, 353, 359, 365, 371, 377, 383, 389, or 395; a VH CDR2 region having an amino acid sequence selected from the group consisting of SEQ ID NOs: 282, 288, 294, 300, 306, 312, 318, 324, 330, 336, 342, 348, 354, 360, 366, 372, 378, 384, 390, and 396 or an amino acid sequence having one, two, three, four or five amino acid substitutions, deletions or additions as compared to SEQ ID NOs: 282, 288, 294, 300, 306, 312, 318, 324, 330, 336, 342, 348, 354, 360, 366, 372, 378, 384, 390, or 396; a VH CDR3 region having an amino acid sequence selected from the group consisting of SEQ ID NOs: 283, 289, 295, 301, 307, 313, 319, 325, 331, 337, 343, 349, 355, 361, 367, 373, 379, 385, 391, and 397, or an amino acid sequence having one, two, three, four or five amino acid substitutions, deletions or additions as compared to SEQ ID NOs: 283, 289, 295, 301, 307, 313, 319, 325, 331, 337, 343, 349, 355, 361, 367, 373, 379, 385, 391, or 397; a VL CDR1 region having an amino acid sequence selected from the group consisting of SEQ ID NOs: 284, 290, 296, 302, 308, 314, 320, 326, 332, 338, 344, 350, 356, 362, 368, 374, 380, 386, 392, and 398, or an amino acid sequence having one, two, three, four or five amino acid substitutions, deletions or additions as compared to SEQ ID NOs: 284, 290, 296, 302, 308, 314, 320, 326, 332, 338, 344, 350, 356, 362, 368, 374, 380, 386, 392, or 398; a VL CDR2 region having an amino acid sequence selected from the group consisting of SEQ ID NOs: 285, 291, 297, 303, 309, 315, 321, 327, 333, 339, 345, 351, 357, 363, 369, 375, 381, 387, 393, and 399, or an amino acid sequence having one, two, three, four or five amino acid substitutions, deletions or additions as compared to SEQ ID NOs: 285, 291, 297, 303, 309, 315, 321, 327, 333, 339, 345, 351, 357, 363, 369, 375, 381, 387, 393, or 399; and a VL CDR3 region having an amino acid sequence selected from the group consisting of SEQ ID NOs: 286, 292, 298, 304, 310, 316, 322, 328, 334, 340, 346, 352, 358, 364, 370, 376, 382, 388, 394, and 400, or an amino acid sequence having one, two, three, four or five amino acid substitutions, deletions or additions as compared to SEQ ID NOs: 286, 292, 298, 304, 310, 316, 322, 328, 334, 340, 346, 352, 358, 364, 370, 376, 382, 388, 394, or 400.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to Factor P. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target Factor P protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (*Pieris* Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company *Pieris* ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The present invention provides fully human antibodies that specifically bind to a Factor P protein. Compared to the chimeric or humanized antibodies, the human Factor P-binding antibodies of the invention have further reduced antigenicity when administered to human subjects.

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as E. coli and are expressed as fusion proteins with bacteriophage and are functional.

Accordingly, a feature of the present invention is a camelid antibody or nanobody having high affinity for Factor P. In certain embodiments herein, the camelid antibody or nanobody is naturally produced in the camelid animal, i.e., is produced by the camelid following immunization with Factor P or a peptide fragment thereof, using techniques described herein for other antibodies. Alternatively, the Factor P-binding camelid nanobody is engineered, i.e., produced by selection for example from a library of phage displaying appropriately mutagenized camelid nanobody proteins using panning procedures with Factor P as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising a Factor P-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for Factor P and a second binding specificity for a second target epitope. For example, the second target epitope is another epitope of Factor P different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the invention are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies of the invention binding to Factor P. The antigen-binding portions can be linked together via protein fusion or covalent or non covalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fc or hinge region.

Trimerizing domain are described for example in Borean patent EP 1 012 280B1. Pentamerizing modules are described for example in PCT/EP97/05897.

Antibodies with Extended Half Life

The present invention provides for antibodies that specifically bind to Factor P protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanoboies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased.

In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622. In addition, in the context of a bispecific antibody as described above, the specificities of the antibody can be designed such that one binding domain of the antibody binds to Factor P while a second binding domain of the antibody binds to serum albumin, preferably HSA.

The strategies for increasing half life is especially useful in nanobodies, fibronectin-based binders, and other antibodies or proteins for which increased in vivo half life is desired.

Antibody Conjugates

The present invention provides antibodies or fragments thereof that specifically bind to a Factor P protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a Factor P protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}I$, $^{125}I$, $^{123}I$, and $^{121}I$,), carbon ($^{14}C$), sulfur ($^{35}S$), tritium ($^{3}H$), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and noradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alphemiters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies of the Invention
Nucleic Acids Encoding the Antibodies The invention provides substantially purified nucleic acid molecules which encode polypeptides comprising segments or domains of the Factor P-binding antibody chains described above. Some of the nucleic acids of the invention comprise the nucleotide sequence encoding the heavy chain variable region shown in SEQ ID NO: 7, 21, 35, 49, 63, 77, 91, 105, 119, 133, 147, 161, 175, 189, 203, 217, 231, 245, 259 or 273, and/or the nucleotide sequence encoding the light chain variable region shown in SEQ ID NO: 8, 22, 36, 50, 64, 78, 92, 106, 120, 134, 148, 162, 176, 190, 204, 218, 232, 246, 260, or 274. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting Factor P antigen binding capacity.

Also provided in the invention are polynucleotides which encode at least one CDR region and usually all three CDR regions from the heavy or light chain of the Factor P-binding antibody set forth above. Some other polynucleotides encode all or substantially all of the variable region sequence of the heavy chain and/or the light chain of the Factor P-binding antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a mature heavy chain sequence that is substantially identical (e.g., at least 80%, 90%, or 99%) to the mature heavy chain sequence set forth in SEQ ID NO: 9, 23, 37, 51, 65, 79, 93, 107, 121, 135, 149, 163, 177, 191, 205, 219, 233, 247, 261 or 275. Some other nucleic acid sequences comprising nucleotide encoding a mature light chain sequence that is substantially identical (e.g., at least 80%, 90%, or 99%) to the mature light chain sequence set forth in SEQ ID NO: 10, 24, 38, 52, 66, 80, 94, 108, 122, 136, 150, 164, 178, 192, 206, 220, 234, 248, 262, or 276.

The polynucleotide sequences can be produced by de novo solid-phase DNA synthesis or by PCR mutagenesis of an existing sequence (e.g., sequences as described in the Examples below) encoding a Factor P-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the Factor P-binding antibodies described above. Various expression vectors can be employed to express the polynucleotides encoding the Factor P-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the Factor P-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a Factor P-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a Factor P-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted Factor P-binding antibody sequences. More often, the inserted Factor P-binding antibody sequences are linked to a signal sequences before inclusion in the vector. Vectors to be used to receive sequences encoding Factor P-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the Factor P-binding antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express Factor P-binding polypeptides of the invention. Insect cells in combination with baculovirus vectors can also be used.

In some preferred embodiments, mammalian host cells are used to express and produce the Factor P-binding polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express Factor P-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal systems for preparing hybridomas include the murine, rat and rabbit systems. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are human monoclonal antibodies. Such human monoclonal antibodies directed against Factor P can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb mouse (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise Factor P-binding antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise Factor P-binding antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise Factor P-binding antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Dower et al.; U.S. Pat. Nos. 5,427,908 and 5,580,717 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the Factor P-binding antibodies having VH and VL sequences or full length heavy and light chain sequences shown herein can be used to create new Factor P-binding antibodies by modifying full length heavy chain and/or light chain sequences, VH and/or VL sequences, or the constant region(s) attached thereto. Thus, in another aspect of the invention, the structural features of a Factor P-binding antibody of the invention are used to create structurally related Factor P-binding antibodies that retain at least one functional property of the antibodies of the invention, such as binding to human Factor P and also inhibiting one or more functional properties of Factor P (e.g., inhibiting MAC deposition in a MAC deposition assay, inhibit red blood cell lysis in a hemolytic assay).

For example, one or more CDR regions of the antibodies of the present invention, or mutations thereof, can be combined recombinantly with known framework regions and/or other CDRs to create additional, recombinantly-engineered, Factor P-binding antibodies of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing a Factor P-binding antibody consisting of a heavy chain variable region antibody sequence having a CDR1 sequence selected from the group consisting of SEQ ID NOs: 1, 15, 29, 43, 57, 71, 85, 99, 113, 127, 141, 155, 169, 183, 197, 211, 225, 239, 253, and 267, a CDR2 sequence selected from the group consisting of SEQ ID NOs: 2, 16, 30, 44, 58, 72, 86, 100, 114, 128, 142, 156, 170, 184, 198, 212, 226, 240, 254, and 268, and/or a CDR3 sequence selected from the group consisting of SEQ ID NOs: 3, 17, 31, 45, 59, 73, 87, 101, 115, 129, 143, 157, 171, 185, 199, 213, 227, 241, 255, and 269; and a light chain variable region antibody sequence having a CDR1 sequence selected from the group consisting of SEQ ID NOs: 4, 18, 32, 46, 60, 74, 88, 102, 116, 130, 144, 158, 172, 186, 200, 214, 228, 242, 256, and 270, a CDR2 sequence selected from the group consisting of SEQ ID NOs: 5, 19, 33, 47, 61, 75, 89, 103, 117, 131, 145, 159, 173, 187, 201, 215, 229, 243, 257, and 271, and/or a CDR3 sequence selected from the group consisting of SEQ ID NOs: 6, 20, 34, 48, 62, 76, 90, 104, 118, 132, 146, 160, 174, 188, 202, 216, 230, 244, 258, and 272; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a Factor P-binding antibody consisting of a heavy chain variable region antibody sequence having a CDR1 sequence selected from the group consisting of SEQ ID NOs: 281, 287, 293, 299, 305, 311, 317, 323, 329, 335, 341, 347, 353, 359, 365, 371, 377, 383, 389, and 395, a CDR2 sequence selected from the group consisting of SEQ ID NOs: 282, 288, 294, 300, 306, 312, 318, 324, 330, 336, 342, 348, 354, 360, 366, 372, 378, 384, 390, and 396, and/or a CDR3 sequence selected from the group consisting of SEQ ID NOs: 283, 289, 295, 301, 307, 313, 319, 325, 331, 337, 343, 349, 355, 361, 367, 373, 379, 385, 391, and 397; and a light chain variable region antibody sequence having a CDR1 sequence selected from the group consisting of SEQ ID NOs: 284, 290, 296, 302, 308, 314, 320, 326, 332, 338, 344, 350, 356, 362, 368, 374, 380, 386, 392, and 398, a CDR2 sequence selected from the group consisting of SEQ ID NOs: 285, 291, 297, 303, 309, 315, 321, 327, 333, 339, 345, 351, 357, 363, 369, 375, 381, 387, 393, and 399, and/or a CDR3 sequence selected from the group consisting of SEQ ID NOs: 286, 292, 298, 304, 310, 316, 322, 328, 334, 340, 346, 352, 358, 364, 370, 376, 382, 388, 394, and 400; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a Factor P-binding antibody optimized for expression in a mammalian cell consisting of: a full length heavy chain antibody sequence having a sequence selected from the group of SEQ ID NOs: 9, 23, 37, 51, 65, 79, 93, 107, 121, 135, 149, 163, 177, 191, 205, 219, 233, 247, 261 and 275; and a full length light chain antibody sequence having a sequence selected from the group of SEQ ID NOs: 10, 24, 38, 52, 66, 80, 94, 108, 122, 136, 150, 164, 178, 192, 206, 220, 234, 248, 262, and 276; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the Factor P-binding antibodies described herein, which functional properties include, but are not limited to, specifically binding to human and/or cynomolgus Factor P; and the antibody inhibit red blood cell lysis in a hemolytic assay.

In certain embodiments of the methods of engineering antibodies of the invention, mutations can be introduced randomly or selectively along all or part of an Factor P-binding antibody coding sequence and the resulting modified Factor P-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments of the invention antibodies have been engineered to remove sites of deamidation. Deamidation is known to cause structural and functional changes in a peptide or protein. Deamindation can result in decreased bioactivity, as well as alterations in pharmacokinetics and antigenicity of the protein pharmaceutical. (*Anal Chem.* 2005 Mar. 1; 77(5):1432-9).

The functional properties of the altered antibodies can be assessed using standard assays available in the art and/or described herein, such as those set forth in the Examples (e.g., ELISAs).

Prophylactic and Therapeutic Uses

Antibodies that binds Factor P as described herein, can be used at a therapeutically useful concentration for the treatment of a disease or disorder associated with increased complement activity by administering to a subject in need thereof an effective amount of the antibodies or antigen binding fragments of the invention. In a specific embodiment, the present invention provides a method of treating age-related macular degeneration (AMD) by administering to a subject in need thereof an effective amount of the antibodies of the invention.

The antibodies of the invention can be used, inter alia, to prevent progression of dry AMD to wet AMD, to slow and/or prevent progression of geographic atrophy, to treat or prevent macular edema, to reduce the frequency of Lucentis injection and to improve vision lost due to dry and wet AMD progression. It can also be used in combination with anti-VEGF therapies for the treatment of wet AMD patients.

Treatment and/or prevention of ocular disease such as AMD can be determined by an ophthalmologist or health care professional using clinically relevant measurements of visual function and/or retinal anatomy. Treatment of AMD means any action (e.g., administration of an anti-Factor P antibody described herein) contemplated to improve or preserve visual function and/or retinal anatomy. In addition, prevention as it relates to AMD means any action (e.g., administration of an anti-Factor P antibody described herein) that prevents or slows a worsening in visual function, retinal anatomy, and/or an AMD disease parameter, as defined herein, in a patient at risk for said worsening.

Visual function may include, for example, visual acuity, visual acuity with low illumination, visual field, central visual field, peripheral vision, contrast sensitivity, dark adaptation, photostress recovery, color discrimination, reading speed, dependence on assistive devices (e.g., large typeface, magnifying devices, telescopes), facial recognition, proficiency at operating a motor vehicle, ability to perform one or more activities of daily living, and/or patient-reported satisfaction related to visual function. THus, treatment of AMD can be said to occur where a subject has an at least 10% decrease or lack of a 10% or more increase in time to a pre-specified degree of dark adaptation. In addition, treatment of AMD can be said to occur where a subject exhibits at least a 10% reduction or lack of a 10% or more increase in total area of central visual scotoma expressed as a visual angle determined by a qualified health care professional (i.e., opthalmologist).

Exemplary measures of visual function include Snellen visual acuity, ETDRS visual acuity, low-luminance visual acuity, Amsler grid, Goldmann visual field, Humphrey visual field, microperimetry, Pelli-Robson charts, SKILL card, Ishihara color plates, Farnsworth D15 or D100 color test, and validated tests for reading speed, facial recognition, driving simulations, and patient reported satisfaction. Thus, treatment of AMD can be said to be achieved upon a gain of or failure to lose 2 or more lines (or 10 letters) of vision on an ETDRS scale. In addition, treatment of AMD can be said to occur where a subject exhibits at least a 10% an increase or lack of 10% decrease in reading speed (words per minute). In addition, treatment of AMD can be said to occur where a subject exhibits at least a 20% increase or lack of a 20% decrease in the proportion of correctly identified plates on an Ishihara test or sequenced disks on a Farnsworth test.

Undesirable aspects of retinal anatomy that may be treated or prevented include, for example, drusen, soft drusen, hard drusen, cuticular drusen, basal laminar drusen, confluent drusen, large drusen (e.g., greater than 125 microns in diameter), RPE atrophy, photoreceptor atrophy, geographic atrophy, choroidal neovascularization, subretinal neovascularization, retinal neovascularization, classic choroidal neovascularization, occult choroidal neovascularization, retinal angiomatous proliferation, chorioretinal anastomosis, an abnormality of choroidal anatomy, subretinal hemorrhage, intraretinal hemorrhage, vitreous hemorrhage, macular scar, subretinal fibrosis, and retinal fibrosis. Thus, treatment of, for example, geographic atrophy can be determined by a 20% or more reduction in lesion growth rate as compared to control or previously documented growth rate in the same subject in the same eye.

Exemplary means of assessing retinal anatomy include funduscopy, fundus photography, fluorescein angiography, indocyanine green angiography, ocular coherence tomography (OCT), spectral domain ocular coherence tomography, scanning laser ophthalmoscopy, confocal microscopy, adaptive optics, fundus autofluorescence, biopsy, necropsy, and immunohistochemistry. Thus, AMD can be said to be treated in a subject upon a 10% reduction in the measurement of macular thickness as determined by OCT, and/or a reduction of hyperfluorescence as determined by fluorescein angiography.

Exemplary measures of retinal anatomy include drusen area, drusen volume, geographic atrophy lesion area, geographic atrophy growth rate, and neovascular membrane area.

In some embodiments, the present invention provides methods of treating a complement related disease or disorder by administering to a subject in need thereof an effective amount of the antibodies of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, post-ischemic reperfusion conditions, myocardial infarction, balloon angioplasty, post-pump syndrome in cardiopulmonary bypass or renal bypass, hemodialysis, renal ischemia, mesenteric artery reperfusion after acrotic reconstruction, infectious disease or sepsis, immune complex disorders and autoimmune diseases, rheumatoid arthritis, systemic lupus erythematosus (SLE), SLE nephritis, proliferative nephritis, hemolytic anemia, and myasthenia gravis. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gasses and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, and immune complex-associated inflammation.

In a specific embodiment, the present invention provides methods of treating a complement related disease or disorder by administering to a subject in need thereof an effective amount of the antibodies of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, aHUS, glomerulonephritis, bullous pemphigoid or MPGN II.

In a specific embodiment, the present invention provides methods of treating glomerulonephritis by administering to a subject in need thereof an effective amount of a composition comprising an antibody of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an antibody of the present invention.

In a specific embodiment, the present invention provides methods of reducing the dysfunction of the immune and hemostatic systems associated with extracorporeal circulation by administering to a subject in need thereof an effective amount of a composition comprising an antibody of the present invention. The antibodies of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient.

Subjects to be treated with therapeutic agents of the present invention can also be administered other therapeutic agents with know methods of treating conditions associated with macular degeneration, such as antibiotic treatments as described in U.S. Pat. No. 6,218,368. In other treatments, immunosuppressive agents such as cyclosporine, are agents capable of suppressing immune responses. These agents include cytotoxic drugs, corticosteriods, nonsteroidal anti-inflammatory drugs (NSAIDs), specific T-lymphocyte immunosuppressants, and antibodies or fragments thereof (see Physicians' Desk Reference, 53rd edition, Medical Economics Company Inc., Montvale, N.J. (1999). Immunosuppressive treatment is typically continued at intervals for a period of a week, a month, three months, six months or a year. In some patients, treatment is administered for up to the rest of a patient's life.

When the therapeutic agents of the present invention are administered together with another agent, the two can be administered sequentially in either order or simultaneously. In some aspects, an antibody of the present invention is administered to a subject who is also receiving therapy with a second agent (e.g., verteporfin). In other aspects, the binding molecule is administered in conjunction with surgical treatments.

Suitable agents for combination treatment with Factor P binding antibodies include agents known in the art that are able to modulate the activities of complement components (see, e.g., U.S. Pat. No. 5,808,109). Other agents have been reported to diminish complement-mediated activity. Such agents include: amino acids (Takada, Y. et al. Immunology 1978, 34, 509); phosphonate esters (Becker, L. Biochem. Biophy. Acta 1967, 147, 289); polyanionic substances (Conrow, R. B. et al. J. Med. Chem. 1980, 23, 242); sulfonyl fluorides (Hansch, C.; Yoshimoto, M. J. Med. Chem. 1974, 17, 1160, and references cited therein); polynucleotides (DeClercq, P. F. et al. Biochem. Biophys. Res. Commun. 1975, 67, 255); pimaric acids (Glovsky, M. M. et al. J. Immunol. 1969, 102, 1); porphines (Lapidus, M. and Tomasco, J. Immunopharmacol. 1981, 3, 137); several anti-inflammatories (Burge, J. J. et al. J. Immunol. 1978, 120, 1625); phenols (Muller-Eberhard, H. J. 1978, in Molecular Basis of Biological Degradative Processes, Berlin, R. D. et al., eds. Academic Press, New York, p. 65); and benzamidines (Vogt, W. et al Immunology 1979, 36, 138). Some of these agents function by general inhibition of proteases and esterases. Others are not specific to any particular intermediate step in the complement pathway, but, rather, inhibit more than one step of complement activation. Examples of the latter compounds include the benzamidines, which block C1, C4 and C3b utilization (see, e.g., Vogt et al. Immunol. 1979, 36, 138).

Additional agents known in the art that can inhibit activity of complement components include K-76, a fungal metabolite from Stachybotrys (Corey et al., J. Amer. Chem. Soc. 104: 5551, 1982). Both K-76 and K-76 COOH have been shown to inhibit complement mainly at the C3b step (Hong et al., J. Immunol. 122: 2418, 1979; Miyazaki et al., Microbiol. Immunol. 24: 1091, 1980), and to prevent the generation of a chemotactic factor from normal human complement (Bumpers et al., Lab. Clinc. Med. 102: 421, 1983). At high concentrations of K-76 or K-76 COOH, some inhibition of the reactions of C2, C3, C6, C7, and C9 with their respective preceding intermediaries is exhibited. K-76 or K-76 COOH has also been reported to inhibit the C3b inactivator system of complement (Hong et al., J. Immunol. 127: 104-108, 1981). Other suitable agents for practicing methods of the present invention include griseofulvin (Weinberg, in Principles of Medicinal Chemistry, 2d Ed., Foye, W. O., ed., Lea & Febiger, Philadelphia, Pa., p. 813, 1981), isopannarin (Djura et al., Aust. J. Chem. 36: 1057, 1983), and metabolites of Siphonodictyon coralli-phagum (Sullivan et al., Tetrahedron 37: 979, 1981).

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related disease as described above with a Factor P binding antibody of the invention and an anti-angiogenic, such as anti-VEGF agent, or another anti-complement antibody such as an antibody or antigen binding fragment thereof that binds to complement factor 5 (C5).

Combination of Anti-Complement Antibodies

In one aspect, the invention provides combinations of any one or more of the anti-Factor P with an additional antibody that binds to and inhibits the activity of a different component of the complement pathway. In particular, the invention includes any one or more of the anti-Factor P antibodies or antigen binding fragments described herein in combination with an antibody or antigen binding fragment that binds complement component 5 (C5). Examples of antibodies or antigen binding fragments thereof that bind to C5 and inhibit complement activation can be found, for example in U.S. Pat. No. 8,241,628 (incorporated herein by reference). More specifically, antibodies or antigen binding fragments thereof that bind to C5 and inhibit the complement pathway are shown and described in Table 2. In one aspect the invention includes a combination of an anti-Factor P antibody or antigen binding fragment thereof as shown and described in Table 1 with the anti-C5 antibody 8109 from Table 2. More specifically, one aspect of the invention relates to a combination of antibody NVS962 from Table 1 (or an antigen binding fragment thereof) with antibody 8109 from Table 2 (or an antigen binding fragment thereof).

In one aspect the combinations of anti-Factor P and anti-C5 antibodies described herein demonstrate a syntergistic inhibition of the complement pathway, particularly the alternative complement pathway. Such inhibition can be demonstrated, for example, using the hemolytic or poly-IC assays described in the Examples below. Synergy in the inhibition of the alternative complement pathway, achieved using a combination of the anti-Factor-P and anti-C5 antibodies described herein can be determined using methods that are well known in the art. For example, a synergistic effect of the combination of anti-Factor P antibody and anti-C5 antibody can be determine relative to a merely additive effect using specific software, such as a Chalice Analyzer.

Briefly, Chalice Analyzer (Lehar et al, Nature Biotechnology 2009, 7:659) software can be used to determine whether the combination of complement inhibiting antibodies (e.g., anti-Factor P and anti-C5) acted synergistically to block complement activation. Combination effects can be characterized by comparing each data point's inhibition to that of a combination reference model that was derived from the single agent curves (Greco, Bravo, Parsons (1995). The search for synergy: a critical review from a response surface perspective. *Pharmacol Rev* 47(2): 331-85). In the Loewe additivity model (Loewe (1928). *Die quantitativen Probleme der Pharmakologie. Ergebn.* Physiol. 27: 47-187), $I_{Loewe}(C_X, C_Y)$ is the inhibition that satisfies $(C_X/C_X)(C_Y/C_Y)=1$, and $IC_{X,Y}$ are the effective concentrations at $I_{Loewe}$ for the fitted single agent curves. Loewe additivity is the generally accepted reference for synergy (Greco et al.), as it represents the combination response generated if X and Y are the same compound.

Potency shifting is usually shown using an isobologram (Greco et al.) which shows how much less drug is required in combination to achieve a desired effect level, when compared to the single agent doses needed to reach that effect. The choice of effect level for the isobologram display and combination index calculations can either be manually or automatically selected in the Chalice Analyzer. The automatic iso-level selection algorithm finds the observed $I_{data}$ with the largest $I_{data}-I_{Loewe}$, excluding those points with $I_{data}$ exceeding the lesser single agent's $I_{max}$. This exclusion is applied to ensure that the isobologram reflects the best synergy at levels covered by both single agents. Having selected an isobologram level $I_{cut}$, the isobologram is drawn by identifying the locus of concentrations that correspond to crossing the chosen iso-level. The isobologram shows the standard isobolographic analysis of synergy compared to the Loewe dose-additive "drug-with-itself" standard. For a specified isobologram level, the observed iso-effect contour (e.g., curved line in FIG. 3) is displayed with the theoretical dose-additive contour (e.g., straight line in FIG. 3), on an $IC_{effect}$-normalized linear concentration scale for both substances in the combination. The Dose-additive reference is always a line connecting the two $IC_{effect}$ concentrations. The $IC_{effect}$ crossing points are found by interpolating the fitted sigmoidal dose response curves.

Potency shifting is scored as the combination index (Chou, Talalay (1984). *Quantitative analysis of dose-effect relationships: the combined effects of multiple drugs or enzyme inhibitors. Adv Enzyme Regul* 22: 27-55) CI. For a chosen iso-effect level $I_{cut}$, $CI_I=(C_X/EC_X)_I+(C_Y/EC_Y)_I$, where $(C_X/EC_X)_I$ for a particular data point is the ratio of the X compound's measured concentration to its effective concentration at the chosen inhibition level. The CI can be thought of as a rough estimate of how much drug was needed in combination relative to the single agent doses required to achieve the chosen effect level, and a value of 0.1 means that only a tenth of equivalent amounts of the single agents were needed for the combination to reach the same effect level. CI values in the range of 0.5-0.7 are typical for in vitro measurements of current clinical combinations (Greco et al.). A CI value of 1.0 is indicative of an additive effect of a combination of antibodies, while a CI value of less than 0.5 is indicative of a strong synergistic effect resulting from the antibody combination. In the Chalice Analyzer, the best CI is reported from the many combination index values calculated for each $I_{cut}$ crossing concentration. Among all the measured CI values, the one with the largest signal-to-noise level is reported as the best combination index.

Combinations of anti-Factor P and anti-C5 antibodies as described herein can be administered singly or as a single composition. In addition, the relative dose of an anti-Factor P and anti-C5 antibody can be in a ratio of 1:1, or may be in a different ratio. The specific dose of an anti-Factor P antibody relative to an anti-C5 antibody may ultimately be determined by a treating physician or health care professional to achieve improvement in the pathological condition being treated. For example, when a combination as described herein is used to treat AMD, a physician or health care professional may taylor the relative doses of the anti-Factor P and anti-C5 antibodies so as to achieve optimal therapeutic benefit as determined using the measurements and criteria described herein.

Pharmaceutical Compositions

The invention provides pharmaceutical compositions comprising the Factor P-binding antibodies (intact or binding fragments) formulated together with a pharmaceutically acceptable carrier. The compositions can additionally contain one or more other therapeutic agents that are suitable for treating or preventing, for example, pathological angiogenesis or tumor growth. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravitreal, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the Factor P-binding antibody is employed in the pharmaceutical compositions of the invention. The Factor P-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of an allergic inflammatory disorder described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. For intravitreal administration with an antibody, the dosage may range from 0.1 mg/eye to 5 mg/eye. For example, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, or 5.0 mg/ml. An exemplary treatment regime entails systemic administration once per every two weeks or once a month or once every 3 to 6 months. An exemplary treatment regime entails systemic administration once per every two weeks or once a month or once every 3 to 6 months Antibody is usually administered on multiple occasions. Intervals between single dosages can be weekly, monthly or yearly. Intervals can also be irregular as indicated by measuring blood levels of Factor P-binding antibody in the patient. In addition alternative dosing intervals can be determined by a physician and administered monthly or as necessary to be efficacious. Efficacy is based on lesion growth, rate of Lucentis rescue, retinal thickness as determined by Spectral Domain-optical Optical Coherence Tomography (SD-OCT), and secondary visual acuity. In some methods of systemic administration, dosage is adjusted to achieve a plasma antibody concentration of 1-1000 μg/ml and in some methods 25-500 μg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the invention will be readily apparent to one of ordinary skill in the art and are encompassed by the appended claims.

Example 1: Generation of Affinity Matured Factor P Antibodies

A fully human phage display library was used to generate the Factor P binding antibodies described herein.

Biotinylated and non-biotinylated human and cynomolgus Factor P were used in solution and solid phase pannings. Standard panning were performed as well as RapMAT approaches (Prassler et al., (2009) Immunotherapy 1(4):571-583). Following affinity maturation (Knappik et al., (2000) J. Mol. Biol., 296:57-86) a set of 10 antibodies were subsequently chosen for conversion to a disulfide-bridged Fab format. The resulting disulfide bridged Fabs are shown in Table 1 (NVS962, NVS963, NVS964, NVS965, NVS966, NVS967).

Example 2: Further Antibody Optimization

The following example describes methods that may be used to further optimize antibodies described herein.

Removal of Deamidation Sites

Deamindation sites were identified by peptide mapping and size exclusion chromatography (SEC), run under reducing conditions. The deamidated material has decreased potency in a MAC deposition assay and decreased affinity for human and cyno FP as measured by BIACORE™ and SET. The extent of deamidation increased over time (3 weeks), at higher temperatures (5 days at 37° C.), and under reducing conditions. Deamidation can be detected using an ion-exchange column resulting in multiple peaks and observation of the additional, deamidated peak. Amino acid sequences that are most prone to deamidation are: SNG, LNG, LNN, ELN (Daugherty, A. and Mrsny, R. (2010) Current Trends in Monoclonal Antibody Development and Manufacturing. Springer. p 103-129.). Accordingly, we engaged in a series of studies to remove the deamidation sites and test the modified antibodies for retained function.

Two Fabs, NVS962 and NVS965, were re-engineered to replace a deamindation site on the heavy chain, specifically occurring at an asparagine at position 30. The following new Fabs were generated to remove the deamination site and corresponding amino acid replacements shown in Table 2.

TABLE 2

Deamidated Fabs

| Deaminadated Fab | N30 replaced with: | Modified Fab |
|---|---|---|
| NVS962 | Serine | NVS962-S |
|  | Glutamine | NVS962-Q |
|  | Glycine | NVS962-G |
|  | Threonine | NVS962-T |
| NVS965 | Threonine | NVS965-T |
|  | Glutamine | NVS965-Q |
|  | Serine | NVS965-S |

An additional Fab that was generated replaced serine 31 with an alanine in Fab NVS962, generating Fab NVS962-S31A. The sequences of the modified Fabs is shown in Table 1.

Removal of Cleavage Sites

Further optimization was conducted on NVS962-S and NVS965-S to remove a cleavage site in the heavy chain CDR3. Specifically the heavy chain was cleaved at Y102S103. The following table describes the amino acid substitutions that were made to destroy the cleavage site. The sequences of the modified Fabs is shown in Table 1.

TABLE 3

Modified Fabs

| Clipped Fab | Y102 replaced with: | S103 replaced with: | Modified Fab |
|---|---|---|---|
| NVS962-S | F | I | NVS808 |
|  | K | V | NVS806 |
|  | S | Y | NVS807 |
| NVS965-S | Y | I | NVS804 |
|  | Y | V | NVS805 |
|  | Y | Y | NVS809 |

Example 3: Characterization of Optimized Antibodies

The following example describes methods that may be used to measure antibody affinity. These and other methods of measuring binding affinity are known in the art.

Affinity Determination

Antibody affinity for Factor P was measured by surface plasmon resonance (SPR) using a BIACORE™ T200 (BIACORE™) and solution equilibrium titration (SET). Explanations of each technology and corresponding mean results for Factor P binding are described below. Modelling assumptions take into account concentrations of Factor P in the system, kinetics of Factor P biosynthesis and half-life, as well as the desired dosing schedule, and suggest that a Fab with an affinity of greater than 500 pM for Factor P is sufficient to lower levels of free Factor P.

BIACORE™ Determination

The kinetics of an interaction, i.e. the rates of complex formation ($k_a$) and dissociation ($k_d$), can be determined from the information in a sensorgram. If binding occurs as sample passes over a prepared sensor surface, the response in the sensorgram increases. If equilibrium is reached a constant signal will be seen. Replacing sample with buffer causes the bound molecules to dissociate and the response decreases. BIACORE™ evaluation software generates the values of $k_a$ and $k_d$ by fitting the data to interaction models (Table 4).

BIACORE™ kinetic experiments were done with the BIACORE™ T100 (GE Healthcare) using CM5 sensor chips (GE Healthcare, BR-1005-30) at 25° C. The running buffer was HBS-EP(+) (GE Healthcare, BR-1001-88). Briefly, the following steps were carried out to determine binding affinity.

Prepare anti-FP IgG immobilized sensor chip: Mouse anti-FP monnoclonal antibody (Quidel, A235) (30 ug/ml in acetate pH5.0 coupling buffer (GE Healthcare, BR-1003-51)) was coupled to two different flow cells (Fc1 and 2) on a CM5 chip at 10 ul/min flow rate for 600 seconds by using amino-coupling procedure according to the supplier's instruction (GE Healthcare, BR-1000-50). The final immobilized level will be >7000RU.

Capture FP on second flow cell: 1 ug/ml of FP in running buffer was injected at 10 ul/min on second flow cell (Fc2) to reach capture level ~20 RU for Fab or ~7 RU for IgG kinetics analysis.

Inject anti-FP Fab or IgG at different concentration on both flow cells: Inject anti-FP solution (0.3125 nM-10 nM in running buffer; at 1:2 serial dilutions) on both flow cells (Fc1 and 2) at 60 ul/min for 240 seconds.

Dissociation: Inject HBS-EP(+) running buffer at 60 ul/min on both flow cells to monitor the dissociation between FP and anti-FP Fab/IgG. Dissociation time was set at 2400 seconds for 5 nM and 2.5M Fab/IgG concentrations and at 300 seconds for all other concentrations including another 5 nM Fab/IgG concentration.

Regeneration: Regeneration was performed at the end of each cycle on both flow cells with 10 mM Glycine-HCl pH1.7 (provided by GE Healthcare)+0.05% P20 surfactant (GE Healthcare, BR-1000-54) at a flow rate of 60 ul/min for 15 seconds twice.

Kinetics analysis: Kinetic rate constants was obtained by applying 1:1 binding model with BIAevaluation 1.1 software, wherein the Rmax values were fit locally.

The results of the BIACORE™ binding kinetics determination are shown in Table 4. As shown the antibodies described herein exhibit high affinity binding to human Factor P, with KD values typically less than or equal to 1 nM, and in many cases less than or equal to 200 pM. These antibodies also show very high affinity to cyno Factor P (binding affinity less than 500 pM).

SET Determination

In contrast to kinetic assays using sensor surfaces, such as SPR, SET is a method which determines affinities in solution. It is an equilibrium measurement that does not deliver kinetic data.

In SET, a constant amount of antibody is incubated with different concentrations of antigen until equilibrium is reached. The concentration of free antibody in the equilibrated solution is determined by applying the solution on an antigen coated MSD™ plate (Meso Scale Discovery™) followed by incubation with an ECL-labeled secondary antibody and measurement of signal intensity. At low antigen concentrations, a strong signal is achieved (high concentration of free antibody which binds to the antigen on the plate) whereas for high antigen concentration, the antibody is completely antigen-captured, resulting in a low signal. If a sufficient number of antigen concentrations in a matching range are available, the titration curve allows for a reasonable determination of the affinity, using the appropriate fit model. For a complete titration, antigen concentrations of at least 10-fold higher than the anticipated $K_D$ have to be applied. The constant concentration of antibody applied in the assay should be in the range of, or below, the $K_D$ (Table 4).

For $K_D$ determination by solution equilibrium titration (SET), monomer fractions of antibody protein were used (at least 90% monomer content, analyzed by analytical SEC; Superdex75 (Amersham Pharmacia) for Fab, or Tosoh G3000SWXL (Tosoh Bioscience) for IgG, respectively).

Affinity determination in solution was basically performed as described in the literature (Friguet et al. 305-19). In order to improve the sensitivity and accuracy of the SET method, it was transferred from classical ELISA to ECL based technology (Haenel et al., 2005).

1 mg/ml goat-anti-human (Fab)$_2$ fragment specific antibodies (Dianova) were labeled with MSD Sulfo-TAG™ NHS-Ester (Meso Scale Discovery, Gaithersburg, Md., USA) according to the manufacturers instructions.

Human Factor P (Complement Technology cat#: A139) and Cyno Factor P purified from cyno serum (protocol adapted from Nakano, et al., (1986) *J Immunol Methods* 90:77-83) were coated on standard binding MSD plates (Meso-Scale Discovery, 384-well: MSD cat#: L21XA, 96-well: MSD cat#: L15XA) at 0.2-0.3 µg/ml in 25 µl PBS and incubated overnight at 4° C. Factor P inhibitors were diluted to a fixed concentration (1 pM or 10 pM) in incubation buffer (PBS with 2% BSA (Sigma cat#: A4503) and 1% Tween20 and 1% Triton-X (Sigma cat#: 234729)), and added to a serial dilution of Factor P (human or cyno) in incubation buffer. Samples were allowed to reach equilibrium by incubation at RT overnight. Plates were washed 3× in wash buffer (PBS with 0.05% Tween20), and blocked with 100 µl incubation buffer at RT for 2 hrs. Plates were washed 3× in wash buffer. Sample containing Factor P inhibitors and Factor P titration were added to the plate (25 µl), and incubated at RT for 15 min. Plates were washed 3× in wash buffer. 25 µl detection antibody was added (Anti-Human (Goat) Sulfo-TAG, 1:1000 in incubation buffer, MSD cat#: R32AJ-1), and incubated at RT for 60 min. Plates were washed 3× in wash buffer, and 50 µl of 1×MSD Read buffer T was added (with surfactant, MSD cat#: R92TC-1). Plates were read on a MSD Spector Imager 6000. Data was analyzed using GraphPad Prism software v4, with background (an average of wells containing no Fab) subtracted from each value. X-axis values (concentration of Factor P in solution) were transformed into log 10x. KD values (KD) were fitted from the following model:

Fab:

$$Y=(Top-((Top/(2\times Fab))\times(((((10^\wedge x)+Fab)+KD)-(((((10^\wedge x)+Fab)+KD)\times(((10^\wedge x)+Fab)+KD))-((4\times(10^\wedge x))\times Fab))^\wedge 0.5))))$$

Top=signal at antigen concentration=0
x=concentration of Factor P in solution
Fab=concentration of applied monovalent analyte (Fab)

TABLE 4

Affinity Binding of Factor P Antibodies

| Factor P Antibody | Factor P Species | SET $K_D$ (pM) | Biacore $K_D$ (pM) | Biacore $K_a$ (1/Ms) | Biacore Kd (1/s) |
|---|---|---|---|---|---|
| NVS962 | Human | 46 | 83 | 1.52 × 10$^6$ | 1.25 × 10$^{-4}$ |
|  | Cyno | 47 | 182 | 1.53 × 10$^6$ | 2.79 × 10$^{-4}$ |
| NVS965 | Human | 36 | 16 | 2.65 × 10$^6$ | 4.10 × 10$^{-5}$ |
|  | Cyno | 14 | 28 | 2.24 × 10$^6$ | 6.22 × 10$^{-5}$ |
| NVS963 | Human | 55 | 90 | 1 × 10$^6$ | 1 × 10$^{-4}$ |
|  | Cyno | 115 | 170 | 1 × 10$^6$ | 2 × 10$^{-4}$ |
| NVs966 | Human | 70 | 160 | 2 × 10$^6$ | 3 × 10$^{-4}$ |
|  | Cyno | 40 | 210 | 1 × 10$^5$ | 2 × 10$^{-4}$ |
| NVS964 | Human | 20 | 35 | 1 × 10$^6$ | 4 × 10$^{-5}$ |
|  | Cyno | 190 | 160 | 1 × 10$^6$ | 2 × 10$^{-4}$ |
| NVS967 | Human | 40 | 60 | 1 × 10$^6$ | 9 × 10$^{-5}$ |
|  | Cyno | 280 | 315 | 1 × 10$^6$ | 6 × 10$^{-4}$ |
| NVS962-Q | Human | 1061 | 496 | 6.27 × 10$^5$ | 3.11 × 10$^{-4}$ |
|  | Cyno | 930 | 475 | 5.55 × 10$^5$ | 2.64 × 10$^{-4}$ |
| NVS962-S | Human | 156 | 161 | 7.3 × 10$^5$ | 1.17 × 10$^{-4}$ |
|  | Cyno | 141 | 127 | 5.24 × 10$^5$ | 6.66 × 10$^{-5}$ |
| NVS962-T | Human | 251 | 131 | 6.39 × 10$^5$ | 8.35 × 10$^{-5}$ |
|  | Cyno | 354 | 175 | 4.88 × 10$^5$ | 8.56 × 10$^{-5}$ |
| NVS962-G | Human | 953 | 1140 | 3.87 × 10$^5$ | 4.4 × 10$^{-4}$ |
|  | Cyno | 567 | 1080 | 3.13 × 10$^5$ | 3.39 × 10$^{-4}$ |
| NVS962-S31A | Human | 189 | 225 | 5.04 × 10$^5$ | 1.13 × 10$^{-4}$ |
|  | Cyno | 189 | 234 | 3.72 × 10$^5$ | 8.7 × 10$^{-5}$ |
| NVS965-Q | Human | 301 | 138 | 2.65 × 10$^6$ | 3.66 × 10$^{-4}$ |
|  | Cyno | 201 | 215 | 2.77 × 10$^6$ | 5.94 × 10$^{-4}$ |
| NVS965-S | Human | 51 | 27 | 3.69 × 10$^6$ | 9.9 × 10$^{-5}$ |
|  | Cyno | 36 | 60 | 2.71 × 10$^6$ | 1.63 × 10$^{-4}$ |
| NVS965-T | Human | 52 | 51.4 | 2.37 × 10$^6$ | 1.03 × 10$^{-4}$ |
|  | Cyno | 44 | 74.6 | 2.17 × 10$^6$ | 1.51 × 10$^{-4}$ |
| NVS808 | Human | 107 | 195 | 7.91 × 10$^5$ | 1.54 × 10$^{-4}$ |
|  | Cyno | ND | ND | ND | ND |
| NVS806 | Human | 18 | 52 | 4.34 × 10$^5$ | 2.24 × 10$^{-5}$ |
|  | Cyno | ND | ND | ND | ND |
| NVS807 | Human | 27 | 106 | 1.21 × 10$^6$ | 1.23 × 10$^{-4}$ |
|  | Cyno | ND | ND | ND | ND |
| NVS804 | Human | 0.8 | 5 | 2.72 × 10$^6$ | 1.29 × 10$^{-5}$ |
|  | Cyno | ND | ND | ND | ND |
| NVS805 | Human | 0.3 | 3 | 3.61 × 10$^6$ | 9.88 × 10$^{-6}$ |
|  | Cyno | ND | ND | ND | ND |

TABLE 4-continued

Affinity Binding of Factor P Antibodies

| Factor P Antibody | Factor P Species | SET $K_D$ (pM) | Biacore $K_D$ (pM) | Biacore $K_a$ (1/Ms) | Biacore Kd (1/s) |
|---|---|---|---|---|---|
| NVS809 | Human | 4.2 | 24.7 | $4.25 \times 10^6$ | $1.04 \times 10^{-4}$ |
|  | Cyno | ND | ND | ND | ND |

Example 4: Factor P Antibodies Inhibit the Alternative Complement Pathway

Hemolysis Assay

In hemolytic techniques, all of the complement components must be present and functional. Therefore hemolytic techniques can screen both functional integrity and deficiencies of the complement system (van et al., 1980; Minh et al., 1983; Tanaka et al., 1986). To measure the functional capacity of the classical pathway, sheep red blood cells coated with hemolysin (rabbit IgG to sheep red blood cells) or chicken red blood cells that are sensitized with rabbit anti-chicken antibodies are used as target cells (sensitized cells). These Ag-Ab complexes activate the classical pathway and result in lysis of the target cells when the components are functional and present in adequate concentration. To determine the functional capacity of the alternative pathway in human and cynomolgus sera, rabbit red blood cells are used as the target cell (see U.S. Pat. No. 6,087,120).

The hemolytic assay is a basic functional assay that tests for complement activation and has been used to evaluate the ability of anti-human FP mAbs and Fab molecules to block lysis of red blood cells (RBCs) by complement pathways. In vitro and in vivo inhibition of complement activity by a single-chain Fv fragment recognizing human C5 can be measured using a haemolytic assay (Thomas et al., 1996; Rinder et al., 1995; Rinder et al., 1995). Blockade of C5a and C5b-9 generation inhibits leukocyte and platelet activation during extracorporeal circulation. Briefly, for classical pathway assays, sensitized red blood cells (e.g., chicken RBCs) are used as targets for lysis by complement proteins present in serum. The following assay is of interest for the characterization and screening of Factor P antibodies for their inhibition of the alternative complement pathway.

This procedure was adapted from (Rinder et al., 1995; Thomas et al., 1996).

Reagents:
Rabbit red blood cells (Rb RBCs)—Lampire, Cat#7246408
Human serum Novartis Blood Research Program; or Cyno serum Alpha Genesis
Gelatin veronal buffer (GVB) Boston BioProducts, Cat# IBB-300
EGTA Boston BioProducts, Cat# BM-151
MgCl2
U-bottom 96-well plate Corning, Cat#3795
Flat-bottom 96-well plate Corning, Cat#3370
NP-40 Sigma, Cat#74385

Protocol:
Rabbit red blood cells (RBCs) were washed and adjusted to $8.33 \times 10^7$ cells/ml in GVB/EGTA/Mg++. 50 µl Fab diluted in GVB was added to wells in a 96-well round bottom plate. 50 µl serum diluted in GVB with EGTA and Mg++ was then added. Control wells were prepared in the following manner: serum without Fab (negative control) and cells plus 0.1% NP-40 (100% lysis control), and NP-40 blank wells. Serum with and without Fab and controls were incubated at room temperature for 30 minutes. At that point, 30 µl Rb RBCs were added to sample and control wells and 30 µl of buffer was added to the blank wells. The cells were generally incubated for 30 minutes at 37° C. and the plate centrifuged at 2000 rpm for 5 min. The supernatant was harvested and transferred to a flat-bottom plate. The absorbance of the supernatant was read at OD415 and OD570. Percent hemolysis was calculated using the formula below.

$$\% \text{ Hemolysis} = \frac{(ODsample - ODserum \cdot \text{blank}) - (OD\ 0\%\ \text{lysis} - ODbuffer \cdot \text{blank})}{(OD\ 100\%\ \text{lysis} - ODNP\ 40 \cdot \text{blank}) - (OD\ 0\%\ \text{lysis} - ODbuffer\ 40 \cdot \text{blank})}$$

Table 5 exemplifies of the ability of the Factor P antibodies and antigen binding fragments to inhibit hemolysis in 10% human or 20% cynomolgus serum. Each of the Factor P antibodies described herein inhibited hemolysis with an 1050 of less than or equal to 50 nM.

In contrast, when the assay was performed using sensitized red blood cells in order to examine activation of the classical complement pathway, the Factor P antibodies described herein were found not to inhibit the classical complement pathway (data not shown).

C3b Deposition Assay

One method of measuring the inhibitor activity against the complement C3 in the alternative pathway is to measure its breakdown product, C3b, depositing on zymosan. This ELISA based assay was performed according to the following steps: 25 µl of 1 mg/ml Zymosan A (Sigma Z4250) in carbonate buffer, pH 9.6 (Pierce Cat#28382) was coated on Maxisorp 384-well ELISA plate (Nunc 464718) overnight at 4° C. On the following day, the zymosan-coated plate was aspirated and blocked with 100 µl per well of ELISA blocking buffer, Synblock (AbD Serotec BUFO34C) for 2 h at room temperature. In a separate reaction, the inhibitors, serially diluted in gelatin veronal buffer (Boston Bioproducts IBB320-10 mM Barbital, 145 mM NaCl, 0.1% Gelatin, 0.5 mM $MgCl_2$, 10 mM EGTA) were added to 10% serum supplemented with $MgCl_2$ and EGTA for a final total reaction concentration of 1 mM $MgCl_2$ and 10 mM EGTA. The positive control contained no inhibitor and negative control had 25 mM EDTA. The mixture was allowed to reach equilibrium by incubating at room temperature for 30 min. To remove the blocking buffer, the buffer was aspirated and the plate was washed once with TBS/0.05% Tween-20. 25 µl per well of the 10% serum containing the inhibitors or controls was added to the plate and incubated at 37° C. for 30 min (previously determined by time-course to be within the linear range of C3b deposition on zymosan.) After the 30 min incubation, the plate was washed three times with TBS/0.05% Tween-20. To detect C3b deposition on zymosan, 25 µl per well of chicken anti-human C3-HRP conjugated polyclonal antibody (Immunology Consultants Laboratory, Inc. Cat# CC3-80P-1) diluted according to manufacturer in PBS with 2% BSA Fraction V (Fisher Cat# ICN 16006980), 0.1% Tween20 (Sigma Cat# P1379), and 0.1% TritonX-100 (Sigma Cat# P234729) was added to the plate and incubate at room temperature for 1 h. Afterward, the plate was washed three times with TBS/0.05% Tween-20 and then add 25 µl of Ultra TMB Substrate Solution (Pierce Cat#34028.) When the solution in the well turned blue, the reaction was stopped with 15 µl of 2N sulfuric acid. The plate was read at 450 nm using the Spectromax with correction for the plastic plate at 570 nm ($OD_{450-570\ nm}$ reading.) The percentage of C3b deposition on zymosan was calculated using the following formula:

$$\% \ C3b \ \text{Deposition} = 100 - 100 * \frac{[(OD_{no\ inhibitor} - OD_{25mM\ EDTA}) - (OD_{sample} - OD_{25mM\ EDTA})]}{(OD_{no\ inhibitor} - OD_{25mM\ EDTA})}$$

Each of the antibodies tested were shown to inhibit C3b deposition with an 1050 of at least less than or equal to 10 nM (Table 5).

MAC Deposition Assay

Another assay that was used to determine the ability of the Factor P antibodies to inhibit the alternative complement pathway was to measure the ability of the antibodies to inhibit the generation of the membrane attack complex (MAC), which is downstream of the C3 convertase and the activity of Factor P. Briefly, Zymosan A (Sigma) was coated on a plate at 1 mg/ml in carbonate buffer, pH 9.5, to activate the Alternative Pathway. Fabs were pre-incubated with serum (20% serum, 5 mM $MgCl_2$, 10 mM EDTA), then added to the plate and incubated overnight at room temperature. After washing the plate three times with TBST, MAC was detected by incubation with anti-C5b-9-ALP (Diatec) for 1 h, followed by three washes with TBST, and incubation with 4-methylumbelliferyl phosphate (Fisher) supplemented with 2 mM $MgCl_2$ for 30 minutes. The reaction was stopped with 0.2M EDTA, and the plate was read at ex=355 nm, em=460 nm. Inhibition of MAC deposition was calculated for each sample relative to baseline (EDTA treated human serum) and positive control (human serum), and used to generate the IC50 curve with PRISM.

Table 5 shows data demonstrating the ability of the Factor P antibodies to inhibit the deposition of MAC, thus indicating that the antibodies inhibited the alternative complement pathway. Specifically, the antibodies inhibited MAC deposition with an IC50 of less than or equal to 25 nM.

C3a Deposition Assay

Another method used to assess the ability of Factor P antibodies to inhibit the alternative complement pathway is to measure the ability of antibodies to inhibit the generation of C3a following cleavage of C3 by C3 convertase. The assay was carried out on zymosan-coated Maxisorp plates coated at 10 mg/ml and 10% and 20% human serum pre-incubated with anti-properdin Fab diluted in a $2^n$ series. The serum was added to the plates for 30 minutes at which time the serum was collected for assessment of C3a generation.

Maxisorp plates were coated with anti-C3a des-arg neo antibody (1 ug/ml) overnight, washed three times, and blocked with diluent for two hours at room temperature. Following aspiration of the diluent, serum was added for one hour. Plates were washed three times and a 100 uL/well detection antibody Mouse anti-Human C3a-Biotin 1:1000 diluted in diluent was added. Following an additional one hour incubation, a streptavidin-HRP secondary antibody diluted 1:5000 in diluent was added to the wells for one hour at room temperature. Plates were washed four times before the addition of TMB detection substrate. The reaction was stopped using standard stop solution and absorbance was read at 450-570 nm.

In parallel to the addition of the serum, a standard curve was produced using purified C3a des-arg diluted in serum. Starting at 5 ug/ml, C3a des-arg was serially diluted 1:4 to generate a 7 point curve. The standard curve wells were treated, washed, and read as above.

TABLE 5

Functional Analysis of Factor P Antibodies

| Factor P Antibody | Factor P Species | MAC Deposition, 20% Serum EC50 (nM) | Zymosan-C3b IC50 10% serum (nM) | Hemolytic assay IC50 10% serum (nM) | Inhibition of C3a generation, 20% human serum (nM) |
|---|---|---|---|---|---|
| NVS962 | Human | 18.79 | 2.63 | 13.18 | 78.42 |
|  | Cyno | 12.08 | 9.91 | 16.14 | ND |
| NVS965 | Human | 17.32 | 1.54 | 7.527 | 31.33 |
|  | Cyno | 22.17 | 6.36 | 13.20 | ND |
| NVS963 | Human | ND | 2.34 | 10.11 | 65.08 |
|  | Cyno | ND | 9.75 | 14.53 | ND |
| NVS966 | Human | ND | 1.66 | 7.154 | 41.11 |
|  | Cyno | ND | 6.62 | 13.00 | ND |
| NVS964 | Human | ND | 1.54 | 9.26 | 42.18 |
|  | Cyno | ND | 6.59 | 13.41 | ND |
| NVS967 | Human | ND | 2.53 | 9.61 | 43.53 |
|  | Cyno | ND | 5.92 | 14.01 | ND |
| NVS962-Q | Human | 23.12 | 0.64 | 15.27 | ND |
|  | Cyno | 20.88 | 1.62 | 14.7 | ND |
| NVS962-S | Human | 6.53 | 1.53 | 8.21 | ND |
|  | Cyno | 15.57 | 1.94 | 12.02 | ND |
| NVS962-T | Human | 6.61 | 1.75 | 9.31 | ND |
|  | Cyno | 5.42 | 3.10 | 12.54 | ND |
| NVS962-G | Human | 12.68 | 1.18 | 13.39 | ND |
|  | Cyno | 9.27 | 2.94 | 14.23 | ND |
| NVS962-S31A | Human | 9.96 | 1.15 | 12.79 | ND |
|  | Cyno | 7.86 | 3.12 | 11.61 | ND |
| NVS965-Q | Human | 15.40 | 1.64 | 9.71 | ND |
|  | Cyno | 9.39 | 3.30 | 14.71 | ND |
| NVS965-S | Human | 7.32 | 1.39 | 7.89 | ND |
|  | Cyno | 8.12 | 1.57 | 12.02 | ND |
| NVS965-T | Human | 13.80 | 0.77 | 7.15 | ND |
|  | Cyno | 10.98 | 1.91 | 12.54 | ND |
| NVS808 | Human | 6.51 | ND | 13.28 | ND |
|  | Cyno | 8.38 | ND | 15.53 | ND |
| NVS806 | Human | 5.74 | ND | 10.14 | ND |
|  | Cyno | 6.51 | ND | 13.93 | ND |
| NVS807 | Human | 5.40 | ND | 12.91 | ND |
|  | Cyno | 6.35 | ND | 12.57 | ND |
| NVS804 | Human | 5.85 | ND | 12.38 | ND |
|  | Cyno | 8.51 | ND | 14.44 | ND |
| NVS805 | Human | 5.90 | ND | 12.82 | ND |
|  | Cyno | 5.95 | ND | 22.11 | ND |
| NVS809 | Human | 6.46 | ND | 12.1 | ND |
|  | Cyno | 5.90 | ND | 12.78 | ND |

ND: Not Determined

Example 5: Species Cross Reactivity

In order to determine whether, in addition to human and cynomolgus, the anti-Factor P antibodies described herein would bind to Factor P from other species, MAC deposition and hemolytic assays were carried out as described above. BIACORE™ analysis, or hemolytic assays were carried out as described above. The serum concentrations used for each species were as follows: 10 and 20% rabbit, 10 and 20% cynomolgus, and 10 and 20% human sera. Rat Factor P binding was assessed by BIACORE™. As shown in Table 6 below, the Factor P antibodies were able to cross react with several species, including rabbit, rat and cynomolgus.

TABLE 6

Species cross-reactivity

| Antibody | Human | Rat | Rabbit | Cyno |
|---|---|---|---|---|
| NVS962 | X | X | X | X |
| NVS962-S | X | X | X | X |
| NVS801 | X | X | X | X |
| NVS965 | X | ND | ND | X |
| NVS965-S | X | ND | ND | X |
| NVS808 | X | ND | X | X |
| NVS806 | X | ND | X | X |

ND: not determined

Example 6: Epitope Mapping

Factor P is comprised of several Thrombospondin repeat domains (TSR 0-6). The TSR0 domain is also referred to as the N terminal domain. Epitope mapping of the Factor P Fabs was performed by creating mouse and human chimeras for each TSR. Previous functional assays showed that the Fabs do not bind to mouse Factor P (hemolytic assays), although each of the chimeras was functional in Factor P-depleted serum. Using this method it was determined that all of the Fabs bind to TSR 5 (SEQ ID NO: 406). FIG. 1C shows the antibodies bind region B of TSR5. The commercially-available antibody, A233, was shown not to bind in this region. Binding can be assessed by ELISA or BIA-CORE™ using standard methods. For one Ab, NVS487, the data was not conclusive due to cross reactivity to mouse Factor P. Sequence alignment between mouse and human Factor P TSR5 domain shows the epitope includes the amino acids of SEQ ID NO: 408.

Example 7: In Vivo Inhibition of the Alternative Complement Pathway

Experiments were performed in cynomolgus money with antibodies of the invention to determine their ability to inhibit the alternative complement pathway.

The test item, NVS962, was administered at the dose levels shown in Table 7. The route of administration was either intravitral (IVT) or intravenous (IV).

TABLE 7

In Vivo Study Design

| Group number | Group description | Dose level | Route of dosing | Dose volume (µL/injection) | Animals/group Male | Animals/group Female |
|---|---|---|---|---|---|---|
| 1 | Control | 0 (vehicle) | IVT<br>IV | 50/IVT injection<br>100/IV injection | 1 | 1 |
| 2 | Low IVT | 1 mg/eye<br>(2 mg/monkey) | IVT | 50/IVT injection | 1 | 1 |
| 3 | IV | 10 mg/monkey | IV | 100/IV injection | 1 | 1 |
| 4 | High IVT | 5 mg/eye<br>(10 mg/monkey) | IVT | 50/IVT injection | 1 | 1 |

The test item and vehicle solutions (vehicle: 10 mM His/His-HCl; 10% trehalose; 0.02% Tween 20; pH 5.5) were administered intravitreally and intravenously on days 1, 15, and 29 of the study as indicated in Table 7.

Assessment of toxicity was based on mortality, clinical observations, body weights, pharmacodynamics (hemolytic analysis), ophthalmic examinations, intraocular pressure measurements, electroretinography, hematology, clinical chemistry, organ weights, and pathology.

There were no mortalities during the study and no test item related findings were seen after evaluation of clinical signs, body weights, ophthalmic examinations, intraocular pressure measurements, electroretinography, hematology, clinical chemistry, organ weights, and pathology.

Complement mediated hemolytic activity was measured using the hemolytic assay described above (see Example 4). Analysis of the hemolytic assay data showed that IV administration of NVS962 led to a complete or nearly complete but short-lived, inhibition of hemolytic complement activity immediately after administration. When administered by the IVT route at a dose of 1 mg/eye, the test item had little or no effect on serum hemolytic complement activity. At 5 mg/eye and in 10% cynomolgus serum, a complete or nearly complete inhibition of hemolytic complement activity was observed.

Example 8: Synergistic Inhibition of the Alternative Complement Pathway by Antibody Combinations Hemolysis Assay Hemolytic assays using the Fab versions of the anti-C5 antibody 8109 from Table 2 and anti-Factor P antibody NVS962 from Table 1 were performed as described in Example 4.

FIG. 2 exemplifies of the ability of the Factor P antibodies and antigen binding fragments in combinations with anti-C5 antibodies and antigen binding fragments to inhibit hemolysis in 20% human serum. 500 nM anti-factor P and 500 nM anti-C5 Fabs individually demonstrate no inhibition of hemolysis when incubated for 60 mins. In contrast, the combination of anti-factor P and anti-C5 antibodies at the same concentration and at concentrations as low as 167 nM demonstrate near complete inhibition of hemolysis. In addition, the near complete inhibition of hemolysis lasts for up to 250 minutes.

Data from the hemolytic assay was used with Chalice Analyzer software to determine whether the combination of complement inhibiting antibodies acted synergistically to block complement activation. Combination effects can be characterized by comparing each data point's inhibition to that of a combination reference model that was derived from the single agent curves (Greco, Bravo, Parsons (1995). The search for synergy: a critical review from a response surface perspective. *Pharmacol Rev* 47(2): 331-85). In the Loewe additivity model (Loewe (1928). *Die quantitativen Probleme der Pharmakologie. Ergebn. Physiol.* 27: 47-187), $I_{Loewe}$ ($C_X, C_Y$) is the inhibition that satisfies ($C_X/C_X$)+($C_Y/C_Y$)=1, and $IC_{X,Y}$ are the effective concentrations at $I_{Loewe}$ for the fitted single agent curves. Loewe additivity is the generally accepted reference for synergy (Greco et al.), as it represents the combination response generated if X and Y are the same compound.

Potency shifting is usually shown using an isobologram (Greco et al.) which shows how much less drug is required in combination to achieve a desired effect level, when compared to the single agent doses needed to reach that effect. The choice of effect level for the isobologram display and combination index calculations can either be manually or automatically selected in the Chalice Analyzer. The automatic iso-level selection algorithm finds the observed $I_{data}$ with the largest $I_{data}-I_{Loewe}$, excluding those points with $I_{data}$ exceeding the lesser single agent's $I_{max}$. This exclusion is applied to ensure that the isobologram reflects the best synergy at levels covered by both single agents. Having selected an isobologram level $I_{cut}$, the isobologram is drawn by identifying the locus of concentrations that correspond to crossing the chosen iso-level. The isobologram shows the standard isobolographic analysis of synergy compared to the Loewe dose-additive "drug-with-itself" standard. For a specified isobologram level, the observed iso-effect contour (e.g., curved line in FIG. 3) is displayed with the theoretical dose-additive contour (e.g., straight line in FIG. 3), on an $IC_{effect}$-normalized linear concentration scale for both substances in the combination. The Dose-additive reference is always a line connecting the two $IC_{effect}$ concentrations. The $IC_{effect}$ crossing points are found by interpolating the fitted sigmoidal dose response curves.

Potency shifting is scored as the combination index (Chou, Talalay (1984). *Quantitative analysis of dose-effect relationships: the combined effects of multiple drugs or enzyme inhibitors. Adv Enzyme Regul* 22: 27-55) CI. For a chosen iso-effect level $I_{cut}$, $CI_I=(C_X/EC_X)_I+(C_Y/EC_Y)_I$, where ($C_X/EC_X)_I$ for a particular data point is the ratio of the X compound's measured concentration to its effective concentration at the chosen inhibition level. The CI can be thought of as a rough estimate of how much drug was needed in combination relative to the single agent doses required to achieve the chosen effect level, and a value of 0.1 means that only a tenth of equivalent amounts of the single agents were needed for the combination to reach the same effect level. CI values in the range of 0.5-0.7 are typical for in vitro measurements of current clinical combinations (Greco et al.). A CI value of 1.0 is indicative of an additive effect of a combination of antibodies, while a CI value of less than 0.5 is indicative of a synergistic effect resulting from the antibody combination. In the Chalice Analyzer, the best CI is reported from the many combination index values calculated for each $I_{cut}$ crossing concentration. Among all the measured CI values, the one with the largest signal-to-noise level is reported as the best combination index.

Data from the hemolytic assay were expressed as % inhibition and loaded into an 8×8 Excel table, in which the antibodies concentrations were expressed as uM values. The Excel template was uploaded to the Chalice software (Lehar et al. 2009) and the combination index was generated by creating an isobologram curve using IC20 for each antibody ($CI=C_X/IC_X+C_Y/IC_Y$, where $IC_X$ and $IC_Y$ are, respectively, the concentrations of anti-factor P antibody and anti-C5 antibody alone that result in a 20% inhibition effect and $C_X$ and $C_Y$ are the concentrations of each drug in the mixture that yield 20% inhibition). The combination index at 20% inhibition is 0.36, indicating synergy between anti-factor P antibody and anti-C5 antibody (FIG. 3).

Macrophage Infiltration

Figure 4:
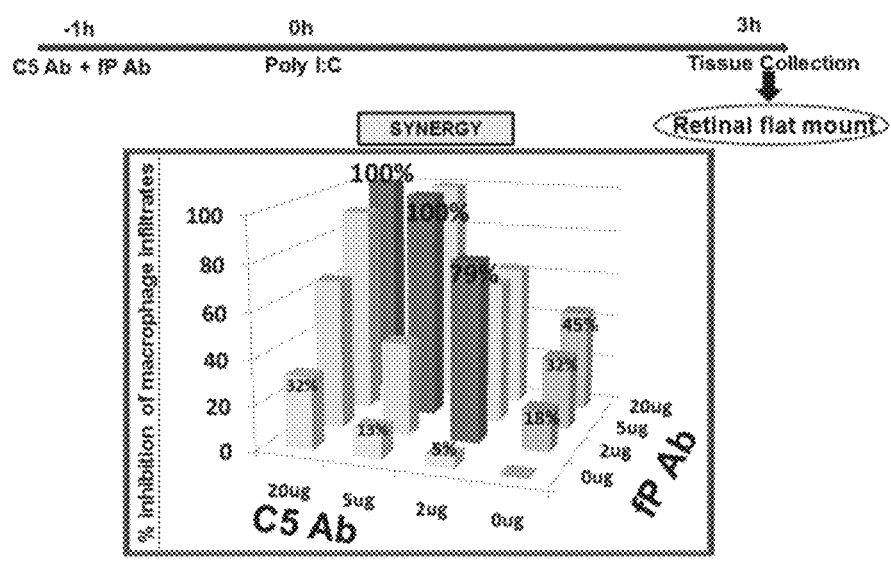
FIG. 4 shows the % inhibition of macrophage infiltrates in a mouse poly-IC model, comparing the inhibition of anti-FactorP and anti-C5 antibodies singly and in combination.

The effect of anti-fP and anti-C5 Fabs individually or in combination were assessed in vivo using the poly-IC murine model of ocular inflammation. Mice were injected i.v. with synthetic dsRNA analog, poly I:C in 0.1 ml PBS systemically into C57BL/6 mice along with anti-fP (antibody NVS962 from Table 1) and anti-C5 antibodies (antibody 8019 from Table 2) individually or in combination. Mice were euthanized at indicated time points. Eyes and retinas were collected and protein extracts were prepared for cytokine and chemokine analysis using a multiplex assay (Pierce). To determine retinal leukocyte infiltration, eyes were fixed in 4% paraformaldehyde and stained with Alexa Fluor-488 conjugated F4/80 antibody for macrophages. The retinas were flat mounted with the retinal vasculature orientated superiorly onto a glass slide and coversliped with a drop of Vectashield mounting medium (Vector Laboratories Inc, Burtingame, Calif.). Fluorescent images of five (500 um) regions on each retina were captured using the Axiocam MR3 camera on a Axio.ImageM1 microscope (Zeiss). The number of neutrophils and macrophages was quantified with Axiovision software (Version 4.5 Zeiss). Using optical coherence tomography (OCT), images of retinas were obtained and analysed from mice treated with poly I:C. These results (FIG. 4) demonstrate that at the highest concentrations tested (20 ug) no greater than 45% inhibition of macrophage inhibition was observed. In contrast, combinations of the anti-Factor P and C5 antibodies at concentrations as low as 2 ug demonstrated 79% inhibition and increasing the concentration achieved 100% inhibition (compared to only 13% and 32% inhibition respectively for the anti-C5 and anti-Factor P antibodies individually).

Figure 5:
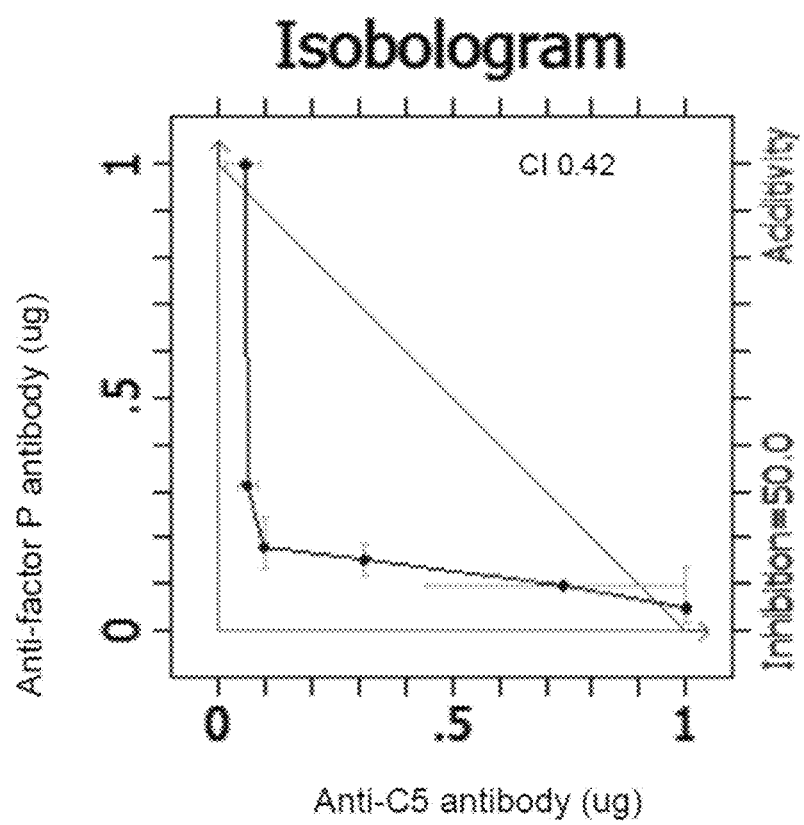
FIG. 5 shows an isobologram generated using the data from the poly-IC results depicted in FIG. 4.

Data from in vivo poly-IC model (macrophage infiltration) described in the preceding paragraph were expressed as % inhibition and loaded into a 4×4 Excel table, in which the antibody doses were expressed as ug values. The Excel template was uploaded to the Chalice analyzer (described above) and the combination index was generated by creating an isobologram curve using IC50 for each antibody ($CI=C_X/IC_X+C_Y/IC_Y$, where $IC_X$ and $IC_Y$ are, respectively, the concentrations of anti-factor P antibody and anti-C5 antibody alone that result in a 50% inhibition effect and $C_X$ and $C_Y$ are the concentrations of each drug in the mixture that yield 50% inhibition). The combination index at 50% inhibition is 0.42 (See FIG. 5), indicating synergy between anti-factor P antibody and anti-C5 antibody.

The invention claimed is:

1. A composition comprising:

a first antibody, or antigen binding fragment thereof, that binds Factor P, wherein the first antibody or antigen binding fragment thereof comprises a heavy chain variable region and a light chain variable region, wherein the heavy chain variable region CDR1, 2, and 3 (HCDR1, HCDR2, and HCDR3) and the light chain variable region CDR1, 2, and 3 (LCDR1, LCDR2, and LCDR3) are selected from the group consisting of:

a) HCDR1, HCDR2, and HCDR3 as set forth in SEQ ID NOs: 1, 2, and 3, respectively, and LCDR1, LCDR2, and LCDR3 as set forth in SEQ ID NOs: 4, 5, and 6, respectively;

b) HCDR1, HCDR2, and HCDR3 as set forth in SEQ ID NOs: 15, 16, and 17, respectively, and LCDR1, LCDR2, and LCDR3 as set forth in SEQ ID NOs: 18, 19, and 20, respectively;

c) HCDR1, HCDR2, and HCDR3 as set forth in SEQ ID NOs: 29, 30, and 31, respectively, and LCDR1, LCDR2, and LCDR3 as set forth in SEQ ID NOs: 32, 33, and 34, respectively;

d) HCDR1, HCDR2, and HCDR3 as set forth in SEQ ID NOs: 43, 44, and 45, respectively, and LCDR1, LCDR2, and LCDR3 as set forth in SEQ ID NOs: 46, 47, and 48, respectively;

e) HCDR1, HCDR2, and HCDR3 as set forth in SEQ ID NOs: 57, 58, and 59, respectively, and LCDR1, LCDR2, and LCDR3 as set forth in SEQ ID NOs: 60, 61, and 62, respectively;

f) HCDR1, HCDR2, and HCDR3 as set forth in SEQ ID NOs: 71, 72, and 73, respectively, and LCDR1, LCDR2, and LCDR3 as set forth in SEQ ID NOs: 74, 75, and 76, respectively;

g) HCDR1, HCDR2 and HCDR3 as set forth in SEQ ID NOs: 85, 86, and 87, respectively, and LCDR1, LCDR2, and LCDR3 as set forth in SEQ ID NOs: 88, 89, and 90, respectively;

h) HCDR1, HCDR2, and HCDR3 as set forth in SEQ ID NOs: 99, 100, and 101, respectively, and LCDR1, LCDR2, and LCDR3 as set forth in SEQ ID NOs: 102, 103, and 104, respectively;

i) HCDR1, HCDR2, and HCDR3 as set forth in SEQ ID NOs: 113, 114, and 115, respectively, and LCDR1, LCDR2, and LCDR3 as set forth in SEQ ID NOs: 116, 117, and 118, respectively;

j) HCDR1, HCDR2, and HCDR3 as set forth in SEQ ID NOs: 127, 128, and 129, respectively, and LCDR1, LCDR2, and LCDR3 as set forth in SEQ ID NOs: 130, 131, and 132, respectively;

k) HCDR1, HCDR2, and HCDR3 as set forth in SEQ ID NOs: 141, 142, and 143, respectively, and LCDR1, LCDR2, and LCDR3 as set forth in SEQ ID NOs: 144, 145, and 146, respectively;

l) HCDR1, HCDR2, and HCDR3 as set forth in SEQ ID NOs: 155, 156, and 157, respectively, and LCDR1, LCDR2, and LCDR3 as set forth in SEQ ID NOs: 158, 159, and 160, respectively;

m) HCDR1, HCDR2, and HCDR3 as set forth in SEQ ID NOs: 169, 170, and 171, respectively, and LCDR1, LCDR2, and LCDR3 as set forth in SEQ ID NOs: 172, 173, and 174, respectively;

n) HCDR1, HCDR2, and HCDR3 as set forth in SEQ ID NOs: 183, 184, and 185, respectively, and LCDR1, LCDR2, and LCDR3 as set forth in SEQ ID NOs: 186, 187, and 188, respectively;

o) HCDR1, HCDR2, and HCDR3 as set forth in SEQ ID NOs: 197, 198, and 199, respectively, and LCDR1, LCDR2, and LCDR3 as set forth in SEQ ID NOs: 200, 201, and 202, respectively;

p) HCDR1, HCDR2, and HCDR3 as set forth in SEQ ID NOs: 211, 212, and 213, respectively, and LCDR1, LCDR2, and LCDR3 as set forth in SEQ ID NOs: 214, 215, and 216, respectively;

q) HCDR1, HCDR2, and HCDR3 as set forth in SEQ ID NOs: 225, 226, and 227, respectively, and LCDR1, LCDR2, and LCDR3 as set forth in SEQ ID NOs: 228, 229, and 230, respectively;

r) HCDR1, HCDR2, and HCDR3 as set forth in SEQ ID NOs: 239, 240, and 241, respectively, and LCDR1, LCDR2, and LCDR3 as set forth in SEQ ID NOs: 242, 243, and 244, respectively;

s) HCDR1, HCDR2, and HCDR3 as set forth in SEQ ID NOs: 253, 254, and 255, respectively, and LCDR1, LCDR2, and LCDR3 as set forth in SEQ ID NOs: 256, 257, and 258, respectively; and t) HCDR1, HCDR2, and HCDR3 as set forth in SEQ ID NOs: 267, 268, and 269, respectively, and LCDR1, LCDR2, and LCDR3 as set forth in SEQ ID NOs: 270, 271, and 272, respectively; and a second antibody, or antigen binding fragment thereof, that binds C5, wherein the second antibody or antigen binding fragment thereof comprises a heavy chain variable region and a light chain variable region, wherein the heavy chain variable region CDR1, 2, and 3 (HCDR1, HCDR2, and HCDR3) and the light chain variable region CDR1, 2, and 3 (LCDR1, LCDR2, and LCDR3) are selected from the group consisting of:

a) HCDR1, HCDR2, and HCDR3 as set forth in SEQ ID NOs: 410, 411, and 412, respectively, and LCDR1, LCDR2, and LCDR3 as set forth in SEQ ID NOs: 413, 414, and 415, respectively;

b) HCDR1, HCDR2, and HCDR3 as set forth in SEQ ID NOs: 426, 427, and 428, respectively, and LCDR1, LCDR2, and LCDR3 as set forth in SEQ ID NOs: 429, 430, and 431, respectively;

c) HCDR1, HCDR2, and HCDR3 as set forth in SEQ ID NOs: 442, 443, and 444, respectively, and LCDR1, LCDR2, and LCDR3 as set forth in SEQ ID NOs: 445, 446, and 447, respectively;

d) HCDR1, HCDR2, and HCDR3 as set forth in SEQ ID NOs: 426, 458, and 428, respectively, and LCDR1, LCDR2, and LCDR3 as set forth in SEQ ID NOs: 429, 430, and 459, respectively; and e) HCDR1, HCDR2, and HCDR3 as set forth in SEQ ID NOs: 470, 471, and 472, respectively, and LCDR1, LCDR2, and LCDR3 as set forth in SEQ ID NOs: 473, 474 and 475, respectively.

2. The composition of claim 1, wherein said composition inhibits ocular inflammation.

3. The composition of claim 2, wherein said ocular inflammation is determined by measuring neutrophil accumulation and/or macrophage recruitment in the retina.

4. The composition of claim 1, wherein said composition inhibits neutrophil accumulation in the retina.

5. The composition of claim 1, wherein said composition inhibits macrophage recruitment in the retina.

6. The composition of claim 1, wherein the first antibody or antigen binding fragment thereof comprises heavy and light chain variable regions having amino acid sequences as set forth in SEQ ID NOs: 7 and 8; SEQ ID NOs: 21 and 22; SEQ ID NOs: 35 and 36; SEQ ID NOs: 49 and 50; SEQ ID NOs: 63 and 64; SEQ ID NOs: 77 and 78; SEQ ID NOs: 91 and 92; SEQ ID NOs: 105 and 106; SEQ ID NOs: 119 and 120; SEQ ID NOs: 133 and 134; SEQ ID NOs: 147 and 148; SEQ ID NOs: 161 and 162; SEQ ID NOs: 175 and 176; SEQ ID NOs: 189 and 190; SEQ ID NOs: 203 and 204; SEQ ID NOs: 217 and 218; SEQ ID NOs: 231 and 232; SEQ ID NOs: 245 and 246; SEQ ID NOs: 259 and 260; or SEQ ID NOs: 273 and 274, respectively.

7. The composition of claim 1, wherein the first antibody, or antigen binding fragment thereof, comprises a heavy chain variable region comprising an amino acid sequence as set forth in SEQ ID NO: 7, 21, 35, 49, 63, 77, 91, 105, 119, 133, 147, 161, 175, 189, 203, 217, 231, 245, 259, or 273, and a light chain variable region, wherein said heavy chain variable region and said light chain variable region combine to form an antigen binding site to Factor P.

8. The composition of claim 1, wherein the first antibody, or antigen binding fragment thereof, comprises a light chain variable domain comprising an amino acid sequence as set forth in SEQ ID NO: 8, 22, 36, 50, 64, 78, 92, 106, 120, 134, 148, 162, 176, 190, 204, 218, 232, 246, 260, or 274, and a heavy chain variable domain, wherein the light chain variable domain and the heavy chain variable domain combine to form an antigen binding site to Factor P.

9. The composition of claim 7, wherein the first antibody or antigen binding fragment thereof comprises the light chain variable region sequence of SEQ ID NO: 8, 22, 36, 50, 64, 78, 92, 106, 120, 134, 148, 162, 176, 190, 204, 218, 232, 246, 260, or 274.

10. The composition of claim 1, wherein the first antibody, or antigen binding fragment thereof, comprises a heavy chain of SEQ ID NO: 9, 23, 37, 51, 65, 79, 93, 107, 121, 135, 149, 163, 177, 191, 205, 219, 233, 247, 261, or 275, and a light chain, wherein the heavy chain and the light chain combine to form an antigen binding site to Factor P.

11. The composition of claim 1, wherein the first antibody, or antigen binding fragment thereof, comprises a light chain of SEQ ID NO: 10, 24, 38, 52, 66, 80, 94, 108, 122, 136, 150, 164, 178, 192, 206, 220, 234, 248, 262, or 276, and a heavy chain, wherein the light chain and the heavy chain combine to form an antigen binding site to Factor P.

12. The composition of claim 10, wherein the first antibody or antigen binding fragment thereof comprises a light chain of SEQ ID NO: 10, 24, 38, 52, 66, 80, 94, 108, 122, 136, 150, 164, 178, 192, 206, 220, 234, 248, 262, or 276.

13. The composition of claim 1, wherein the first antibody, or antigen binding fragment thereof, comprises a heavy chain with an amino acid sequence as set forth in SEQ ID NO: 9, 23, 37, 51, 65, 79, 93, 107, 121, 135, 149, 163, 177, 191, 205, 219, 233, 247, 261, or 275, and a light chain with an amino acid sequence as set forth in SEQ ID NO: 10, 24, 38, 52, 66, 80, 94, 108, 122, 136, 150, 164, 178, 192, 206, 220, 234, 248, 262, or 276.

14. The composition of claim 1, wherein the first antibody, or antigen binding fragment thereof, comprises a heavy chain and a light chain with an amino acid sequence as set forth in SEQ ID NO: 9 and 10, 23 and 24, 37 and 38, 51 and 52, 65 and 66, 79 and 80, 93 and 94, 107 and 108, 121 and 122, 135 and 136, 149 and 150, 163 and 164, 177 and 178, 191 and 192, 205 and 206, 219 and 220, 233 and 234, 247 and 248, 261 and 262, or 275 and 276, respectively.

15. The composition of claim 1, wherein the second antibody or antigen binding fragment thereof comprises heavy and light chain variable regions having amino acid sequences as set forth in SEQ ID NOs: 416 and 417; SEQ ID NOs: 432 and 433; SEQ ID NOs: 448 and 449; SEQ ID NOs: 460 and 461; or SEQ ID NOs: 476 and 477, respectively.

16. The composition of claim 6, wherein the second antibody or antigen binding fragment thereof comprises heavy and light chain variable regions having amino acid sequences as set forth in SEQ ID NOs: 416 and 417; SEQ ID NOs: 432 and 433; SEQ ID NOs: 448 and 449; SEQ ID NOs: 460 and 461; or SEQ ID NOs: 476 and 477, respectively.

17. The composition of claim 1, wherein the second antibody or antigen binding fragment thereof comprises a heavy chain variable region comprising an amino acid sequence as set forth in SEQ ID NO: 416, 432, 448, 460, or 476, and a light chain variable region, wherein said heavy chain variable region and said light chain variable region combine to form an antigen binding site to C5.

18. The composition of claim 7, wherein the second antibody or antigen binding fragment thereof comprises a heavy chain variable region comprising an amino acid sequence as set forth in SEQ ID NO: 416, 432, 448, 460, or 476, and a light chain variable region, wherein said heavy chain variable region and said light chain variable region combine to form an antigen binding site to C5.

19. The composition of claim 1, wherein the second antibody or antigen binding fragment thereof comprises a light chain variable region comprising an amino acid sequence as set forth in SEQ ID NO: 417, 433, 449, 461, or 477, and a heavy chain variable domain, wherein the light chain variable domain and the heavy chain variable domain combine to form an antigen binding site to C5.

20. The composition of claim 8, wherein the second antibody or antigen binding fragment thereof comprises a light chain variable region comprising an amino acid sequence as set forth in SEQ ID NO: 417, 433, 449, 461, or 477, and a heavy chain variable domain, wherein the light chain variable domain and the heavy chain variable domain combine to form an antigen binding site to C5.

21. The composition of claim 7, wherein the second antibody or antigen binding fragment thereof comprises the light chain variable region sequence of SEQ ID NO: 417, 433, 449, 461, or 477.

22. The composition of claim 9, wherein the second antibody or antigen binding fragment thereof comprises the light chain variable region sequence of SEQ ID NO: 417, 433, 449, 461, or 477.

23. The composition of claim 1, wherein the second antibody or antigen binding fragment thereof comprises a heavy chain sequence of SEQ ID NO: 418, 434, 450, 462, or 478, and a light chain, wherein the heavy chain and the light chain combine to form an antigen binding site to C5.

24. The composition of claim 10, wherein the second antibody or antigen binding fragment thereof comprises a heavy chain sequence of SEQ ID NO: 418, 434, 450, 462, or 478, and a light chain, wherein the heavy chain and the light chain combine to form an antigen binding site to C5.

25. The composition of claim 1, wherein the second antibody or antigen binding fragment thereof comprises a light chain sequence of SEQ ID NO: 419, 435, 451, 463, or 479, and a heavy chain, wherein the light chain and the heavy chain combine to form an antigen binding site to C5.

26. The composition of claim 11, wherein the second antibody or antigen binding fragment thereof comprises a light chain sequence of SEQ ID NO: 419, 435, 451, 463, or 479, and a heavy chain, wherein the light chain and the heavy chain combine to form an antigen binding site to C5.

27. The composition of claim 10, wherein the second antibody or antigen binding fragment thereof comprises a light chain sequence of SEQ ID NO: 419, 435, 451, 463, or 479.

28. The composition of claim 12, wherein the second antibody or antigen binding fragment thereof comprises a light chain sequence of SEQ ID NO: 419, 435, 451, 463, or 479.

29. The composition of claim 1, wherein the second antibody or antigen binding fragment thereof comprises a heavy chain with an amino acid sequence as set forth in SEQ ID NO: 418, 434, 450, 462, or 478, and a light chain with an amino acid sequence as set forth in SEQ ID NO: 419, 435, 451, 463, or 479.

30. The composition of claim 13, wherein the second antibody or antigen binding fragment thereof comprises a heavy chain with an amino acid sequence as set forth in SEQ ID NO: 418, 434, 450, 462, or 478, and a light chain with an amino acid sequence as set forth in SEQ ID NO: 419, 435, 451, 463, or 479.

31. The composition of claim 1, wherein the second antibody or antigen binding fragment thereof comprises a heavy chain and a light chain with an amino acid sequence as set forth in SEQ ID NOs: 418 and 419, 434 and 435; 450 and 451; 462 and 463; or 478 and 479, respectively.

32. The composition of claim 14, wherein the second antibody or antigen binding fragment thereof comprises a heavy chain and a light chain with an amino acid sequence as set forth in SEQ ID NOs: 418 and 419, 434 and 435; 450 and 451; 462 and 463; or 478 and 479, respectively.

33. The composition of claim 1, wherein the composition inhibits the alternative complement pathway.

* * * * *

SEQUENCE LISTING

<160> NUMBER OF SEQ ID NOS: 487

<210> SEQ ID NO 1
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 1

Ser Tyr Ala Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ile Ile Pro Ile Phe Gly Thr Ala Asn Tyr Ala Gln Lys Phe Gln
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Gly Gly Tyr Ser Phe Asp Ser
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Gly Asp Asn Leu Gly Ser Lys Tyr Val Asp
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Asp Asn Asn Arg Pro Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

Gln Thr Tyr Thr Ser Gly Asn Asn Tyr Leu
1               5                   10

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser
            115

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
                20                  25                  30

Asp Trp Tyr Gln Gln Lys Pro Gly Gln Ala Pro Val Leu Val Ile Tyr
            35                  40                  45

Ser Asp Asn Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu
            100                 105

<210> SEQ ID NO 9
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
    210                 215                 220

<210> SEQ ID NO 10
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
     130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 11
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtgcagc tggtgcagag cggagccgaa gtgaagaaac ccggcagcag cgtgaaggtg      60
tcctgcaagg ccagcggcgg caccttcaac agctacgcca tcagctgggt gcgccaggct     120
cctggacagg gcctggaatg gatgggccgg atcatcccca tcttcggcac cgccaactac     180
gcccagaaat tccagggcag agtgaccatc accgccgacg agagcaccag caccgcctac     240
atggaactga gcagcctgag aagcgaggac accgccgtgt actactgtgc ccggcacggc     300
ggctacagct cgatagctg gggccagggc accctggtga ccgtgagctc a               351

<210> SEQ ID NO 12
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
agctacgagc tgactcagcc ccctctgtg tctgtggccc ctggccagac cgccagaatc       60
agctgcagcg gcgacaacct gggcagcaaa tacgtggact ggtatcagca gaagcccggc     120
caggctcccg tgctggtgat ctacagcgac aacaaccggc ccagcggcat ccctgagcgg     180
ttcagcggca gcaacagcgg caataccgcc accctgacca tcagcggcac ccaggccgag     240
gacgaggccg actactactg ccagacctac accagcggca caactaccct ggtgttcgga     300
ggcggaacaa agttaaccgt ccta                                            324

<210> SEQ ID NO 13
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gaggtgcagc tggtgcagag cggagccgaa gtgaagaaac ccggcagcag cgtgaaggtg      60
tcctgcaagg ccagcggcgg caccttcaac agctacgcca tcagctgggt gcgccaggct     120

```
cctggacagg gcctggaatg gatgggccgg atcatcccca tcttcggcac cgccaactac    180
gcccagaaat tccagggcag agtgaccatc accgccgacg agagcaccag caccgcctac    240
atggaactga gcagcctgag aagcgaggac accgccgtgt actactgtgc ccggcacggc    300
ggctacagct tcgatagctg gggccagggc accctggtga ccgtgagctc agcctccacc    360
aagggtccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
```

<210> SEQ ID NO 14
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
agctacgagc tgactcagcc cccttctgtg tctgtggccc ctggccagac cgccagaatc    60
agctgcagcg gcgacaacct gggcagcaaa tacgtggact ggtatcagca gaagcccggc    120
caggctcccg tgctggtgat ctacagcgac aacaaccggc cagcggcat ccctgagcgg    180 ttcagcggca gcaacagcgg caataccgcc accctgacca tcagcggcac ccaggccgag    240
gacgaggccg actactactg ccagacctac accagcggca caactaccct ggtgttcgga    300
ggcggaacaa agttaaccgt cctaggtcag cccaaggctg ccccctcggt cactctgttc    360 ccgcccctcct ctgaggagct tcaagccaac aaggccacac tggtgtgtct cataagtgac    420
ttctacccgg gagccgtgac agtggcctgg aaggcagata gcagccccgt caaggcggga    480
gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                       642
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Tyr Ala Ile Ser
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Ile Asn Pro Tyr Tyr Gly Asp Ala Ile Tyr Ala Gln Lys Phe Gln
1               5                   10                  15

Gly

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Tyr Ser Asp Tyr Met Asp Tyr
1               5

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Gly Ser Ser Ser Asn Ile Gly Ala Gly Tyr Asp Val His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Asn Ser His Arg Pro Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ser Tyr Asp Glu Ser Ala His Ser
1               5

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Pro Ile Asn Pro Tyr Tyr Gly Asp Ala Ile Tyr Ala Gln Lys Phe

-continued

```
                    50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Tyr Tyr Ser Asp Tyr Met Asp Tyr Trp Gly Gln Gly Thr Leu
                100                 105                 110

Val Thr Val Ser Ser
            115

<210> SEQ ID NO 22
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile His Asp Asn Ser His Arg Pro Ser Gly Val Pro Asp Arg Phe
        50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Ala Ser Tyr Asp Glu Ser
                     85                  90                  95

Ala His Ser Val Phe Gly Gly Gly Thr Lys Leu Thr Val Leu
                100                 105                 110

<210> SEQ ID NO 23
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Pro Ile Asn Pro Tyr Tyr Asp Ala Ile Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Tyr Tyr Ser Asp Tyr Met Asp Tyr Trp Gly Gln Gly Thr Leu
                100                 105                 110

Val Thr Val Ser Ser Ala Ser Thr Lys Gly Pro Ser Val Phe Pro Leu
```

```
                115                 120                 125
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys
        210                 215                 220

<210> SEQ ID NO 24
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile His Asp Asn Ser His Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Tyr Asp Glu Ser
                85                  90                  95

Ala His Ser Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 25
<211> LENGTH: 351
<212> TYPE: DNA
<213> ORGANISM: Artificial Sequence
<220> FEATURE:
```

-continued

<223> OTHER INFORMATION: Description of Artificial Sequence: Synthetic
      polynucleotide

<400> SEQUENCE: 25
gaggtgcagc tggtgcagag cggagccgaa gtgaagaaac ccggcagcag cgtgaaggtg      60
tcctgcaagg ccagcggcgg cacctttagc agctacgcca tcagctgggt gcgccaggct     120
ccaggacagg gcctggaatg gatgggcccc atcaacccct actacggcga cgccatctac     180
gcccagaaat tccagggcag agtgaccatc accgccgacg agagccacag caccgcctac     240
atggaactga gcagcctgag aagcgaggac accgccgtgt actactgcgc ccggtactac     300
agcgactaca tggactactg gggccagggc accctggtga ccgtgagctc a              351

<210> SEQ ID NO 26
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
cagtcagtgc tgacccagcc tccctctgtg tctggcgccc ctggccagag agtgaccatc      60
agctgcaccg gctccagcag caacatcgga gctggatacg acgtgcactg gtatcagcag     120
ctgcccggca gcccctaa gctgctgatc acgacaaca gccacagacc cagcggcgtg         180
cccgatagat tcagcggcag caagagcggc accagcgcca gcctggccat caccggcctg     240
cagagcgagg acgaggccga ctactactgc gccagctacg acgagagcgc ccacagcgtg     300
ttcggaggcg gaacaaagtt aaccgtccta                                      330

<210> SEQ ID NO 27
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gaggtgcagc tggtgcagag cggagccgaa gtgaagaaac ccggcagcag cgtgaaggtg      60
tcctgcaagg ccagcggcgg cacctttagc agctacgcca tcagctgggt gcgccaggct     120
ccaggacagg gcctggaatg gatgggcccc atcaacccct actacggcga cgccatctac     180
gcccagaaat tccagggcag agtgaccatc accgccgacg agagccacag caccgcctac     240
atggaactga gcagcctgag aagcgaggac accgccgtgt actactgcgc ccggtactac     300
agcgactaca tggactactg gggccagggc accctggtga ccgtgagctc agcctccacc     360
aagggtccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga gagttgagcc caaatcttgt     660

<210> SEQ ID NO 28
<211> LENGTH: 648
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 28

```
cagtcagtgc tgacccagcc tccctctgtg tctggcgccc ctggccagag agtgaccatc    60
agctgcaccg gctccagcag caacatcgga gctggatacg acgtgcactg gtatcagcag   120
ctgcccggca gccccctaa gctgctgatc cacgacaaca gccacagacc cagcggcgtg    180
cccgatagat tcagcggcag caagagcggc accagcgcca gctggccat caccggcctg    240
cagagcgagg acgaggccga ctactactgc gccagctacg acgagagcgc ccacagcgtg   300
ttcggaggcg gaacaaagtt aaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca caagtacgc ggccagcagc    540
tatctgagcc tgacgcctga gcagtggaag tcccacagaa gctacagctg ccaggtcacg   600
catgaaggga gcaccgtgga aagacagtg gcccctacag aatgttca                 648
```

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser His Tyr Met His
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Ile Asn Ala Asp Leu Gly Asp Thr Asn Tyr Ala Gln Lys Phe Gln
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Gly Ile Glu His Gly Gly His Tyr Tyr Trp Gly Tyr Leu Phe Asp
1               5                   10                  15

Ile

<210> SEQ ID NO 32
<211> LENGTH: 11
<212> TYPE: PRT
<213> ORGANISM: Artificial Sequence
<220> FEATURE:

<223> OTHER INFORMATION: Description of Artificial Sequence: Synthetic
       peptide

<400> SEQUENCE: 32

Ser Gly Asp Ser Ile Arg Glu Tyr Tyr Val His
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 33

Asp Asp Thr Asn Arg Pro Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 34

Ala Ala Trp Asp Phe Ser Pro Ala Ile
1               5

<210> SEQ ID NO 35
<211> LENGTH: 126
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Tyr Met His Trp Val Arg Gln Ala Pro Gly Gln Gly Leu Glu Trp Met
            35                  40                  45

Gly Lys Ile Asn Ala Asp Leu Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Ile Glu His Gly Gly His Tyr Tyr Trp Gly Tyr Leu
            100                 105                 110

Phe Asp Ile Trp Gly Gln Gly Thr Leu Val Thr Val Ser Ser
        115                 120                 125

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 36

Ser Tyr Glu Leu Thr Gln Pro Pro Ser Val Ser Val Ala Pro Gly Gln
1               5                   10                  15

Thr Ala Arg Ile Ser Cys Ser Gly Asp Ser Ile Arg Glu Tyr Tyr Val
            20                  25                  30

His Trp Tyr Gln Gln Lys Pro Gly Gln Ala Pro Val Leu Val Ile Gly
        35                  40                  45

Asp Asp Thr Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ala Trp Asp Phe Ser Pro Ala Ile
                85                  90                  95

Val Phe Gly Gly Gly Thr Lys Leu Thr Val Leu
            100                 105

<210> SEQ ID NO 37
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Lys Ile Asn Ala Asp Leu Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Ile Glu His Gly Gly His Tyr Tyr Trp Gly Tyr Leu
            100                 105                 110

Phe Asp Ile Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys
225

<210> SEQ ID NO 38
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Ser Tyr Glu Leu Thr Gln Pro Pro Ser Val Ser Val Ala Pro Gly Gln
 1               5                  10                  15

Thr Ala Arg Ile Ser Cys Ser Gly Asp Ser Ile Arg Glu Tyr Tyr Val
             20                  25                  30

His Trp Tyr Gln Gln Lys Pro Gly Gln Ala Pro Val Leu Val Ile Gly
         35                  40                  45

Asp Asp Thr Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Ala Trp Asp Phe Ser Pro Ala Ile
                 85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 39
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
gaggtgcagc tggtgcagag cggagccgaa gtgaagaaac tggcgccag cgtgaaggtg      60 tcctgcaagg ccagcggcta caccttcacc agccactaca tgcactgggt gcgccaggct    120
ccaggacagg gcctggaatg gatgggcaag atcaacgccg acctgggcga caccaactac    180
gcccagaaat tccagggcag agtgaccatg acccgggaca ccagcatcag caccgcctac    240
atggaactga gcagcctgag aagcgaggac accgccgtgt actactgcgc caggacggc    300 atcgagcacg gcgccactac tactggggc tacctgttcg acatctgggg ccagggcacc    360
ctggtgaccg tgagctca                                                   378
```

<210> SEQ ID NO 40
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

| agctacgagc tgactcagcc cccttctgtg tctgtggccc ctggccagac cgccagaatc | 60 |
| agctgcagcg gcgacagcat ccgggagtac tacgtgcact ggtatcagca gaagcccggc | 120 |
| caggctcctg tgctggtgat cggcgacgac accaacagac ccagcggcat ccccgagaga | 180 |
| ttcagcggca gcaacagcgg caataccgcc accctgacca tcagcggcac ccaggccgag | 240 |
| gacgaggccg attactactg cgccgcctgg gacttcagcc ctgccatcgt gttcggaggc | 300 |
| ggaacaaagt taaccgtcct a | 321 |

<210> SEQ ID NO 41
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

| gaggtgcagc tggtgcagag cggagccgaa gtgaagaaac ctggcgccag cgtgaaggtg | 60 |
| tcctgcaagg ccagcggcta caccttcacc agccactaca tgcactgggt gcgccaggct | 120 |
| ccaggacagg gcctggaatg gatgggcaag atcaacgccg acctgggcga caccaactac | 180 |
| gcccagaaat tccagggcag agtgaccatg acccgggaca ccagcatcag caccgcctac | 240 |
| atggaactga gcagcctgag aagcgaggac accgccgtgt actactgcgc cagggacggc | 300 |
| atcgagcacg gcgccactac tactggggc tacctgttcg acatctgggg ccagggcacc | 360 |
| ctggtgaccg tgagctcagc atccaccaag ggtccatcgg tcttccccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca caccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagagag ttgagcccaa atcttgt | 687 |

<210> SEQ ID NO 42
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

| agctacgagc tgactcagcc cccttctgtg tctgtggccc ctggccagac cgccagaatc | 60 |
| agctgcagcg gcgacagcat ccgggagtac tacgtgcact ggtatcagca gaagcccggc | 120 |
| caggctcctg tgctggtgat cggcgacgac accaacagac ccagcggcat ccccgagaga | 180 |
| ttcagcggca gcaacagcgg caataccgcc accctgacca tcagcggcac ccaggccgag | 240 |
| gacgaggccg attactactg cgccgcctgg gacttcagcc ctgccatcgt gttcggaggc | 300 |

```
ggaacaaagt taaccgtcct aggtcagccc aaggctgccc cctcggtcac tctgttcccg    360
ccctcctctg aggagcttca agccaacaag gccacactgg tgtgtctcat aagtgacttc    420
tacccgggag ccgtgacagt ggcctggaag gcagatagca gccccgtcaa ggcgggagtg    480
gagaccacca cccctccaa acaaagcaac aacaagtacg cggccagcag ctatctgagc     540
ctgacgcctg agcagtggaa gtcccacaga agctacagct gccaggtcac gcatgaaggg    600
agcaccgtgg agaagacagt ggcccctaca gaatgttca                          639
```

```
<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asn Tyr Trp Ile Gly
1               5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ile Asp Pro Gly Glu Ser Leu Thr Asn Tyr Ala Pro Ser Phe Gln
1               5                   10                  15
Gly

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Gly Val Ala Asp Val Asp Met Pro Phe Ala His
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Gly Asp Asn Leu Gly Ser Tyr Tyr Val Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Gly Asp Ser Glu Arg Pro Ser
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Ser Trp Asp Ile Thr Ser Phe
1               5

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Gly Arg Ile Asp Pro Gly Glu Ser Leu Thr Asn Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Thr Gly Val Ala Asp Val Asp Met Pro Phe Ala His Trp Gly
            100                 105                 110

Gln Gly Thr Leu Val Thr Val Ser Ser
        115                 120

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Tyr Tyr Val
                20                  25                  30

Asn Trp Tyr Gln Gln Lys Pro Gly Gln Ala Pro Val Leu Val Ile Tyr
            35                  40                  45

Gly Asp Ser Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80
```

Asp Glu Ala Asp Tyr Tyr Cys Gly Ser Trp Asp Ile Thr Ser Phe Val
                 85                  90                  95

Phe Gly Gly Gly Thr Lys Leu Thr Val Leu
            100                 105

<210> SEQ ID NO 51
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Gly Arg Ile Asp Pro Gly Glu Ser Leu Thr Asn Tyr Ala Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Thr Gly Val Ala Asp Val Asp Met Pro Phe Ala His Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

<210> SEQ ID NO 52
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Tyr Tyr Val
                20                  25                  30

Asn Trp Tyr Gln Gln Lys Pro Gly Gln Ala Pro Val Leu Val Ile Tyr
            35                  40                  45

Gly Asp Ser Glu Arg Pro Ser Gly Ile Pro Glu Arg Phe Ser Gly Ser
 50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Gly Ser Trp Asp Ile Thr Ser Phe Val
                 85                  90                  95

Phe Gly Gly Gly Thr Lys Leu Thr Val Leu Gly Gln Pro Lys Ala Ala
             100                 105                 110

Pro Ser Val Thr Leu Phe Pro Pro Ser Ser Glu Glu Leu Gln Ala Asn
         115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 53
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gaggtgcagc tggtgcagag cggagccgaa gtgaagaagc tggcgagag cctgaagatc      60 agctgcaagg gcagcggcta cagcttcacc aactactgga tcggctgggt gcgccagatg     120
cctggcaagg gcctggaatg gatgggcaga atcgaccccg cgagtccct gaccaactac      180 gcccccagct ccagggcca ggtgacaatc agcgccgaca agagcatcag caccgcctat     240
ctgcagtgga gcagcctgaa ggccagcgac accgccatgt actactgcgc cagaaccggc    300
gtggccgacg tggacatgcc ttttgcccac tggggccagg gcaccctggt gaccgtgagc    360
tca                                                                  363

<210> SEQ ID NO 54
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
agctacgtgc tgactcagcc cccttctgtg tctgtggccc ctggcaagac cgccagaatc      60
agctgcagcg gcgacaacct gggcagctac tacgtgaact ggtatcagca gaagcccggc    120
caggctcccg tgctggtgat ctacggcgac agcgagaggc ctagcggcat ccccgagcgg    180
ttcagcggca gcaacagcgg caataccgcc accctgacca tctctagagc ccaggccggc    240
gacgaggccg attactactg cggctcctgg gacatcacca gcttcgtgtt cggaggcgga    300

```
acaaagttaa ccgtccta                                                      318

<210> SEQ ID NO 55
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gaggtgcagc tggtgcagag cggagccgaa gtgaagaagc ctggcgagag cctgaagatc        60
agctgcaagg gcagcggcta cagcttcacc aactactgga tcggctgggt gcgccagatg       120
cctggcaagg gcctggaatg gatgggcaga atcgaccccg cgagtccct gaccaactac        180 gcccccagct tccagggcca ggtgacaatc agcgccgaca gagcatcag caccgcctat        240 ctgcagtgga gcagcctgaa ggccagcgac accgccatgt actactgcgc cagaaccggc      300
gtggccgacg tggacatgcc ttttgcccac tggggccagg gcaccctggt gaccgtgagc       360
tcagcctcca ccaagggtcc atcggtcttc ccctggcac cctcctccaa gagcacctct       420
gggggcacag cggccctggg ctgcctggtc aaggactact ccccgaacc ggtgacggtg        480 tcgtggaact caggcgccct gaccagcggc gtgcacacct tccggctgt cctacagtcc       540 tcaggactct actccctcag cagcgtggtg accgtgccct ccagcagctt gggcacccag       600
acctacatct gcaacgtgaa tcacaagccc agcaacacca aggtggacaa gagagttgag      660
cccaaatctt gt                                                           672

<210> SEQ ID NO 56
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
agctacgtgc tgactcagcc cccttctgtg tctgtggccc ctggcaagac cgccagaatc       60
agctgcagcg gcgacaacct gggcagctac tacgtgaact ggtatcagca gaagcccggc      120
caggctcccg tgctggtgat ctacggcgac agcgagaggc ctagcggcat ccccgagcgg      180
ttcagcggca gcaacagcgg caataccgcc accctgacca tctctagagc ccaggccggc      240
gacgaggcca attactactg cggctcctgg gacatcacca gcttcgtgtt cggaggcgga      300
acaaagttaa ccgtcctagg tcagcccaag gctgccccct cggtcactct gttcccgccc      360
tcctctgagg agcttcaagc caacaaggcc acactggtgt gtctcataag tgacttctac      420
ccgggagccg tgacagtggc ctggaaggca gatagcagcc ccgtcaaggc gggagtggag      480
accaccacac cctccaaaca aagcaacaac aagtacgcgg ccagcagcta tctgagcctg      540
acgcctgagc agtggaagtc cacagaagc tacagctgcc aggtcacgca tgaagggagc      600
accgtggaga agacagtggc ccctacagaa tgttca                                636

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 57

Ser Tyr Ala Ile Ser
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ile Ile Pro Ile Phe Gly Thr Ala Asn Tyr Ala Gln Lys Phe Gln
1               5                   10                  15

Gly

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Gly Gly Tyr Ser Phe Asp Ser
1               5

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Gly Asp Asn Leu Gly Ser Lys Tyr Val Asp
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Asp Asn Asn Arg Pro Ser
1               5

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Thr Tyr Asp Ser Ser Pro Arg Thr Glu
1               5                   10

```
<210> SEQ ID NO 63
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser
        115

<210> SEQ ID NO 64
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                85                  90                  95

Glu Val Phe Gly Gly Gly Thr Lys Leu Thr Val Leu
            100                 105

<210> SEQ ID NO 65
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
210                 215                 220

<210> SEQ ID NO 66
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                85                  90                  95

Glu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly

```
                145                 150                 155                 160
Val Glu Thr Thr Thr Pro Ser Lys Gln Ser Asn Asn Lys Tyr Ala Ala
                    165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser
    210

<210> SEQ ID NO 67
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gaggtgcagc tggtgcagag cggagccgaa gtgaagaaac cggcagcag cgtgaaggtg         60 tcctgcaagg ccagcggcgg caccttcaac agctacgcca tcagctgggt gcgccaggct       120
cctggacagg gcctggaatg gatgggccgg atcatcccca tcttcggcac cgccaactac       180
gcccagaaat tccagggcag agtgaccatc accgccgacg agagcaccag caccgcctac       240
atggaactga gcagcctgag aagcgaggac accgccgtgt actactgtgc ccggcacggc       300
ggctacagct cgatagctg gggccagggc accctggtga ccgtgagctc a                 351

<210> SEQ ID NO 68
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
agctacgtgc tgactcagcc ccctctgtg tctgtggccc ctggcaagac cgccagaatc         60
agctgcagcg gcgacaacct gggcagcaaa tacgtggact ggtatcagca gaagcccggc       120
caggctcccg tgctggtgat ctacagcgac aacaaccggc cagcggcat ccctgagcgg        180 ttcagcggca gcaacagcgg caataccgcc accctgacca tcagcggcac ccaggccatg       240
gacgaggccg actactactg cgccacctac gacagcagcc cagaaccga ggtgttcgga        300 ggcggaacaa agttaaccgt ccta                                              324

<210> SEQ ID NO 69
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gaggtgcagc tggtgcagag cggagccgaa gtgaagaaac cggcagcag cgtgaaggtg         60 tcctgcaagg ccagcggcgg caccttcaac agctacgcca tcagctgggt gcgccaggct       120
cctggacagg gcctggaatg gatgggccgg atcatcccca tcttcggcac cgccaactac       180
gcccagaaat tccagggcag agtgaccatc accgccgacg agagcaccag caccgcctac       240
```

```
atggaactga gcagcctgag aagcgaggac accgccgtgt actactgtgc ccggcacggc      300
ggctacagct tcgatagctg gggccagggc accctggtga ccgtgagctc agcctccacc      360
aagggtccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga gagttgagcc caaatcttgt      660
```

<210> SEQ ID NO 70
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
agctacgtgc tgactcagcc cccttctgtg tctgtggccc ctggcaagac cgccagaatc       60
agctgcagcg gcgacaacct gggcagcaaa tacgtggact ggtatcagca gaagcccggc      120
caggctcccg tgctggtgat ctacagcgac aacaaccggc ccagcggcat ccctgagcgg      180
ttcagcggca gcaacagcgg caataccgcc accctgacca tcagcggcac ccaggccatg      240
gacgaggccg actactactg cgccacctac gacagcagcc cagaaccga ggtgttcgga      300 ggcggaacaa agttaaccgt cctaggtcag cccaaggctg cccccctcggt cactctgttc      360 ccgcccctcct ctgaggagct tcaagccaac aaggccacac tggtgtgtct cataagtgac      420
ttctacccgg gagccgtgac agtggcctgg aaggcagata gcagccccgt caaggcggga      480
gtggagacca ccacaccctc caaacaaagc aacaacaagt acgcggccag cagctatctg      540
agcctgacgc ctgagcagtg gaagtcccac agaagctaca gctgccaggt cacgcatgaa      600
gggagcaccg tggagaagac agtggcccct acagaatgtt ca                        642
```

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser His Tyr Met His
1               5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asn Ile Asn Pro Val Asp Gly Gly Thr Glu Tyr Ala Gln Lys Phe Gln
1               5                   10                  15

Gly

<210> SEQ ID NO 73

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Gly Ile Glu His Gly Gly His Tyr Tyr Trp Gly Tyr Leu Phe Asp
1               5                   10                  15
Ile

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Gly Asp Ser Ile Arg Glu Tyr Tyr Val His
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Asp Thr Asn Arg Pro Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Ala Trp Asp Phe Ser Pro Ala Ile
1               5

<210> SEQ ID NO 77
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Asn Ile Asn Pro Val Asp Gly Gly Thr Glu Tyr Ala Gln Lys Phe
    50                  55                  60
```

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Ile Glu His Gly Gly His Tyr Tyr Trp Gly Tyr Leu
            100                 105                 110

Phe Asp Ile Trp Gly Gln Gly Thr Leu Val Thr Val Ser Ser
            115                 120                 125

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ser Tyr Val Leu Thr Gln Pro Pro Ser Val Ser Val Ala Pro Gly Lys
1               5                   10                  15

Thr Ala Arg Ile Ser Cys Ser Gly Asp Ser Ile Arg Glu Tyr Tyr Val
            20                  25                  30

His Trp Tyr Gln Gln Lys Pro Gly Gln Ala Pro Val Leu Val Ile Gly
        35                  40                  45

Asp Asp Thr Asn Arg Pro Ser Gly Ile Pro Glu Arg Phe Ser Gly Ser
50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Ala Ala Trp Asp Phe Ser Pro Ala Ile
                85                  90                  95

Val Phe Gly Gly Gly Thr Lys Leu Thr Val Leu
            100                 105

<210> SEQ ID NO 79
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Asn Ile Asn Pro Val Asp Gly Gly Thr Glu Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Ile Glu His Gly Gly His Tyr Tyr Trp Gly Tyr Leu
            100                 105                 110

Phe Asp Ile Trp Gly Gln Gly Thr Leu Val Thr Val Ser Ser Ala Ser
            115                 120                 125

```
Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Arg Val
210                 215                 220

Glu Pro Lys Ser Cys
225
```

<210> SEQ ID NO 80
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Ser Tyr Val Leu Thr Gln Pro Pro Ser Val Ser Val Ala Pro Gly Lys
1               5                   10                  15

Thr Ala Arg Ile Ser Cys Ser Gly Asp Ser Ile Arg Glu Tyr Tyr Val
            20                  25                  30

His Trp Tyr Gln Gln Lys Pro Gly Gln Ala Pro Val Leu Val Ile Gly
        35                  40                  45

Asp Asp Thr Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Ala Ala Trp Asp Phe Ser Pro Ala Ile
                85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 81
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
gaggtgcagc tggtgcagag cggagccgaa gtgaagaaac ctggcgccag cgtgaaggtg    60
tcctgcaagg ccagcggcta caccttcacc agccactaca tgcactgggt gcgccaggct   120
ccaggacagg gcctggaatg gatgggcaac atcaacccccg tggacggcgg caccgagtac   180
gcccagaaat tccagggcag agtgaccatg acccgggaca ccagcatcag caccgcctac   240
atggaactga gcagcctgag aagcgaggac accgccgtgt actactgcgc cagggacggc   300
atcgagcacg gcggccacta ctactggggc tacctgttcg acatctgggg ccagggcacc   360
ctggtgaccg tgagctca                                                378
```

<210> SEQ ID NO 82
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

```
tcttacgtgc tgactcagcc ccccttctgtg tctgtggccc ctggcaagac cgccagaatc    60
agctgcagcg gcgacagcat ccgggagtac tacgtgcact ggtatcagca gaagcccggc   120
caggctcctg tgctggtgat cggcgacgac accaacagac ccagcggcat ccccgagaga   180
ttcagcggca gcaacagcgg caataccgcc accctgacca tctctagagc ccaggccggc   240
gacgaggccg attactactg cgccgcctgg gacttcagcc tgccatcgt gttcggaggc   300
ggaacaaagt taaccgtcct a                                             321
```

<210> SEQ ID NO 83
<211> LENGTH: 687
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
gaggtgcagc tggtgcagag cggagccgaa gtgaagaaac ctggcgccag cgtgaaggtg    60
tcctgcaagg ccagcggcta caccttcacc agccactaca tgcactgggt gcgccaggct   120
ccaggacagg gcctggaatg gatgggcaac atcaacccccg tggacggcgg caccgagtac   180
gcccagaaat tccagggcag agtgaccatg acccgggaca ccagcatcag caccgcctac   240
atggaactga gcagcctgag aagcgaggac accgccgtgt actactgcgc cagggacggc   300
atcgagcacg gcggccacta ctactggggc tacctgttcg acatctgggg ccagggcacc   360
ctggtgaccg tgagctcagc ctccaccaag ggtccatcgg tcttccccct ggcaccctcc   420
tccaagagca cctctggggg cacagcggcc ctgggctgcc tggtcaagga ctacttcccc   480
gaaccggtga cggtgtcgtg gaactcaggc gccctgacca gcggcgtgca caccttcccg   540
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagagag ttgagcccaa atcttgt                                       687
```

<210> SEQ ID NO 84
<211> LENGTH: 639
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
tcttacgtgc tgactcagcc cccttctgtg tctgtggccc ctggcaagac cgccagaatc      60
agctgcagcg gcgacagcat ccgggagtac tacgtgcact ggtatcagca gaagcccggc     120
caggctcctg tgctggtgat cggcgacgac accaacagac ccagcggcat ccccgagaga     180
ttcagcggca gcaacagcgg caataccgcc accctgacca tctctagagc ccaggccggc     240
gacgaggccg attactactg cgccgcctgg gacttcagcc ctgccatcgt gttcggaggc     300
ggaacaaagt taaccgtcct aggtcagccc aaggctgccc cctcggtcac tctgttcccg     360
ccctcctctg aggagcttca agccaacaag gccacactgg tgtgtctcat aagtgacttc     420
tacccgggag ccgtgacagt ggcctggaag gcagatagca gccccgtcaa ggcgggagtg     480
gagaccacca cccctccaa acaaagcaac aacaagtacg cggccagcag ctatctgagc     540
ctgacgcctg agcagtggaa gtcccacaga agctacagct gccaggtcac gcatgaaggg     600
agcaccgtgg agaagacagt ggcccctaca gaatgttca                            639
```

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Ser Tyr Ala Ile Ser
1               5

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Arg Ile Ile Pro Ile Phe Gly Thr Ala Asn Tyr Ala Gln Lys Phe Gln
1               5                   10                  15
Gly

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

His Gly Gly Tyr Ser Tyr Phe Asp Ser
1               5

<210> SEQ ID NO 88
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Gly Asp Asn Leu Gly Ser Lys Tyr Val Asp
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Asp Asn Asn Arg Pro Ser
1               5

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Thr Tyr Thr Ser Gly Asn Asn Tyr Leu
1               5                   10

<210> SEQ ID NO 91
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Tyr Phe Asp Ser Trp Gly Gln Gly Thr Leu
                100                 105                 110

Val Thr Val Ser Ser
        115

<210> SEQ ID NO 92
<211> LENGTH: 108
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 92

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu
            100                 105

<210> SEQ ID NO 93
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Tyr Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
    210                 215                 220
```

<210> SEQ ID NO 94
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 95
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
gaggtgcagc tggtgcagag cggagccgaa gtgaagaaac cggcagcag cgtgaaggtg      60 tcctgcaagg ccagcggcgg caccttcagc agctacgcca tcagctgggt gcgccaggct    120
cctggacagg gcctggaatg gatgggccgg atcatcccca tcttcggcac cgccaactac    180
gcccagaaat tccagggcag agtgaccatc accgccgacg agagcaccag caccgcctac    240
atggaactga gcagcctgag aagcgaggac accgccgtgt actactgtgc ccggcacggc    300
ggctactact cgatagctg gggccagggc accctggtga ccgtgagctc a              351
```

<210> SEQ ID NO 96

-continued

```
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
agctacgagc tgactcagcc cccttctgtg tctgtggccc ctggccagac cgccagaatc    60
agctgcagcg gcgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccgag   240
gacgaggccg actactactg ccagacctac accagcggca caactacct ggtgttcgga    300 ggcggaacaa agttaaccgt ccta                                          324

<210> SEQ ID NO 97
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gaggtgcagc tggtgcagag cggagccgaa gtgaagaaac ccggcagcag cgtgaaggtg    60
tcctgcaagg ccagcggcgg caccttcagc agctacgcca tcagctgggt gcgccaggct   120
cctggacagg gcctggaatg gatgggccgg atcatcccca tcttcggcac cgccaactac   180
gcccagaaat ccagggcag agtgaccatc accgccgacg agagcaccag caccgcctac   240
atggaactga gcagcctgag aagcgaggac accgccgtgt actactgtgc ccggcacggc   300
ggctactact cgatagctg gggccagggc accctggtga ccgtgagctc agcctccacc   360
aagggtccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga gagttgagcc caaatcttgt   660

<210> SEQ ID NO 98
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
agctacgagc tgactcagcc cccttctgtg tctgtggccc ctggccagac cgccagaatc    60
agctgcagcg gcgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccgag   240
gacgaggccg actactactg ccagacctac accagcggca caactacct ggtgttcgga    300 ggcggaacaa agttaaccgt cctaggtcag cccaaggctg ccccctcggt cactctgttc   360
ccgccctcct ctgaggagct tcaagccaac aaggccacac tggtgtgtct cataagtgac   420
```

```
ttctacccgg gagccgtgac agtggcctgg aaggcagata gcagccccgt caaggcggga    480
gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                      642
```

```
<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Tyr Ala Ile Ser
1               5

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Ile Ile Pro Ile Phe Gly Thr Ala Asn Tyr Ala Gln Lys Phe Gln
1               5                   10                  15

Gly

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

His Gly Gly Tyr Ile Phe Asp Ser
1               5

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Gly Asp Asn Leu Gly Ser Lys Tyr Val Asp
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Asp Asn Asn Arg Pro Ser
1               5
```

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Thr Tyr Thr Ser Gly Asn Asn Tyr Leu
1               5                   10

<210> SEQ ID NO 105
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ile Phe Asp Ser Trp Gly Gln Gly Thr Leu
            100                 105                 110

Val Thr Val Ser Ser
        115

<210> SEQ ID NO 106
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu
            100                 105

<210> SEQ ID NO 107
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ile Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
210                 215                 220

<210> SEQ ID NO 108
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
50                  55                  60

```
Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Tyr Thr Ser Gly Asn Asn Tyr
                 85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 109
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
gaggtgcagc tggtgcagag cggagccgaa gtgaagaaac ccggcagcag cgtgaaggtg      60
tcctgcaagg ccagcggcgg caccttcagc agctacgcca tcagctgggt gcgccaggct     120
cctggacagg gcctggaatg gatgggccgg atcatcccca tcttcggcac cgccaactac     180
gcccagaaat tccagggcag agtgaccatc accgccgacg agagcaccag caccgcctac     240
atggaactga gcagcctgag aagcgaggac accgccgtgt actactgtgc ccggcacggc     300
ggctacattt tcgatagctg gggccagggc accctggtga ccgtgagctc a              351
```

<210> SEQ ID NO 110
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
agctacgagc tgactcagcc cccttctgtg tctgtggccc ctggccagac cgccagaatc      60
agctgcagcg gcgacaacct gggcagcaaa tactggactg gtatcagca gaagcccggc     120 caggctcccg tgctggtgat ctacagcgac aacaaccggc ccagcggcat ccctgagcgg     180
ttcagcggca gcaacagcgg caataccgcc accctgacca tcagcggcac ccaggccgag     240
gacgaggccg actactactg ccagacctac accagcggca caactacct ggtgttcgga     300 ggcggaacaa agttaaccgt ccta                                           324
```

<210> SEQ ID NO 111
<211> LENGTH: 660

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
gaggtgcagc tggtgcagag cggagccgaa gtgaagaaac ccggcagcag cgtgaaggtg        60
tcctgcaagg ccagcggcgg caccttcagc agctacgcca tcagctgggt gcgccaggct       120
cctggacagg gcctggaatg gatgggccgg atcatcccca tcttcggcac cgccaactac       180
gcccagaaat tccagggcag agtgaccatc accgccgacg agagcaccag caccgcctac       240
atggaactga gcagcctgag aagcgaggac accgccgtgt actactgtgc ccggcacggc       300
ggctacattt tcgatagctg gggccagggc accctggtga ccgtgagctc agcctccacc       360
aagggtccat cggtcttccc cctggcaccc tcctccaaga gcacctctgg gggcacagcg       420
gccctgggct gcctggtcaa ggactacttc cccgaaccgg tgacggtgtc gtggaactca       480
ggcgccctga ccagcggcgt gcacaccttc ccggctgtcc tacagtcctc aggactctac       540
tccctcagca gcgtggtgac cgtgccctcc agcagcttgg gcacccagac ctacatctgc       600
aacgtgaatc acaagcccag caacaccaag gtggacaaga gagttgagcc caaatcttgt       660
```

<210> SEQ ID NO 112
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
agctacgagc tgactcagcc cccttctgtg tctgtggccc ctggccagac cgccagaatc        60
agctgcagcg gcgacaacct gggcagcaaa tacgtggact ggtatcagca gaagcccggc       120
caggctcccg tgctggtgat ctacagcgac aacaaccggc cagcggcat ccctgagcgg        180
ttcagcggca gcaacagcgg caataccgcc accctgacca tcagcggcac ccaggccgag       240
gacgaggccg actactactg ccagacctac accagcggca caactacct ggtgttcgga        300
ggcggaacaa agttaaccgt cctaggtcag cccaaggctg cccccctcggt cactctgttc       360
ccgcccctcct ctgaggagct tcaagccaac aaggccacac tggtgtgtct cataagtgac       420
ttctacccgg gagccgtgac agtggcctgg aaggcagata gcagccccgt caaggcggga       480
gtggagacca ccacacctctc caaacaaagc aacaacaagt acgcggccag cagctatctg       540
agcctgacgc ctgagcagtg gaagtcccac agaagctaca gctgccaggt cacgcatgaa       600
gggagcaccg tggagaagac agtggcccct acagaatgtt ca                         642
```

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Tyr Ala Ile Ser
1               5

<210> SEQ ID NO 114

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ile Ile Pro Ile Phe Gly Thr Ala Asn Tyr Ala Gln Lys Phe Gln
1               5                   10                  15

Gly

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

His Gly Gly Tyr Val Phe Asp Ser
1               5

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Gly Asp Asn Leu Gly Ser Lys Tyr Val Asp
1               5                   10

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Asp Asn Asn Arg Pro Ser
1               5

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Thr Tyr Thr Ser Gly Asn Asn Tyr Leu
1               5                   10

<210> SEQ ID NO 119
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 119

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Val Phe Asp Ser Trp Gly Gln Gly Thr Leu
            100                 105                 110

Val Thr Val Ser Ser
            115

<210> SEQ ID NO 120
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu
            100                 105

<210> SEQ ID NO 121
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe

```
            50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Gly Gly Tyr Val Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
    210                 215                 220

<210> SEQ ID NO 122
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ser Tyr Glu Leu Thr Gln Pro Pro Ser Val Ser Val Ala Pro Gly Gln
 1               5                  10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Tyr Thr Ser Gly Asn Asn Tyr
                 85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

Tyr Ser Cys Gln Val Thr His Glu Gly Ser Thr Val Glu Lys Thr Val
            195                 200                 205

Ala Pro Thr Glu Cys Ser
    210

<210> SEQ ID NO 123
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
gaggtgcagc tggtgcagag cggagccgaa gtgaagaaac ccggcagcag cgtgaaggtg      60
tcctgcaagg ccagcggcgg caccttcagc agctacgcca tcagctgggt gcgccaggct     120
cctggacagg gcctggaatg gatgggccgg atcatcccca tcttcggcac cgccaactac     180
gcccagaaat tccagggcag agtgaccatc accgccgacg agagccacag caccgcctac     240
atggaactga gcagcctgag aagcgaggac accgccgtgt actactgtgc ccggcacggc     300
ggctacgtct cgatagctg gggccagggc accctggtga ccgtgagctc a               351

<210> SEQ ID NO 124
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
agctacgagc tgactcagcc cccttctgtg tctgtggccc ctggccagac cgccagaatc      60
agctgcagcg gcgacaacct gggcagcaaa tacgtggact ggtatcagca gaagcccggc     120
caggctcccg tgctggtgat ctacagcgac aacaaccggc cagcggcat ccctgagcgg      180 ttcagcggca gcaacagcgg caataccgcc accctgacca tcagcggcac ccaggccgag     240
gacgaggccg actactactg ccagacctac accagcggca caactacct ggtgttcgga      300 ggcggaacaa agttaaccgt ccta                                             324

<210> SEQ ID NO 125
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gaggtgcagc tggtgcagag cggagccgaa gtgaagaaac ccggcagcag cgtgaaggtg      60
tcctgcaagg ccagcggcgg caccttcagc agctacgcca tcagctgggt gcgccaggct     120
cctggacagg gcctggaatg gatgggccgg atcatcccca tcttcggcac cgccaactac     180
gcccagaaat tccagggcag agtgaccatc accgccgacg agagccacag caccgcctac     240
atggaactga gcagcctgag aagcgaggac accgccgtgt actactgtgc ccggcacggc     300
ggctacgtct cgatagctg gggccagggc accctggtga ccgtgagctc agcctccacc     360
aagggtccat cggtcttccc cctggcaccc tcctccaaga gcacctctgg gggcacagcg     420
gccctgggct gcctggtcaa ggactacttc cccgaaccgg tgacggtgtc gtggaactca     480

-continued

```
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
```

<210> SEQ ID NO 126
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

```
agctacgagc tgactcagcc cccttctgtg tctgtggccc ctggccagac cgccagaatc     60
agctgcagcg gcgacaacct gggcagcaaa tacgtggact ggtatcagca gaagcccggc    120
caggctcccg tgctggtgat ctacagcgac aacaaccggc ccagcggcat ccctgagcgg    180
ttcagcggca gcaacagcgg caataccgcc accctgacca tcagcggcac ccaggccgag    240
gacgaggccg actactactg ccagacctac accagcggca caactacct ggtgttcgga     300 ggcggaacaa agttaaccgt cctaggtcag cccaaggctg ccccctcggt cactctgttc    360
ccgccctcct ctgaggagct tcaagccaac aaggccacac tggtgtgtct cataagtgac    420
ttctacccgg gagccgtgac agtggcctgg aaggcagata gcagcccgt caaggcggga    480 gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggccccct acagaatgtt ca                      642
```

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Tyr Ala Ile Ser
1               5

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Ile Ile Pro Ile Phe Gly Thr Ala Asn Tyr Ala Gln Lys Phe Gln
1               5                   10                  15

Gly

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

His Gly Gly Tyr Val Phe Asp Ser
1               5

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Gly Asp Asn Leu Gly Ser Lys Tyr Val Asp
1               5                   10

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Asp Asn Asn Arg Pro Ser
1               5

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Thr Tyr Asp Ser Ser Pro Arg Thr Glu
1               5                   10

<210> SEQ ID NO 133
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ile Phe Asp Ser Trp Gly Gln Gly Thr Leu
            100                 105                 110

Val Thr Val Ser Ser
        115

115

<210> SEQ ID NO 134
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                85                  90                  95

Glu Val Phe Gly Gly Gly Thr Lys Leu Thr Val Leu
            100                 105

<210> SEQ ID NO 135
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ile Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser

```
                    180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys
    210                 215                 220

<210> SEQ ID NO 136
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                85                  90                  95

Glu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 137
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gaggtgcagc tggtgcagag cggagccgaa gtgaagaaac ccggcagcag cgtgaaggtg      60
tcctgcaagg ccagcggcgg caccttcagc agctacgcca tcagctgggt gcgccaggct     120
cctggacagg gcctggaatg gatgggccgg atcatcccca tcttcggcac cgccaactac     180
gcccagaaat tccagggcag agtgaccatc accgccgacg agagcaccag caccgcctac     240
```

```
atggaactga gcagcctgag aagcgaggac accgccgtgt actactgtgc cggcacggc    300 ggctacattt cgatagctg gggccagggc accctggtga ccgtgagctc a             351
```

<210> SEQ ID NO 138
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

```
agctacgtgc tgactcagcc cccttctgtg tctgtggccc ctggcaagac cgccagaatc    60
agctgcagcg cgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccatg   240
gacgaggccg actactactg cgccacctac gacagcagcc cagaaccga ggtgttcgga    300 ggcggaacaa agttaaccgt ccta                                          324
```

<210> SEQ ID NO 139
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139

```
gaggtgcagc tggtgcagag cggagccgaa gtgaagaaac ccggcagcag cgtgaaggtg    60
tcctgcaagg ccagcggcgg caccttcagc agctacgcca tcagctgggt gcgccaggct   120
cctggacagg gcctggaatg gatgggccgg atcatcccca tcttcggcac cgccaactac   180
gcccagaaat tccagggcag agtgaccatc accgccgacg agagccacag caccgcctac   240
atggaactga gcagcctgag aagcgaggac accgccgtgt actactgtgc cggcacggc    300 ggctacattt cgatagctg gggccagggc accctggtga ccgtgagctc agcctccacc    360
aagggtccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga gagttgagcc caaatcttgt   660
```

<210> SEQ ID NO 140
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140

```
agctacgtgc tgactcagcc cccttctgtg tctgtggccc ctggcaagac cgccagaatc    60
agctgcagcg cgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccatg   240
```

```
gacgaggccg actactactg cgccacctac gacagcagcc ccagaaccga ggtgttcgga    300
ggcggaacaa agttaaccgt cctaggtcag cccaaggctg cccctcggt cactctgttc    360 ccgcccctcct ctgaggagct tcaagccaac aaggccacac tggtgtgtct cataagtgac    420
ttctacccgg gagccgtgac agtggcctgg aaggcagata gcagcccgt caaggcggga    480 gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                      642
```

```
<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Tyr Ala Ile Ser
1               5

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Ile Ile Pro Ile Phe Gly Thr Ala Asn Tyr Ala Gln Lys Phe Gln
1               5                   10                  15
Gly

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

His Gly Gly Tyr Tyr Phe Asp Ser
1               5

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Gly Asp Asn Leu Gly Ser Lys Tyr Val Asp
1               5                   10

<210> SEQ ID NO 145
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 145

Ser Asp Asn Asn Arg Pro Ser
1               5

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Thr Tyr Asp Ser Ser Pro Arg Thr Glu
1               5                   10

<210> SEQ ID NO 147
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Tyr Phe Asp Ser Trp Gly Gln Gly Thr Leu
            100                 105                 110

Val Thr Val Ser Ser
        115

<210> SEQ ID NO 148
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60
```

Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Asp Ser Ser Pro Arg Thr
                 85                  90                  95

Glu Val Phe Gly Gly Gly Thr Lys Leu Thr Val Leu
            100                 105

<210> SEQ ID NO 149
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Gly Gly Tyr Tyr Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
    210                 215                 220

<210> SEQ ID NO 150
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
         35                  40                  45

Ser Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Asp Ser Ser Pro Arg Thr
                 85                  90                  95

Glu Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
             115                 120                 125

Ala Asn Lys Ala Thr Leu Val Cys Leu Ile Ser Asp Phe Tyr Pro Gly
         130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
             180                 185                 190

Tyr Ser Cys Gln Val Thr His Glu Gly Ser Thr Val Glu Lys Thr Val
         195                 200                 205

Ala Pro Thr Glu Cys Ser
    210

<210> SEQ ID NO 151
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
gaggtgcagc tggtgcagag cggagccgaa gtgaagaaac cggcagcag cgtgaaggtg      60 tcctgcaagg ccagcggcgg caccttcagc agctacgcca tcagctgggt gcgccaggct    120
cctggacagg gcctggaatg gatgggccgg atcatcccca tcttcggcac cgccaactac    180
gcccagaaat tccagggcag agtgaccatc accgccgacg agagcaccag caccgcctac    240
atggaactga gcagcctgag aagcgaggac accgccgtgt actactgtgc ccggcacggc    300
ggctactact cgatagctg gggccagggc accctggtga ccgtgagctc a              351

<210> SEQ ID NO 152
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
agctacgtgc tgactcagcc cccttctgtg tctgtggccc tggcaagac cgccagaatc      60 agctgcagcg gcgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccatg   240

```
gacgaggccg actactactg cgccacctac gacagcagcc ccagaaccga ggtgttcgga      300
ggcggaacaa agttaaccgt ccta                                            324
```

<210> SEQ ID NO 153
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153

```
gaggtgcagc tggtgcagag cggagccgaa gtgaagaaac ccggcagcag cgtgaaggtg       60
tcctgcaagg ccagcggcgg caccttcagc agctacgcca tcagctgggt gcgccaggct      120
cctggacagg gcctggaatg gatgggccgg atcatcccca tcttcggcac cgccaactac      180
gcccagaaat tccagggcag agtgaccatc accgccgacg agagcaccag caccgcctac      240
atggaactga gcagcctgag aagcgaggac accgccgtgt actactgtgc ccggcacggc      300
ggctactact cgatagctg gggccagggc accctggtga ccgtgagctc agcctccacc      360
aagggtccat cggtcttccc cctggcaccc tcctccaaga gcacctctgg ggcacagcg      420 gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga gagttgagcc caaatcttgt      660
```

<210> SEQ ID NO 154
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154

```
agctacgtgc tgactcagcc cccttctgtg tctgtggccc ctggcaagac cgccagaatc       60
agctgcagcg gcgacaacct gggcagcaaa tacgtggact ggtatcagca gaagcccggc      120
caggctcccg tgctggtgat ctacagcgac aacaaccggc ccagcggcat ccctgagcgg      180
ttcagcggca gcaacagcgg caataccgcc accctgacca tcagcggcac ccaggccatg      240
gacgaggccg actactactg cgccacctac gacagcagcc ccagaaccga ggtgttcgga      300
ggcggaacaa agttaaccgt cctaggtcag cccaaggctg cccctcggt cactctgttc      360 ccgcccctcct ctgaggagct tcaagccaac aaggccacac tggtgtgtct cataagtgac      420
ttctacccgg gagccgtgac agtggcctgg aaggcagata gcagcccgt caaggcggga      480 gtggagacca ccacaccctc caaacaaagc aacaacaagt acgcggccag cagctatctg      540
agcctgacgc ctgagcagtg gaagtccac agaagctaca gctgccaggt cacgcatgaa      600
gggagcaccg tggagaagac agtggcccct acagaatgtt ca                        642
```

<210> SEQ ID NO 155
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 155

Ser Tyr Ala Ile Ser
1               5

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Arg Ile Ile Pro Ile Phe Gly Thr Ala Asn Tyr Ala Gln Lys Phe Gln
1               5                   10                  15

Gly

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

His Gly Gly Tyr Val Phe Asp Ser
1               5

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Gly Asp Asn Leu Gly Ser Lys Tyr Val Asp
1               5                   10

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ser Asp Asn Asn Arg Pro Ser
1               5

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Thr Tyr Asp Ser Ser Pro Arg Thr Glu
1               5                   10

<210> SEQ ID NO 161
```

-continued

```
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161
```

Glu Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Val Phe Asp Ser Trp Gly Gln Gly Thr Leu
            100                 105                 110

Val Thr Val Ser Ser
        115

```
<210> SEQ ID NO 162
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162
```

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                85                  90                  95

Glu Val Phe Gly Gly Gly Thr Lys Leu Thr Val Leu
            100                 105

```
<210> SEQ ID NO 163
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163
```

Glu Val Gln Leu Val Gln Ser Gly Ala Glu Val Lys Lys Pro Gly Ser
1               5                   10                  15

```
Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Arg Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Gly Gly Tyr Val Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
210                 215                 220

<210> SEQ ID NO 164
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
             20                  25                  30

Asp Trp Tyr Gln Gln Lys Pro Gly Gln Ala Pro Val Leu Val Ile Tyr
         35                  40                  45

Ser Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                 85                  90                  95

Glu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160
```

Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
        180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 165
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
gaggtgcagc tggtgcagag cggagccgaa gtgaagaaac cggcagcag cgtgaaggtg      60 tcctgcaagg ccagcggcgg caccttcagc agctacgcca tcagctgggt gcgccaggct    120
cctggacagg gcctggaatg gatgggccgg atcatcccca tcttcggcac cgccaactac    180
gcccagaaat tccagggcag agtgaccatc accgccgacg agagccacag caccgcctac    240
atggaactga gcagcctgag aagcgaggac accgccgtgt actactgtgc ccggcacggc    300
ggctacgtct tcgatagctg gggccagggc accctggtga ccgtgagctc a             351

<210> SEQ ID NO 166
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166
agctacgtgc tgactcagcc cccttctgtg tctgtggccc ctggcaagac cgccagaatc     60
agctgcagcg gcgacaacct gggcagcaaa tacgtggact ggtatcagca gaagcccggc    120
caggctcccg tgctggtgat ctacagcgac aacaaccggc cagcggcat ccctgagcgg     180 ttcagcggca gcaacagcgg caataccgcc accctgacca tcagcggcac ccaggccatg    240
gacgaggccg actactactg cgccacctac gacagcagcc cagaaccga ggtgttcgga     300 ggcggaacaa agttaaccgt ccta                                           324

<210> SEQ ID NO 167
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
gaggtgcagc tggtgcagag cggagccgaa gtgaagaaac cggcagcag cgtgaaggtg      60 tcctgcaagg ccagcggcgg caccttcagc agctacgcca tcagctgggt gcgccaggct    120
cctggacagg gcctggaatg gatgggccgg atcatcccca tcttcggcac cgccaactac    180
gcccagaaat tccagggcag agtgaccatc accgccgacg agagccacag caccgcctac    240
atggaactga gcagcctgag aagcgaggac accgccgtgt actactgtgc ccggcacggc    300

```
ggctacgtct tcgatagctg gggccagggc accctggtga ccgtgagctc agcctccacc    360
aagggtccat cggtcttccc cctggcaccc tcctccaaga gcacctctgg ggcacagcg     420 gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
```

<210> SEQ ID NO 168
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168

```
agctacgtgc tgactcagcc cccttctgtg tctgtggccc ctggcaagac cgccagaatc     60
agctgcagcg gcgacaacct gggcagcaaa tacgtggact ggtatcagca gaagcccggc    120
caggctcccg tgctggtgat ctacagcgac aacaaccggc ccagcggcat ccctgagcgg    180
ttcagcggca gcaacagcgg caataccgcc accctgacca tcagcggcac ccaggccatg    240
gacgaggcca actactactg cgccacctac gacagcagcc cagaaccga ggtgttcgga     300 ggcggaacaa agttaaccgt cctaggtcag cccaaggctg cccctcggt cactctgttc     360 ccgccctcct ctgaggagct tcaagccaac aaggccacac tggtgtgtct cataagtgac    420
ttctacccgg agccgtgac agtggcctgg aaggcagata gcagccccgt caaggcggga    480
gtggagacca ccacaccctc caacaaagc aacaacaagt acgcggccag cagctatctg    540
agcctgacgc ctgagcagtg gaagtcccac agaagctaca gctgccaggt cacgcatgaa    600
gggagcaccg tggagaagac agtggccccct acagaatgtt ca                      642
```

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ser Tyr Ala Ile Ser
1               5

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Arg Ile Ile Pro Ile Phe Gly Thr Ala Asn Tyr Ala Gln Lys Phe Gln
1               5                   10                  15

Gly

<210> SEQ ID NO 171
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

His Gly Gly Tyr Ser Phe Asp Ser
1               5

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Gly Asp Asn Leu Gly Ser Lys Tyr Val Asp
1               5                   10

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Asp Asn Asn Arg Pro Ser
1               5

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gln Thr Tyr Thr Ser Gly Asn Asn Tyr Leu
1               5                   10

<210> SEQ ID NO 175
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser
        115

<210> SEQ ID NO 176
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu
            100                 105

<210> SEQ ID NO 177
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys
        210                 215                 220

<210> SEQ ID NO 178
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 179
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
```

```
gaggtgcagc tggtgcagag cggagccgaa gtgaagaaac ccggcagcag cgtgaaggtg      60
tcctgcaagg ccagcggcgg caccttcagc agctacgcca tcagctgggt gcgccaggct     120
cctggacagg gcctggaatg gatgggccgg atcatcccca tcttcggcac cgccaactac     180
gcccagaaat tccagggcag agtgaccatc accgccgacg agagccacag caccgcctac     240
atggaactga gcagcctgag aagcgaggac accgccgtgt actactgtgc ccggcacggc     300
ggctacagct tcgatagctg gggccagggc accctggtga ccgtgagctc a              351
```

<210> SEQ ID NO 180
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 180

```
agctacgagc tgactcagcc cccttctgtg tctgtggccc ctggccagac cgccagaatc      60
agctgcagcg gcgacaacct gggcagcaaa tacgtggact ggtatcagca gaagcccggc     120
caggctcccg tgctggtgat ctacagcgac aacaaccggc ccagcggcat ccctgagcgg     180
ttcagcggca gcaacagcgg caataccgcc accctgacca tcagcggcac ccaggccgag     240
gacgaggccg actactactg ccagacctac accagcggca caaactacct ggtgttcgga     300
ggcggaacaa agttaaccgt ccta                                            324
```

<210> SEQ ID NO 181
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 181

```
gaggtgcagc tggtgcagag cggagccgaa gtgaagaaac ccggcagcag cgtgaaggtg      60
tcctgcaagg ccagcggcgg caccttcagc agctacgcca tcagctgggt gcgccaggct     120
cctggacagg gcctggaatg gatgggccgg atcatcccca tcttcggcac cgccaactac     180
gcccagaaat tccagggcag agtgaccatc accgccgacg agagccacag caccgcctac     240
atggaactga gcagcctgag aagcgaggac accgccgtgt actactgtgc ccggcacggc     300
ggctacagct tcgatagctg gggccagggc accctggtga ccgtgagctc agcctccacc     360
aagggtccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga gagttgagcc caaatcttgt     660
```

<210> SEQ ID NO 182
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 182

```
agctacgagc tgactcagcc cccttctgtg tctgtggccc tggccagac cgccagaatc    60 agctgcagcg gcgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccgag   240
gacgaggccg actactactg ccagacctac accagcggca caactacct ggtgttcgga   300 ggcggaacaa agttaaccgt cctaggtcag cccaaggctg cccccctcggt cactctgttc   360 ccgcccctcct ctgaggagct tcaagccaac aaggccacac tggtgtgtct cataagtgac   420
ttctacccgg gagccgtgac agtggcctgg aaggcagata gcagcccgt caaggcggga   480 gtggagacca ccacaccctc caaacaaagc aacaacaagt acgcggccag cagctatctg   540
agcctgacgc ctgagcagtg gaagtcccac agaagctaca gctgccaggt cacgcatgaa   600
gggagcaccg tggagaagac agtggcccct acagaatgtt ca                     642
```

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Tyr Ala Ile Ser
1               5

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ile Ile Pro Ile Phe Gly Thr Ala Asn Tyr Ala Gln Lys Phe Gln
1               5                   10                  15

Gly

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

His Gly Gly Tyr Ser Phe Asp Ser
1               5

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Gly Asp Asn Leu Gly Ser Lys Tyr Val Asp
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Asp Asn Asn Arg Pro Ser
1               5

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Thr Tyr Thr Ser Gly Asn Asn Tyr Leu
1               5                   10

<210> SEQ ID NO 189
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gln Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser
        115

<210> SEQ ID NO 190
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val

```
            20                  25                  30
Asp Trp Tyr Gln Gln Lys Pro Gly Gln Ala Pro Val Leu Val Ile Tyr
            35                  40                  45

Ser Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu
            100                 105
```

<210> SEQ ID NO 191
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gln Ser Tyr
            20                  25                  30

Ala Ile Ser Trp Val Arg Gln Ala Pro Gly Gln Gly Leu Glu Trp Met
            35                  40                  45

Gly Arg Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
        210                 215                 220
```

<210> SEQ ID NO 192
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 193
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
gaggtgcagc tggtgcagag cggagccgaa gtgaagaaac ccggcagcag cgtgaaggtg     60
tcctgcaagg ccagcggcgg caccttccaa agctacgcca tcagctgggt gcgccaggct    120
cctggacagg gcctggaatg gatgggccgg atcatcccca tcttcggcac cgccaactac    180
gcccagaaat tccagggcag agtgaccatc accgccacg agagcaccag caccgcctac    240
atggaactga gcagcctgag aagcgaggac accgccgtgt actactgtgc ccggcacggc    300
ggctacagct cgatagctg gggccagggc accctggtga ccgtgagctc a              351

<210> SEQ ID NO 194
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
agctacgagc tgactcagcc cccttctgtg tctgtggccc ctggccagac cgccagaatc     60
agctgcagcg gcgacaacct gggcagcaaa tacgtggact ggtatcagca gaagcccggc    120
caggctcccg tgctggtgat ctacagcgac aacaaccggc ccagcggcat ccctgagcgg    180
ttcagcggca gcaacagcgg caataccgcc accctgacca tcagcggcac ccaggccgag    240
gacgaggccg actactactg ccagacctac accagcggca caactacct ggtgttcgga    300 ggcggaacaa agttaaccgt ccta    324

<210> SEQ ID NO 195
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
gaggtgcagc tggtgcagag cggagccgaa gtgaagaaac ccggcagcag cgtgaaggtg     60
tcctgcaagg ccagcggcgg caccttccaa agctacgcca tcagctgggt gcgccaggct    120
cctggacagg gcctggaatg gatgggccgg atcatcccca tcttcggcac cgccaactac    180
gcccagaaat tccagggcag agtgaccatc accgccgacg agagcaccag caccgcctac    240
atggaactga gcagcctgag aagcgaggac accgccgtgt actactgtgc ccggcacggc    300
ggctacagct cgatagctg gggccagggc accctggtga ccgtgagctc agcctccacc    360
aagggtccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660

<210> SEQ ID NO 196
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
agctacgagc tgactcagcc ccctctgtg tctgtggccc ctggccagac cgccagaatc     60
agctgcagcg gcgacaacct gggcagcaaa tacgtggact ggtatcagca gaagcccggc    120
caggctcccg tgctggtgat ctacagcgac aacaaccggc ccagcggcat ccctgagcgg    180
ttcagcggca gcaacagcgg caataccgcc accctgacca tcagcggcac ccaggccgag    240
gacgaggccg actactactg ccagacctac accagcggca caactacct ggtgttcgga    300 ggcggaacaa agttaaccgt cctaggtcag cccaaggctg cccccctcggt cactctgttc    360 ccgccctcct ctgaggagct tcaagccaac aaggccacac tggtgtgtct cataagtgac    420
ttctacccgg gagccgtgac agtggcctgg aaggcagata gcagcccgt caaggcggga    480 gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca    642

<210> SEQ ID NO 197

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Tyr Ala Ile Ser
1               5

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Arg Ile Ile Pro Ile Phe Gly Thr Ala Asn Tyr Ala Gln Lys Phe Gln
1               5                  10                  15

Gly

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

His Gly Gly Tyr Ser Phe Asp Ser
1               5

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ser Gly Asp Asn Leu Gly Ser Lys Tyr Val Asp
1               5                  10

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Asp Asn Asn Arg Pro Ser
1               5

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 202

Gln Thr Tyr Thr Ser Gly Asn Asn Tyr Leu
1               5                   10

<210> SEQ ID NO 203
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ala Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser
        115

<210> SEQ ID NO 204
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu
            100                 105

<210> SEQ ID NO 205
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ala Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
    210                 215                 220

<210> SEQ ID NO 206
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Ser Gly Asn Asn Tyr
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln

```
            115                 120                 125
Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 207
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207
gaggtgcagc tggtgcagag cggagccgaa gtgaagaaac ccggcagcag cgtgaaggtg      60
tcctgcaagg ccagcggcgg caccttcaac gcctacgcca tcagctgggt cgcccaggct     120
cctggacagg gcctggaatg gatgggccgg atcatcccca tcttcggcac cgccaactac     180
gcccagaaat tccagggcag agtgaccatc accgccgacg agagccagca ccgcctac      240 atggaactga gcagcctgag aagcgaggac accgccgtgt actactgtgc ccggcacggc     300
ggctacagct cgatagctg gggccagggc accctggtga ccgtgagctc a               351

<210> SEQ ID NO 208
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208
agctacgagc tgactcagcc cccttctgtg tctgtggccc ctggccagac cgccagaatc      60
agctgcagcg gcgacaacct gggcagcaaa tacgtggact ggtatcagca gaagcccggc     120
caggctcccg tgctggtgat ctacagcgac aacaaccggc cagcggcat ccctgagcgg     180 ttcagcggca gcaacagcgg caataccgcc accctgacca tcagcggcac ccaggccgag     240
gacgaggccg actactactg ccagacctac accagcggca caactacct ggtgttcgga     300 ggcggaacaa agttaaccgt ccta                                            324

<210> SEQ ID NO 209
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209
gaggtgcagc tggtgcagag cggagccgaa gtgaagaaac ccggcagcag cgtgaaggtg      60
```

```
tcctgcaagg ccagcggcgg caccttcaac gcctacgcca tcagctgggt gcgccaggct    120
cctggacagg gcctggaatg gatgggccgg atcatcccca tcttcggcac cgccaactac    180
gcccagaaat tccagggcag agtgaccatc accgccgacg agagcaccag caccgcctac    240
atggaactga gcagcctgag aagcgaggac ccgccgtgt actactgtgc ccggcacggc    300
ggctacagct tcgatagctg gggccagggc accctggtga ccgtgagctc agcctccacc    360
aagggtccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc cggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
```

<210> SEQ ID NO 210
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
agctacgagc tgactcagcc cccttctgtg tctgtggccc ctggccagac cgccagaatc     60
agctgcagcg gcgacaacct gggcagcaaa tacgtggact ggtatcagca gaagcccggc    120
caggctcccg tgctggtgat ctacagcgac aacaaccggc ccagcggcat ccctgagcgg    180
ttcagcggca gcaacagcgg caataccgcc accctgacca tcagcggcac ccaggccgag    240
gacgaggccg actactactg ccagacctac accagcggca caactacct ggtgttcgga    300 ggcggaacaa agttaaccgt cctaggtcag cccaaggctg ccccctcggt cactctgttc    360
ccgccctcct ctgaggagct tcaagccaac aaggccacac tggtgtgtct cataagtgac    420
ttctacccgg gagccgtgac agtggcctgg aaggcagata gcagccccgt caaggcggga    480
gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                      642
```

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Tyr Ala Ile Ser
1               5

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Arg Ile Ile Pro Ile Phe Gly Thr Ala Asn Tyr Ala Gln Lys Phe Gln

```
1               5                   10                  15
Gly

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

His Gly Gly Tyr Ser Phe Asp Ser
1               5

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ser Gly Asp Asn Leu Gly Ser Lys Tyr Val Asp
1               5                   10

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Asp Asn Asn Arg Pro Ser
1               5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gln Thr Tyr Thr Ser Gly Asn Asn Tyr Leu
1               5                   10

<210> SEQ ID NO 217
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Ser Tyr
            20                  25                  30

Ala Ile Ser Trp Val Arg Gln Ala Pro Gly Gln Gly Leu Glu Trp Met
        35                  40                  45
```

```
Gly Arg Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
                100                 105                 110

Val Thr Val Ser Ser
            115

<210> SEQ ID NO 218
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Ser Tyr Glu Leu Thr Gln Pro Pro Ser Val Ser Val Ala Pro Gly Gln
 1               5                  10                  15

Thr Ala Arg Ile Ser Cys Ser Gly Asp Asn Leu Gly Ser Lys Tyr Val
                20                  25                  30

Asp Trp Tyr Gln Gln Lys Pro Gly Gln Ala Pro Val Leu Val Ile Tyr
                35                  40                  45

Ser Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu
                100                 105

<210> SEQ ID NO 219
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Gly Ser Tyr
                20                  25                  30

Ala Ile Ser Trp Val Arg Gln Ala Pro Gly Gln Gly Leu Glu Trp Met
                35                  40                  45

Gly Arg Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
                100                 105                 110
```

-continued

```
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys
210                 215                 220

<210> SEQ ID NO 220
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
        210

<210> SEQ ID NO 221
<211> LENGTH: 351
<212> TYPE: DNA
```

```
<213> ORGANISM: Artificial Sequence
<220> FEATURE:
<223> OTHER INFORMATION: Description of Artificial Sequence: Synthetic
      polynucleotide

<400> SEQUENCE: 221
gaggtgcagc tggtgcagag cggagccgaa gtgaagaaac ccggcagcag cgtgaaggtg      60
tcctgcaagg ccagcggcgg caccttcggc agctacgcca tcagctgggt gcgccaggct     120
cctggacagg gcctggaatg gatgggccgg atcatcccca tcttcggcac cgccaactac     180
gcccagaaat ccagggcag agtgaccatc accgccgacg agagcaccag caccgcctac     240
atggaactga gcagcctgag aagcgaggac accgccgtgt actactgtgc ccggcacggc     300
ggctacagct tcgatagctg gggccagggc accctggtga ccgtgagctc a              351

<210> SEQ ID NO 222
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
agctacgagc tgactcagcc ccccttctgtg tctgtggccc ctggccagac cgccagaatc      60
agctgcagcg gcgacaacct gggcagcaaa tacgtggact ggtatcagca gaagcccggc     120
caggctcccg tgctggtgat ctacagcgac aacaaccggc ccagcggcat ccctgagcgg     180
ttcagcggca gcaacagcgg caataccgcc accctgacca tcagcggcac ccaggccgag     240
gacgaggccg actactactg ccagacctac accagcggca caactaccct ggtgttcgga     300
ggcggaacaa agttaaccgt ccta                                             324

<210> SEQ ID NO 223
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
gaggtgcagc tggtgcagag cggagccgaa gtgaagaaac ccggcagcag cgtgaaggtg      60
tcctgcaagg ccagcggcgg caccttcggc agctacgcca tcagctgggt gcgccaggct     120
cctggacagg gcctggaatg gatgggccgg atcatcccca tcttcggcac cgccaactac     180
gcccagaaat ccagggcag agtgaccatc accgccgacg agagcaccag caccgcctac     240
atggaactga gcagcctgag aagcgaggac accgccgtgt actactgtgc ccggcacggc     300
ggctacagct tcgatagctg gggccagggc accctggtga ccgtgagctc agcctccacc     360
aagggtccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga gagttgagcc caaatcttgt     660

<210> SEQ ID NO 224
<211> LENGTH: 642
<212> TYPE: DNA
```

<213> ORGANISM: Artificial Sequence
<220> FEATURE:
<223> OTHER INFORMATION: Description of Artificial Sequence: Synthetic
polynucleotide

<400> SEQUENCE: 224

```
agctacgagc tgactcagcc cccttctgtg tctgtggccc ctggccagac cgccagaatc      60
agctgcagcg gcgacaacct gggcagcaaa tacgtggact ggtatcagca gaagcccggc     120
caggctcccg tgctggtgat ctacagcgac aacaaccggc cagcggcat ccctgagcgg      180 ttcagcggca gcaacagcgg caataccgcc accctgacca tcagcggcac ccaggccgag     240
gacgaggccg actactactg ccagacctac accagcggca caactacct ggtgttcgga      300 ggcggaacaa agttaaccgt cctaggtcag cccaaggctg cccctcggt cactctgttc      360 ccgcccctcct ctgaggagct tcaagccaac aaggccacac tggtgtgtct cataagtgac    420
ttctacccgg agccgtgac agtggcctgg aaggcagata gcagcccgt caaggcggga      480 gtggagacca ccacccctc caaacaaagc aacaacaagt acgcggccag cagctatctg     540
agcctgacgc ctgagcagtg gaagtcccac agaagctaca gctgccaggt cacgcatgaa    600
gggagcaccg tggagaagac agtggcccct acagaatgtt ca                        642
```

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 225

Ser Tyr Ala Ile Ser
1               5

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 226

Arg Ile Ile Pro Ile Phe Gly Thr Ala Asn Tyr Ala Gln Lys Phe Gln
1               5                   10                  15

Gly

<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 227

His Gly Gly Tyr Ser Phe Asp Ser
1               5

<210> SEQ ID NO 228
<211> LENGTH: 11
<212> TYPE: PRT
<213> ORGANISM: Artificial Sequence
<220> FEATURE:

<223> OTHER INFORMATION: Description of Artificial Sequence: Synthetic
    peptide

<400> SEQUENCE: 228

Ser Gly Asp Asn Leu Gly Ser Lys Tyr Val Asp
1               5                   10

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 229

Ser Asp Asn Asn Arg Pro Ser
1               5

<210> SEQ ID NO 230
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 230

Gln Thr Tyr Thr Ser Gly Asn Asn Tyr Leu
1               5                   10

<210> SEQ ID NO 231
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 231

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser
        115

<210> SEQ ID NO 232
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 232

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu
            100                 105

<210> SEQ ID NO 233
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
    210                 215                 220

<210> SEQ ID NO 234

<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 234

```
Ser Tyr Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Ser Gly Asn Asn Tyr
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 235
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 235

```
gaggtgcagc tggtgcagag cggagccgaa gtgaagaaac ccggcagcag cgtgaaggtg     60
tcctgcaagg ccagcggcgg caccttcacc agctacgcca tcagctgggt cgcccaggct    120
cctggacagg gcctggaatg gatgggccgg atcatcccca tcttcggcac cgccaactac    180
gcccagaaat tccagggcag agtgaccatc accgccgacg agagcaccag caccgcctac    240
atggaactga gcagcctgag aagcgaggac accgccgtgt actactgtgc ccggcacggc    300
ggctacagct tcgatagctg gggccagggc accctggtga ccgtgagctc a             351
```

<210> SEQ ID NO 236
<211> LENGTH: 324
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 236
agctacgagc tgactcagcc cccttctgtg tctgtggccc ctggccagac cgccagaatc    60
agctgcagcg gcgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccgag   240
gacgaggccg actactactg ccagacctac accagcggca caactacct ggtgttcgga    300 ggcggaacaa agttaaccgt ccta                                          324

<210> SEQ ID NO 237
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237
gaggtgcagc tggtgcagag cggagccgaa gtgaagaaac ccggcagcag cgtgaaggtg    60
tcctgcaagg ccagcggcgg cacctTcacc agctacgcca tcagctgggt gcgcaggct   120 cctggacagg gcctggaatg gatgggccgg atcatcccca tcttcggcac cgccaactac   180
gcccagaaat ccagggcag agtgaccatc accgccgacg agagccacag caccgcctac   240
atggaactga gcagcctgag aagcgaggac accgccgtgt actactgtgc ccggcacggc   300
ggctacagct tcgatagctg gggccagggc accctggtga ccgtgagctc agcctccacc   360
aagggtccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga gagttgagcc caaatcttgt   660

<210> SEQ ID NO 238
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
agctacgagc tgactcagcc cccttctgtg tctgtggccc ctggccagac cgccagaatc    60
agctgcagcg gcgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccgag   240
gacgaggccg actactactg ccagacctac accagcggca caactacct ggtgttcgga    300 ggcggaacaa agttaaccgt cctaggtcag cccaaggctg cccctcggt cactctgttc    360 ccgccctcct ctgaggagct tcaagccaac aaggccacac tggtgtgtct cataagtgac   420
ttctacccgg gagccgtgac agtggcctgg aaggcagata gcagcccgt caaggcggga   480 gtggagacca ccacaccctc caaacaaagc aacaacaagt acgcggccag cagctatctg   540
```
agcctgacgc ctgagcagtg gaagtcccac agaagctaca gctgccaggt cacgcatgaa      600
gggagcaccg tggagaagac agtggcccct acagaatgtt ca                         642

<210> SEQ ID NO 239
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Tyr Ala Ile Ser
1               5

<210> SEQ ID NO 240
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Arg Ile Ile Pro Ile Phe Gly Thr Ala Asn Tyr Ala Gln Lys Phe Gln
1               5                   10                  15

Gly

<210> SEQ ID NO 241
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

His Gly Gly Tyr Ser Phe Asp Ser
1               5

<210> SEQ ID NO 242
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Gly Asp Asn Leu Gly Ser Lys Tyr Val Asp
1               5                   10

<210> SEQ ID NO 243
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ser Asp Asn Asn Arg Pro Ser
1               5

<210> SEQ ID NO 244

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Thr Tyr Asp Ser Ser Pro Arg Thr Glu
1               5                   10

<210> SEQ ID NO 245
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser
        115

<210> SEQ ID NO 246
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                85                  90                  95

Glu Val Phe Gly Gly Gly Thr Lys Leu Thr Val Leu
            100                 105
```

```
<210> SEQ ID NO 247
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
    210                 215                 220

<210> SEQ ID NO 248
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80
```

Asp Glu Ala Asp Tyr Tyr Cys Ala Thr Tyr Asp Ser Ser Pro Arg Thr
            85                  90                  95

Glu Val Phe Gly Gly Gly Thr Lys Leu Thr Val Leu Gly Gln Pro Lys
        100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 249
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
gaggtgcagc tggtgcagag cggagccgaa gtgaagaaac ccggcagcag cgtgaaggtg      60
tcctgcaagg ccagcggcgg caccttcacc agctacgcca tcagctgggt gcgccaggct     120
cctggacagg gcctggaatg gatgggccgg atcatcccca tcttcggcac cgccaactac     180
gcccagaaat tccagggcag agtgaccatc accgccgacg agagccacag caccgcctac     240
atggaactga gcagcctgag aagcgaggac accgccgtgt actactgtgc ccggcacggc     300
ggctacagct cgatagctg gggccagggc accctggtga ccgtgagctc a              351

<210> SEQ ID NO 250
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250
agctacgtgc tgactcagcc ccctctgtg tctgtggccc ctggcaagac cgccagaatc      60
agctgcagcg gcgacaacct gggcagcaaa tacgtggact ggtatcagca gaagcccggc     120
caggctcccg tgctggtgat ctacagcgac aacaaccggc caagcggcat ccctgagcgg     180
ttcagcggca gcaacagcgg caataccgcc accctgacca tcagcggcac ccaggccatg     240
gacgaggccg actactactg cgccacctac gacagcagcc cagaaccgga ggtgttcgga     300
ggcggaacaa agttaaccgt ccta                                            324

<210> SEQ ID NO 251
<211> LENGTH: 660
<212> TYPE: DNA
<213> ORGANISM: Artificial Sequence
<220> FEATURE:

<223> OTHER INFORMATION: Description of Artificial Sequence: Synthetic
    polynucleotide

<400> SEQUENCE: 251
gaggtgcagc tggtgcagag cggagccgaa gtgaagaaac ccggcagcag cgtgaaggtg    60
tcctgcaagg ccagcggcgg caccttcacc agctacgcca tcagctgggt gcgccaggct    120
cctggacagg gcctggaatg gatgggccgg atcatcccca tcttcggcac cgccaactac    180
gcccagaaat tccagggcag agtgaccatc accgccgacg agagccagag caccgcctac    240
atggaactga gcagcctgag aagcgaggac accgccgtgt actactgtgc ccggcacggc    300
ggctacagct tcgatagctg gggccagggc accctggtga ccgtgagctc agcctccacc    360
aagggtccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660

<210> SEQ ID NO 252
<211> LENGTH: 642
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 252
agctacgtgc tgactcagcc cccttctgtg tctgtggccc ctggcaagac cgccagaatc    60
agctgcagcg gcgacaacct gggcagcaaa tacgtggact ggtatcagca gaagcccggc    120
caggctcccg tgctggtgat ctacagcgac aacaaccggc ccagcggcat ccctgagcgg    180
ttcagcggca gcaacagcgg caataccgcc accctgacca tcagcggcac ccaggccatg    240
gacgaggccg actactactg cgccacctac gacagcagcc cagaaccga ggtgttcgga    300 ggcggaacaa agttaaccgt cctaggtcag cccaaggctg ccccctcggt cactctgttc    360
ccgccctcct ctgaggagct tcaagccaac aaggccacac tggtgtgtct cataagtgac    420
ttctacccgg gagccgtgac agtggcctgg aaggcagata gcagccccgt caaggcggga    480
gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca              642

<210> SEQ ID NO 253
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 253

Ser Tyr Ala Ile Ser
1               5

<210> SEQ ID NO 254
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 254

Arg Ile Ile Pro Ile Phe Gly Thr Ala Asn Tyr Ala Gln Lys Phe Gln
1               5                   10                  15

Gly

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

His Gly Gly Tyr Ser Phe Asp Ser
1               5

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ser Gly Asp Asn Leu Gly Ser Lys Tyr Val Asp
1               5                   10

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ser Asp Asn Asn Arg Pro Ser
1               5

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ala Thr Tyr Asp Ser Ser Pro Arg Thr Glu
1               5                   10

<210> SEQ ID NO 259
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Glu Val Gln Leu Val Gln Ser Gly Ala Glu Val Lys Lys Pro Gly Ser
```

```
                1               5                   10                  15
            Ser Val Lys Val Ser Cys Lys Ala Ser Gly Gly Thr Phe Gln Ser Tyr
                            20                  25                  30

Ala Ile Ser Trp Val Arg Gln Ala Pro Gly Gln Gly Leu Glu Trp Met
                        35                  40                  45

Gly Arg Ile Ile Pro Ile Phe Gly Thr Ala Asn Tyr Ala Gln Lys Phe
                    50                  55                  60

Gln Gly Arg Val Thr Ile Thr Ala Asp Glu Ser Thr Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg His Gly Gly Tyr Ser Phe Asp Ser Trp Gly Gln Gly Thr Leu
                        100                 105                 110

Val Thr Val Ser Ser
                        115

<210> SEQ ID NO 260
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Ser Tyr Val Leu Thr Gln Pro Pro Ser Val Ser Val Ala Pro Gly Lys
            1               5                   10                  15

Thr Ala Arg Ile Ser Cys Ser Gly Asp Asn Leu Gly Ser Lys Tyr Val
                            20                  25                  30

Asp Trp Tyr Gln Gln Lys Pro Gly Gln Ala Pro Val Leu Val Ile Tyr
                        35                  40                  45

Ser Asp Asn Asn Arg Pro Ser Gly Ile Pro Glu Arg Phe Ser Gly Ser
                    50                  55                  60

Asn Ser Gly Asn Thr Ala Thr Leu Thr Ile Ser Gly Thr Gln Ala Met
            65                  70                  75                  80

Asp Glu Ala Asp Tyr Tyr Cys Ala Thr Tyr Asp Ser Ser Pro Arg Thr
                            85                  90                  95

Glu Val Phe Gly Gly Gly Thr Lys Leu Thr Val Leu
                        100                 105

<210> SEQ ID NO 261
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Glu Val Gln Leu Val Gln Ser Gly Ala Glu Val Lys Lys Pro Gly Ser
            1               5                   10                  15

Ser Val Lys Val Ser Cys Lys Ala Ser Gly Gly Thr Phe Gln Ser Tyr
                            20                  25                  30

Ala Ile Ser Trp Val Arg Gln Ala Pro Gly Gln Gly Leu Glu Trp Met
                        35                  40                  45

Gly Arg Ile Ile Pro Ile Phe Gly Thr Ala Asn Tyr Ala Gln Lys Phe
                    50                  55                  60

Gln Gly Arg Val Thr Ile Thr Ala Asp Glu Ser Thr Ser Thr Ala Tyr
```

```
              65                  70                  75                  80
Met Glu Leu Ser Ser Leu Arg Ser Glu Asp Thr Ala Val Tyr Tyr Cys
                    85                  90                  95

Ala Arg His Gly Gly Tyr Ser Phe Asp Ser Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys
            210                 215                 220

<210> SEQ ID NO 262
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
                20                  25                  30

Asp Trp Tyr Gln Gln Lys Pro Gly Gln Ala Pro Val Leu Val Ile Tyr
            35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                85                  90                  95

Glu Val Phe Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205
```

Ala Pro Thr Glu Cys Ser
    210

<210> SEQ ID NO 263
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263
gaggtgcagc tggtgcagag cggagccgaa gtgaagaaac ccggcagcag cgtgaaggtg    60
tcctgcaagg ccagcggcgg caccttccaa agctacgcca tcagctgggt gcgccaggct   120
cctggacagg gcctggaatg gatgggccgg atcatcccca tcttcggcac cgccaactac   180
gcccagaaat tccagggcag agtgaccatc accgccgacg agagcaccag caccgcctac   240
atggaactga gcagcctgag aagcgaggac accgccgtgt actactgtgc ccggcacggc   300
ggctacagct tcgatagctg gggccagggc accctggtga ccgtgagctc a           351

<210> SEQ ID NO 264
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264
agctacgtgc tgactcagcc cccttctgtg tctgtggccc ctggcaagac cgccagaatc    60
agctgcagcg gcgacaacct gggcagcaaa tacgtggact ggtatcagca gaagcccggc   120
caggctcccg tgctggtgat ctacagcgac aacaaccggc cagcggcat ccctgagcgg    180 ttcagcggca gcaacagcgg caataccgcc accctgacca tcagcggcac ccaggccatg   240
gacgaggccg actactactg cgccacctac gacagcagcc cagaaccga ggtgttcgga    300 ggcggaacaa agttaaccgt ccta                                          324

<210> SEQ ID NO 265
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
gaggtgcagc tggtgcagag cggagccgaa gtgaagaaac ccggcagcag cgtgaaggtg    60
tcctgcaagg ccagcggcgg caccttccaa agctacgcca tcagctgggt gcgccaggct   120
cctggacagg gcctggaatg gatgggccgg atcatcccca tcttcggcac cgccaactac   180
gcccagaaat tccagggcag agtgaccatc accgccgacg agagcaccag caccgcctac   240
atggaactga gcagcctgag aagcgaggac accgccgtgt actactgtgc ccggcacggc   300
ggctacagct tcgatagctg gggccagggc accctggtga ccgtgagctc agcctccacc   360
aagggtccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600

```
aacgtgaatc acaagcccag caacaccaag gtggacaaga gagttgagcc caaatcttgt    660
```

<210> SEQ ID NO 266
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 266

```
agctacgtgc tgactcagcc cccttctgtg tctgtggccc ctggcaagac cgccagaatc     60
agctgcagcg gcgacaacct gggcagcaaa tacgtggact ggtatcagca gaagcccggc    120
caggctcccg tgctggtgat ctacagcgac aacaaccggc ccagcggcat ccctgagcgg    180
ttcagcggca gcaacagcgg caataccgcc accctgacca tcagcggcac ccaggccatg    240
gacgaggccg actactactg cgccacctac gacagcagcc ccagaaccga ggtgttcgga    300
ggcggaacaa agttaaccgt cctaggtcag cccaaggctg ccccctcggt cactctgttc    360 ccgcccctcct ctgaggagct tcaagccaac aaggccacac tggtgtgtct cataagtgac    420
ttctacccgg gagccgtgac agtggcctgg aaggcagata gcagcccgt caaggcggga    480 gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                      642
```

<210> SEQ ID NO 267
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Tyr Ala Ile Ser
1               5

<210> SEQ ID NO 268
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Arg Ile Ile Pro Ile Phe Gly Thr Ala Asn Tyr Ala Gln Lys Phe Gln
1               5                   10                  15

Gly

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

His Gly Gly Tyr Ser Phe Asp Ser
1               5

-continued

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ser Gly Asp Asn Leu Gly Ser Lys Tyr Val Asp
1               5                   10

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ser Asp Asn Asn Arg Pro Ser
1               5

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ala Thr Tyr Asp Ser Ser Pro Arg Thr Glu
1               5                   10

<210> SEQ ID NO 273
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser
        115

```
<210> SEQ ID NO 274
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                85                  90                  95

Glu Val Phe Gly Gly Gly Thr Lys Leu Thr Val Leu
            100                 105

<210> SEQ ID NO 275
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Tyr Ser Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

```
                195                 200                 205
Thr Lys Val Asp Lys Arg Val Glu Pro Lys Ser Cys
    210                 215                 220

<210> SEQ ID NO 276
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Ser Tyr Val Leu Thr Gln Pro Pro Ser Val Ser Val Ala Pro Gly Lys
1               5                   10                  15

Thr Ala Arg Ile Ser Cys Ser Gly Asp Asn Leu Gly Ser Lys Tyr Val
            20                  25                  30

Asp Trp Tyr Gln Gln Lys Pro Gly Gln Ala Pro Val Leu Val Ile Tyr
        35                  40                  45

Ser Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Asp Ser Ser Pro Arg Thr
                85                  90                  95

Glu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 277
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277
gaggtgcagc tggtgcagag cggagccgaa gtgaagaaac cggcagcag cgtgaaggtg      60 tcctgcaagg ccagcggcgg caccttcagc agctacgcca tcagctgggt gcgccaggct    120
cctggacagg gcctggaatg gatgggccgg atcatcccca tcttcggcac cgccaactac    180
gcccagaaat tccagggcag agtgaccatc accgccgacg agagccacag caccgcctac    240
atggaactga gcagcctgag aagcgaggac accgccgtgt actactgtgc ccggcacggc    300
```

<210> SEQ ID NO 278
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278

```
agctacgtgc tgactcagcc cccttctgtg tctgtggccc ctggcaagac cgccagaatc    60
agctgcagcg gcgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccatg   240
gacgaggccg actactactg cgccacctac gacagcagcc cagaaccga ggtgttcgga    300
ggcggaacaa agttaaccgt ccta                                          324
```

<210> SEQ ID NO 279
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279

```
gaggtgcagc tggtgcagag cggagccgaa gtgaagaaac ccggcagcag cgtgaaggtg    60
tcctgcaagg ccagcggcgg caccttcagc agctacgcca tcagctgggt gcgccaggct   120
cctggacagg gcctggaatg gatgggccgg atcatcccca tcttcggcac cgccaactac   180
gcccagaaat tccagggcag agtgaccatc accgccgacg agagcaccag caccgcctac   240
atggaactga gcagcctgag aagcgaggac accgccgtgt actactgtgc ccggcacggc   300
ggctacagct cgatagctg gggccagggc accctggtga ccgtgagctc agcctccacc   360
aagggtccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga gagttgagcc caaatcttgt   660
```

<210> SEQ ID NO 280
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 280

```
agctacgtgc tgactcagcc cccttctgtg tctgtggccc ctggcaagac cgccagaatc    60
agctgcagcg gcgacaacct gggcagcaaa tacgtggact ggtatcagca gaagcccggc   120
caggctcccg tgctggtgat ctacagcgac aacaaccggc ccagcggcat ccctgagcgg   180
ttcagcggca gcaacagcgg caataccgcc accctgacca tcagcggcac ccaggccatg   240
gacgaggccg actactactg cgccacctac gacagcagcc cagaaccga ggtgttcgga    300
```

```
ggcggaacaa agttaaccgt cctaggtcag cccaaggctg cccctcggt cactctgttc    360 ccgcccctcct ctgaggagct tcaagccaac aaggccacac tggtgtgtct cataagtgac   420
ttctacccgg gagccgtgac agtggcctgg aaggcagata gcagcccgt caaggcggga    480 gtggagacca ccacaccctc caaacaaagc aacaacaagt acgcggccag cagctatctg   540
agcctgacgc ctgagcagtg gaagtcccac agaagctaca gctgccaggt cacgcatgaa   600
gggagcaccg tggagaagac agtggcccct acagaatgtt ca                     642
```

```
<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gly Gly Thr Phe Asn Ser Tyr
1               5

<210> SEQ ID NO 282
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ile Pro Ile Phe Gly Thr
1               5

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

His Gly Gly Tyr Ser Phe Asp Ser
1               5

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Asp Asn Leu Gly Ser Lys Tyr
1               5

<210> SEQ ID NO 285
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285
```

```
Ser Asp Asn
1

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Tyr Thr Ser Gly Asn Asn Tyr Leu
1               5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Gly Gly Thr Phe Ser Ser Tyr
1               5

<210> SEQ ID NO 288
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Asn Pro Tyr Tyr Gly Asp
1               5

<210> SEQ ID NO 289
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Tyr Tyr Ser Asp Tyr Met Asp Tyr
1               5

<210> SEQ ID NO 290
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ser Ser Ser Asn Ile Gly Ala Gly Tyr Asp
1               5                   10

<210> SEQ ID NO 291
<211> LENGTH: 3
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 291

Asp Asn Ser
1

<210> SEQ ID NO 292
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Tyr Asp Glu Ser Ala His Ser
1               5

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gly Tyr Thr Phe Thr Ser His
1               5

<210> SEQ ID NO 294
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Asn Ala Asp Leu Gly Asp
1               5

<210> SEQ ID NO 295
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Asp Gly Ile Glu His Gly Gly His Tyr Tyr Trp Gly Tyr Leu Phe Asp
1               5                   10                  15

Ile

<210> SEQ ID NO 296
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Asp Ser Ile Arg Glu Tyr Tyr
1               5

```
<210> SEQ ID NO 297
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Asp Asp Thr
1

<210> SEQ ID NO 298
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Trp Asp Phe Ser Pro Ala Ile
1               5

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Tyr Ser Phe Thr Asn Tyr
1               5

<210> SEQ ID NO 300
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Asp Pro Gly Glu Ser Leu
1               5

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Thr Gly Val Ala Asp Val Asp Met Pro Phe Ala His
1               5                   10

<210> SEQ ID NO 302
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 302

Asp Asn Leu Gly Ser Tyr Tyr
1               5

<210> SEQ ID NO 303
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gly Asp Ser
1

<210> SEQ ID NO 304
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Trp Asp Ile Thr Ser Phe
1               5

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Gly Thr Phe Asn Ser Tyr
1               5

<210> SEQ ID NO 306
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ile Pro Ile Phe Gly Thr
1               5

<210> SEQ ID NO 307
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

His Gly Gly Tyr Ser Phe Asp Ser
1               5

<210> SEQ ID NO 308
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Asp Asn Leu Gly Ser Lys Tyr
1               5

<210> SEQ ID NO 309
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Asp Asn
1

<210> SEQ ID NO 310
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Tyr Asp Ser Ser Pro Arg Thr Glu
1               5

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Tyr Thr Phe Thr Ser His
1               5

<210> SEQ ID NO 312
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Asn Pro Val Asp Gly Gly
1               5

<210> SEQ ID NO 313
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Asp Gly Ile Glu His Gly Gly His Tyr Tyr Trp Gly Tyr Leu Phe Asp
```

```
1               5               10              15
Ile
```

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

```
Asp Ser Ile Arg Glu Tyr Tyr
1               5
```

<210> SEQ ID NO 315
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

```
Asp Asp Thr
1
```

<210> SEQ ID NO 316
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

```
Trp Asp Phe Ser Pro Ala Ile
1               5
```

<210> SEQ ID NO 317
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

```
Gly Gly Thr Phe Ser Ser Tyr
1               5
```

<210> SEQ ID NO 318
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

```
Ile Pro Ile Phe Gly Thr
1               5
```

<210> SEQ ID NO 319
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 319

His Gly Gly Tyr Tyr Phe Asp Ser
1               5

<210> SEQ ID NO 320
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Asp Asn Leu Gly Ser Lys Tyr
1               5

<210> SEQ ID NO 321
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Ser Asp Asn
1

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Tyr Thr Ser Gly Asn Asn Tyr Leu
1               5

<210> SEQ ID NO 323
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Gly Gly Thr Phe Ser Ser Tyr
1               5

<210> SEQ ID NO 324
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ile Pro Ile Phe Gly Thr
1               5
```

<210> SEQ ID NO 325
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

His Gly Gly Tyr Ile Phe Asp Ser
1               5

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Asp Asn Leu Gly Ser Lys Tyr
1               5

<210> SEQ ID NO 327
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Ser Asp Asn
1

<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Tyr Thr Ser Gly Asn Asn Tyr Leu
1               5

<210> SEQ ID NO 329
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Gly Thr Phe Ser Ser Tyr
1               5

<210> SEQ ID NO 330
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 330

Ile Pro Ile Phe Gly Thr
1               5

<210> SEQ ID NO 331
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

His Gly Gly Tyr Val Phe Asp Ser
1               5

<210> SEQ ID NO 332
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Asp Asn Leu Gly Ser Lys Tyr
1               5

<210> SEQ ID NO 333
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ser Asp Asn
1

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Tyr Thr Ser Gly Asn Asn Tyr Leu
1               5

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gly Gly Thr Phe Ser Ser Tyr
1               5

<210> SEQ ID NO 336
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 336

Ile Pro Ile Phe Gly Thr
1               5

<210> SEQ ID NO 337
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

His Gly Gly Tyr Ile Phe Asp Ser
1               5

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Asp Asn Leu Gly Ser Lys Tyr
1               5

<210> SEQ ID NO 339
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ser Asp Asn
1

<210> SEQ ID NO 340
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Tyr Asp Ser Ser Pro Arg Thr Glu
1               5

<210> SEQ ID NO 341
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gly Gly Thr Phe Ser Ser Tyr
1               5
```

<210> SEQ ID NO 342
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ile Pro Ile Phe Gly Thr
1               5

<210> SEQ ID NO 343
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

His Gly Gly Tyr Tyr Phe Asp Ser
1               5

<210> SEQ ID NO 344
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Asp Asn Leu Gly Ser Lys Tyr
1               5

<210> SEQ ID NO 345
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ser Asp Asn
1

<210> SEQ ID NO 346
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Tyr Asp Ser Ser Pro Arg Thr Glu
1               5

<210> SEQ ID NO 347
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gly Gly Thr Phe Ser Ser Tyr
1               5

<210> SEQ ID NO 348
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ile Pro Ile Phe Gly Thr
1               5

<210> SEQ ID NO 349
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

His Gly Gly Tyr Val Phe Asp Ser
1               5

<210> SEQ ID NO 350
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Asp Asn Leu Gly Ser Lys Tyr
1               5

<210> SEQ ID NO 351
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Ser Asp Asn
1

<210> SEQ ID NO 352
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Tyr Asp Ser Ser Pro Arg Thr Glu
1               5

<210> SEQ ID NO 353
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Gly Gly Thr Phe Ser Ser Tyr
1               5

<210> SEQ ID NO 354
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ile Pro Ile Phe Gly Thr
1               5

<210> SEQ ID NO 355
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

His Gly Gly Tyr Ser Phe Asp Ser
1               5

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Asp Asn Leu Gly Ser Lys Tyr
1               5

<210> SEQ ID NO 357
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Ser Asp Asn
1

<210> SEQ ID NO 358
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Tyr Thr Ser Gly Asn Asn Tyr Leu
```

```
1               5
```

<210> SEQ ID NO 359
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

```
Gly Gly Thr Phe Gln Ser Tyr
1               5
```

<210> SEQ ID NO 360
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

```
Ile Pro Ile Phe Gly Thr
1               5
```

<210> SEQ ID NO 361
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

```
His Gly Gly Tyr Ser Phe Asp Ser
1               5
```

<210> SEQ ID NO 362
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

```
Asp Asn Leu Gly Ser Lys Tyr
1               5
```

<210> SEQ ID NO 363
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

```
Ser Asp Asn
1
```

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Tyr Thr Ser Gly Asn Asn Tyr Leu
1               5

<210> SEQ ID NO 365
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Gly Gly Thr Phe Asn Ala Tyr
1               5

<210> SEQ ID NO 366
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ile Pro Ile Phe Gly Thr
1               5

<210> SEQ ID NO 367
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

His Gly Gly Tyr Ser Phe Asp Ser
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Asp Asn Leu Gly Ser Lys Tyr
1               5

<210> SEQ ID NO 369
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ser Asp Asn
1

<210> SEQ ID NO 370

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Tyr Thr Ser Gly Asn Asn Tyr Leu
1               5

<210> SEQ ID NO 371
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Gly Gly Thr Phe Gly Ser Tyr
1               5

<210> SEQ ID NO 372
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ile Pro Ile Phe Gly Thr
1               5

<210> SEQ ID NO 373
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

His Gly Gly Tyr Ser Phe Asp Ser
1               5

<210> SEQ ID NO 374
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Asp Asn Leu Gly Ser Lys Tyr
1               5

<210> SEQ ID NO 375
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375
```

Ser Asp Asn
1

<210> SEQ ID NO 376
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Tyr Thr Ser Gly Asn Asn Tyr Leu
1               5

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gly Gly Thr Phe Thr Ser Tyr
1               5

<210> SEQ ID NO 378
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ile Pro Ile Phe Gly Thr
1               5

<210> SEQ ID NO 379
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

His Gly Gly Tyr Ser Phe Asp Ser
1               5

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Asp Asn Leu Gly Ser Lys Tyr
1               5

<210> SEQ ID NO 381
<211> LENGTH: 3
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 381

Ser Asp Asn
1

<210> SEQ ID NO 382
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Tyr Thr Ser Gly Asn Asn Tyr Leu
1               5

<210> SEQ ID NO 383
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Gly Gly Thr Phe Thr Ser Tyr
1               5

<210> SEQ ID NO 384
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ile Pro Ile Phe Gly Thr
1               5

<210> SEQ ID NO 385
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

His Gly Gly Tyr Ser Phe Asp Ser
1               5

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Asp Asn Leu Gly Ser Lys Tyr
1               5
```

```
<210> SEQ ID NO 387
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ser Asp Asn
1

<210> SEQ ID NO 388
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Tyr Asp Ser Ser Pro Arg Thr Glu
1               5

<210> SEQ ID NO 389
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Gly Gly Thr Phe Gln Ser Tyr
1               5

<210> SEQ ID NO 390
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Ile Pro Ile Phe Gly Thr
1               5

<210> SEQ ID NO 391
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

His Gly Gly Tyr Ser Phe Asp Ser
1               5

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392
```

```
Asp Asn Leu Gly Ser Lys Tyr
1               5

<210> SEQ ID NO 393
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ser Asp Asn
1

<210> SEQ ID NO 394
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Tyr Asp Ser Ser Pro Arg Thr Glu
1               5

<210> SEQ ID NO 395
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Gly Gly Thr Phe Ser Ser Tyr
1               5

<210> SEQ ID NO 396
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Ile Pro Ile Phe Gly Thr
1               5

<210> SEQ ID NO 397
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

His Gly Gly Tyr Ser Phe Asp Ser
1               5

<210> SEQ ID NO 398
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 398

Asp Asn Leu Gly Ser Lys Tyr
1               5

<210> SEQ ID NO 399
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Ser Asp Asn
1

<210> SEQ ID NO 400
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Tyr Asp Ser Ser Pro Arg Thr Glu
1               5

<210> SEQ ID NO 401
<211> LENGTH: 441
<212> TYPE: PRT
<213> ORGANISM: Homo sapiens

<400> SEQUENCE: 401

Pro Val Leu Cys Phe Thr Gln Tyr Glu Glu Ser Ser Gly Lys Cys Lys
1               5                   10                  15

Gly Leu Leu Gly Gly Gly Val Ser Val Glu Asp Cys Cys Leu Asn Thr
            20                  25                  30

Ala Phe Ala Tyr Gln Lys Arg Ser Gly Gly Leu Cys Gln Pro Cys Arg
        35                  40                  45

Ser Pro Arg Trp Ser Leu Trp Ser Thr Trp Ala Pro Cys Ser Val Thr
    50                  55                  60

Cys Ser Glu Gly Ser Gln Leu Arg Tyr Arg Arg Cys Val Gly Trp Asn
65                  70                  75                  80

Gly Gln Cys Ser Gly Lys Val Ala Pro Gly Thr Leu Glu Trp Gln Leu
                85                  90                  95

Gln Ala Cys Glu Asp Gln Gln Cys Cys Pro Glu Met Gly Gly Trp Ser
            100                 105                 110

Gly Trp Gly Pro Trp Glu Pro Cys Ser Val Thr Cys Ser Lys Gly Thr
        115                 120                 125

Arg Thr Arg Arg Arg Ala Cys Asn His Pro Ala Pro Lys Cys Gly Gly
    130                 135                 140

His Cys Pro Gly Gln Ala Gln Glu Ser Glu Ala Cys Asp Thr Gln Gln
145                 150                 155                 160

Val Cys Pro Thr His Gly Ala Trp Ala Thr Trp Gly Pro Trp Thr Pro
                165                 170                 175

Cys Ser Ala Ser Cys His Gly Gly Pro His Glu Pro Lys Glu Thr Arg
```

```
              180                 185                 190
Ser Arg Lys Cys Ser Ala Pro Glu Pro Ser Gln Lys Pro Pro Gly Lys
            195                 200                 205

Pro Cys Pro Gly Leu Ala Tyr Glu Gln Arg Cys Thr Gly Leu Pro
            210                 215                 220

Pro Cys Pro Val Ala Gly Gly Trp Gly Pro Trp Gly Pro Val Ser Pro
225                 230                 235                 240

Cys Pro Val Thr Cys Gly Leu Gly Gln Thr Met Glu Gln Arg Thr Cys
                245                 250                 255

Asn His Pro Val Pro Gln His Gly Gly Pro Phe Cys Ala Gly Asp Ala
            260                 265                 270

Thr Arg Thr His Ile Cys Asn Thr Ala Val Pro Cys Pro Val Asp Gly
        275                 280                 285

Glu Trp Asp Ser Trp Gly Glu Trp Ser Pro Cys Ile Arg Arg Asn Met
    290                 295                 300

Lys Ser Ile Ser Cys Gln Glu Ile Pro Gly Gln Gln Ser Arg Gly Arg
305                 310                 315                 320

Thr Cys Arg Gly Arg Lys Phe Asp Gly His Arg Cys Ala Gly Gln Gln
                325                 330                 335

Gln Asp Ile Arg His Cys Tyr Ser Ile Gln His Cys Pro Leu Lys Gly
            340                 345                 350

Ser Trp Ser Glu Trp Ser Thr Trp Gly Leu Cys Met Pro Pro Cys Gly
            355                 360                 365

Pro Asn Pro Thr Arg Ala Arg Gln Arg Leu Cys Thr Pro Leu Leu Pro
        370                 375                 380

Lys Tyr Pro Pro Thr Val Ser Met Val Glu Gly Gln Gly Glu Lys Asn
385                 390                 395                 400

Val Thr Phe Trp Gly Arg Pro Leu Pro Arg Cys Glu Glu Leu Gln Gly
                405                 410                 415

Gln Lys Leu Val Val Glu Glu Lys Arg Pro Cys Leu His Val Pro Ala
            420                 425                 430

Cys Lys Asp Pro Glu Glu Glu Leu
        435                 440

<210> SEQ ID NO 402
<211> LENGTH: 469
<212> TYPE: PRT
<213> ORGANISM: Pan troglodytes

<400> SEQUENCE: 402

Met Ile Thr Glu Gly Ala Gln Ala Pro Cys Leu Leu Leu Pro Pro Leu
1               5                   10                  15

Leu Leu Leu Leu Thr Leu Pro Ala Thr Gly Ser Asp Pro Val Leu Cys
            20                  25                  30

Phe Thr Gln Tyr Glu Glu Ser Ser Gly Lys Cys Lys Gly Leu Leu Gly
        35                  40                  45

Gly Gly Val Ser Val Lys Asp Cys Cys Leu Asn Thr Ala Tyr Ala Tyr
    50                  55                  60

Gln Glu Arg Asn Gly Gly Leu Cys Gln Pro Cys Arg Ser Pro Arg Trp
65                  70                  75                  80

Ser Leu Trp Ser Thr Trp Ala Pro Cys Ser Val Thr Cys Ser Glu Gly
                85                  90                  95

Ser Gln Leu Arg Tyr Arg Arg Cys Val Gly Trp Asn Gly Gln Cys Ser
            100                 105                 110
```

Glu Arg Val Ala Leu Gly Thr Leu Glu Trp Gln Leu Gln Ala Cys Glu
            115                 120                 125

Asp Lys Gln Cys Cys Pro Glu Met Gly Gly Trp Ser Asp Trp Gly Pro
        130                 135                 140

Trp Glu Pro Cys Ser Val Thr Cys Ser Lys Gly Met Arg Thr Arg Arg
145                 150                 155                 160

Arg Ala Cys Asn His Pro Ala Pro Lys Cys Gly Gly His Cys Pro Gly
                165                 170                 175

Glu Ala Gln Glu Ser Glu Ala Cys Asp Thr Gln Gln Val Cys Pro Thr
            180                 185                 190

His Gly Ala Trp Ala Ala Trp Gly Pro Trp Ser Pro Cys Ser Gly Ser
        195                 200                 205

Cys His Gly Gly Pro His Glu Pro Lys Glu Thr Arg Ser Arg Thr Cys
    210                 215                 220

Ser Ala Pro Glu Pro Ser Gln Lys Pro Gly Lys Pro Cys Pro Gly
225                 230                 235                 240

Pro Ala Tyr Glu His Arg Lys Cys Thr Gly Leu Pro Pro Cys Pro Val
                245                 250                 255

Ala Gly Gly Trp Gly Pro Trp Gly Pro Val Ser Pro Cys Pro Val Thr
            260                 265                 270

Cys Gly Leu Gly Gln Thr Ile Glu Arg Arg Thr Cys Asn Arg Pro Val
        275                 280                 285

Pro Gln His Gly Gly Pro Ser Cys Ala Gly Asp Ala Thr Arg Thr His
    290                 295                 300

Ile Cys Asn Thr Ala Ala Pro Cys Pro Val Asp Gly Glu Trp Asp Leu
305                 310                 315                 320

Trp Gly Gln Trp Ser Thr Cys Val Arg Arg Asn Met Lys Ser Ile Ser
                325                 330                 335

Cys Glu Glu Ile Pro Gly Gln Gln Ser Arg Trp Arg Thr Cys Lys Gly
            340                 345                 350

Arg Lys Phe Asp Gly His Arg Cys Thr Gly Gln Gln Asp Ile Arg
        355                 360                 365

His Cys Tyr Ser Ile Gln His Cys Pro Leu Lys Gly Ser Trp Ser Glu
    370                 375                 380

Trp Ser Thr Trp Gly Leu Cys Met Pro Pro Cys Gly Pro Asn Pro Thr
385                 390                 395                 400

Arg Ala Arg Gln Arg Leu Cys Thr Pro Leu Leu Pro Lys Tyr Pro Pro
                405                 410                 415

Thr Val Ser Met Val Glu Gly Gln Gly Glu Lys Asn Val Thr Phe Trp
            420                 425                 430

Gly Arg Pro Leu Pro Arg Cys Glu Glu Leu Gln Gly Gln Lys Leu Val
        435                 440                 445

Val Glu Glu Lys Arg Pro Cys Leu His Val Pro Ala Cys Lys Asp Pro
    450                 455                 460

Glu Glu Glu Lys Leu
465

<210> SEQ ID NO 403
<211> LENGTH: 465
<212> TYPE: PRT
<213> ORGANISM: Rattus norvegicus

<400> SEQUENCE: 403

Met Pro Val Gly Met Gln Ala Pro Gln Trp Leu Leu Leu Leu Leu Leu
1               5                   10                  15

```
Ile Leu Pro Thr Thr Gly Ser Asp Pro Val Leu Cys Phe Thr Gln Tyr
            20                  25                  30

Glu Glu Pro Ser Gly Arg Cys Lys Gly Leu Leu Gly Arg Asp Ile Arg
        35                  40                  45

Val Glu Asp Cys Cys Leu Asn Thr Ala Tyr Ala Phe Gln Glu His Asp
50                  55                  60

Gly Gly Leu Cys Gln Ser Cys Arg Ser Pro Gln Trp Ser Ala Trp Ser
65                  70                  75                  80

Ser Trp Gly Pro Cys Ser Val Thr Cys Ser Glu Gly Ser Gln Leu Arg
                85                  90                  95

His Arg Arg Cys Val Gly Arg Gly Gly Gln Cys Ser Glu Lys Ala Ala
            100                 105                 110

Pro Gly Thr Leu Glu Trp Gln Leu Gln Ala Cys Glu Asp Gln Leu Cys
        115                 120                 125

Cys Pro Glu Met Gly Gly Trp Ser Glu Trp Gly Pro Trp Gly Pro Cys
130                 135                 140

Ser Val Thr Cys Ser Lys Gly Thr Gln Thr Arg Gln Arg Leu Cys Asp
145                 150                 155                 160

Asn Pro Ala Pro Lys Cys Gly Gly His Cys Pro Gly Glu Ala Gln Gln
                165                 170                 175

Ser Gln Ala Cys Asp Thr Gln Lys Ile Cys Pro Thr His Gly Ala Trp
            180                 185                 190

Ala Ser Trp Gly Pro Trp Ser Ala Cys Ser Gly Ser Cys Leu Gly Gly
        195                 200                 205

Ala Gln Glu Pro Lys Glu Thr Arg Ser Arg Ser Cys Ser Ala Pro Ala
        210                 215                 220

Pro Ser His Gln Pro Pro Gly Lys Pro Cys Ser Gly Thr Ala Tyr Glu
225                 230                 235                 240

His Arg Gly Cys Ser Gly Leu Pro Pro Cys Pro Val Ala Gly Gly Trp
                245                 250                 255

Gly Pro Trp Gly Pro Ser Ser Pro Cys Pro Val Thr Cys Gly Leu Gly
            260                 265                 270

Gln Thr Leu Glu Arg Arg Thr Cys Asp His Pro Val Pro Arg His Gly
        275                 280                 285

Gly Pro Phe Cys Ala Gly Asp Ala Thr Arg Lys His Val Cys Asn Thr
        290                 295                 300

Ala Met Pro Cys Pro Val Asn Gly Glu Trp Glu Ala Trp Gly Lys Trp
305                 310                 315                 320

Ser His Cys Ser Arg Val Arg Met Lys Ser Ile Ser Cys Asp Glu Ile
                325                 330                 335

Pro Gly Gln Gln Ser Arg Ser Arg Ser Cys Gly Gly Arg Lys Phe Asp
            340                 345                 350

Gly Gln Pro Cys Thr Gly Lys Leu Gln Asp Ile Arg His Cys Tyr Asp
        355                 360                 365

Ile His Asn Cys Val Leu Lys Gly Ser Trp Ser Gln Trp Ser Thr Trp
        370                 375                 380

Gly Leu Cys Thr Pro Cys Gly Pro Asn Pro Thr Arg Val Arg Gln
385                 390                 395                 400

Arg Leu Cys Thr Pro Leu Leu Pro Lys Tyr Ser Pro Thr Val Ser Met
                405                 410                 415

Val Glu Gly Gln Gly Glu Lys Asn Val Thr Phe Trp Gly Ile Pro Arg
            420                 425                 430
```

Pro Leu Cys Glu Val Leu Gln Gly Gln Lys Leu Val Glu Glu Lys
            435                 440                 445

Arg Pro Cys Leu His Val Pro Ser Cys Arg Asp Pro Glu Glu Lys Lys
450                 455                 460

Pro
465

<210> SEQ ID NO 404
<211> LENGTH: 466
<212> TYPE: PRT
<213> ORGANISM: Oryctolagus cuniculus

<400> SEQUENCE: 404

Met Pro Ala Gln Ala Gln Pro Pro Leu Pro Leu Leu Leu Pro Leu
1               5                   10                  15

Leu Leu Thr Leu Pro Ala Thr Gly Ala Asp Pro Val Val Cys Phe Thr
            20                  25                  30

Glu Tyr Asp Glu Pro Ser Gly Lys Cys Lys Gly Leu Leu Gly Gly Gly
            35                  40                  45

Val Ser Val Glu His Cys Cys Leu Asn Ala Ala Tyr Ala Phe Gln Glu
50                  55                  60

Pro Gly Ser Gly Leu Cys His Ala Cys Arg Ser Pro Leu Trp Ser Pro
65                  70                  75                  80

Trp Ser Ala Trp Ala Pro Cys Ser Val Thr Cys Ser Glu Gly Ser Gln
                85                  90                  95

Leu Arg His Arg Arg Cys Val Gly Gln Gly Gly Pro Cys Ser Glu Lys
            100                 105                 110

Ala Ala Pro Gly Thr Leu Gln Trp Gln Leu Gln Ala Cys Glu Asp Gln
            115                 120                 125

Pro Cys Cys Pro Glu Ile Gly Gly Trp Ser Asp Trp Gly Pro Trp Arg
130                 135                 140

Pro Cys Ser Val Thr Cys Ser Lys Gly Thr Lys Thr Arg Gln Arg Ala
145                 150                 155                 160

Cys Asp Arg Pro Ala Pro Lys Cys Gly Gly Arg Cys Pro Gly Glu Ala
                165                 170                 175

Gln Glu Ser Glu Ala Cys Asp Thr Lys Gln Val Cys Pro Thr His Gly
            180                 185                 190

Leu Trp Ala Ala Trp Gly Pro Trp Ser Pro Cys Ser Gly Ser Cys His
            195                 200                 205

Gly Gly Pro Gln Val Pro Lys Glu Thr Arg Ser Arg Thr Cys Ser Ala
210                 215                 220

Pro Glu Pro Ser Lys Gln Pro Pro Gly Lys Pro Cys Ser Gly Pro Ala
225                 230                 235                 240

Tyr Glu Glu Gln Ser Cys Ala Gly Leu Pro Pro Cys Pro Val Ala Gly
                245                 250                 255

Gly Trp Gly Pro Trp Gly Pro Val Ser Ser Cys Ser Val Thr Cys Gly
            260                 265                 270

Leu Gly Lys Thr Leu Glu Lys Arg Thr Cys Asp His Pro Val Pro Gln
            275                 280                 285

His Gly Gly Pro Phe Cys Thr Gly Asp Ala Thr Arg Thr His Ile Cys
290                 295                 300

Asn Thr Ala Val Pro Cys Pro Val Asn Gly Glu Trp Glu Ala Trp Gly
305                 310                 315                 320

Glu Trp Ser Glu Cys Ser Arg Pro Gly Arg Lys Ser Ile Ser Cys Glu
                325                 330                 335

```
Glu Val Pro Gly Gln Gln Arg Arg Thr Arg Val Cys Lys Gly Arg Lys
            340                 345                 350

Phe Asp Gly Gln Arg Cys Ala Gly Glu Tyr Gln Asp Ile Arg His Cys
            355                 360                 365

Tyr Asn Ile Gln Arg Cys Arg Leu Lys Gly Ser Trp Leu Glu Trp Ser
            370                 375                 380

Ser Trp Gly Leu Cys Thr Pro Pro Cys Gly Ser Pro Thr Arg Thr
385                 390                 395                 400

Arg Gln Arg Leu Cys Thr Ala Leu Leu Pro Lys Phe Pro Pro Thr Ile
            405                 410                 415

Ser Leu Val Glu Gly Gln Gly Glu Lys Asn Val Thr Phe Trp Gly Lys
            420                 425                 430

Pro Trp Pro Gln Cys Glu Gln Leu Gln Gly Gln Lys Leu Val Val Glu
            435                 440                 445

Glu Lys Arg Pro Cys Leu His Val Pro Ala Cys Lys Asp Pro Glu Glu
            450                 455                 460

Lys Pro
465

<210> SEQ ID NO 405
<211> LENGTH: 464
<212> TYPE: PRT
<213> ORGANISM: Mus musculus

<400> SEQUENCE: 405

Met Pro Ala Glu Met Gln Ala Pro Gln Trp Leu Leu Leu Leu Leu Val
1               5                   10                  15

Ile Leu Pro Ala Thr Gly Ser Asp Pro Val Leu Cys Phe Thr Gln Tyr
            20                  25                  30

Glu Glu Ser Ser Gly Arg Cys Lys Gly Leu Leu Gly Arg Asp Ile Arg
            35                  40                  45

Val Glu Asp Cys Cys Leu Asn Ala Ala Tyr Ala Phe Gln Glu His Asp
50                  55                  60

Gly Gly Leu Cys Gln Ala Cys Arg Ser Pro Gln Trp Ser Ala Trp Ser
65                  70                  75                  80

Leu Trp Gly Pro Cys Ser Val Thr Cys Ser Glu Gly Ser Gln Leu Arg
            85                  90                  95

His Arg Arg Cys Val Gly Arg Gly Gly Gln Cys Ser Glu Asn Val Ala
            100                 105                 110

Pro Gly Thr Leu Glu Trp Gln Leu Gln Ala Cys Glu Asp Gln Pro Cys
            115                 120                 125

Cys Pro Glu Met Gly Gly Trp Ser Glu Trp Gly Pro Trp Gly Pro Cys
            130                 135                 140

Ser Val Thr Cys Ser Lys Gly Thr Gln Ile Arg Gln Arg Val Cys Asp
145                 150                 155                 160

Asn Pro Ala Pro Lys Cys Gly Gly His Cys Pro Gly Glu Ala Gln Gln
            165                 170                 175

Ser Gln Ala Cys Asp Thr Gln Lys Thr Cys Pro Thr His Gly Ala Trp
            180                 185                 190

Ala Ser Trp Gly Pro Trp Ser Pro Cys Ser Gly Ser Cys Leu Gly Gly
            195                 200                 205

Ala Gln Glu Pro Lys Glu Thr Arg Ser Arg Ser Cys Ser Ala Pro Ala
            210                 215                 220

Pro Ser His Gln Pro Pro Gly Lys Pro Cys Ser Gly Pro Ala Tyr Glu
```

```
                225                 230                 235                 240
        His Lys Ala Cys Ser Gly Leu Pro Pro Cys Pro Val Ala Gly Gly Trp
                        245                 250                 255
        Gly Pro Trp Ser Pro Leu Ser Pro Cys Ser Val Thr Cys Gly Leu Gly
                    260                 265                 270
        Gln Thr Leu Glu Gln Arg Thr Cys Asp His Pro Ala Pro Arg His Gly
                275                 280                 285
        Gly Pro Phe Cys Ala Gly Asp Ala Thr Arg Asn Gln Met Cys Asn Lys
            290                 295                 300
        Ala Val Pro Cys Pro Val Asn Gly Glu Trp Glu Ala Trp Gly Lys Trp
        305                 310                 315                 320
        Ser Asp Cys Ser Arg Leu Arg Met Ser Ile Asn Cys Glu Gly Thr Pro
                        325                 330                 335
        Gly Gln Gln Ser Arg Ser Arg Ser Cys Gly Gly Arg Lys Phe Asn Gly
                    340                 345                 350
        Lys Pro Cys Ala Gly Lys Leu Gln Asp Ile Arg His Cys Tyr Asn Ile
                355                 360                 365
        His Asn Cys Ile Met Lys Gly Ser Trp Ser Gln Trp Ser Thr Trp Ser
            370                 375                 380
        Leu Cys Thr Pro Pro Cys Ser Pro Asn Ala Thr Arg Val Arg Gln Arg
        385                 390                 395                 400
        Leu Cys Thr Pro Leu Leu Pro Lys Tyr Pro Pro Thr Val Ser Met Val
                        405                 410                 415
        Glu Gly Gln Gly Glu Lys Asn Val Thr Phe Trp Gly Thr Pro Arg Pro
                    420                 425                 430
        Leu Cys Glu Ala Leu Gln Gly Gln Lys Leu Val Val Glu Glu Lys Arg
                435                 440                 445
        Ser Cys Leu His Val Pro Val Cys Lys Asp Pro Glu Glu Lys Lys Pro
            450                 455                 460

<210> SEQ ID NO 406
<211> LENGTH: 64
<212> TYPE: PRT
<213> ORGANISM: Homo sapiens

<400> SEQUENCE: 406

Val Asp Gly Glu Trp Asp Ser Trp Gly Glu Trp Ser Pro Cys Ile Arg
        1               5                   10                  15
        Arg Asn Met Lys Ser Ile Ser Cys Gln Glu Ile Pro Gly Gln Gln Ser
                    20                  25                  30
        Arg Gly Arg Thr Cys Arg Gly Arg Lys Phe Asp Gly His Arg Cys Ala
                35                  40                  45
        Gly Gln Gln Gln Asp Ile Arg His Cys Tyr Ser Ile Gln His Cys Pro
            50                  55                  60

<210> SEQ ID NO 407
<211> LENGTH: 23
<212> TYPE: PRT
<213> ORGANISM: Homo sapiens

<400> SEQUENCE: 407

Pro Cys Ile Arg Arg Asn Met Lys Ser Ile Ser Cys Gln Glu Ile Pro
        1               5                   10                  15
        Gly Gln Gln Ser Arg Gly Arg
                    20
```

```
<210> SEQ ID NO 408
<211> LENGTH: 5
<212> TYPE: PRT
<213> ORGANISM: Homo sapiens

<400> SEQUENCE: 408

Lys Ser Ile Ser Cys
1               5

<210> SEQ ID NO 409
<211> LENGTH: 63
<212> TYPE: PRT
<213> ORGANISM: Mus musculus

<400> SEQUENCE: 409

Val Asn Gly Glu Trp Glu Ala Trp Gly Lys Trp Ser Asp Cys Ser Arg
1               5                   10                  15

Leu Arg Met Ser Ile Asn Cys Glu Gly Thr Pro Gly Gln Gln Ser Arg
            20                  25                  30

Ser Arg Ser Cys Gly Gly Arg Lys Phe Asn Gly Lys Pro Cys Ala Gly
        35                  40                  45

Lys Leu Gln Asp Ile Arg His Cys Tyr Asn Ile His Asn Cys Ile
    50                  55                  60

<210> SEQ ID NO 410
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Ser Tyr Ala Ile Ser
1               5

<210> SEQ ID NO 411
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gly Ile Gly Pro Phe Phe Gly Thr Ala Asn Tyr Ala Gln Lys Phe Gln
1               5                   10                  15

Gly

<210> SEQ ID NO 412
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Asp Thr Pro Tyr Phe Asp Tyr
1               5

<210> SEQ ID NO 413
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 413

Ser Gly Asp Ser Ile Pro Asn Tyr Tyr Val Tyr
1               5                   10

<210> SEQ ID NO 414
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Asp Asp Ser Asn Arg Pro Ser
1               5

<210> SEQ ID NO 415
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Gln Ser Phe Asp Ser Ser Leu Asn Ala Glu Val
1               5                   10

<210> SEQ ID NO 416
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Gly Pro Phe Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
                100                 105                 110

Thr Val Ser Ser
            115

<210> SEQ ID NO 417
<211> LENGTH: 108
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 417

```
Ser Tyr Glu Leu Thr Gln Pro Leu Ser Val Ser Val Ala Leu Gly Gln
1               5                   10                  15

Thr Ala Arg Ile Thr Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu
            100                 105
```

<210> SEQ ID NO 418
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
```

```
                225                 230                 235                 240
Leu Phe Pro Pro Lys Pro Lys Asp Thr Leu Met Ile Ser Arg Thr Pro
                    245                 250                 255

Glu Val Thr Cys Val Val Val Asp Val Ser His Glu Asp Pro Glu Val
                    260                 265                 270

Lys Phe Asn Trp Tyr Val Asp Gly Val Glu Val His Asn Ala Lys Thr
                    275                 280                 285

Lys Pro Arg Glu Glu Gln Tyr Asn Ser Thr Tyr Arg Val Val Ser Val
                    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                    325                 330                 335

Lys Ala Lys Gly Gln Pro Arg Glu Pro Gln Val Tyr Thr Leu Pro Pro
                    340                 345                 350

Ser Arg Glu Glu Met Thr Lys Asn Gln Val Ser Leu Thr Cys Leu Val
                    355                 360                 365

Lys Gly Phe Tyr Pro Ser Asp Ile Ala Val Glu Trp Glu Ser Asn Gly
                    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                    405                 410                 415

Gln Gln Gly Asn Val Phe Ser Cys Ser Val Met His Glu Ala Leu His
                    420                 425                 430

Asn His Tyr Thr Gln Lys Ser Leu Ser Leu Ser Pro Gly Lys
                    435                 440                 445

<210> SEQ ID NO 419
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Ser Tyr Glu Leu Thr Gln Pro Leu Ser Val Ser Val Ala Leu Gly Gln
1               5                   10                  15

Thr Ala Arg Ile Thr Cys Ser Gly Asp Ser Ile Pro Asn Tyr Tyr Val
                    20                  25                  30

Tyr Trp Tyr Gln Gln Lys Pro Gly Gln Ala Pro Val Leu Val Ile Tyr
                35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140
```

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 420
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 420
gaggtgcaat tggttcagtc tggcgcggaa gtgaaaaaac cgggcagcag cgtgaaagtg      60
agctgcaaag cctccggagg cacttttcct tcttatgcca tttcttgggt gcgccaagcc     120
cctgggcagg gtctcgagtg gatgggcggt atcggtccgt tttttggcac tgcgaattac     180
gcgcagaagt ttcagggccg ggtgaccatt accgcggatg aaagcaccag caccgcgtat     240
atggaactga gcagcctgcg tagcgaagat acggccgtgt attattgcgc gcgtgatact     300 ccttatttg attattgggg ccaaggcacc ctggtgacgg ttagctca                   348

<210> SEQ ID NO 421
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 421
tcctatgaac tcacacagcc cctgagcgtg agcgtggccc tgggccagac cgcccggatc      60
acctgctccg gcgacagcat ccccaactac tacgtgtact ggtaccagca gaagcccggc     120
caggcccccg tgctggtgat ctacgacgac agcaaccggc cagcggcat ccccgagcgg     180 ttcagcggca gcaacagcgg caacaccgcc accctgacca tttccagagc acaggcaggc     240
gacgaggccg actactactg ccagagcttc gacagcagcc tgaacgccga ggtgttcggc     300
ggagggacca gttaaccgt ccta                                             324

<210> SEQ ID NO 422
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 422
gaggtgcaat tggttcagtc tggcgcggaa gtgaaaaaac cgggcagcag cgtgaaagtg      60
agctgcaaag cctccggagg cacttttctt tcttatgcca tttcttgggt gcgccaagcc     120
cctgggcagg gtctcgagtg gatgggcggt atcggtccgt tttttggcac tgcgaattac     180
gcgcagaagt ttcagggccg ggtgaccatt accgcggatg aaagcaccag caccgcgtat     240

```
atggaactga gcagcctgcg tagcgaagat acggccgtgt attattgcgc gcgtgatact       300
ccttattttg attattgggg ccaaggcacc ctggtgacgg ttagctcagc ctccaccaag       360
ggtccatcgg tcttccccct ggcaccctcc tccaagagca cctctggggg cacagcggcc       420
ctgggctgcc tggtcaagga ctacttcccc gaaccggtga cggtgtcgtg aactcaggc        480 gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaggtg acaagagag ttgagcccaa atcttgtgac        660
aaaactcaca catgcccacc gtgcccagca cctgaagcag cggggggacc gtcagtcttc       720
ctcttccccc caaaacccaa ggacaccctc atgatctccc ggacccctga ggtcacatgc       780
gtggtggtgg acgtgagcca cgaagaccct gaggtcaagt tcaactggta cgtggacggc       840
gtggaggtgc ataatgccaa gacaaagccg cgggaggagc agtacaacag cacgtaccgg       900
gtggtcagcg tcctcaccgt cctgcaccag gactggctga atggcaagga gtacaagtgc       960
aaggtctcca acaaagccct cccagccccc atcgagaaaa ccatctccaa agccaaaggg      1020
cagccccgag aaccacaggt gtacaccctg cccccatccc gggaggagat gaccaagaac      1080
caggtcagcc tgacctgcct ggtcaaaggc ttctatccca gcgacatcgc cgtggagtgg      1140
gagagcaatg ggcagccgga gaacaactac aagaccacgc ctcccgtgct ggactccgac      1200
ggctccttct tcctctacag caagctcacc gtggacaaga gcaggtggca gcaggggaac      1260
gtcttctcat gctccgtgat gcatgaggct ctgcacaacc actacacgca gaagagcctc      1320
tccctgtctc cgggtaaa                                                    1338
```

<210> SEQ ID NO 423
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 423

```
tcctatgaac tcacacagcc cctgagcgtg agcgtggccc tgggccagac cgcccggatc        60
acctgctccg gcgacagcat ccccaactac tacgtgtact ggtaccagca gaagcccggc       120
caggcccccg tgctggtgat ctacgacgac agcaaccggc ccagcggcat ccccgagcgg       180
ttcagcggca gcaacagcgg caacaccgcc accctgacca tttccagagc acaggcaggc       240
gacgaggccg actactactg ccagagcttc gacagcagcc tgaacgccga ggtgttcggc       300
ggagggacca gttaaccgt cctaggtcag cccaaggctg cccctcggt cactctgttc         360 ccgccctcct ctgaggagct tcaagccaac aaggccacac tggtgtgtct cataagtgac       420
ttctacccgg gagccgtgac agtggcctgg aaggcagata gcagccccgt caaggcggga      480
gtggagacca ccacaccctc caaacaaagc aacaacaagt acgcggccag cagctatctg      540
agcctgacgc ctgagcagtg gaagtcccac agaagctaca gctgccaggt cacgcatgaa      600
gggagcaccg tggagaagac agtggcccct acagaatgtt ca                         642
```

<210> SEQ ID NO 424
<211> LENGTH: 1338
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 424

```
gaggtgcagc tggtgcagag cggagccgag gtgaagaagc ccggtagcag cgtcaaggtg      60
tcctgcaagg ccagcggcgg caccttcagc agctacgcca tcagctgggt gcggcaggcc     120
ccaggccagg gcctggagtg gatgggcggc atcggcccat tcttcggcac cgccaactac     180
gcccagaagt tccagggcag ggtcaccatc accgccgacg agagcaccag caccgcctac     240
atggagctgt ccagcctgag aagcgaggac accgccgtgt actactgcgc cagagacacc     300
ccctacttcg actactgggg ccagggcacc ctggtgaccg tgagcagcgc tagcaccaag     360
ggccccagcg tgttccccct ggcccccagc agcaagagca cctccggcgg cacagccgcc     420
ctgggctgcc tggtgaagga ctacttcccc gagcccgtga ccgtgtcctg gaacagcgga     480
gccctgacca gcggcgtgca caccttcccc gccgtgctgc agagcagcgg cctgtacagc     540
ctgtccagcg tggtgacagt gcccagcagc agcctgggca cccagaccta catctgcaac     600
gtgaaccaca gcccagcaa caccaaggtg gacaagagag tggagcccaa gagctgcgac     660
aagacccaca cctgccccc ctgcccagcc cccgaagctg caggcggccc ttccgtgttc     720
ctgttccccc ccaagcccaa ggacaccctg atgatcagca ggaccccga ggtgacctgc     780
gtggtggtgg acgtgagcca cgaggaccca gaggtgaagt tcaactggta cgtggacggc     840
gtggaggtgc acaacgccaa gaccaagccc agagaggagc agtacaacag cacctacagg     900
gtggtgtccg tgctgaccgt gctgcaccag gactggctga acggcaaaga atacaagtgc     960
aaggtctcca acaaggccct gcctgccccc atcgaaaaga ccatcagcaa ggccaagggc    1020
cagccacggg agcccagg tgtacaccctg ccccttctc gggaggagat gaccaagaac    1080
caggtgtccc tgacctgtct ggtgaagggc ttctacccca gcgacatcgc cgtggagtgg    1140
gagagcaacg gccagcccga gaacaactac aagaccaccc ccccagtgct ggacagcgac    1200
ggcagcttct tcctgtacag caagctgacc gtggacaaga gcaggtggca gcagggcaac    1260
gtgttcagct gcagcgtgat gcacgaggcc ctgcacaacc actacaccca gaagagcctg    1320
agcctgtcac ccggcaag                                                  1338
```

<210> SEQ ID NO 425
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 425

```
agctacgagc tgacccagcc cctgagcgtg agcgtggccc tgggccagac cgccaggatc      60
acctgcagcg gcgacagcat ccccaactac tacgtgtact ggtatcagca gaagcccggc     120
caggcccccg tgctggtgat ctacgacgac agcaacaggc cagcggcat ccccgagagg     180
ttcagcggca gcaacagcgg caacaccgcc accctgacca tcagcagagc ccaggccggc     240
gacgaggccg actactactg ccagagcttc gacagctcac tgaacgccga ggtgttcggc     300
ggagggacca agctgaccgt gctgggccag cctaaggctg cccccagcgt gaccctgttc     360
ccccccagca gcgaggagct gcaggccaac aaggccaccc tggtgtgcct gatcagcgac     420
ttctacccag cgccgtgac cgtggcctgg aaggccgaca gcagccccgt gaaggccggc     480
gtggagacca ccaccccag caagcagagc aacaacaagt acgccgccag cagctacctg     540
```

```
agcctgaccc ccgagcagtg gaagagccac aggtcctaca gctgccaggt gacccacgag      600
ggcagcaccg tggaaaagac cgtggcccca accgagtgca gc                        642
```

<210> SEQ ID NO 426
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Asn Tyr Ile Ser
1

<210> SEQ ID NO 427
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ile Ile Asp Pro Asp Asp Ser Tyr Thr Glu Tyr Ser Pro Ser Phe Gln
1               5                   10                  15

Gly

<210> SEQ ID NO 428
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Tyr Glu Tyr Gly Gly Phe Asp Ile
1               5

<210> SEQ ID NO 429
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Ser Gly Asp Asn Ile Gly Asn Ser Tyr Val His
1               5                   10

<210> SEQ ID NO 430
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Lys Asp Asn Asp Arg Pro Ser
1               5

<210> SEQ ID NO 431
<211> LENGTH: 9

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Gly Thr Tyr Asp Ile Glu Ser Tyr Val
1               5

<210> SEQ ID NO 432
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Ile Ser Trp Val Arg Gln Met Pro Gly Lys Gly Leu Glu Trp Met Gly
            35                  40                  45

Ile Ile Asp Pro Asp Asp Ser Tyr Thr Glu Tyr Ser Pro Ser Phe Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115

<210> SEQ ID NO 433
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
                20                  25                  30

His Trp Tyr Gln Gln Lys Pro Gly Gln Ala Pro Val Leu Val Ile Tyr
            35                  40                  45

Lys Asp Asn Asp Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95

Phe Gly Gly Gly Thr Lys Leu Thr Val Leu
            100                 105

<210> SEQ ID NO 434
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 434

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 435
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 436
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 436
```

```
gaggtgcaat tggttcagag cggcgcggaa gtgaaaaaac cgggcgaaag cctgaaaatt      60
agctgcaaag gttccggata ttcctttact aattatattt cttgggtgcg ccagatgcct     120
gggaagggtc tcgagtggat gggcattatt gatcctgatg attcttatac tgagtattct     180 ccttctttc agggtcaggt caccattagc gcggataaaa gcattagcac cgcgtatctt     240
caatggagca gcctgaaagc gagcgatacg gccatgtatt attgcgcgcg ttatgagtat     300
ggtggttttg atatttgggg ccaaggcacc ctggtgacgg ttagctca                  348
```

```
<210> SEQ ID NO 437
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 437
agttacgaac tgacccagcc gccttcagtg agcgttgcac caggtcagac cgcgcgtatc      60
tcgtgtagcg gcgataatat tggtaattct tatgttcatt ggtaccagca gaaacccggg     120
caggcgccag ttcttgtgat ttataaggat aatgatcgtc cctcaggcat cccggaacgc     180
tttagcggat ccaacagcgg caacaccgcg accctgacca ttagcggcac tcaggcggaa     240
gacgaagcgg attattattg cggtacttat gatattgagt cttatgtgtt tggcggcggc     300
acgaagttaa ccgtccta                                                   318
```

```
<210> SEQ ID NO 438
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 438
gaggtgcaat tggttcagag cggcgcggaa gtgaaaaaac cgggcgaaag cctgaaaatt      60
agctgcaaag gttccggata ttcctttact aattatattt cttgggtgcg ccagatgcct     120
gggaagggtc tcgagtggat gggcattatt gatcctgatg attcttatac tgagtattct     180 ccttctttc agggtcaggt caccattagc gcggataaaa gcattagcac cgcgtatctt     240
caatggagca gcctgaaagc gagcgatacg gccatgtatt attgcgcgcg ttatgagtat     300
ggtggttttg atatttgggg ccaaggcacc ctggtgacgg ttagctcagc tccaccaag     360 ggtccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagagag ttgagcccaa atcttgtgac    660
aaaactcaca catgcccacc gtgcccagca cctgaagcag cgggggggacc gtcagtcttc    720 ctcttccccc caaaacccaa ggacaccctc atgatctccc ggaccctga ggtcacatgc    780 gtggtggtgg acgtgagcca cgaagaccct gaggtcaagt tcaactggta cgtggacggc    840
gtggaggtgc ataatgccaa gacaaagccg cgggaggagc agtacaacag cacgtaccgg    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
```

```
cagccccgag aaccacaggt gtacaccctg cccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 439
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 439

```
agttacgaac tgacccagcc gccttcagtg agcgttgcac aggtcagac cgcgcgtatc     60 tcgtgtagcg gcgataatat tggtaattct tatgttcatt ggtaccagca gaaacccggg   120
caggcgccag ttcttgtgat ttataaggat aatgatcgtc cctcaggcat cccggaacgc   180
tttagcggat ccaacagcgg caacaccgcg accctgacca ttagcggcac tcaggcggaa   240
gacgaagcgg attattattg cggtacttat gatattgagt cttatgtgtt tggcggcggc   300
acgaagttaa ccgtcctagg tcagcccaag gctgccccct cggtcactct gttcccgccc   360
tcctctgagg agcttcaagc caacaaggcc acactggtgt gtctcataag tgacttctac   420
ccgggagccg tgacagtggc ctggaaggca gatagcagcc ccgtcaaggc gggagtggag   480
accaccacac cctccaaaca aagcaacaac aagtacgcgg ccagcagcta tctgagcctg   540
acgcctgagc agtggaagtc ccacagaagc tacagctgcc aggtcacgca tgaagggagc   600
accgtggaga agacagtggc ccctacagaa tgttca                             636
```

<210> SEQ ID NO 440
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 440

```
gaggtgcagc tggtgcagag cggagccgag gtgaaaaagc ccggtgagag cctgaagatc    60
agctgcaagg gcagcggcta cagcttcacc aactacatca gctgggtgcg gcagatgccc   120
ggcaagggcc tggagtggat gggcatcatc gaccccgacg acagctacac cgagtacagc   180
cccagcttcc agggccaggt gaccatcagc gccgacaaga gcatcagcac cgcctacctg   240
cagtggagca gcctgaaggc cagcgacacc gccatgtact actgcgccag atacgagtac   300
ggcggcttcg acatctgggg ccagggcacc ctggtgaccg tcagctcagc tagcaccaag   360 ggcccccagcg tgttccccct ggccccagc agcaagagca cctccggcgg cacagccgcc   420
ctgggctgcc tggtgaagga ctacttcccc gagcccgtga ccgtgtcctg gaacagcgga   480
gccctgacca gcggcgtgca caccttcccc gccgtgctgc agagcagcgg cctgtacagc   540
ctgtccagcg tggtgacagt gcccagcagc agcctgggca cccagaccta catctgcaac   600
gtgaaccaca gcccagcaa caccaaggtg gacaagagag tggagcccaa gagctgcgac   660
```

```
aagacccaca cctgccccccc ctgcccagcc cccgaagctg caggcggccc ttccgtgttc    720 ctgttcccccc ccaagcccaa ggacaccctg atgatcagca ggaccccccga ggtgacctgc    780 gtggtggtgg acgtgagcca cgaggaccca gaggtgaagt tcaactggta cgtggacggc    840
gtggaggtgc acaacgccaa gaccaagccc agagaggagc agtacaacag cacctacagg    900
gtggtgtccg tgctgaccgt gctgcaccag gactggctga acggcaaaga atacaagtgc    960
aaggtctcca acaaggccct gcctgccccc atcgaaaaga ccatcagcaa ggccaagggc   1020
cagccacggg agcccaggt gtacaccctg ccccttctc gggaggagat gaccaagaac    1080
caggtgtccc tgacctgtct ggtgaagggc ttctacccca gcgacatcgc cgtggagtgg   1140
gagagcaacg gccagcccga gaacaactac aagaccaccc cccagtgct ggacagcgac    1200 ggcagcttct tcctgtacag caagctgacc gtggacaaga gcaggtggca gcagggcaac   1260
gtgttcagct gcagcgtgat gcacgaggcc ctgcacaacc actacaccca aagagcctg   1320 agcctgtcac ccggcaag                                                   1338
```

<210> SEQ ID NO 441
<211> LENGTH: 636
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 441

```
agctacgagc tgacccagcc ccccagcgtg agcgtggccc caggccagac cgccaggatc     60
agctgcagcg gcgacaacat cggcaacagc tacgtgcact ggtatcagca gaagcccggc    120 caggccccccg tgctggtgat ctacaaggac aacgacaggc ccagcggcat ccccgagagg    180
ttcagcggca gcaactccgg caacaccgcc accctgacca tcagcggcac ccaggccgag    240
gacgaggccg actactactg cggcacctac gatatcgagt catacgtgtt cggcggaggg    300
accaagctga ccgtgctggg ccagcctaag gctgcccccca gcgtgaccct gttcccccccc    360 agcagcgagg agctgcaggc caacaaggcc accctggtgt gcctgatcag cgacttctac    420
ccaggcgccg tgaccgtggc ctggaaggcc gacagcagcc ccgtgaaggc cggcgtggag    480 accaccaccccc ccagcaagca gagcaacaac aagtacgccg ccagcagcta cctgagcctg    540 accccccgagc agtggaagag ccacaggtcc tacagctgcc aggtgacccca cgagggcagc    600 accgtggaaa agaccgtggc cccaaccgag tgcagc                              636
```

<210> SEQ ID NO 442
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 442

Thr Ser Gly Gly Gly Val Ser
1               5

<210> SEQ ID NO 443
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 443

Asn Ile Asp Asp Ala Asp Ile Lys Asp Tyr Ser Pro Ser Leu Lys Ser
1               5                   10                  15

<210> SEQ ID NO 444
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Gly Pro Tyr Gly Phe Asp Ser
1               5

<210> SEQ ID NO 445
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Thr Gly Thr Ser Ser Asp Ile Gly Thr Tyr Asn Tyr Val Ser
1               5                   10

<210> SEQ ID NO 446
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Asp Asp Ser Asn Arg Pro Ser
1               5

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Gln Ser Tyr Asp Ser Gln Ser Ile Val
1               5

<210> SEQ ID NO 448
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

-continued

Gly Gly Gly Val Ser Trp Ile Arg Gln Pro Pro Gly Lys Ala Leu Glu
            35                  40                  45

Trp Leu Ala Asn Ile Asp Asp Ala Asp Ile Lys Asp Tyr Ser Pro Ser
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Gly Pro Tyr Gly Phe Asp Ser Trp Gly Gln Gly Thr Leu
            100                 105                 110

Val Thr Val Ser Ser
            115

<210> SEQ ID NO 449
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Glu Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Ile Gly Thr Tyr
                 20                  25                  30

Asn Tyr Val Ser Trp Tyr Gln Gln His Pro Gly Lys Ala Pro Lys Leu
            35                  40                  45

Met Ile Tyr Asp Asp Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Ser Gln
                 85                  90                  95

Ser Ile Val Phe Gly Gly Gly Thr Lys Leu Thr Val Leu
            100                 105

<210> SEQ ID NO 450
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Glu Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
                 20                  25                  30

Gly Gly Gly Val Ser Trp Ile Arg Gln Pro Pro Gly Lys Ala Leu Glu
            35                  40                  45

Trp Leu Ala Asn Ile Asp Asp Ala Asp Ile Lys Asp Tyr Ser Pro Ser
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Gly Pro Tyr Gly Phe Asp Ser Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 451
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Glu Ser Ala Leu Thr Gln Pro Ala Ser Val Ser Gly Ser Pro Gly Gln
1               5                   10                  15

-continued

```
Ser Ile Thr Ile Ser Cys Thr Gly Thr Ser Ser Asp Ile Gly Thr Tyr
         20                  25                  30

Asn Tyr Val Ser Trp Tyr Gln Gln His Pro Gly Lys Ala Pro Lys Leu
     35                  40                  45

Met Ile Tyr Asp Asp Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Asp Ser Gln
                 85                  90                  95

Ser Ile Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 452
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 452
gaggtgacat tgaaagaaag cggcccggcc ctggtgaaac cgacccaaac cctgaccctg      60
acctgtacct tttccggatt tagcctgtct acttctggtg gtggtgtgtc ttggattcgc     120
cagccgcctg ggaaagccct cgagtggctg gctaatattg atgatgctga tattaaggat     180
tattctcctt ctcttaagtc tcgtctgacc attagcaaag atacttcgaa aaatcaggtg     240
gtgctgacta tgaccaacat ggacccggtg gataccggcca cctattattg cgcgcgtggt     300
ccttatggtt ttgattcttg gggccaaggc accctggtga cggttagctc a              351

<210> SEQ ID NO 453
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 453
gaaagcgcac tgacccagcc agcttcagtg agcggctcac caggtcagag cattaccatc      60
tcgtgtacgg gtactagcag cgatattggt acttataatt atgtgtcttg gtaccagcag     120
catcccggga aggcgccgaa acttatgatt tatgatgatt ctaatcgtcc ctcaggcgtg     180
```

| | | |
|---|---|---|
| agcaaccgtt ttagcggatc caaaagcggc aacaccgcga gcctgaccat tagcggcctg | 240 | |
| caagcggaag acgaagcgga ttattattgc cagtcttatg attctcagtc tattgtgttt | 300 | |
| ggcggcggca cgaagttaac cgtccta | 327 | |

<210> SEQ ID NO 454
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 454

| | |
|---|---|
| gaggtgacat tgaaagaaag cggcccggcc ctggtgaaac cgacccaaac cctgaccctg | 60 |
| acctgtacct tttccggatt tagcctgtct acttctggtg gtggtgtgtc ttggattcgc | 120 |
| cagccgcctg ggaaagccct cgagtggctg gctaatattg atgatgctga tattaaggat | 180 |
| tattctcctt ctcttaagtc tcgtctgacc attagcaaag atacttcgaa aaatcaggtg | 240 |
| gtgctgacta tgaccaacat ggacccggtg gatacggcca cctattattg cgcgcgtggt | 300 |
| ccttatggtt ttgattcttg gggccaaggc accctggtga cggttagctc agcctccacc | 360 |
| aagggtccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga gagttgagcc caaatcttgt | 660 |
| gacaaaactc acacatgccc accgtgccca gcacctgaag cagcgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgggtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa a | 1341 |

<210> SEQ ID NO 455
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 455

| | |
|---|---|
| gaaagcgcac tgacccagcc agcttcagtg agcggctcac caggtcagag cattaccatc | 60 |
| tcgtgtacgg gtactagcag cgatattggt acttataatt atgtgtcttg gtaccagcag | 120 |

```
catcccggga aggcgccgaa acttatgatt tatgatgatt ctaatcgtcc ctcaggcgtg      180
agcaaccgtt ttagcggatc caaaagcggc aacaccgcga gcctgaccat tagcggcctg      240
caagcggaag acgaagcgga ttattattgc cagtcttatg attctcagtc tattgtgttt      300
ggcggcggca cgaagttaac cgtcctaggt cagcccaagg ctgccccctc ggtcactctg      360
ttcccgccct cctctgagga gcttcaagcc aacaaggcca cactggtgtg tctcataagt      420
gacttctacc cggagccgt gacagtggcc tggaaggcag atagcagccc cgtcaaggcg       480
ggagtggaga ccaccacacc ctccaaacaa agcaacaaca gtacgcggc cagcagctat       540 ctgagcctga cgcctgagca gtggaagtcc cacagaagct acagctgcca ggtcacgcat      600
gaagggagca ccgtggagaa gacagtggcc cctacagaat gttca                      645
```

<210> SEQ ID NO 456
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 456

```
gaggtgaccc tgaaggagag cggcccagcc ctggtgaagc ccacccagac cctgaccctg       60
acttgcacct tcagcggctt cagcctgagc accagcggag ggggcgtgag ctggatcagg      120
cagcccccag gtaaggccct ggagtggctg gccaatatcg acgacgccga tatcaaggac      180
tacagcccca gcctgaagag caggctgacc atcagcaagg acaccagcaa gaaccaggtg      240
gtgctgacca tgaccaatat ggaccccgtg acaccgcca cctactactg cgccagaggc       300
ccctacggct tcgacagctg gggccagggc accctggtga ccgtcagctc agctagcacc      360
aagggcccca gcgtgttccc cctggccccc agcagcaaga gcacctccgg cggcacagcc      420
gccctgggct gcctggtgaa ggactacttc cccgagcccg tgaccgtgtc ctggaacagc      480
ggagccctga ccagcggcgt gcacaccttc cccgccgtgc tgcagagcag cggcctgtac      540
agcctgtcca gcgtggtgac agtgcccagc agcagcctgg gcacccagac ctacatctgc      600
aacgtgaacc acaagcccag caacaccaag gtggacaaga gagtggagcc caagagctgc      660
gacaagaccc acacctgccc ccctgccca gcccccgaag ctgcaggcgg ccccttccgtg     720 ttcctgttcc ccccaagcc caaggacacc ctgatgatca gcaggacccc cgaggtgacc      780
tgcgtggtgg tggacgtgag ccacgaggac ccagaggtga agttcaactg gtacgtggac      840
ggcgtggagg tgcacaacgc caagaccaag cccagagagg agcagtacaa cagcacctac      900
agggtggtgt ccgtgctgac cgtgctgcac caggactggc tgaacggcaa agaatacaag      960
tgcaaggtct ccaacaaggc cctgcctgcc ccatcgaaa agaccatcag caaggccaag     1020
ggccagccac gggagcccca ggtgtacacc ctgcccccctt ctcgggagga tgaccaag      1080 aaccaggtgt ccctgacctg tctggtgaag ggcttctacc ccagcgacat cgccgtggag     1140
tgggagagca acggccagcc cgagaacaac tacaagacca ccccccccagt gctggacagc     1200 gacggcagct tcttcctgta cagcaagctg accgtggaca gagcaggtg gcagcagggc     1260 aacgtgttca gctgcagcgt gatgcacgag gccctgcaca accactacac ccagaagagc     1320
ctgagcctgt cacccggcaa g                                               1341
```

<210> SEQ ID NO 457
<211> LENGTH: 645
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 457

```
gagagcgccc tgacccagcc cgccagcgtg agcggcagcc caggccagtc tatcacaatc      60
agctgcaccg gcacctccag cgatatcggc acctacaact acgtgagctg gtatcagcag     120
cacccggca aggcccccaa gctgatgatc tacgacgaca gcaacaggcc cagcggcgtg      180
agcaacaggt tcagcggcag caagagcggc aacaccgcca gcctgacaat cagcggcctg     240
caggccgagg acgaggccga ctactactgc cagagctacg acagccagtc aatcgtgttc     300
ggcggaggga ccaagctgac cgtgctgggc cagcctaagg ctgcccccag cgtgaccctg     360
ttccccccca gcagcgagga gctgcaggcc aacaaggcca ccctggtgtg cctgatcagc     420
gacttctacc caggcgccgt gaccgtggcc tggaaggccg acagcagccc cgtgaaggcc     480
ggcgtggaga ccaccacccc cagcaagcag agcaacaaca gtacgccgc cagcagctac     540
ctgagcctga ccccgagca gtggaagagc acaggtcct acagctgcca ggtgacccac      600
gagggcagca ccgtggaaaa gaccgtggcc ccaaccgagt gcagc                     645
```

<210> SEQ ID NO 458
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 458

Ile Ile Asp Pro Asp Asp Ser Tyr Thr Arg Tyr Ser Pro Ser Phe Gln
1               5                   10                  15
Gly

<210> SEQ ID NO 459
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 459

Ala Thr Trp Gly Ser Glu Asp Gln Val
1               5

<210> SEQ ID NO 460
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 460

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Ile Ser Trp Val Arg Gln Met Pro Gly Lys Gly Leu Glu Trp Met Gly
            35                  40                  45

Ile Ile Asp Pro Asp Asp Ser Tyr Thr Arg Tyr Ser Pro Ser Phe Gln
50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
            115

<210> SEQ ID NO 461
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Thr Trp Ser Glu Asp Gln Val
                85                  90                  95

Phe Gly Gly Gly Thr Lys Leu Thr Val Leu
            100                 105

<210> SEQ ID NO 462
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Arg Tyr Ser Pro Ser Phe Gln
50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 463
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30
```

His Trp Tyr Gln Gln Lys Pro Gly Gln Ala Pro Val Leu Val Ile Tyr
              35                  40                  45

Lys Asp Asn Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Thr Trp Gly Ser Glu Asp Gln Val
                 85                  90                  95

Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 464
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 464
gaggtgcaat tggttcagag cggcgcggaa gtgaaaaaac cgggcgaaag cctgaaaatt     60
agctgcaaag gttccggata ttcctttact aattatattt cttgggtgcg ccagatgcct    120
gggaagggtc tcgagtggat gggcattatc gatccggatg atagctatac ccgttattct    180
ccgagctttc agggacaggt gaccattagc gcggataaaa gcattagcac cgcgtatctt    240
caatggagca gcctgaaagc gagcgatacg gccatgtatt attgcgcgcg ttatgagtat    300
ggtggttttg atatttgggg ccaaggcacc ctggtgacgg ttagctca                 348

<210> SEQ ID NO 465
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 465
agttacgaac tgacccagcc gccttcagtg agcgttgcac aggtcagac cgcgcgtatc      60 tcgtgtagcg gcgataatat tggtaattct tatgttcatt ggtaccagca gaaacccggg    120
caggcgccag ttcttgtgat ttataaggat aatgatcgtc cctcaggcat cccggaacgc    180
tttagcggat ccaacagcgg caacaccgcg accctgacca ttagcggcac tcaggcggaa    240

```
gacgaagcgg attattattg cgctacttgg ggttctgagg atcaggtgtt tggcggcggc    300
acgaagttaa ccgtccta                                                  318
```

<210> SEQ ID NO 466
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 466

```
gaggtgcaat tggttcagag cggcgcggaa gtgaaaaaac cgggcgaaag cctgaaaatt    60
agctgcaaag gttccggata ttcctttact aattatattt cttgggtgcg ccagatgcct   120
gggaagggtc tcgagtggat gggcattatc gatccggatg atagctatac ccgttattct   180
ccgagctttc agggacaggt gaccattagc gcggataaaa gcattagcac cgcgtatctt   240
caatggagca gcctgaaagc gagcgatacg gccatgtatt attgcgcgcg ttatgagtat   300
ggtggttttg atatttgggg ccaaggcacc ctggtgacgg ttagctcagc ctccaccaag   360
ggtccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagagag ttgagcccaa atcttgtgac   660
aaaactcaca catgcccacc gtgcccagca cctgaagcag cggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgg   900
gtggtcagcg tcctcaccgt cctgcaccag gactggctga atggcaagga gtacaagtgc   960
aaggtctcca acaaagccct cccagccccc atcgagaaaa ccatctccaa agccaaaggg  1020
cagccccgag aaccacaggt gtacaccctg cccccatccc gggaggagat gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaa                                                1338
```

<210> SEQ ID NO 467
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 467

```
agttacgaac tgacccagcc gccttcagtg agcgttgcac caggtcagac cgcgcgtatc    60
tcgtgtagcg gcgataatat tggtaattct tatgttcatt ggtaccagca gaaacccggg   120
caggcgccag ttcttgtgat ttataaggat aatgatcgtc cctcaggcat cccggaacgc   180
tttagcggat ccaacagcgg caacaccgcg accctgacca ttagcggcac tcaggcggaa   240
```

```
gacgaagcgg attattattg cgctacttgg ggttctgagg atcaggtgtt tggcggcggc    300
acgaagttaa ccgtcctagg tcagcccaag gctgccccct cggtcactct gttcccgccc    360
tcctctgagg agcttcaagc caacaaggcc acactggtgt gtctcataag tgacttctac    420
ccgggagccg tgacagtggc ctggaaggca gatagcagcc ccgtcaaggc gggagtggag    480
accaccacac cctccaaaca aagcaacaac aagtacgcgg ccagcagcta tctgagcctg    540
acgcctgagc agtggaagtc ccacagaagc tacagctgcc aggtcacgca tgaagggagc    600
accgtggaga agacagtggc ccctacagaa tgttca                              636
```

<210> SEQ ID NO 468
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 468

```
gaggtgcagc tggtgcagag cggagccgag gtgaaaaagc ccggtgagag cctgaagatc    60
agctgcaagg gcagcggcta cagcttcacc aactacatca gctgggtgcg gcagatgccc    120
ggcaagggcc tggagtggat gggcatcatc gaccccgacg acagctacac caggtacagc    180
cccagcttcc agggccaggt gaccatcagc gccgacaaga gcatcagcac cgcctacctg    240
cagtggagca gcctgaaggc cagcgacacc gccatgtact actgcgccag atacgagtac    300
ggcggcttcg acatctgggg ccagggcacc ctggtgaccg tcagctcagc tagcaccaag    360
ggccccagcg tgttccccct ggccccagc agcaagagca cctccggcgg cacagccgcc    420
ctgggctgcc tggtgaagga ctacttcccc gagcccgtga ccgtgtcctg aacagcgga    480 gccctgacca gcggcgtgca caccttcccc gccgtgctgc agagcagcgg cctgtacagc    540
ctgtccagcg tggtgacagt gcccagcagc agcctgggca cccagaccta catctgcaac    600
gtgaaccaca agcccagcaa caccaaggtg gacaagagag tggagcccaa agctgcgac    660 aagacccaca cctgcccccc ctgcccagcc cccgaagctg caggcggccc ttccgtgttc    720
ctgttccccc ccaagcccaa ggacaccctg atgatcagca ggacccccga ggtgacctgc    780
gtggtggtgg acgtgagcca cgaggaccca gaggtgaagt tcaactggta cgtggacggc    840
gtggaggtgc acaacgccaa gaccaagccc agagaggagc agtacaacag cacctacagg    900
gtggtgtccg tgctgaccgt gctgcaccag gactggctga acggcaaaga atacaagtgc    960
aaggtctcca acaaggccct gcctgccccc atcgaaaaga ccatcagcaa ggccaagggc    1020
cagccacggg agccccaggt gtacaccctg ccccttctc gggaggagat gaccaagaac    1080
caggtgtccc tgacctgtct ggtgaagggc ttctacccca gcgacatcgc cgtggagtgg    1140
gagagcaacg gccagcccga gaacaactac aagaccaccc cccagtgct ggacagcgac    1200 ggcagcttct tcctgtacag caagctgacc gtggacaaga gcaggtggca gcagggcaac    1260
gtgttcagct gcagcgtgat gcacgaggcc ctgcacaacc actacaccca gaagagcctg    1320
agcctgtcac ccggcaag                                                 1338
```

<210> SEQ ID NO 469
<211> LENGTH: 636
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 469

```
agctacgagc tgacccagcc ccccagcgtg agcgtggccc caggccagac cgccaggatc    60
agctgcagcg gcgacaatat cggcaacagc tacgtgcact ggtatcagca gaagcccggc   120
caggcccccg tgctggtgat ctacaaggac aacgacaggc ccagcggcat ccccgagagg   180
ttcagcggca gcaactccgg caacaccgcc accctgacaa tcagcggcac ccaggccgag   240
gacgaggccg actactactg cgccacctgg ggctcagagg accaggtgtt cggcggaggg   300
accaagctga ccgtgctggg ccagcctaag gctgccccca gcgtgaccct gttcccccca   360
agcagcgagg agctgcaggc caacaaggcc accctggtgt gcctgatcag cgacttctac   420
ccaggcgccg tgaccgtggc ctggaaggcc gacagcagcc ccgtgaaggc cggcgtggag   480
accaccaccc ccagcaagca gagcaacaac aagtacgccg ccagcagcta cctgagcctg   540
acccccgagc agtggaagag ccacaggtcc tacagctgcc aggtgaccca cgagggcagc   600
accgtggaaa agaccgtggc ccaaaccgag tgcagc                             636
```

<210> SEQ ID NO 470
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Ser Tyr Tyr Ile Gly
1               5

<210> SEQ ID NO 471
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Ile Ile Asp Pro Thr Asp Ser Gln Thr Ala Tyr Ser Pro Ser Phe Gln
1               5                   10                  15

Gly

<210> SEQ ID NO 472
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Tyr Met Met Arg Gly Phe Asp His
1               5

<210> SEQ ID NO 473
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Ser Gly Asp Ser Leu Gly Asp Tyr Tyr Ala Tyr
1               5                   10

<210> SEQ ID NO 474
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Lys Asp Asn Asn Arg Pro Ser
1               5

<210> SEQ ID NO 475
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Gln Thr Trp Asp Thr Gly Glu Ser Gly Val
1               5                   10

<210> SEQ ID NO 476
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Tyr Ile Gly Trp Val Arg Gln Met Pro Gly Lys Gly Leu Glu Trp Met
        35                  40                  45

Gly Ile Ile Asp Pro Thr Asp Ser Gln Thr Ala Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Met Met Arg Gly Phe Asp His Trp Gly Gln Gly Thr Leu
            100                 105                 110

Val Thr Val Ser Ser
        115

<210> SEQ ID NO 477
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

```
Ser Tyr Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Thr Gly Glu Ser Gly
                85                  90                  95

Val Phe Gly Gly Gly Thr Lys Leu Thr Val Leu
            100                 105
```

<210> SEQ ID NO 478
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Tyr Ile Gly Trp Val Arg Gln Met Pro Gly Lys Gly Leu Glu Trp Met
        35                  40                  45

Gly Ile Ile Asp Pro Thr Asp Ser Gln Thr Ala Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Met Met Arg Gly Phe Asp His Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 479
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Ser Tyr Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Ala
            20                  25                  30

Tyr Trp Tyr Gln Gln Lys Pro Gly Gln Ala Pro Val Leu Val Ile Tyr
        35                  40                  45

Lys Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Thr Gly Glu Ser Gly
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
```

|  |  | 165 |  |  |  | 170 |  |  |  | 175 |  |
|---|---|---|---|---|---|---|---|---|---|---|---|

Ser Tyr Leu Ser Leu Thr Pro Glu Gln Trp Lys Ser His Arg Ser Tyr
                180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 480
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 480
gaggtgcaat tggttcagag cggcgcggaa gtgaaaaaac cgggcgaaag cctgaaaatt        60
agctgcaaag gttccggata ttcctttact tcttattata ttggttgggt gcgccagatg       120
cctgggaagg gtctcgagtg gatgggcatt attgatccta ctgattctca gactgcttat       180
tctccttctt ttcagggtca ggtgaccatt agcgcggata aaagcattag caccgcgtat       240
cttcaatgga gcagcctgaa agcgagcgat acggccatgt attattgcgc gcgttatatg       300
atgcgtggtt ttgatcattg gggccaaggc accctggtga cggttagctc a               351

<210> SEQ ID NO 481
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 481
agttacgaac tgacccagcc gccttcagtg agcgttgcac caggtcagac cgcgcgtatc        60
tcgtgtagcg gcgattctct tggtgattat tatgcttatt ggtaccagca gaaacccggg       120
caggcgccag ttcttgtgat ttataaggat aataatcgtc cctcaggcat cccggaacgc       180
tttagcggat ccaacagcgg caacaccgcg accctgacca ttagcggcac tcaggcggaa       240
gacgaagcgg attattattg ccagacttgg gatactggtg agtctggtgt gtttggcggc       300
ggcacgaagt taaccgtcct a                                                  321

<210> SEQ ID NO 482
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 482
gaggtgcaat tggttcagag cggcgcggaa gtgaaaaaac cgggcgaaag cctgaaaatt        60
agctgcaaag gttccggata ttcctttact tcttattata ttggttgggt gcgccagatg       120
cctgggaagg gtctcgagtg gatgggcatt attgatccta ctgattctca gactgcttat       180
tctccttctt ttcagggtca ggtgaccatt agcgcggata aaagcattag caccgcgtat       240
cttcaatgga gcagcctgaa agcgagcgat acggccatgt attattgcgc gcgttatatg       300
atgcgtggtt ttgatcattg gggccaaggc accctggtga cggttagctc agcctccacc       360

```
aagggtccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaag cagcgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgggtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga tgaccaag    1080 aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                             1341
```

<210> SEQ ID NO 483
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 483

```
agttacgaac tgacccagcc gccttcagtg agcgttgcac aggtcagac cgcgcgtatc    60 tcgtgtagcg gcgattctct tggtgattat tatgcttatt ggtaccagca gaaacccggg    120
caggcgccag ttcttgtgat ttataaggat aataatcgtc cctcaggcat cccggaacgc    180
tttagcggat ccaacagcgg caacaccgcg accctgacca ttagcggcac tcaggcggaa   240
gacgaagcgg attattattg ccagacttgg gatactggtg agtctggtgt gtttggcggc    300
ggcacgaagt taaccgtcct aggtcagccc aaggctgccc cctcggtcac tctgttcccg    360
ccctcctctg aggagcttca agccaacaag gccacactgg tgtgtctcat aagtgacttc    420
tacccgggag ccgtgacagt ggcctggaag gcagatagca gccccgtcaa ggcgggagtg    480
gagaccacca cacctccaa acaaagcaac aacaagtacg cggccagcag ctatctgagc    540
ctgacgcctg agcagtggaa gtcccacaga agctacagct gccaggtcac gcatgaaggg   600
agcaccgtgg agaagacagt ggcccctaca gaatgttca                          639
```

<210> SEQ ID NO 484
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 484

```
gaggtgcagc tggtgcagag cggagccgag gtgaaaaagc ccggtgagag cctgaagatc    60
agctgcaagg gcagcggcta cagcttcacc agctactaca tcggctgggt gcggcagatg   120
cccggcaagg gcctggagtg gatgggcatc atcgaccccca ccgacagcca gaccgcctac   180
agccccagct ccagggccca ggtgaccatc agcgccgaca gagcatcag caccgcctac   240 ctgcagtgga gcagcctgaa ggccagcgac accgccatgt actactgcgc ccggtacatg   300
atgaggggct tcgaccactg gggtcagggc accctggtga ccgtcagctc agctagcacc   360
aagggcccca gcgtgttccc cctggccccc agcagcaaga gcacctccgg cggcacagcc   420
gccctgggct gcctggtgaa ggactacttc cccgagcccg tgaccgtgtc ctggaacagc   480
ggagccctga ccagcggcgt gcacaccttc cccgccgtgc tgcagagcag cggcctgtac   540
agcctgtcca gcgtggtgac agtgcccagc agcagcctgg gcacccagac ctacatctgc   600
aacgtgaacc acaagcccag caacaccaag gtggacaaga gagtggagcc caagagctgc   660
gacaagaccc acacctgccc ccctgcccca gcccccgaag ctgcaggcgg ccctccgtg   720 ttcctgttcc cccccaagcc caaggacacc ctgatgatca gcaggacccc cgaggtgacc   780
tgcgtggtgg tggacgtgag ccacgaggac ccagaggtga agttcaactg gtacgtggac   840
ggcgtggagg tgcacaacgc caagaccaag cccagagagg agcagtacaa cagcacctac   900
agggtggtgt ccgtgctgac cgtgctgcac caggactggc tgaacggcaa agaatacaag   960
tgcaaggtct ccaacaaggc cctgcctgcc cccatcgaaa agaccatcag caaggccaag  1020
ggccagccac gggagcccca ggtgtacacc ctgcccccctt ctcgggagga tgaccaag   1080 aaccaggtgt ccctgacctg tctggtgaag ggcttctacc ccagcgacat cgccgtggag  1140
tgggagagca acggccagcc cgagaacaac tacaagacca cccccccagt gctggacagc  1200
gacggcagct tcttcctgta cagcaagctg accgtggaca gagcaggtg gcagcagggc  1260 aacgtgttca gctgcagcgt gatgcacgag gccctgcaca accactacac ccagaagagc  1320
ctgagcctgt cacccggcaa g                                            1341

<210> SEQ ID NO 485
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 485
agctacgagc tgacccagcc ccccagcgtg agcgtggccc caggccagac cgccaggatc    60
agctgcagcg gcgacagcct gggcgactac tacgcctact ggtatcagca gaagcccggc   120 caggccccg tgctggtgat ctacaaggac aacaacaggc ccagcggcat ccccgagagg   180
ttcagcggca gcaacagcgg caacaccgcc accctgacaa tcagcggcac ccaggccgag   240
gacgaggcca ctactactg ccagacctgg gacaccggcg agtcaggcgt gttcggcgga   300
gggaccaagc tgaccgtgct gggtcagcct aaggctgccc ccagcgtgac cctgttcccc   360
cccagcagcg aggagctgca ggccaacaag gccaccctgg tgtgcctgat cagcgacttc   420
tacccaggcg ccgtgaccgt ggcctggaag gccgacagca ccccgtgaa ggccggcgtg   480 gagaccacca cccccagcaa gcagagcaac aacaagtacg ccgccagcag ctacctgagc   540
ctgacccccg agcagtggaa gagccacagg tcctacagct gccaggtgac ccacgagggc   600
agcaccgtgg aaaagaccgt ggcccccaacc gagtgcagc                          639
```

```
<210> SEQ ID NO 486
<211> LENGTH: 68
<212> TYPE: PRT
<213> ORGANISM: Homo sapiens

<400> SEQUENCE: 486

Pro Val Asp Gly Glu Trp Asp Ser Trp Glu Trp Ser Pro Cys Ile
1               5                   10                  15

Arg Arg Asn Met Lys Ser Ile Ser Cys Gln Glu Ile Pro Gly Gln Gln
            20                  25                  30

Ser Arg Gly Arg Thr Cys Arg Gly Arg Lys Phe Asp Gly His Arg Cys
        35                  40                  45

Ala Gly Gln Gln Gln Asp Ile Arg His Cys Tyr Ser Ile Gln His Cys
    50                  55                  60

Pro Leu Lys Gly
65

<210> SEQ ID NO 487
<211> LENGTH: 67
<212> TYPE: PRT
<213> ORGANISM: Mus musculus

<400> SEQUENCE: 487

Pro Val Asn Gly Glu Trp Glu Ala Trp Gly Lys Trp Ser Asp Cys Ser
1               5                   10                  15

Arg Leu Arg Met Ser Ile Asn Cys Glu Gly Thr Pro Gly Gln Gln Ser
            20                  25                  30

Arg Ser Arg Ser Cys Gly Gly Arg Lys Phe Asn Gly Lys Pro Cys Ala
        35                  40                  45

Gly Lys Leu Gln Asp Ile Arg His Cys Tyr Asn Ile His Asn Cys Ile
    50                  55                  60

Met Lys Gly
65
```